US009663533B2

(12) United States Patent
Amans et al.

(10) Patent No.: US 9,663,533 B2
(45) Date of Patent: May 30, 2017

(54) THIENO[3,2-C]PYRIDIN-4(5H)-ONES AS BET INHIBITORS

(71) Applicant: GlaxoSmithKline LLC, Wilmington, New Castle, DE (US)

(72) Inventors: Dominique Amans, Stevenage (GB); Paul Bamborough, Stevenage (GB); Rino Antonio Bit, Stevenage (GB); John Alexander Brown, Stevenage (GB); Matthew Campbell, Stevenage (GB); Matthew John Lindon, Stevenage (GB); Tracy Jane Shipley, Stevenage (GB); Natalie Hope Theodoulou, Stevenage (GB); Christopher Roland Wellaway, Stevenage (GB); Susan Marie Westaway, Stevenage (GB)

(73) Assignee: GlaxoSmithKline LLC, Wilmington, DE (US)

(*) Notice: Subject to any disclaimer, the term of this patent is extended or adjusted under 35 U.S.C. 154(b) by 71 days.

(21) Appl. No.: 14/442,122

(22) PCT Filed: Nov. 12, 2013

(86) PCT No.: PCT/US2013/069541
§ 371 (c)(1),
(2) Date: May 12, 2015

(87) PCT Pub. No.: WO2014/078257
PCT Pub. Date: May 22, 2014

(65) Prior Publication Data
US 2016/0297832 A1 Oct. 13, 2016

Related U.S. Application Data

(60) Provisional application No. 61/726,184, filed on Nov. 14, 2012, provisional application No. 61/781,742, filed on Mar. 14, 2013.

(51) Int. Cl.
| | |
|---|---|
| *C07D 495/04* | (2006.01) |
| *A61K 45/06* | (2006.01) |
| *A61K 31/4365* | (2006.01) |
| *A61K 31/4427* | (2006.01) |
| *A61K 31/4439* | (2006.01) |
| *A61K 31/4545* | (2006.01) |
| *A61K 31/496* | (2006.01) |
| *A61K 31/5377* | (2006.01) |
| *A61K 31/551* | (2006.01) |
| *A61K 31/553* | (2006.01) |

(52) U.S. Cl.
CPC ........ *C07D 495/04* (2013.01); *A61K 31/4365* (2013.01); *A61K 31/4427* (2013.01); *A61K 31/4439* (2013.01); *A61K 31/4545* (2013.01); *A61K 31/496* (2013.01); *A61K 31/5377* (2013.01); *A61K 31/551* (2013.01); *A61K 31/553* (2013.01); *A61K 45/06* (2013.01)

(58) Field of Classification Search
CPC .................................................. C07D 495/04
See application file for complete search history.

(56) References Cited

U.S. PATENT DOCUMENTS

| 3,845,065 A | 10/1974 | Shen et al. |
|---|---|---|
| 2002/0055497 A1 | 5/2002 | Butler et al. |
| 2002/0115656 A1 | 8/2002 | Butler et al. |

FOREIGN PATENT DOCUMENTS

| EP | 0652218 | 5/1995 |
|---|---|---|
| JP | H08337583 A | 12/1996 |
| WO | WO 02/14315 | 2/2002 |
| WO | WO 02/20011 | 3/2002 |
| WO | WO 2013/097052 | 7/2013 |
| WO | WO 2013/097601 | 7/2013 |

OTHER PUBLICATIONS

Muller, Susanne. Expert Reviews in Molecular Medicine. vol. 13 (2011) 1-21.*
Zhang, Guangtao. Chem. Rev. (2015) 115, 11625-11668.*
Y. Ikeura et al. "Potent NK1 Receptor Agonists: Synthesis and Antagonistic Activity of Various Heterocycles with an N-[3,5-Bis(trifluoromethyl)benzyl]-N-methylcarbamoyl Substituent." Chem. Pharm. Bull., 1997, vol. 45, No. 10, pp. 1642-1652.
G. Gentile et al. "Identification of 2-(4-pyridyl)thienopyridinones as GSK-3.beta. inhibitors." Bioorg. Med. Chem. Lett., Jun. 29, 2011, vol. 21, No. 16, pp. 4823-4827.
M.J.R.P. Queiroz et al. "New strategies for the synthesis of heteroannulated 2-pyridinones, substituted 2-quinolinones and coumarins from dehydroamino acid derivatives." Tetrahedron, Mar. 21, 2008, vol. 64, No. 22, pp. 5139-5146.

* cited by examiner

*Primary Examiner* — Golam M M Shameem
*Assistant Examiner* — Laura Daniel
(74) *Attorney, Agent, or Firm* — Jane F. Djung; Kathryn A. Lutomski

(57) ABSTRACT

Thienopyridone compounds of formula (I):

(I)

or a salt thereof, pharmaceutical compositions containing such compounds and their use in therapy, in particular in the treatment of diseases or conditions for which a bromodomain inhibitor is indicated.

13 Claims, No Drawings

THIENO[3,2-C]PYRIDIN-4(5H)-ONES AS BET INHIBITORS

CROSS-REFERENCE TO RELATED APPLICATIONS

This application is filed pursuant to 35 USC 371 as a United States National Phase Application of International Patent Application Ser. No. PCT/US2013/069541 filed on Nov. 12, 2013, which claims priority from 61/726,184 filed on Nov. 14, 2012 and 61/781,742 filed on Mar. 14, 2013 in the United States.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.* 2011, 54, 3827-3838).

A novel class of compounds have been found which inhibit the binding of bromodomains with its cognate acetylated proteins, more particularly a class of compounds that inhibit the binding of BET family bromodomains to aceylated lysine residues, even more particularly a class of compounds that selectively inhibit the binding and function of BET family bromodomains via Binding Domain 1 (BD1). Such compounds will hereafter be referred to as "bromodomain inhibitors".

SUMMARY OF THE INVENTION

In a first aspect of the present invention, there is provided a compound of formula (I)

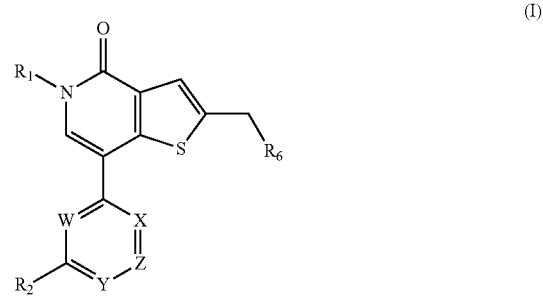

(I)

or a salt thereof, more particularly a compound of formula (I) or a pharmaceutically acceptable salt thereof.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to a compound of formula (I)

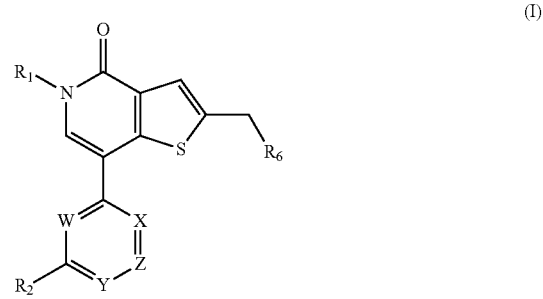

(I)

wherein:

W is N or C—R$_8$;

X is N, CH or C(CH$_3$);

Z is N or C—R$_{14}$;

Y is N or C—R$_5$ (subject to proviso that no more than 2 of W, X, Y and Z are N);

R$_1$ is C$_{1-4}$alkyl;

R$_2$ is H, OH, C$_{1-4}$alkyl, —N(CH$_3$)$_2$, —NH(CH$_3$), halo, —CF$_3$, —NH$_2$, —OC$_{1-4}$alkyl, —NHC(O)H, —NHC(O)C$_{1-4}$alkyl, —N(CH$_3$)C(O)C$_{1-4}$alkyl, —NHCH(CH$_3$)CH$_2$OCH$_3$, —N(CH$_3$)CH$_2$CH$_2$OCH$_3$, —OCH$_2$CH$_2$OCH$_3$, —OCH$_2$CH$_2$CH$_2$OH, —OCH(CH$_3$)CH$_2$OCH$_3$, or R$_2$ is a group selected from -G-CH$_2$CH(R$_3$)(R$_4$), -G-CH(R$_3$)(R$_4$) and -G-R$_3$ in which G is NH, N(CH$_3$), O, C(O)NH or NHC(O);

R$_3$ is phenyl, pyridinyl, C$_{3-7}$cycloalkyl or a heterocycle optionally substituted by =O; and R$_4$ is H or C$_{1-4}$ alkyl;

R$_5$ is H, C$_{1-4}$alkyl, halo, —CF$_3$, CN, OH, —OC$_{1-4}$alkyl, —CH$_2$NH$_2$, —OCF$_3$ or —SO$_2$CH$_3$;

R$_6$ is —NR$_{11}$R$_{12}$ or a group

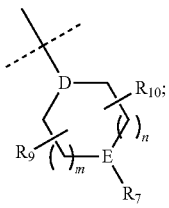

D is CH or N;

E is N, O, CH or SO$_2$;

R$_7$, when present, is H, OH, C$_{1-4}$alkyl, —NH$_2$, —SO$_2$C$_{1-4}$alkyl, —SO$_2$phenyl, —SO$_2$benzyl, —SO$_2$N(CH$_3$)$_2$, —NHSO$_2$CH$_3$, —C(O)C$_{1-4}$alkyl or —C(O)phenyl;

R$_8$ is H, C$_{1-4}$alkyl, halo, —CF$_3$, CN, OH, —OC$_{1-4}$ alkyl, —OCF$_3$, —OCH$_2$phenyl or —OCH$_2$C$_{3-7}$cycloalkyl;

R$_9$ is H, C$_{1-4}$alkyl, —C(O)NH$_2$, —CO$_2$CH$_3$, —CF$_3$, halo, OH, —OC$_{1-4}$alkyl, —CH$_2$OH, —C(O)NHCH$_3$, —C(O)N(CH$_3$)$_2$, —CH$_2$OC$_{1-4}$alkyl, —CH$_2$OCH$_2$C$_{3-7}$cycloalkyl or oxo;

R$_{10}$ is H, C$_{1-4}$alkyl, —C(O)NH$_2$, —CO$_2$CH$_3$, —CF$_3$, halo, OH or —OC$_{1-4}$alkyl;

R$_{11}$ is H, C$_{1-4}$alkyl or SO$_2$CH$_3$;

R$_{12}$ is H, C$_{1-4}$alkyl, C$_{1-4}$alkyleneNHR$_{13}$, C$_{1-4}$alkyleneOH, SO$_2$CH$_3$, a heterocycle or a heterocycle comprising SO$_2$;

R$_{13}$ is H or SO$_2$CH$_3$;

R$_{14}$ is H, C$_{1-4}$alkyl or NHC(O)C$_{1-4}$alkyl; and n and m are each an integer independently selected from 0, 1 and 2; or a salt thereof.

In one embodiment, W is C—R$_8$. In another embodiment W is N. In one embodiment R$_8$ is hydrogen, methyl, ethyl, —OCH$_3$, fluoro, —OCH$_2$cyclopropyl or —OCH$_2$phenyl. In another embodiment R$_8$ is hydrogen, methyl or ethyl. In another embodiment R$_8$ is hydrogen. In a further embodiment R$_8$ is hydrogen or —OCH$_2$cyclopropyl.

In one embodiment X is CH. In another embodiment X is C(CH$_3$). In further embodiment X is N.

In one embodiment Z is C—R$_{14}$. In another embodiment Z is N. In one embodiment R$_{14}$ is H.

In one embodiment Y is C—R$_5$. In another embodiment Y is N.

In one embodiment R$_5$ is hydrogen, —OCH$_3$, fluoro, chloro, —CF$_3$, CN, methyl, —SO$_2$CH$_3$ or —CH$_2$NH$_2$. In another embodiment R$_5$ is H, —CF$_3$, CN, —OCH$_3$, —CH$_2$NH$_2$ or —SO$_2$CH$_3$. In another embodiment R$_5$ is H or —OCH$_3$. In another embodiment R$_5$ is H. In a further embodiment R$_5$ is —OCH$_3$.

In one embodiment R$_1$ is methyl or ethyl. In another embodiment R$_1$ is methyl.

In one embodiment R$_2$ is H, OH, methyl, —N(CH$_3$)$_2$, fluoro, chloro, —CF$_3$, —NH$_2$, —OCH$_3$, —OCH(CH$_3$)$_2$, —NHC(O)H, —NHC(O)Me, —N(CH$_3$)CH$_2$CH$_2$OCH$_3$, —OCH$_2$CH$_2$OCH$_3$, —OCH$_2$CH$_2$CH$_2$OH or —OCH(CH$_3$)CH$_2$OCH$_3$. In one embodiment R$_2$ is H, OH, methyl, fluoro, chloro, —CF$_3$, —NH$_2$, —OCH$_3$, —OCH(CH$_3$)$_2$, —NHC(O)H, —NHC(O)Me, —N(CH$_3$)CH$_2$CH$_2$OCH$_3$, —OCH$_2$CH$_2$OCH$_3$, —OCH$_2$CH$_2$CH$_2$OH or —OCH(CH$_3$)CH$_2$OCH$_3$. In another embodiment R$_2$ is H, —OCH$_3$, —OCH(CH$_3$)$_2$, —NHC(O)Me or —N(CH$_3$)CH$_2$CH$_2$OCH$_3$. In another embodiment R$_2$ is H, OH, methyl, chloro, —CF$_3$, —NH$_2$, —OCH$_3$, —OCH$_2$CH$_3$, —OCH(CH$_3$)$_2$, —NHC(O)H, —NHC(O)CH$_3$, —NHC(O)CH$_2$CH$_3$, —NHCH(CH$_3$)CH$_2$OCH$_3$, —N(CH$_3$)CH$_2$CH$_2$OCH$_3$, —N(CH$_3$)C(O)CH$_3$, —OCH$_2$CH$_2$OCH$_3$, —OCH$_2$CH$_2$CH$_2$OH or —OCH(CH$_3$)CH$_2$OCH$_3$. In a further embodiment R$_2$ is H, —OCH$_3$, —NHC(O)CH$_3$, —NHC(O)CH$_2$CH$_3$ or —N(CH$_3$)CH$_2$CH$_2$OCH$_3$.

In one embodiment R$_2$ is a group -G-CH(R$_3$)(R$_4$).

In one embodiment G is NH, N(CH$_3$) or O. In another embodiment G is NH, O or C(O)NH. In a further embodiment G is NH or O.

In one embodiment R$_3$ is phenyl, pyridinyl, cyclopropyl, tetrahydropyranyl or tetrahydrofuranyl. In another embodiment R$_3$ is phenyl, pyridin-2-yl, cyclopropyl, tetrahydropyran-4-yl or tetrahydrofuran-3-yl. In another embodiment R$_3$ is phenyl, pyridin-2-yl, cyclopropyl, tetrahydropyran-4-yl or tetrahydrofuran-2-yl. In a further embodiment R$_3$ is phenyl or pyridin-2-yl.

In one embodiment R$_4$ is H or methyl.

In one embodiment R$_2$ is a group -G-CH$_2$CH(R$_3$)(R$_4$).

In one embodiment G is NH, N(CH$_3$) or O. In another embodiment G is NH, O or C(O)NH. In a further embodiment G is NH or O.

In one embodiment R$_3$ is pyrrolidinyl or pyrrolidin-2-one.

In one embodiment R$_4$ is H or methyl.

In one embodiment R$_6$ is —NR$_{11}$R$_{12}$.

In one embodiment R$_{11}$ is H, methyl or —SO$_2$CH$_3$. In another embodiment R$_{11}$ is H or methyl.

In one embodiment R$_{12}$ is —CH$_2$CH$_2$CH$_2$NH$_2$, —CH$_2$CH$_2$NH$_2$, —CH$_2$CH$_2$OH—CH$_2$CH$_2$NHSO$_2$CH$_3$, —SO$_2$CH$_3$, —CH$_3$ or

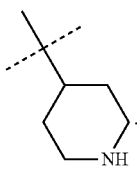

In another embodiment R$_{12}$ is —CH$_2$CH$_2$CH$_2$NH$_2$, —CH$_2$CH$_2$NH$_2$, —CH$_2$CH$_2$NHSO$_2$CH$_3$, —SO$_2$CH$_3$, —CH$_3$ or

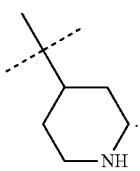

In one embodiment $R_6$ is a group

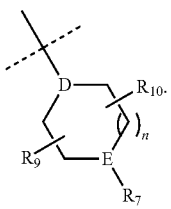

In one embodiment D is CH. In another embodiment D is N.

In one embodiment E is N. In another embodiment E is O. In another embodiment E is CH. In a further embodiment E is $SO_2$.

In one embodiment $R_7$ is H, methyl, ethyl, iso-propyl, —$NH_2$, —$SO_2CH_3$, —$SO_2CH_2CH_3$, —$SO_2CH(CH_3)_2$, —$SO_2CH_2$phenyl, —$SO_2$phenyl, —$SO_2N(CH_3)_2$, —C(O)$CH_3$ or C(O)phenyl. In another embodiment $R_7$ is H, methyl, ethyl, iso-propyl, —$SO_2CH_3$, —$SO_2CH_2CH_3$ or —C(O)phenyl. In a further embodiment $R_7$ is —$SO_2CH_3$.

In one embodiment E is N and $R_7$ is H, methyl, ethyl, iso-propyl, —$NH_2$, —$SO_2CH_3$, —$SO_2CH_2CH_3$, —$SO_2CH(CH_3)_2$, —$SO_2CH_2$phenyl, —$SO_2$phenyl, —$SO_2N(CH_3)_2$, —C(O)$CH_3$ or C(O)phenyl.

In another embodiment E is N and $R_7$ is H, methyl, ethyl, iso-propyl, —$SO_2CH_3$, —$SO_2CH_2CH_3$ or —C(O)phenyl. In a further embodiment E is N and $R_7$ is —$SO_2CH_3$.

In one embodiment E and D are both N and $R_7$ is H, methyl, ethyl, iso-propyl, —$SO_2CH_3$, —$SO_2CH_2CH_3$ or —C(O)phenyl. In another embodiment E and D are both N and $R_7$ is H, methyl, ethyl, iso-propyl, —$NH_2$, —$SO_2CH_3$, —$SO_2CH_2CH_3$, —$SO_2CH(CH_3)_2$, —$SO_2CH_2$phenyl, —$SO_2$phenyl, —$SO_2N(CH_3)_2$, —C(O)$CH_3$ or C(O)phenyl. In a further embodiment E and D are both N and $R_7$ is —$SO_2CH_3$.

In one embodiment $R_9$ is H, methyl, ethyl, butyl, —$CONH_2$, —$CO_2CH_3$, —$CF_3$, fluoro, OH, —$OCH_3$ or oxo. In one embodiment $R_9$ is H, methyl, ethyl, butyl, —$CONH_2$, —$CO_2CH_3$, —$CF_3$, fluoro, OH or —$OCH_3$. In another embodiment $R_9$ is H, methyl, ethyl, butyl, —C(O)$NH_2$ or —$CO_2CH_3$. In another embodiment $R_9$ is H or methyl. In another embodiment $R_9$ is H. In a further embodiment $R_9$ is methyl.

In one embodiment $R_{10}$ is H or methyl. In another embodiment $R_{10}$ is H. In a further embodiment $R_{10}$ is methyl.

In one embodiment $R_9$ and $R_{10}$ are attached to the same atom. In another embodiment $R_9$ and $R_{10}$ are attached to different atoms.

In one embodiment n is 1 or 2. In another embodiment n is 0. In another embodiment n is 1. In a further embodiment n is 2.

In one embodiment m is 1 or 2. In another embodiment m is 0. In another embodiment m is 1. In a further embodiment m is 2.

In one embodiment both n and m are 1. In another embodiment n is 1 and m is 2.

In one embodiment $R_6$ is selected from:

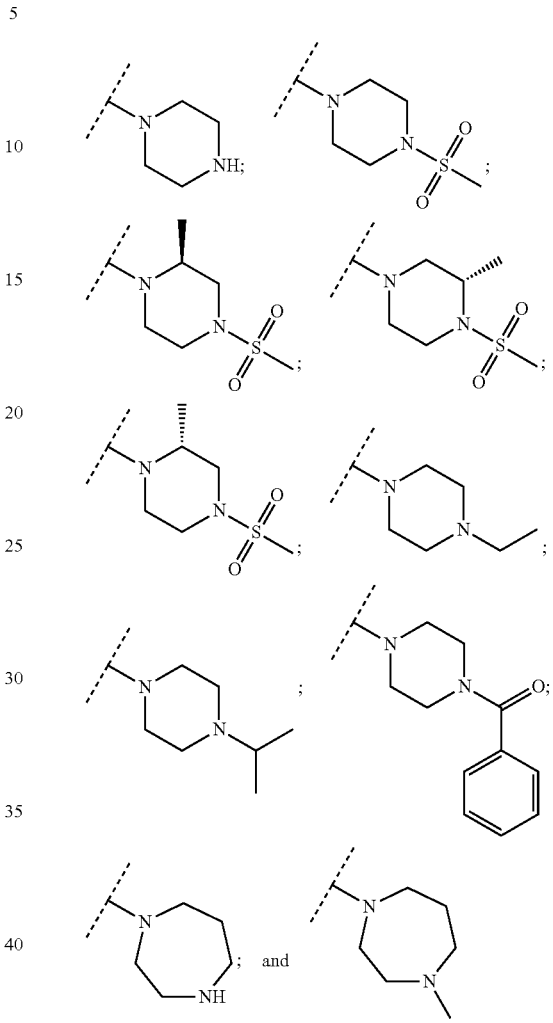

In another embodiment $R_6$ is selected from:

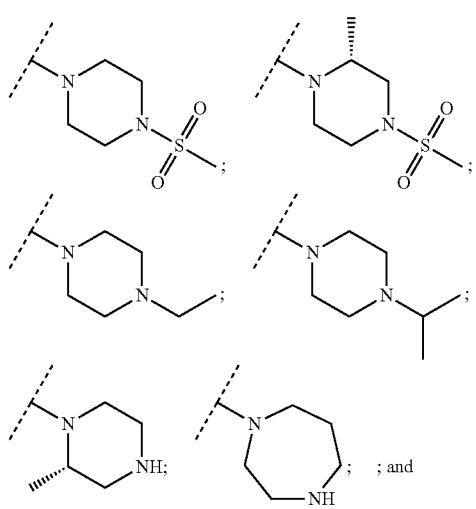

-continued

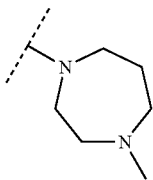

In another embodiment R$_6$ is selected from:

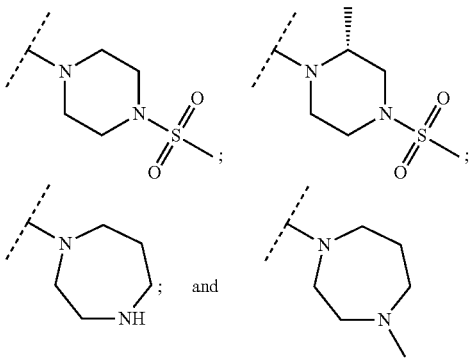

In a further embodiment R$_6$ is:

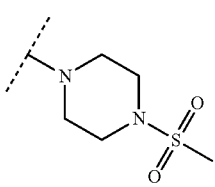

In one embodiment the compound of formula (I) is a compound of formula (IA)

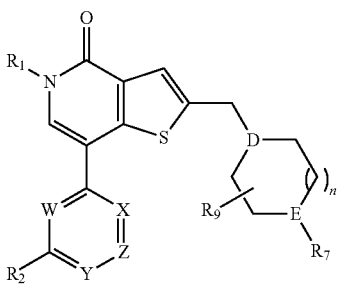

wherein:
W is N, CH or C(OCH$_2$cyclopropyl)
X and Z are each independently N or CH;
Y is N or C—R$_5$ (subject to proviso that no more than 2 of W, X, Y and Z are N);
R$_1$ is C$_{1-4}$ alkyl;
R$_2$ is H, OH, —OC$_{1-4}$alkyl, —NHC(O)H, —NHC(O)CH$_3$, —NHC(O)CH$_2$CH$_3$, —N(CH$_3$)CH$_2$CH$_2$OCH$_3$ or
R$_2$ is a group -G-CH(R$_3$)(R$_4$) or -G-CH$_2$CH(R$_3$)(R$_4$) in which
G is NH, N(CH$_3$) or O;
R$_3$ is phenyl, pyridinyl or a heterocycle optionally substituted by =O; and
R$_4$ is H or C$_{1-4}$ alkyl;
R$_5$ is H, C$_{1-4}$alkyl, halo, —CF$_3$, CN, OH, —OC$_{1-4}$ alkyl, —CH$_2$NH$_2$, —OCF$_3$ or —SO$_2$CH$_3$;
D is CH or N;
E is N, O or CH;
R$_7$, when present, is H, C$_{1-4}$alkyl, SO$_2$C$_{1-4}$alkyl or —C(O)phenyl;
R$_9$ is H, C$_{1-4}$ alkyl or —CONH$_2$; and
n is 1 or 2; or a salt thereof.

In one embodiment the compound of formula (I) is a compound of formula (IB)

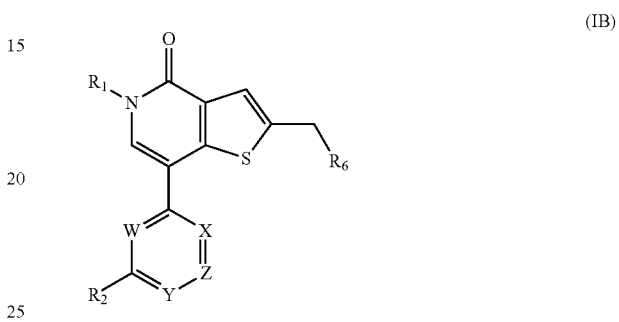

wherein:
W is N or C—R$_8$;
X and Z are independently N, CH or C(CH$_3$);
Y is N or C—R$_5$ (subject to proviso that no more than 2 of W, X, Y and Z are N);
R$_1$ is C$_{1-4}$ alkyl; R$_2$ is H, OH, C$_{1-4}$alkyl, halo, —CF$_3$, —NH$_2$, —OC$_{1-4}$alkyl, —NHC(O)H, —NHC(O)Me, —NHCH(CH$_3$)CH$_2$OCH$_3$, —N(CH$_3$)CH$_2$CH$_2$OCH$_3$, —OCH$_2$CH$_2$OCH$_3$, —OCH$_2$CH$_2$CH$_2$OH, —OCH(CH$_3$)CH$_2$OCH$_3$, or
R$_2$ is a group -G-CH(R$_3$)(R$_4$) in which
G is NH, N(CH$_3$), O or C(O)NH;
R$_3$ is phenyl, pyridinyl, C$_3$-$_7$cycloalkyl or a heterocycle; and
R$_4$ is H or C$_{1-4}$ alkyl;
R$_5$ is H, C$_{1-4}$alkyl, halo, —CF$_3$, CN, OH, —OC$_{1-4}$alkyl, —CH$_2$NH$_2$, —OCF$_3$ or —SO$_2$CH$_3$;
R$_6$ is —NR$_{11}$R$_{12}$ or a group

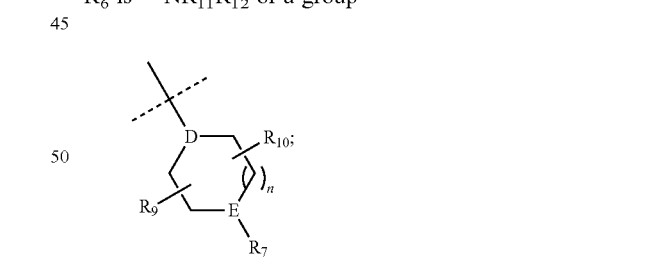

D is CH or N;
E is N, O, CH or SO$_2$;
R$_7$, when present, is H, OH, C$_{1-4}$alkyl, —NH$_2$, —SO$_2$C$_{1-4}$ alkyl, —SO$_2$phenyl, —SO$_2$benzyl, —SO$_2$N(CH$_3$)$_2$, —NHSO$_2$CH$_3$, —C(O)C$_{1-4}$alkyl or —C(O)phenyl;
R$_8$ is H, C$_{1-4}$alkyl, halo, —CF$_3$, CN, OH, —OC$_{1-4}$alkyl, —OCF$_3$ or —OCH$_2$phenyl;
R$_9$ is H, C$_{1-4}$ alkyl, —CONH$_2$, —CO$_2$CH$_3$, —CF$_3$, halo, OH or —OC$_{1-4}$alkyl;
R$_{10}$ is H, C$_{1-4}$alkyl, —CONH$_2$, —CO$_2$CH$_3$, —CF$_3$, halo, OH or —OC$_{1-4}$alkyl;
R$_{11}$ is H or C$_{1-4}$alkyl;

$R_{12}$ is H, $C_{1-4}$ alkyl, $C_{1-4}$alkyleneNHR$_{13}$, SO$_2$CH$_3$ or a heterocycle;
$R_{13}$ is H or SO$_2$CH$_3$; and
n is 0, 1 or 2; or a salt thereof.

In one embodiment, W is C—R$_8$. In another embodiment W is N.

In one embodiment R$_8$ is hydrogen, methyl or ethyl. In another embodiment R$_8$ is hydrogen.

In one embodiment X is CH. In another embodiment X is C(CH$_3$). In further embodiment X is N.

In one embodiment Z is CH. In another embodiment Z is N.

In one embodiment Y is C—R$_5$. In another embodiment Y is N.

In one embodiment R$_5$ is H, —CF$_3$, CN, —OCH$_3$, —CH$_2$NH$_2$ or —SO$_2$CH$_3$. In another embodiment R$_5$ is H or —OCH$_3$.

In one embodiment R$_1$ is methyl or ethyl. In another embodiment R$_1$ is methyl.

In one embodiment R$_2$ is H, OH, methyl, fluoro, chloro, —CF$_3$, —NH$_2$, —OCH$_3$, —OCH(CH$_3$)$_2$, —NHC(O)H, —NHC(O)Me, —N(CH$_3$)CH$_2$CH$_2$OCH$_3$, —OCH$_2$CH$_2$OCH$_3$, —OCH$_2$CH$_2$CH$_2$OH or —OCH(CH$_3$)CH$_2$OCH$_3$. In another embodiment R$_2$ is H, —OCH$_3$, —OCH(CH$_3$)$_2$, —NHC(O)Me or —N(CH$_3$)CH$_2$CH$_2$OCH$_3$. In a further embodiment R$_2$ is a group -G-CH(R$_3$)(R$_4$).

In one embodiment G is NH, N(CH$_3$) or O. In another embodiment G is NH or O.

In one embodiment R$_3$ is phenyl, pyridinyl, cyclopropyl, tetrahydropyranyl or tetrahydrofuranyl. In another embodiment R$_3$ is phenyl, pyridin-2-yl, cyclopropyl, tetrahydropyran-4-yl or tetrahydrofuran-3-yl. In a further embodiment R$_3$ is phenyl or pyridin-2-yl.

In one embodiment R$_4$ is H or methyl.
In one embodiment R$_6$ is —NR$_{11}$R$_{12}$.
In one embodiment R$_{11}$ is H or methyl.
In one embodiment R$_{12}$ is —CH$_2$CH$_2$CH$_2$NH$_2$, —CH$_2$CH$_2$NH$_2$, —CH$_2$CH$_2$NHSO$_2$CH$_3$, —SO$_2$CH$_3$, —CH$_3$ or

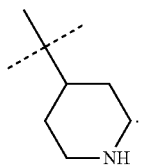

In one embodiment R$_6$ is a group

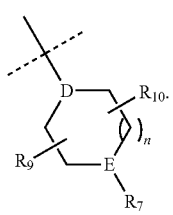

In one embodiment D is CH. In another embodiment D is N.

In one embodiment E is N. In another embodiment E is O. In another embodiment E is CH. In a further embodiment E is SO$_2$.

In one embodiment R$_7$ is H, methyl, ethyl, iso-propyl, —SO$_2$CH$_3$, —SO$_2$CH$_2$CH$_3$ or —C(O)phenyl. In another embodiment R$_7$ is —SO$_2$CH$_3$.

In one embodiment E is N and R$_7$ is H, methyl, ethyl, iso-propyl, —SO$_2$CH$_3$, —SO$_2$CH$_2$CH$_3$ or —C(O)phenyl.

In one embodiment E and D are both N and R$_7$ is H, methyl, ethyl, iso-propyl, —SO$_2$CH$_3$, —SO$_2$CH$_2$CH$_3$ or —C(O)phenyl.

In one embodiment R$_9$ is H, methyl, ethyl, butyl, —CONH$_2$, —CO$_2$CH$_3$, —CF$_3$, fluoro, OH or —OCH$_3$. In another embodiment R$_9$ is H or methyl.

In one embodiment R$_{10}$ is H or methyl.
In one embodiment n is 0. In another embodiment n is 1. In a further embodiment n is 2.

In one embodiment the compound of formula (I) is a compound of formula (IC)

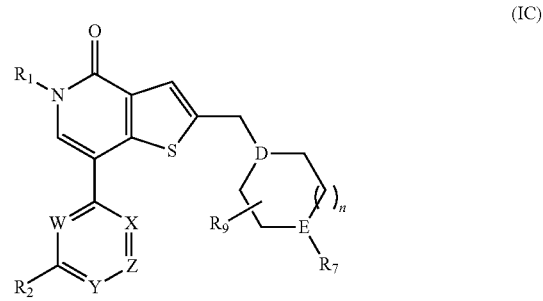

wherein:
W, X and Z are independently N or CH;
Y is N or C—R$_5$ (subject to proviso that no more than 2 of W, X, Y and Z are N);
R$_1$ is C$_{1-4}$ alkyl;
R$_2$ is H, OH, —OC$_{1-4}$alkyl, —NHC(O)H, —NHC(O)Me or R$_2$ is a group -G-CH(R$_3$)(R$_4$) in which
 G is NH, N(CH$_3$) or O;
 R$_3$ is phenyl, pyridinyl or a heterocycle; and
 R$_4$ is H or C$_{1-4}$ alkyl;
R$_5$ is H, C$_{1-4}$alkyl, halo, —CF$_3$, CN, OH, —OC$_{1-4}$ alkyl, —CH$_2$NH$_2$ or —OCF$_3$;
D is CH or N;
E is N, O or CH;
R$_7$, when present, is H, C$_{1-4}$alkyl or —SO$_2$C$_{1-4}$alkyl;
R$_9$ is H, C$_{1-4}$ alkyl or —CONH$_2$; and
n is 0, 1 or 2; or a salt thereof.

In one embodiment the compound of formula (I) is a compound of formula (ID)

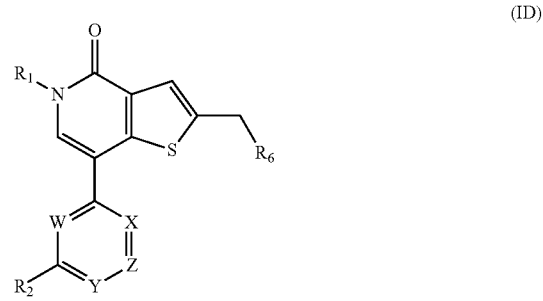

wherein:
W is N or C—R$_8$;

X is N, CH or C(CH₃);
Z is N or C—R₁₄;
Y is N or C—R₅ (subject to proviso that no more than 2 of W, X, Y and Z are N);
R₁ is C₁₋₄ alkyl;
R₂ is H, OH, C₁₋₄alkyl, halo, —CF₃, —NH₂, —OC₁₋₄alkyl, —NHC(O)H, —NHC(O)C₁₋₄alkyl, —N(CH₃)C(O)C₁₋₄alkyl, —NHCH(CH₃)CH₂OCH₃, —N(CH₃)CH₂CH₂OCH₃, —OCH₂CH₂OCH₃, —OCH₂CH₂CH₂OH, —OCH(CH₃)CH₂OCH₃, or
R₂ is a group selected from -G-CH₂CH(R₃)(R₄), -G-CH(R₃)(R₄) and -G-R₃ in which
  G is NH, N(CH₃), O, C(O)NH or NHC(O);
  R₃ is phenyl, pyridinyl, C₃₋₇cycloalkyl or a heterocycle optionally substituted by =O; and
  R₄ is H or C₁₋₄ alkyl;
R₅ is H, C₁₋₄alkyl, halo, —CF₃, CN, OH, —OC₁₋₄alkyl, —CH₂NH₂, —OCF₃ or —SO₂CH₃;
R₆ is —NR₁₁R₁₂ or a group

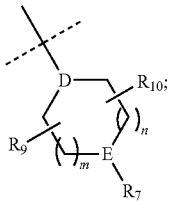

D is CH or N;
E is N, O, CH or SO₂;
R₇, when present, is H, OH, C₁₋₄alkyl, —NH₂, —SO₂C₁₋₄alkyl, —SO₂phenyl, —SO₂benzyl, —SO₂N(CH₃)₂, —NHSO₂CH₃, —C(O)C₁₋₄alkyl, —C(O)phenyl,
R₈ is H, C₁₋₄alkyl, halo, —CF₃, CN, OH, —OC₁₋₄ alkyl, —OCF₃, —OCH₂phenyl or —OCH₂C₃₋₇cycloalkyl;
R₉ is H, C₁₋₄ alkyl, —C(O)NH₂, —CO₂CH₃, —CF₃, halo, OH, —OC₁₋₄alkyl, —CH₂OH, —C(O)NHCH₃ or —C(O)NH(CH₃)₂; —CH₂OC₁₋₄alkyl or —CH₂OCH₂C₃₋₇cycloalkyl;
R₁₀ is H, C₁₋₄alkyl, —C(O)NH₂, —CO₂CH₃, —CF₃, halo, OH or —OC₁₋₄alkyl;
R₁₁ is H, C₁₋₄alkyl or SO₂CH₃;
R₁₂ is H, C₁₋₄alkyl, C₁₋₄alkyleneNHR₁₃, SO₂CH₃, a heterocycle or a heterocycle comprising SO₂;
R₁₃ is H or SO₂CH₃;
R₁₄ is H, C₁₋₄alkyl or NHC(O)C₁₋₄alkyl; and
n and m are each an integer independently selected from 0, 1 and 2; or a salt thereof.

It is to be understood that the present invention covers all combinations of substituent groups described hereinabove.

Compounds of the invention include the compounds of Examples 1 to 207 and salts thereof. In another embodiment compounds of the invention include the compounds of Examples 1 to 197 and salts thereof. In a further embodiment compounds of the invention include the compounds of Examples 1 to 139 and salts thereof.

In another embodiment, the compound of formula (I) is
5-methyl-2-((4-(methylsulphonyl)piperazin-1-yl)methyl)-7-(5-(1-phenylethoxy)pyridin-3-yl)thieno[3,2-c]pyridin-4(5H)-one;
5-methyl-2-((4-(methylsulphonyl)piperazin-1-yl)methyl)-7-(3-(1-(pyridin-2-yl)ethoxy)phenyl)thieno[3,2-c]pyridin-4(5H)-one;
5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one;
(R)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one;
(S)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one;
7-(5-(benzyloxy)pyridin-3-yl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(3-((tetrahydro-2H-pyran-4-yl)methoxy)phenyl)thieno[3,2-c]pyridin-4(5H)-one;
7-(3-isopropoxyphenyl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(2-((tetrahydro-2H-pyran-4-yl)methoxy)pyridin-4-yl)thieno[3,2-c]pyridin-4(5H)-one;
7-(3-(2-methoxyethoxy)phenyl)-5-methyl-2-((4-(methylsulphonyl)piperazin-1-yl)methyl)thieno[3,2-c]pyridin-4(5H)-one;
7-(3-(3-hydroxypropoxy)phenyl)-5-methyl-2-((4-(methylsulphonyl)piperazin-1-yl)methyl)thieno[3,2-c]pyridin-4(5H)-one;
7-(3-hydroxyphenyl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(5-((tetrahydro-2H-pyran-4-yl)methoxy)pyridin-3-yl)thieno[3,2-c]pyridin-4(5H)-one;
7-(5-hydroxypyridin-3-yl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(2-(1-(pyridin-2-yl)ethoxy)pyridin-4-yl)thieno[3,2-c]pyridin-4(5H)-one;
7-(5-((1-methoxypropan-2-yl)oxy)pyridin-3-yl)-5-methyl-2-((4-(methylsulphonyl)piperazin-1-yl)methyl)thieno[3,2-c]pyridin-4(5H)-one;
7-(3-methoxyphenyl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(3-(1-phenylethoxy)phenyl)thieno[3,2-c]pyridin-4(5H)-one;
5-methyl-2-((4-(methylsulphonyl)piperazin-1-yl)methyl)-7-(3-((1-phenylethyl)amino)phenyl)thieno[3,2-c]pyridin-4(5H)-one;
(R)-N-(3-(5-methyl-2-((2-methyl-4-(methylsulphonyl)piperazin-1-yl)methyl)-4-oxo-4,5-dihydrothieno[3,2-c]pyridin-7-yl)phenyl)acetamide;
5-methyl-2-((4-(methylsulphonyl)piperazin-1-yl)methyl)-7-(3-(((tetrahydro-2H-2H-pyran-4-yl)methyl)amino)phenyl)thieno[3,2-c]pyridin-4(5H)-one;
N-(3-(5-methyl-2-((4-(methylsulphonyl)piperazin-1-yl)methyl)-4-oxo-4,5-dihydrothieno[3,2-c]pyridin-7-yl)phenyl)acetamide;
7-(2-((2-methoxyethyl)(methyl)amino)pyridin-4-yl)-5-methyl-2-((4-(methylsulphonyl)piperazin-1-yl)methyl)thieno[3,2-c]pyridin-4(5H)-one;
7-(2-((1-methoxypropan-2-yl)amino)pyridin-4-yl)-5-methyl-2-((4-(methylsulphonyl)piperazin-1-yl)methyl)thieno[3,2-c]pyridin-4(5H)-one;
7-(2-((cyclopropylmethyl)amino)pyridin-4-yl)-5-methyl-2-((4-(methylsulphonyl)piperazin-1-yl)methyl)thieno[3,2-c]pyridin-4(5H)-one;

N-(3-(5-methyl-2-((4-(methylsulphonyl)piperazin-1-yl) methyl)-4-oxo-4,5-dihydrothieno[3,2-c]pyridin-7-yl)phenyl)formamide;

7-(3-aminophenyl)-5-methyl-2-((4-(methylsulphonyl)piperazin-1-yl)methyl)thieno[3,2-c]pyridin-4(5H)-one;

7-(3-(benzylamino)phenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-(((tetrahydrofuran-2-yl)methyl)amino)pyridin-4-yl) thieno[3,2-c]pyridin-4(5H)-one;

7-(3-(benzyloxy)phenyl)-2-((4-ethylpiperazin-1-yl)methyl)-5-methylthieno[3,2-c]pyridin-4(5H)-one;

7-(3-(benzyloxy)phenyl)-2-((4-isopropylpiperazin-1-yl) methyl)-5-methylthieno[3,2-c]pyridin-4(5H)-one;

2-((4-benzoylpiperazin-1-yl)methyl)-7-(3,4-dimethoxyphenyl)-5-methylthieno[3,2-c]pyridin-4(5H)-one;

7-(3,4-dimethoxyphenyl)-2-((4-(ethylsulphonyl)piperazin-1-yl)methyl)-5-methylthieno[3,2-c]pyridin-4(5H)-one;

N-(3-(5-methyl-2-((4-methylpiperazin-1-yl)methyl)-4-oxo-4,5-dihydrothieno[3,2-c]pyridin-7-yl)phenyl)acetamide;

2-((4-(benzylsulphonyl)piperazin-1-yl)methyl)-7-(3,4-dimethoxyphenyl)-5-methylthieno[3,2-c]pyridin-4(5H)-one;

7-(3,4-dimethoxyphenyl)-5-methyl-2-((4-(phenylsulphonyl)piperazin-1-yl)methyl)thieno[3,2-c]pyridin-4(5H)-one;

2-((4-acetylpiperazin-1-yl)methyl)-5-methyl-7-phenylthieno[3,2-c]pyridin-4(5H)-one;

7-(3,4-dimethoxyphenyl)-2-((4-(isopropylsulphonyl)piperazin-1-yl)methyl)-5-methylthieno[3,2-c]pyridin-4(5H)-one;

7-(3,4-dimethoxyphenyl)-5-methyl-2-((4-methylpiperazin-1-yl)methyl)thieno[3,2-c]pyridin-4(5H)-one;

4-((7-(3,4-dimethoxyphenyl)-5-methyl-4-oxo-4,5-dihydrothieno[3,2-c]pyridin-2-yl)methyl)-N,N-dimethylpiperazine-1-sulphonamide;

2-((4-acetylpiperazin-1-yl)methyl)-7-(3,4-dimethoxyphenyl)-5-methylthieno[3,2-c]pyridin-4(5H)-one;

7-(3-(benzyloxy)phenyl)-5-methyl-2-((4-methyl-1,4-diazepan-1-yl)methyl)thieno[3,2-c]pyridin-4(5H)-one;

N-(3-(5-methyl-2-((1-(methylsulphonyl)piperidin-4-yl) methyl)-4-oxo-4,5-dihydrothieno[3,2-c]pyridin-7-yl)phenyl)acetamide;

7-(2,4-difluorophenyl)-5-methyl-2-((4-(methylsulphonyl) piperazin-1-yl)methyl)thieno[3,2-c]pyridin-4(5H)-one;

5-methyl-2-((4-(methylsulphonyl)piperazin-1-yl)methyl)-7-(pyridin-2-yl)thieno[3,2-c]pyridin-4(5H)-one;

5-methyl-2-((4-(methylsulphonyl)piperazin-1-yl)methyl)-7-phenylthieno[3,2-c]pyridin-4(5H)-one;

2-((2,4-dimethylpiperazin-1-yl)methyl)-5-methyl-7-(5-((tetrahydro-2H-2H-pyran-4-yl)methoxy)pyridin-3-yl) thieno[3,2-c]pyridin-4(5H)-one;

2-((1,4-diazepan-1-yl)methyl)-7-(3,4-dimethoxyphenyl)-5-methylthieno[3,2-c]pyridin-4(5H)-one;

2-(((3-aminopropyl)amino)methyl)-7-(3-(benzyloxy)phenyl)-5-methylthieno[3,2-c]pyridin-4(5H)-one;

N-(2-(((7-(3-(benzyloxy)phenyl)-5-methyl-4-oxo-4,5-dihydrothieno[3,2-c]pyridin-2-yl)methyl)amino)ethyl)methanesulphonamide;

N-((7-(3-(benzyloxy)phenyl)-5-methyl-4-oxo-4, 5-dihydrothieno[3,2-c]pyridin-2-yl)methyl)-N-(2-(methylsulfonamido)ethyl)methanesulfonamide;

N-(4-(5-methyl-2-((1-(methylsulphonyl)piperidin-4-yl) methyl)-4-oxo-4,5-dihydrothieno[3,2-c]pyridin-7-yl) pyridin-2-yl)acetamide;

N-(3-(5-methyl-2-((4-methyl-1,4-diazepan-1-yl)methyl)-4-oxo-4,5-dihydrothieno[3,2-c]pyridin-7-yl)phenyl)acetamide;

7-(3,4-dimethoxyphenyl)-5-methyl-2-((1-(methylsulphonyl)piperidin-4-yl)methyl)thieno[3,2-c]pyridin-4(5H)-one;

2-(((3-aminopropyl)amino)methyl)-7-(3,4-dimethoxyphenyl)-5-methylthieno[3,2-c]pyridin-4(5H)-one;

2-(((2-aminoethyl)amino)methyl)-7-(3-(benzyloxy)phenyl)-5-methylthieno[3,2-c]pyridin-4(5H)-one;

5-methyl-2-((4-(methylsulphonyl)piperazin-1-yl)methyl)-7-(pyridin-4-yl)thieno[3,2-c]pyridin-4(5H)-one;

7-(3,4-dimethoxyphenyl)-5-methyl-2-((4-(methylsulphonyl)-1,4-diazepan-1-yl)methyl)thieno[3,2-c]pyridin-4 (5H)-one;

7-(3,4-dimethoxyphenyl)-5-methyl-2-((3-methyl-4-(methylsulphonyl)piperazin-1-yl)methyl)thieno[3,2-c]pyridin-4(5H)-one;

7-(3,4-dimethoxyphenyl)-5-methyl-2-((4-(methylsulphonyl)piperazin-1-yl)methyl)thieno[3,2-c]pyridin-4(5H)-one;

7-(5-methoxy-2-methylphenyl)-5-methyl-2-((4-(methylsulphonyl)piperazin-1-yl)methyl)thieno[3,2-c]pyridin-4 (5H)-one;

7-(3-methoxy-2-methylphenyl)-5-methyl-2-((4-(methylsulphonyl)piperazin-1-yl)methyl)thieno[3,2-c]pyridin-4 (5H)-one;

7-(2-ethylphenyl)-5-methyl-2-((4-(methylsulphonyl)piperazin-1-yl)methyl)thieno[3,2-c]pyridin-4(5H)-one N-(3-(5-methyl-2-((N-methylmethylsulphonamido) methyl)-4-oxo-4,5-dihydrothieno[3,2-c]pyridin-7-yl)phenyl)acetamide;

7-(4-methoxyphenyl)-5-methyl-2-((4-(methylsulphonyl) piperazin-1-yl)methyl)thieno[3,2-c]pyridin-4(5H)-one;

5-methyl-7-(4-(methylsulphonyl)phenyl)-2-((4-(methylsulphonyl)piperazin-1-yl)methyl)thieno[3,2-c]pyridin-4 (5H)-one;

7-(3,4-dimethoxyphenyl)-5-methyl-2-(piperazin-1-ylmethyl)thieno[3,2-c]pyridin-4(5H)-one;

2-(((2-aminoethyl)amino)methyl)-7-(3,4-dimethoxyphenyl)-5-methylthieno[3,2-c]pyridin-4(5H)-one;

7-(3,4-dimethoxyphenyl)-5-methyl-2-((3-methylpiperazin-1-yl)methyl)thieno[3,2-c]pyridin-4(5H)-one;

N-(2-(((7-(3,4-dimethoxyphenyl)-5-methyl-4-oxo-4,5-dihydrothieno[3,2-c]pyridin-2-yl)methyl)amino)ethyl)methanesulphonamide;

N-((7-(3,4-dimethoxyphenyl)-5-methyl-4-oxo-4,5-dihydrothieno[3,2-c]pyridin-2-yl)methyl)-N-(2-(methylsulfonamido)ethyl)methanesulfonamide;

5-methyl-2-((4-(methylsulphonyl)piperazin-1-yl)methyl)-7-(m-tolyl)thieno[3,2-c]pyridin-4(5H)-one;

7-(3,4-dimethoxyphenyl)-2-((1,1-dioxidothiomorpholino) methyl)-5-methylthieno[3,2-c]pyridin-4(5H)-one;

(R)-7-(3,4-dimethoxyphenyl)-5-methyl-2-((3-methylmorpholino)methyl)thieno[3,2-c]pyridin-4(5H)-one;

7-(2-(benzyloxy)phenyl)-5-methyl-2-((4-(methylsulphonyl) piperazin-1-yl)methyl)thieno[3,2-c]pyridin-4(5H)-one;

5-methyl-2-((4-(methylsulphonyl)piperazin-1-yl)methyl)-7-(4-(trifluoromethyl)phenyl)thieno[3,2-c]pyridin-4(5H)-one;

2-((1,4-oxazepan-4-yl)methyl)-7-(2-((2-methoxyethyl) (methyl)amino)pyridin-4-yl)-5-methylthieno[3,2-c]pyridin-4(5H)-one;

7-(3,4-dimethoxyphenyl)-2-((4-hydroxypiperidin-1-yl) methyl)-5-methylthieno[3,2-c]pyridin-4(5H)-one;

7-(4-methoxy-2-methylphenyl)-5-methyl-2-((4-(methylsulphonyl)piperazin-1-yl)methyl)thieno[3,2-c]pyridin-4(5H)-one;

4-(5-methyl-2-((4-(methylsulphonyl)piperazin-1-yl)methyl)-4-oxo-4,5-dihydrothieno[3,2-c]pyridin-7-yl)benzonitrile;

N-(4-(5-methyl-2-((3-methylmorpholino)methyl)-4-oxo-4,5-dihydrothieno[3,2-c]pyridin-7-yl)pyridin-2-yl)acetamide;

(S)-7-(3-(benzyloxy)phenyl)-5-methyl-2-((3-methylmorpholino)methyl)thieno[3,2-c]pyridin-4(5H)-one;

N-(3-(5-methyl-2-((3-methylmorpholino)methyl)-4-oxo-4,5-dihydrothieno[3,2-c]pyridin-7-yl)phenyl)acetamide;

7-(2-((2-methoxyethyl)(methyl)amino)pyridin-4-yl)-5-methyl-2-((4-(methylsulphonyl)piperidin-1-yl)methyl)thieno[3,2-c]pyridin-4(5H)-one;

(S)-7-(3-hydroxyphenyl)-5-methyl-2-((3-methylmorpholino)methyl)thieno[3,2-c]pyridin-4(5H)-one;

(S)-7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-(piperidin-1-ylmethyl)thieno[3,2-c]pyridin-4(5H)-one;

2-((1,4-oxazepan-4-yl)methyl)-7-(2-chloropyridin-4-yl)-5-methylthieno[3,2-c]pyridin-4(5H)-one;

7-(2-aminopyridin-4-yl)-5-methyl-2-((3-methylmorpholino)methyl)thieno[3,2-c]pyridin-4(5H)-one:

5-methyl-2-((methylamino)methyl)-7-(2-((tetrahydro-2H-2H-pyran-4-yl)methoxy)pyridin-4-yl)thieno[3,2-c]pyridin-4(5H)-one;

7-(3,4-dimethoxyphenyl)-5-methyl-2-(pyrrolidin-1-ylmethyl)thieno[3,2-c]pyridin-4(5H)-one;

N-((7-(3,4-dimethoxyphenyl)-5-methyl-4-oxo-4,5-dihydrothieno[3,2-c]pyridin-2-yl)methyl)-N-methylmethanesulphonamide;

7-(3,4-dimethoxyphenyl)-2-((3,5-dimethylpiperazin-1-yl)methyl)-5-methylthieno[3,2-c]pyridin-4(5H)-one;

(S)-5-methyl-2-((3-methylmorpholino)methyl)-7-(3-((tetrahydro-2H-2H-pyran-4-yl)methoxy)phenyl)thieno[3,2-c]pyridin-4(5H)-one;

(R)-7-(3,4-dimethoxyphenyl)-5-methyl-2-((2-methylpiperazin-1-yl)methyl)thieno[3,2-c]pyridin-4(5H)-one;

(R)-1-((7-(3,4-dimethoxyphenyl)-5-methyl-4-oxo-4,5-dihydrothieno[3,2-c]pyridin-2-yl)methyl)piperazine-2-carboxamide;

(S)-7-(3,4-dimethoxyphenyl)-5-methyl-2-((3-methylpiperazin-1-yl)methyl)thieno[3,2-c]pyridin-4(5H)-one;

methyl 1-((7-(3,4-dimethoxyphenyl)-5-methyl-4-oxo-4,5-dihydrothieno[3,2-c]pyridin-2-yl)methyl)piperazine-2-carboxylate;

7-(3,4-dimethoxyphenyl)-2-((cis-2,6-dimethylpiperazin-1-yl)methyl)-5-methylthieno[3,2-c]pyridin-4(5H)-one;

(R)-2-((3-butylpiperazin-1-yl)methyl)-7-(3,4-dimethoxyphenyl)-5-methylthieno[3,2-c]pyridin-4(5H)-one;

(S)-7-(3,4-dimethoxyphenyl)-2-((3-ethylpiperazin-1-yl)methyl)-5-methylthieno[3,2-c]pyridin-4(5H)-one;

7-(3,4-dimethoxyphenyl)-5-methyl-2-((piperidin-4-ylamino)methyl)thieno[3,2-c]pyridin-4(5H)-one;

(S)-7-(3,4-dimethoxyphenyl)-5-methyl-2-((2-methylpiperazin-1-yl)methyl)thieno[3,2-c]pyridin-4(5H)-one;

2-((3-aminopyrrolidin-1-yl)methyl)-7-(3,4-dimethoxyphenyl)-5-methylthieno[3,2-c]pyridin-4(5H)-one;

2-((4-aminopiperidin-1-yl)methyl)-7-(3,4-dimethoxyphenyl)-5-methylthieno[3,2-c]pyridin-4(5H)-one;

2-(((2-aminoethyl)(methyl)amino)methyl)-7-(3,4-dimethoxyphenyl)-5-methylthieno[3,2-c]pyridin-4(5H)-one;

(R)-7-(3,4-dimethoxyphenyl)-5-methyl-2-((2-methyl-4-(methylsulphonyl)piperazin-1-yl)methyl)thieno[3,2-c]pyridin-4(5H)-one;

(S)-7-(3,4-dimethoxyphenyl)-5-methyl-2-((3-methyl-4-(methylsulphonyl)piperazin-1-yl)methyl)thieno[3,2-c]pyridin-4(5H)-one;

methyl 1-((7-(3,4-dimethoxyphenyl)-5-methyl-4-oxo-4,5-dihydrothieno[3,2-c]pyridin-2-yl)methyl)-4-(methylsulphonyl)piperazine-2-carboxylate;

(R)-2-((3-butyl-4-(methylsulphonyl)piperazin-1-yl)methyl)-7-(3,4-dimethoxyphenyl)-5-methylthieno[3,2-c]pyridin-4(5H)-one;

(S)-7-(3,4-dimethoxyphenyl)-2-((3-ethyl-4-(methylsulphonyl)piperazin-1-yl)methyl)-5-methylthieno[3,2-c]pyridin-4(5H)-one;

(S)-7-(3,4-dimethoxyphenyl)-5-methyl-2-((2-methyl-4-(methylsulphonyl)piperazin-1-yl)methyl)thieno[3,2-c]pyridin-4(5H)-one;

N-(1-((7-(3,4-dimethoxyphenyl)-5-methyl-4-oxo-4,5-dihydrothieno[3,2-c]pyridin-2-yl)methyl)pyrrolidin-3-yl)methanesulphonamide;

7-(4-((2-methoxyethyl)(methyl)amino)pyridin-2-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(pyridin-3-yl)thieno[3,2-c]pyridin-4(5H)-one;

7-(3,4-dichlorophenyl)-5-methyl-2-((4-(methylsulphonyl)piperazin-1-yl)methyl)thieno[3,2-c]pyridin-4(5H)-one;

7-(4-(aminomethyl)phenyl)-5-methyl-2-((4-(methylsulphonyl)piperazin-1-yl)methyl)thieno[3,2-c]pyridin-4(5H)-one;

7-(3-(benzyloxy)-4-methoxyphenyl)-5-methyl-2-((4-(methylsulphonyl)piperazin-1-yl)methyl)thieno[3,2-c]pyridin-4(5H)-one;

(R)-7-(4-methoxyphenyl)-5-methyl-2-((2-methyl-4-(methylsulphonyl)piperazin-1-yl)methyl)thieno[3,2-c]pyridin-4(5H)-one;

5-methyl-2-(((R)-2-methyl-4-(methylsulphonyl)piperazin-1-yl)methyl)-7-(5-(1-(pyridin-2-yl)ethoxy)pyridin-3-yl)thieno[3,2-c]pyridin-4(5H)-one;

(R)-7-(3-methoxyphenyl)-5-methyl-2-((2-methyl-4-(methylsulphonyl)piperazin-1-yl)methyl)thieno[3,2-c]pyridin-4(5H)-one;

(R)-N-(4-(5-methyl-2-((2-methyl-4-(methylsulphonyl)piperazin-1-yl)methyl)-4-oxo-4,5-dihydrothieno[3,2-c]pyridin-7-yl)pyridin-2-yl)acetamide;

(R)-5-methyl-2-((2-methyl-4-(methylsulphonyl)piperazin-1-yl)methyl)-7-phenylthieno[3,2-c]pyridin-4(5H)-one;

5-methyl-2-((4-(methylsulphonyl)piperazin-1-yl)methyl)-7-(p-tolyl)thieno[3,2-c]pyridin-4(5H)-one;

(R)-7-(2-methoxypyridin-4-yl)-5-methyl-2-((2-methyl-4-(methylsulphonyl)piperazin-1-yl)methyl)thieno[3,2-c]pyridin-4(5H)-one (R)-7-(5-methoxypyridin-3-yl)-5-methyl-2-((2-methyl-4-(methylsulphonyl)piperazin-1-yl)methyl)thieno[3,2-c]pyridin-4(5H)-one;

(R)-7-(6-methoxypyridin-3-yl)-5-methyl-2-((2-methyl-4-(methylsulphonyl)piperazin-1-yl)methyl)thieno[3,2-c]pyridin-4(5H)-one;

(R)-5-methyl-2-((2-methyl-4-(methylsulphonyl)piperazin-1-yl)methyl)-7-(pyridin-2-yl)thieno[3,2-c]pyridin-4(5H)-one;

5-methyl-2-((4-(methylsulphonyl)piperazin-1-yl)methyl)-7-(3-(trifluoromethyl)phenyl)thieno[3,2-c]pyridin-4(5H)-one;

N-benzyl-3-(5-methyl-2-((4-(methylsulphonyl)piperazin-1-yl)methyl)-4-oxo-4,5-dihydrothieno[3,2-c]pyridin-7-yl)benzamide;
(R)-7-(6-hydroxypyrimidin-4-yl)-5-methyl-2-((2-methyl-4-(methylsulphonyl)piperazin-1-yl)methyl)thieno[3,2-c]pyridin-4(5H)-one;
5-methyl-2-((4-(methylsulphonyl)piperazin-1-yl)methyl)-7-(o-tolyl)thieno[3,2-c]pyridin-4(5H)-one;
(S)-7-(6-methoxypyridin-3-yl)-5-methyl-2-((2-methyl-4-(methylsulphonyl)piperazin-1-yl)methyl)thieno[3,2-c]pyridin-4(5H)-one;
(S)-5-methyl-2-((2-methyl-4-(methylsulphonyl)piperazin-1-yl)methyl)-7-(pyridin-4-yl)thieno[3,2-c]pyridin-4(5H)-one;
(S)-5-methyl-2-((2-methyl-4-(methylsulphonyl)piperazin-1-yl)methyl)-7-(pyridin-3-yl)thieno[3,2-c]pyridin-4(5H)-one;
(S)-7-(5-methoxypyridin-3-yl)-5-methyl-2-((2-methyl-4-(methylsulphonyl)piperazin-1-yl)methyl)thieno[3,2-c]pyridin-4(5H)-one;
(S)-7-(4-methoxy-2-methylphenyl)-5-methyl-2-((2-methyl-4-(methylsulphonyl)piperazin-1-yl)methyl)thieno[3,2-c]pyridin-4(5H)-one;
(S)-7-(3-(benzyloxy)-4-methoxyphenyl)-5-methyl-2-((2-methylpiperazin-1-yl)methyl)thieno[3,2-c]pyridin-4(5H)-one;
5-ethyl-2-((4-(methylsulphonyl)piperazin-1-yl)methyl)-7-phenylthieno[3,2-c]pyridin-4(5H)-one;
7-(3,4-dimethoxyphenyl)-5-ethyl-2-((4-(methylsulphonyl)piperazin-1-yl)methyl)thieno[3,2-c]pyridin-4(5H)-one;
2-((4-acetylpiperazin-1-yl)methyl)-5-ethyl-7-phenylthieno[3,2-c]pyridin-4(5H)-one;
2-((4-acetylpiperazin-1-yl)methyl)-7-(3,4-dimethoxyphenyl)-5-ethylthieno[3,2-c]pyridin-4(5H)-one;
(R)-N-(4-(2-((4-(ethylsulfonyl)-2-methylpiperazin-1-yl)methyl)-5-methyl-4-oxo-4,5-dihydrothieno[3,2-c]pyridin-7-yl)pyridin-2-yl)acetamide;
N-(4-(2-((3-isopropylmorpholino)methyl)-5-methyl-4-oxo-4,5-dihydrothieno[3,2-c]pyridin-7-yl)pyridin-2-yl)acetamide;
(R)-N-(4-(2-((3-fluoropyrrolidin-1-yl)methyl)-5-methyl-4-oxo-4,5-dihydrothieno[3,2-c]pyridin-7-yl)pyridin-2-yl)acetamide;
(R)-N-(4-(2-((3-hydroxypyrrolidin-1-yl)methyl)-5-methyl-4-oxo-4,5-dihydrothieno[3,2-c]pyridin-7-yl)pyridin-2-yl)acetamide;
N-(4-(2-((3-fluoropiperidin-1-yl)methyl)-5-methyl-4-oxo-4,5-dihydrothieno[3,2-c]pyridin-7-yl)pyridin-2-yl)acetamide;
(R)-N-(4-(2-((3-fluoropiperidin-1-yl)methyl)-5-methyl-4-oxo-4,5-dihydrothieno[3,2-c]pyridin-7-yl)pyridin-2-yl)acetamide;
(S)-N-(4-(2-((3-fluoropiperidin-1-yl)methyl)-5-methyl-4-oxo-4,5-dihydrothieno[3,2-c]pyridin-7-yl)pyridin-2-yl)acetamide;
N-(4-(5-methyl-4-oxo-2-((3-(trifluoromethyl)pyrrolidin-1-yl)methyl)-4,5-dihydrothieno[3,2-c]pyridin-7-yl)pyridin-2-yl)acetamide;
1-((7-(2-acetamidopyridin-4-yl)-5-methyl-4-oxo-4,5-dihydrothieno[3,2-c]pyridin-2-yl)methyl)piperidine-2-carboxamide;
N-(4-(5-methyl-2-((2-methylmorpholino)methyl)-4-oxo-4,5-dihydrothieno[3,2-c]pyridin-7-yl)pyridin-2-yl)acetamide;
N-(4-(2-((2,6-dimethylmorpholino)methyl)-5-methyl-4-oxo-4,5-dihydrothieno[3,2-c]pyridin-7-yl)pyridin-2-yl)acetamide;
N-(4-(2-((3,5-dimethylmorpholino)methyl)-5-methyl-4-oxo-4,5-dihydrothieno[3,2-c]pyridin-7-yl)pyridin-2-yl)acetamide;
N-(4-(2-(((3R,5S)-3,5-dimethylmorpholino)methyl)-5-methyl-4-oxo-4,5-dihydrothieno[3,2-c]pyridin-7-yl)pyridin-2-yl)acetamide;
N-(4-(2-(((2R,3R)-2,3-dimethylmorpholino)methyl)-5-methyl-4-oxo-4,5-dihydrothieno[3,2-c]pyridin-7-yl)pyridin-2-yl)acetamide;
N-(4-(2-((3-fluoropyrrolidin-1-yl)methyl)-5-methyl-4-oxo-4,5-dihydrothieno[3,2-c]pyridin-7-yl)pyridin-2-yl)acetamide;
N-(4-(2-(((2S,6R)-2,6-dimethylmorpholino)methyl)-5-methyl-4-oxo-4,5-dihydrothieno[3,2-c]pyridin-7-yl)pyridin-2-yl)acetamide;
N-(4-(5-methyl-4-oxo-2-((2-(trifluoromethyl)pyrrolidin-1-yl)methyl)-4,5-dihydrothieno[3,2-c]pyridin-7-yl)pyridin-2-yl)acetamide;
N-(4-(2-((2,5-dimethylmorpholino)methyl)-5-methyl-4-oxo-4,5-dihydrothieno[3,2-c]pyridin-7-yl)pyridin-2-yl)acetamide;
(S)-N-(4-(2-((3-hydroxypiperidin-1-yl)methyl)-5-methyl-4-oxo-4,5-dihydrothieno[3,2-c]pyridin-7-yl)pyridin-2-yl)acetamide;
(S)-N-(4-(2-((3-hydroxypyrrolidin-1-yl)methyl)-5-methyl-4-oxo-4,5-dihydrothieno[3,2-c]pyridin-7-yl)pyridin-2-yl)acetamide;
(R)-N-(4-(2-((3-hydroxypiperidin-1-yl)methyl)-5-methyl-4-oxo-4,5-dihydrothieno[3,2-c]pyridin-7-yl)pyridin-2-yl)acetamide;
(S)-N-(4-(2-((3-fluoropyrrolidin-1-yl)methyl)-5-methyl-4-oxo-4,5-dihydrothieno[3,2-c]pyridin-7-yl)pyridin-2-yl)acetamide;
N-(4-(2-((3-methoxypiperidin-1-yl)methyl)-5-methyl-4-oxo-4,5-dihydrothieno[3,2-c]pyridin-7-yl)pyridin-2-yl)acetamide;
N-(4-(2-((3-hydroxyazetidin-1-yl)methyl)-5-methyl-4-oxo-4,5-dihydrothieno[3,2-c]pyridin-7-yl)pyridin-2-yl)acetamide;
N-(4-(2-((3,3-difluoropiperidin-1-yl)methyl)-5-methyl-4-oxo-4,5-dihydrothieno[3,2-c]pyridin-7-yl)pyridin-2-yl)acetamide;
(R)-7-(2-ethoxypyridin-4-yl)-5-methyl-2-((2-methyl-4-(methylsulfonyl)piperazin-1-yl)methyl)thieno[3,2-c]pyridin-4(5H)-one;
(R)-7-(2-(cyclopropylmethoxy)pyridin-4-yl)-5-methyl-2-((2-methyl-4-(methylsulfonyl)piperazin-1-yl)methyl)thieno[3,2-c]pyridin-4(5H)-one;
(R)-5-methyl-2-((2-methyl-4-(methylsulfonyl)piperazin-1-yl)methyl)-7-(2-(2-(pyrrolidin-1-yl)ethoxy)pyridin-4-yl)thieno[3,2-c]pyridin-4(5H)-one;
(R)-7-(2-(2-methoxyethoxy)pyridin-4-yl)-5-methyl-2-((2-methyl-4-(methylsufonyl)piperazin-1-yl)methyl)thieno[3,2-c]pyridin-4(5H)-one;
(R)-7-(3-methoxypyridin-4-yl)-5-methyl-2-((2-methyl-4-(methylsulfonyl)piperazin-1-yl)methyl)thieno[3,2-c]pyridin-4(5H)-one;
(R)-7-(3-(cyclopropylmethoxy)pyridin-4-yl)-5-methyl-2-((2-methyl-4-(methylsulfonyl)piperazin-1-yl)methyl)thieno[3,2-c]pyridin-4(5H)-one;
(R)-5-methyl-2-((2-methyl-4-(methylsulfonyl)piperazin-1-yl)methyl)-7-(2-(2-(2-oxopyrrolidin-1-yl)ethoxy)pyridin-4-yl)thieno[3,2-c]pyridin-4(5H)-one;
(R)-7-(5-(cyclopropylmethoxy)pyridin-3-yl)-5-methyl-2-((2-methyl-4-(methylsulfonyl)piperazin-1-yl)methyl)thieno[3,2-c]pyridin-4(5H)-one;

2-((3-hydroxypiperidin-1-yl)methyl)-7-(2-methoxypyridin-4-yl)-5-methylthieno[3,2-c]pyridin-4(5H)-one;

7-(2-ethoxypyridin-4-yl)-2-((3-hydroxypiperidin-1-yl)methyl)-5-methylthieno[3,2-c]pyridin-4(5H)-one;

(R)-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)propionamide;

(R)-2-cyclopropyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

(R)-N-methyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

(R)-N-(6-(cyclopropylmethoxy)-4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

2-((1,4-oxazepan-4-yl)methyl)-5-methyl-7-(2-((tetrahydro-2H-2H-pyran-4-yl)methoxy)pyridin-4-yl)thieno[3,2-c]pyridin-4(5H)-one;

5-methyl-2-(morpholinomethyl)-7-(2-((tetrahydro-2H-pyran-4-yl)methoxy)pyridin-4-yl)thieno[3,2-c]pyridin-4(5H)-one;

2-((1,4-diazepan-1-yl)methyl)-5-methyl-7-(2-((tetrahydro-2H-pyran-4-yl)methoxy)pyridin-4-yl)thieno[3,2-c]pyridin-4(5H)-one;

5-methyl-2-((4-methyl-1,4-diazepan-1-yl)methyl)-7-(2-((tetrahydro-2H-pyran-4-yl)methoxy)pyridin-4-yl)thieno[3,2-c]pyridin-4(5H)-one;

2-((1,4-diazepan-1-yl)methyl)-5-methyl-7-(2-((pyridin-2-ylmethyl)amino)pyridin-4-yl)thieno[3,2-c]pyridin-4(5H)-one;

2-((1,4-diazepan-1-yl)methyl)-5-methyl-7-(3-(pyridin-2-ylmethoxy)phenyl)thieno[3,2-c]pyridin-4(5H)-one;

2-((1,4-diazepan-1-yl)methyl)-5-methyl-7-(2-(pyridin-2-ylmethoxy)pyridin-4-yl)thieno[3,2-c]pyridin-4(5H)-one;

2-((1,4-diazepan-1-yl)methyl)-7-(2-(benzyloxy)pyridin-4-yl)-5-methylthieno[3,2-c]pyridin-4(5H)-one;

1-((7-(3,4-dimethoxyphenyl)-5-methyl-4-oxo-4,5-dihydrothieno[3,2-c]pyridin-2-yl)methyl)-N, 3-dimethylpiperidine-3-carboxamide;

7-(3,4-dimethoxyphenyl)-2-((3-(hydroxymethyl)-3-methylpiperidin-1-yl)methyl)-5-methylthieno[3,2-c]pyridin-4(5H)-one;

7-(3,4-dimethoxyphenyl)-2-(((1,1-dioxidotetrahydrothiophen-3-yl)amino)methyl)-5-methylthieno[3,2-c]pyridin-4(5H)-one;

7-(3,4-dimethoxyphenyl)-2-(((1,1-dioxidotetrahydro-2H-thiopyran-4-yl)amino)methyl)-5-methylthieno[3,2-c]pyridin-4(5H)-one;

7-(3,4-dimethoxyphenyl)-5-methyl-2-((methylamino)methyl)thieno[3,2-c]pyridin-4(5H)-one;

7-(3,4-dimethoxyphenyl)-2-((3-(methoxymethyl)-3-methylpiperidin-1-yl)methyl)-5-methylthieno[3,2-c]pyridin-4(5H)-one;

2-((3-((cyclopropylmethoxy)methyl)-3-methylpiperidin-1-yl)methyl)-7-(3,4-dimethoxyphenyl)-5-methylthieno[3,2-c]pyridin-4(5H)-one;

7-(2,6-dimethylphenyl)-5-methyl-2-((4-(methylsulfonyl)piperazin-1-yl)methyl)thieno[3,2-c]pyridin-4(5H)-one;

5-methyl-7-(5-((tetrahydro-2H-pyran-4-yl)methoxy)pyridin-3-yl)-2-((2,2,4-trimethylpiperazin-1-yl)methyl)thieno[3,2-c]pyridin-4(5H)-one;

N-(3-(5-methyl-2-((2-methylpyrrolidin-1-yl)methyl)-4-oxo-4,5-dihydrothieno[3,2-c]pyridin-7-yl)phenyl)acetamide;

N-(4-(2-((2,3-dimethylpiperidin-1-yl)methyl)-5-methyl-4-oxo-4,5-dihydrothieno[3,2-c]pyridin-7-yl)pyridin-2-yl)acetamide;

N-(4-(5-methyl-4-oxo-2-(piperidin-1-ylmethyl)-4,5-dihydrothieno[3,2-c]pyridin-7-yl)pyridin-2-yl)acetamide;

1-((7-(3,4-dimethoxyphenyl)-5-methyl-4-oxo-4,5-dihydrothieno[3,2-c]pyridin-2-yl)methyl)-N,N,3-trimethylpiperidine-3-carboxamide;

or a salt thereof.

In another embodiment, the compound of formula (I) is 5-methyl-2-((4-(methylsulphonyl)piperazin-1-yl)methyl)-7-(5-(1-phenylethoxy)pyridin-3-yl)thieno[3,2-c]pyridin-4(5H)-one;

5-methyl-2-((4-(methylsulphonyl)piperazin-1-yl)methyl)-7-(3-(1-(pyridin-2-yl)ethoxy)phenyl)thieno[3,2-c]pyridin-4(5H)-one;

5-methyl-2-((4-(methylsulphonyl)piperazin-1-yl)methyl)-7-(5-(1-(pyridin-2-yl)ethoxy)pyridin-3-yl)thieno[3,2-c]pyridin-4(5H)-one;

7-(5-(benzyloxy)pyridin-3-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(3-((tetrahydro-2H-pyran-4-yl)methoxy)phenyl)thieno[3,2-c]pyridin-4(5H)-one;

7-(3-isopropoxyphenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-((tetrahydro-2H-pyran-4-yl)methoxy)pyridin-4-yl)thieno[3,2-c]pyridin-4(5H)-one;

7-(3-(2-methoxyethoxy)phenyl)-5-methyl-2-((4-(methylsulphonyl)piperazin-1-yl)methyl)thieno[3,2-c]pyridin-4(5H)-one;

7-(3-(3-hydroxypropoxy)phenyl)-5-methyl-2-((4-(methylsulphonyl)piperazin-1-yl)methyl)thieno[3,2-c]pyridin-4(5H)-one;

7-(3-hydroxyphenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(5-((tetrahydro-2H-pyran-4-yl)methoxy)pyridin-3-yl)thieno[3,2-c]pyridin-4(5H)-one;

7-(5-hydroxypyridin-3-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-(1-(pyridin-2-yl)ethoxy)pyridin-4-yl)thieno[3,2-c]pyridin-4(5H)-one;

7-(5-((1-methoxypropan-2-yl)oxy)pyridin-3-yl)-5-methyl-2-((4-(methylsulphonyl)piperazin-1-yl)methyl)thieno[3,2-c]pyridin-4(5H)-one;

7-(3-methoxyphenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(3-(1-phenylethoxy)phenyl)thieno[3,2-c]pyridin-4(5H)-one;

5-methyl-2-((4-(methylsulphonyl)piperazin-1-yl)methyl)-7-(3-((1-phenylethyl)amino)phenyl)thieno[3,2-c]pyridin-4(5H)-one;

(R)-N-(3-(5-methyl-2-((2-methyl-4-(methylsulphonyl)piperazin-1-yl)methyl)-4-oxo-4,5-dihydrothieno[3,2-c]pyridin-7-yl)phenyl)acetamide;

5-methyl-2-((4-(methylsulphonyl)piperazin-1-yl)methyl)-7-(3-(((tetrahydro-2H-pyran-4-yl)methyl)amino)phenyl)thieno[3,2-c]pyridin-4(5H)-one;

N-(3-(5-methyl-2-((4-(methylsulphonyl)piperazin-1-yl)methyl)-4-oxo-4,5-dihydrothieno[3,2-c]pyridin-7-yl)phenyl)acetamide;

7-(2-((2-methoxyethyl)(methyl)amino)pyridin-4-yl)-5-methyl-2-((4-(methylsulphonyl)piperazin-1-yl)methyl)thieno[3,2-c]pyridin-4(5H)-one;

7-(2-((1-methoxypropan-2-yl)amino)pyridin-4-yl)-5-methyl-2-((4-(methylsulphonyl)piperazin-1-yl)methyl)thieno[3,2-c]pyridin-4(5H)-one;

7-(2-((cyclopropylmethyl)amino)pyridin-4-yl)-5-methyl-2-((4-(methylsulphonyl)piperazin-1-yl)methyl)thieno[3,2-c]pyridin-4(5H)-one;

N-(3-(5-methyl-2-((4-(methylsulphonyl)piperazin-1-yl)methyl)-4-oxo-4,5-dihydrothieno[3,2-c]pyridin-7-yl)phenyl)formamide;

7-(3-aminophenyl)-5-methyl-2-((4-(methylsulphonyl)piperazin-1-yl)methyl)thieno[3,2-c]pyridin-4(5H)-one;

7-(3-(benzylamino)phenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-(((tetrahydrofuran-2-yl)methyl)amino)pyridin-4-yl)thieno[3,2-c]pyridin-4(5H)-one;

7-(3-(benzyloxy)phenyl)-2-((4-ethylpiperazin-1-yl)methyl)-5-methylthieno[3,2-c]pyridin-4(5H)-one;

7-(3-(benzyloxy)phenyl)-2-((4-isopropylpiperazin-1-yl)methyl)-5-methylthieno[3,2-c]pyridin-4(5H)-one;

2-((4-benzoylpiperazin-1-yl)methyl)-7-(3,4-dimethoxyphenyl)-5-methylthieno[3,2-c]pyridin-4(5H)-one;

7-(3,4-dimethoxyphenyl)-2-((4-(ethylsulphonyl)piperazin-1-yl)methyl)-5-methylthieno[3,2-c]pyridin-4(5H)-one;

N-(3-(5-methyl-2-((4-methylpiperazin-1-yl)methyl)-4-oxo-4,5-dihydrothieno[3,2-c]pyridin-7-yl)phenyl)acetamide;

2-((4-(benzylsulphonyl)piperazin-1-yl)methyl)-7-(3,4-dimethoxyphenyl)-5-methylthieno[3,2-c]pyridin-4(5H)-one;

7-(3,4-dimethoxyphenyl)-5-methyl-2-((4-(phenylsulphonyl)piperazin-1-yl)methyl)thieno[3,2-c]pyridin-4(5H)-one;

2-((4-acetylpiperazin-1-yl)methyl)-5-methyl-7-phenylthieno[3,2-c]pyridin-4(5H)-one;

7-(3,4-dimethoxyphenyl)-2-((4-(isopropylsulphonyl)piperazin-1-yl)methyl)-5-methylthieno[3,2-c]pyridin-4(5H)-one;

7-(3,4-dimethoxyphenyl)-5-methyl-2-((4-methylpiperazin-1-yl)methyl)thieno[3,2-c]pyridin-4(5H)-one;

4-((7-(3,4-dimethoxyphenyl)-5-methyl-4-oxo-4,5-dihydrothieno[3,2-c]pyridin-2-yl)methyl)-N,N-dimethylpiperazine-1-sulphonamide;

2-((4-acetylpiperazin-1-yl)methyl)-7-(3,4-dimethoxyphenyl)-5-methylthieno[3,2-c]pyridin-4(5H)-one;

7-(3-(benzyloxy)phenyl)-5-methyl-2-((4-methyl-1,4-diazepan-1-yl)methyl)thieno[3,2-c]pyridin-4(5H)-one;

N-(3-(5-methyl-2-((1-(methylsulphonyl)piperidin-4-yl)methyl)-4-oxo-4,5-dihydrothieno[3,2-c]pyridin-7-yl)phenyl)acetamide;

7-(2,4-difluorophenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(pyridin-2-yl)thieno[3,2-c]pyridin-4(5H)-one;

5-methyl-2-((4-(methylsulphonyl)piperazin-1-yl)methyl)-7-phenylthieno[3,2-c]pyridin-4(5H)-one;

2-((2,4-dimethylpiperazin-1-yl)methyl)-5-methyl-7-(5-((tetrahydro-2H-pyran-4-yl)methoxy)pyridin-3-yl)thieno[3,2-c]pyridin-4(5H)-one;

2-((1,4-diazepan-1-yl)methyl)-7-(3,4-dimethoxyphenyl)-5-methylthieno[3,2-c]pyridin-4(5H)-one;

2-(((3-aminopropyl)amino)methyl)-7-(3-(benzyloxy)phenyl)-5-methylthieno[3,2-c]pyridin-4(5H)-one;

N-(2-(((7-(3-(benzyloxy)phenyl)-5-methyl-4-oxo-4,5-dihydrothieno[3,2-c]pyridin-2-yl)methyl)amino)ethyl)methanesulphonamide;

N-(4-(5-methyl-2-((1-(methylsulphonyl)piperidin-4-yl)methyl)-4-oxo-4,5-dihydrothieno[3,2-c]pyridin-7-yl)pyridin-2-yl)acetamide;

N-(3-(5-methyl-2-((4-methyl-1,4-diazepan-1-yl)methyl)-4-oxo-4,5-dihydrothieno[3,2-c]pyridin-7-yl)phenyl)acetamide;

7-(3,4-dimethoxyphenyl)-5-methyl-2-((1-(methylsulphonyl)piperidin-4-yl)methyl)thieno[3,2-c]pyridin-4(5H)-one;

2-(((3-aminopropyl)amino)methyl)-7-(3,4-dimethoxyphenyl)-5-methylthieno[3,2-c]pyridin-4(5H)-one;

2-(((2-aminoethyl)amino)methyl)-7-(3-(benzyloxy)phenyl)-5-methylthieno[3,2-c]pyridin-4(5H)-one;

5-methyl-2-((4-(methylsulphonyl)piperazin-1-yl)methyl)-7-(pyridin-4-yl)thieno[3,2-c]pyridin-4(5H)-one;

7-(3,4-dimethoxyphenyl)-5-methyl-2-((4-(methylsulphonyl)-1,4-diazepan-1-yl)methyl)thieno[3,2-c]pyridin-4(5H)-one;

7-(3,4-dimethoxyphenyl)-5-methyl-2-((3-methyl-4-(methylsulphonyl)piperazin-1-yl)methyl)thieno[3,2-c]pyridin-4(5H)-one;

7-(3,4-dimethoxyphenyl)-5-methyl-2-((4-(methylsulphonyl)piperazin-1-yl)methyl)thieno[3,2-c]pyridin-4(5H)-one;

7-(5-methoxy-2-methylphenyl)-5-methyl-2-((4-(methylsulphonyl)piperazin-1-yl)methyl)thieno[3,2-c]pyridin-4(5H)-one;

7-(3-methoxy-2-methylphenyl)-5-methyl-2-((4-(methylsulphonyl)piperazin-1-yl)methyl)thieno[3,2-c]pyridin-4(5H)-one;

7-(2-ethylphenyl)-5-methyl-2-((4-(methylsulphonyl)piperazin-1-yl)methyl)thieno[3,2-c]pyridin-4(5H)-one N-(3-(5-methyl-2-((N-methylmethylsulphonamido)methyl)-4-oxo-4,5-dihydrothieno[3,2-c]pyridin-7-yl)phenyl)acetamide;

7-(4-methoxyphenyl)-5-methyl-2-((4-(methylsulphonyl)piperazin-1-yl)methyl)thieno[3,2-c]pyridin-4(5H)-one;

5-methyl-7-(4-(methylsulphonyl)phenyl)-2-((4-(methylsulphonyl)piperazin-1-yl)methyl)thieno[3,2-c]pyridin-4(5H)-one;

7-(3,4-dimethoxyphenyl)-5-methyl-2-(piperazin-1-ylmethyl)thieno[3,2-c]pyridin-4(5H)-one;

2-(((2-aminoethyl)amino)methyl)-7-(3,4-dimethoxyphenyl)-5-methylthieno[3,2-c]pyridin-4(5H)-one;

7-(3,4-dimethoxyphenyl)-5-methyl-2-((3-methylpiperazin-1-yl)methyl)thieno[3,2-c]pyridin-4(5H)-one;

N-(2-(((7-(3,4-dimethoxyphenyl)-5-methyl-4-oxo-4,5-dihydrothieno[3,2-c]pyridin-2-yl)methyl)amino)ethyl)methanesulphonamide;

5-methyl-2-((4-(methylsulphonyl)piperazin-1-yl)methyl)-7-(m-tolyl)thieno[3,2-c]pyridin-4(5H)-one;

7-(3,4-dimethoxyphenyl)-2-((1,1-dioxidothiomorpholino)methyl)-5-methylthieno[3,2-c]pyridin-4(5H)-one;

(R)-7-(3,4-dimethoxyphenyl)-5-methyl-2-((3-methylmorpholino)methyl)thieno[3,2-c]pyridin-4(5H)-one;

7-(2-(benzyloxy)phenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(4-(trifluoromethyl)phenyl)thieno[3,2-c]pyridin-4(5H)-one;

2-((1,4-oxazepan-4-yl)methyl)-7-(2-((2-methoxyethyl)(methyl)amino)pyridin-4-yl)-5-methylthieno[3,2-c]pyridin-4(5H)-one;

7-(3,4-dimethoxyphenyl)-2-((4-hydroxypiperidin-1-yl)methyl)-5-methylthieno[3,2-c]pyridin-4(5H)-one;

7-(4-methoxy-2-methylphenyl)-5-methyl-2-((4-(methylsulphonyl)piperazin-1-yl)methyl)thieno[3,2-c]pyridin-4(5H)-one;

4-(5-methyl-2-((4-(methylsulphonyl)piperazin-1-yl)methyl)-4-oxo-4,5-dihydrothieno[3,2-c]pyridin-7-yl)benzonitrile;

N-(4-(5-methyl-2-((3-methylmorpholino)methyl)-4-oxo-4,5-dihydrothieno[3,2-c]pyridin-7-yl)pyridin-2-yl)acetamide;

(S)-7-(3-(benzyloxy)phenyl)-5-methyl-2-((3-methylmorpholino)methyl)thieno[3,2-c]pyridin-4(5H)-one;

N-(3-(5-methyl-2-((3-methylmorpholino)methyl)-4-oxo-4,5-dihydrothieno[3,2-c]pyridin-7-yl)phenyl)acetamide;

7-(2-((2-methoxyethyl)(methyl)amino)pyridin-4-yl)-5-methyl-2-((4-(methylsulphonyl)piperidin-1-yl)methyl)thieno[3,2-c]pyridin-4(5H)-one;

(S)-7-(3-hydroxyphenyl)-5-methyl-2-((3-methylmorpholino)methyl)thieno[3,2-c]pyridin-4(5H)-one;

(S)-7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-(piperidin-1-ylmethyl)thieno[3,2-c]pyridin-4(5H)-one;

2-((1,4-oxazepan-4-yl)methyl)-7-(2-chloropyridin-4-yl)-5-methylthieno[3,2-c]pyridin-4(5H)-one;

7-(2-aminopyridin-4-yl)-5-methyl-2-((3-methylmorpholino)methyl)thieno[3,2-c]pyridin-4(5H)-one:

5-methyl-2-((methylamino)methyl)-7-(2-((tetrahydro-2H-pyran-4-yl)methoxy)pyridin-4-yl)thieno[3,2-c]pyridin-4(5H)-one;

7-(3,4-dimethoxyphenyl)-5-methyl-2-(pyrrolidin-1-ylmethyl)thieno[3,2-c]pyridin-4(5H)-one;

N-((7-(3,4-dimethoxyphenyl)-5-methyl-4-oxo-4,5-dihydrothieno[3,2-c]pyridin-2-yl)methyl)-N-methylmethanesulphonamide;

7-(3,4-dimethoxyphenyl)-2-((3,5-dimethylpiperazin-1-yl)methyl)-5-methylthieno[3,2-c]pyridin-4(5H)-one;

(S)-5-methyl-2-((3-methylmorpholino)methyl)-7-(3-((tetrahydro-2H-pyran-4-yl)methoxy)phenyl)thieno[3,2-c]pyridin-4(5H)-one;

(R)-7-(3,4-dimethoxyphenyl)-5-methyl-2-((2-methylpiperazin-1-yl)methyl)thieno[3,2-c]pyridin-4(5H)-one;

(R)-1-((7-(3,4-dimethoxyphenyl)-5-methyl-4-oxo-4,5-dihydrothieno[3,2-c]pyridin-2-yl)methyl)piperazine-2-carboxamide;

(S)-7-(3,4-dimethoxyphenyl)-5-methyl-2-((3-methylpiperazin-1-yl)methyl)thieno[3,2-c]pyridin-4(5H)-one;

methyl 1-((7-(3,4-dimethoxyphenyl)-5-methyl-4-oxo-4,5-dihydrothieno[3,2-c]pyridin-2-yl)methyl)piperazine-2-carboxylate;

7-(3,4-dimethoxyphenyl)-2-((cis-2,6-dimethylpiperazin-1-yl)methyl)-5-methylthieno[3,2-c]pyridin-4(5H)-one;

(R)-2-((3-butylpiperazin-1-yl)methyl)-7-(3,4-dimethoxyphenyl)-5-methylthieno[3,2-c]pyridin-4(5H)-one;

(S)-7-(3,4-dimethoxyphenyl)-2-((3-ethylpiperazin-1-yl)methyl)-5-methylthieno[3,2-c]pyridin-4(5H)-one;

7-(3,4-dimethoxyphenyl)-5-methyl-2-((piperidin-4-ylamino)methyl)thieno[3,2-c]pyridin-4(5H)-one;

(S)-7-(3,4-dimethoxyphenyl)-5-methyl-2-((2-methylpiperazin-1-yl)methyl)thieno[3,2-c]pyridin-4(5H)-one;

2-((3-aminopyrrolidin-1-yl)methyl)-7-(3,4-dimethoxyphenyl)-5-methylthieno[3,2-c]pyridin-4(5H)-one;

2-((4-aminopiperidin-1-yl)methyl)-7-(3,4-dimethoxyphenyl)-5-methylthieno[3,2-c]pyridin-4(5H)-one;

2-(((2-aminoethyl)(methyl)amino)methyl)-7-(3,4-dimethoxyphenyl)-5-methylthieno[3,2-c]pyridin-4(5H)-one;

(R)-7-(3,4-dimethoxyphenyl)-5-methyl-2-((2-methyl-4-(methylsulphonyl)piperazin-1-yl)methyl)thieno[3,2-c]pyridin-4(5H)-one;

(S)-7-(3,4-dimethoxyphenyl)-5-methyl-2-((3-methyl-4-(methylsulphonyl)piperazin-1-yl)methyl)thieno[3,2-c]pyridin-4(5H)-one;

methyl 1-((7-(3,4-dimethoxyphenyl)-5-methyl-4-oxo-4,5-dihydrothieno[3,2-c]pyridin-2-yl)methyl)-4-(methylsulphonyl)piperazine-2-carboxylate;

(R)-2-((3-butyl-4-(methylsulphonyl)piperazin-1-yl)methyl)-7-(3,4-dimethoxyphenyl)-5-methylthieno[3,2-c]pyridin-4(5H)-one;

(S)-7-(3,4-dimethoxyphenyl)-2-((3-ethyl-4-(methylsulphonyl)piperazin-1-yl)methyl)-5-methylthieno[3,2-c]pyridin-4(5H)-one;

(S)-7-(3,4-dimethoxyphenyl)-5-methyl-2-((2-methyl-4-(methylsulphonyl)piperazin-1-yl)methyl)thieno[3,2-c]pyridin-4(5H)-one;

N-(1-((7-(3,4-dimethoxyphenyl)-5-methyl-4-oxo-4,5-dihydrothieno[3,2-c]pyridin-2-yl)methyl)pyrrolidin-3-yl)methanesulphonamide;

7-(4-((2-methoxyethyl)(methyl)amino)pyridin-2-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(pyridin-3-yl)thieno[3,2-c]pyridin-4(5H)-one;

7-(3,4-dichlorophenyl)-5-methyl-2-((4-(methylsulphonyl)piperazin-1-yl)methyl)thieno[3,2-c]pyridin-4(5H)-one;

7-(4-(aminomethyl)phenyl)-5-methyl-2-((4-(methylsulphonyl)piperazin-1-yl)methyl)thieno[3,2-c]pyridin-4(5H)-one;

7-(3-(benzyloxy)-4-methoxyphenyl)-5-methyl-2-((4-(methylsulphonyl)piperazin-1-yl)methyl)thieno[3,2-c]pyridin-4(5H)-one;

(R)-7-(4-methoxyphenyl)-5-methyl-2-((2-methyl-4-(methylsulphonyl)piperazin-1-yl)methyl)thieno[3,2-c]pyridin-4(5H)-one;

5-methyl-2-(((R)-2-methyl-4-(methylsulphonyl)piperazin-1-yl)methyl)-7-(5-(1-(pyridin-2-yl)ethoxy)pyridin-3-yl)thieno[3,2-c]pyridin-4(5H)-one;

(R)-7-(3-methoxyphenyl)-5-methyl-2-((2-methyl-4-(methylsulphonyl)piperazin-1-yl)methyl)thieno[3,2-c]pyridin-4(5H)-one;

(R)-N-(4-(5-methyl-2-((2-methyl-4-(methylsulphonyl)piperazin-1-yl)methyl)-4-oxo-4,5-dihydrothieno[3,2-c]pyridin-7-yl)pyridin-2-yl)acetamide;

(R)-5-methyl-2-((2-methyl-4-(methylsulphonyl)piperazin-1-yl)methyl)-7-phenylthieno[3,2-c]pyridin-4(5H)-one;

5-methyl-2-((4-(methylsulphonyl)piperazin-1-yl)methyl)-7-(p-tolyl)thieno[3,2-c]pyridin-4(5H)-one;

(R)-7-(2-methoxypyridin-4-yl)-5-methyl-2-((2-methyl-4-(methylsulphonyl)piperazin-1-yl)methyl)thieno[3,2-c]pyridin-4(5H)-one (R)-7-(5-methoxypyridin-3-yl)-5-methyl-2-((2-methyl-4-(methylsulphonyl)piperazin-1-yl)methyl)thieno[3,2-c]pyridin-4(5H)-one;

(R)-7-(6-methoxypyridin-3-yl)-5-methyl-2-((2-methyl-4-(methylsulphonyl)piperazin-1-yl)methyl)thieno[3,2-c]pyridin-4(5H)-one;

(R)-5-methyl-2-((2-methyl-4-(methylsulphonyl)piperazin-1-yl)methyl)-7-(pyridin-2-yl)thieno[3,2-c]pyridin-4(5H)-one;

5-methyl-2-((4-(methylsulphonyl)piperazin-1-yl)methyl)-7-(3-(trifluoromethyl)phenyl)thieno[3,2-c]pyridin-4(5H)-one;

N-benzyl-3-(5-methyl-2-((4-(methylsulphonyl)piperazin-1-yl)methyl)-4-oxo-4,5-dihydrothieno[3,2-c]pyridin-7-yl)benzamide;

(R)-7-(6-hydroxypyrimidin-4-yl)-5-methyl-2-((2-methyl-4-(methylsulphonyl)piperazin-1-yl)methyl)thieno[3,2-c]pyridin-4(5H)-one;

5-methyl-2-((4-(methylsulphonyl)piperazin-1-yl)methyl)-7-(o-tolyl)thieno[3,2-c]pyridin-4(5H)-one;

(S)-7-(6-methoxypyridin-3-yl)-5-methyl-2-((2-methyl-4-(methylsulphonyl)piperazin-1-yl)methyl)thieno[3,2-c]pyridin-4(5H)-one;

(S)-5-methyl-2-((2-methyl-4-(methylsulphonyl)piperazin-1-yl)methyl)-7-(pyridin-4-yl)thieno[3,2-c]pyridin-4(5H)-one;

(S)-5-methyl-2-((2-methyl-4-(methylsulphonyl)piperazin-1-yl)methyl)-7-(pyridin-3-yl)thieno[3,2-c]pyridin-4(5H)-one;

(S)-7-(5-methoxypyridin-3-yl)-5-methyl-2-((2-methyl-4-(methylsulphonyl)piperazin-1-yl)methyl)thieno[3,2-c]pyridin-4(5H)-one;

(S)-7-(4-methoxy-2-methylphenyl)-5-methyl-2-((2-methyl-4-(methylsulphonyl)piperazin-1-yl)methyl)thieno[3,2-c]pyridin-4(5H)-one;

(S)-7-(3-(benzyloxy)-4-methoxyphenyl)-5-methyl-2-((2-methylpiperazin-1-yl)methyl)thieno[3,2-c]pyridin-4(5H)-one;

5-ethyl-2-((4-(methylsulphonyl)piperazin-1-yl)methyl)-7-phenylthieno[3,2-c]pyridin-4(5H)-one;

7-(3,4-dimethoxyphenyl)-5-ethyl-2-((4-(methylsulphonyl)piperazin-1-yl)methyl)thieno[3,2-c]pyridin-4(5H)-one;

2-((4-acetylpiperazin-1-yl)methyl)-5-ethyl-7-phenylthieno[3,2-c]pyridin-4(5H)-one;

2-((4-acetylpiperazin-1-yl)methyl)-7-(3,4-dimethoxyphenyl)-5-ethylthieno[3,2-c]pyridin-4(5H)-one; or a salt thereof.

The term "$C_{1-4}$alkyl" means a straight or branched alkyl containing at least one, and at most four, carbon atoms. Examples of "$C_1$-$C_4$alkyl" as used herein include, but are not limited to, methyl, ethyl, n-propyl, n-butyl, isobutyl, isopropyl and t-butyl.

The term "$C_{1-4}$alkylene" means a straight or branched alkyl chain containing at least one, and at most four, carbon atoms. Examples of "$C_1$-$C_4$alkylene" as used herein include, but are not limited to, methylene, ethylene, propylene and butylene.

The term "$C_{3-7}$cycloalkyl" is used to describe a non-aromatic carbocyclic ring containing at least three and at most seven carbon atoms. Examples of $C_{3-7}$cycloalkyl groups include cyclopropyl, cyclobutyl, cyclopentyl, cyclohexyl and cycloheptyl.

The term "heterocycle" refers to a 5 or 6 membered saturated ring that includes one or more (e.g. 2) ring heteroatoms selected from nitrogen, oxygen and sulfur. Examples of saturated heterocycle groups include, but are not limited to, tetrahydropyran, tetrahydrofuran, tetrahydrothiophene, piperidine, piperazine, morpholine, 1,4-dioxane, thiomorpholine, 1,4-oxathiane and 1,4-dithane. The point of attachment to the rest of the molecule may be by any suitable carbon or nitrogen atom.

The term "heterocycle comprising $SO_2$ as one of the ring heteroatoms" refers to a 5 or 6 membered saturated ring that includes one or more (e.g. 2) ring heteroatoms selected from nitrogen, oxygen, sulfur and sulfur dioxide wherein at least one of the heteroatoms is sulfur dioxide.

Examples of heterocycle groups comprising $SO_2$ include, but are not limited to, tetrahydrothiophenyl 1,2-dioxide and tetrahydro-2H-thiopyranyl 1,1-dioxide.

The term "halo" as used herein refers to fluoro, chloro, bromo or iodo.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example the *Journal of the American Chemical Society* or the *Journal of Biological Chemistry*. Unless otherwise noted, all starting materials were obtained from commercial suppliers and used without further purification.

The compounds of formula (I) may contain a chiral atom such that optical isomers, e.g. enantiomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

It will be appreciated that the present invention covers compounds of formula (I) as the free base and as salts thereof, for example as a pharmaceutically acceptable salt thereof. In one embodiment the invention relates to compounds of formula (I) in the form of a free base. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, glutamaic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formula (I), and are included within the scope of this invention The invention includes within its scope all possible stoichiometric and non-stoichiometric forms of the salts of the compounds of formula (I).

It will be appreciated that many organic compounds can form complexes with solvents in which they are reacted or from which they are precipitated or crystallised. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognisable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Illustrative general synthetic methods are set out below and then specific compounds of formula (I) and pharmaceutically acceptable salts thereof, are prepared in the Examples.

Compounds of formula (I) may be prepared as described in Schemes 1 to 9 below:

Scheme 1

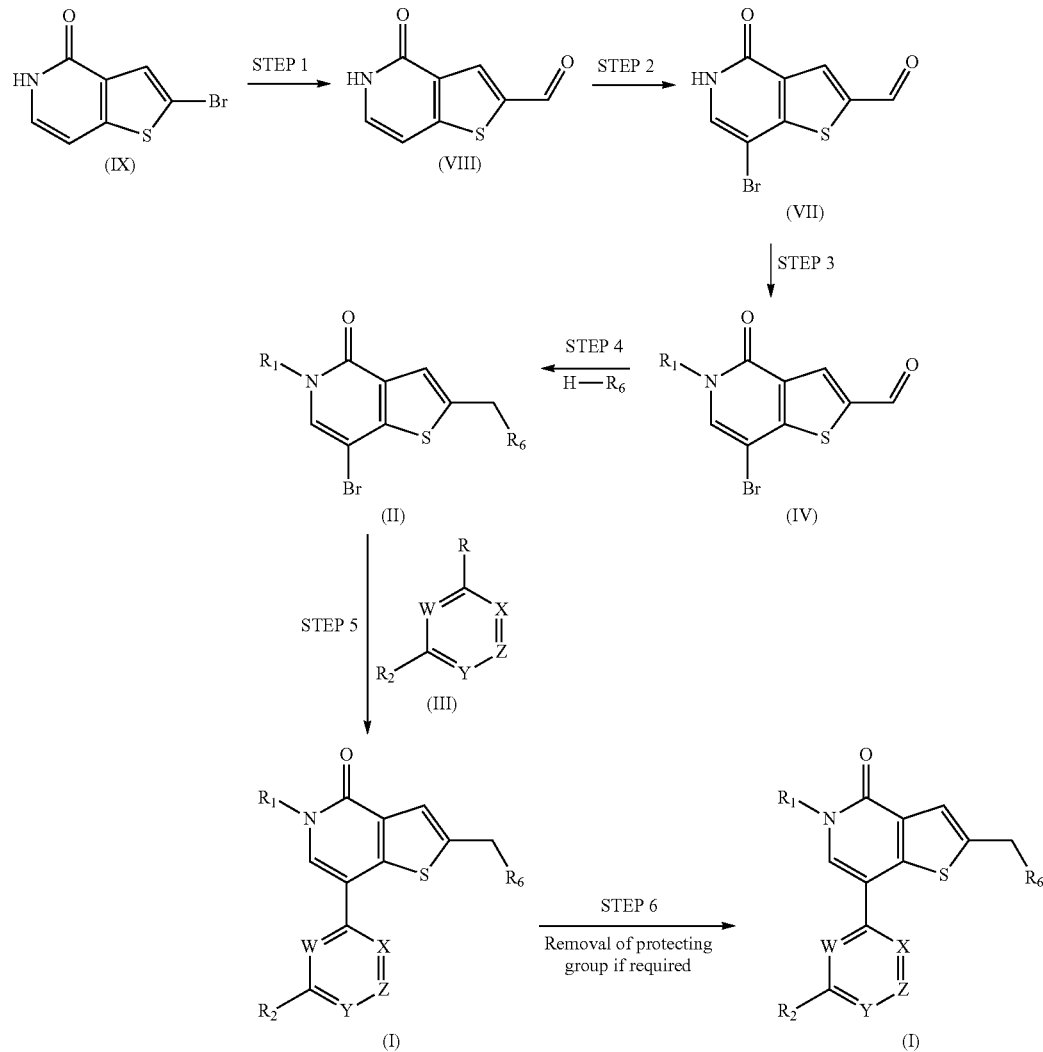

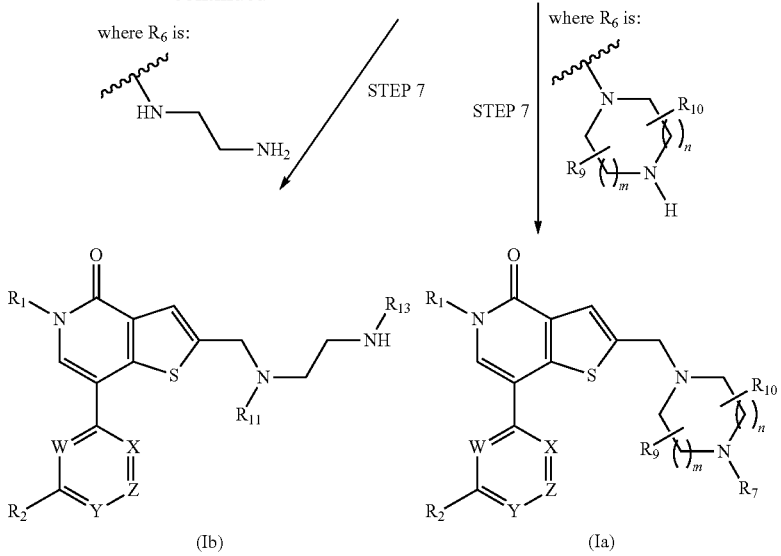

wherein m, n, $R_1$, $R_2$, $R_6$, $R_7$, $R_9$, $R_{10}$, $R_{11}$, $R_{13}$, W, X, Y and Z are as defined for a compound of formula (I); and R is selected from —B(OH)$_2$, —BF$_3$K,

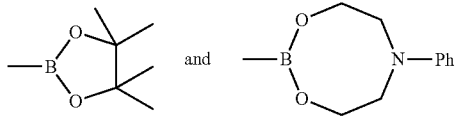

H—$R_6$ is a compound of formula (V) or a compound of formula (VI)

wherein m, n, $R_7$, $R_9$, $R_{10}$, $R_{11}$, $R_{12}$ and E are as defined for a compound of formula (I).

In respect of steps shown in Scheme 1 the following reactions conditions may be utilised.

Step 1 may be carried out by treating with a suitable strong base, such as nBuLi, followed by a suitable formylating agent, such as N,N-dimethylformamide, in a suitable solvent, such as THF, at a suitable temperature, such as −78° C. and for suitable time period, such as 3 hours.

Step 2 may be carried out by treating with a suitable brominating agent, such as n-bromosuccinimide or Br$_2$, in a suitable solvent, such as THF, AcOH or CH$_3$CN, at a suitable temperature and time period, such as room temperature when using NBS for, for example 6 hours or under reflux if using Br$_2$, for, for example 30 min.

Step 3 may be carried out by treatment with a suitable alkylating agent, such as iodomethane or iodoethane, in the presence of a suitable base, for example Cs$_2$CO$_3$, K$_2$CO$_3$ or NaH, in a suitable solvent, such as THF or DMF, at a suitable temperature, such as room temperature for a period of, for example overnight.

Step 4 may be carried out with a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

Step 5 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, s$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

When the protecting group is BOC, Step 6 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Step 7 may be carried out by treatment with a suitable sulfonylating or acylating agent, such as a sulfonyl chloride, an acyl chloride, or an acyl anhydride, in the presence of a suitable base, such as pyridine, pyridine/DMAP, or triethylamine, in a suitable solvent, such as DCM, acetonitrile or 1,2-DCE, at a suitable temperature, such as room temperature or 40° C. and for a suitable time period, such as 1 hr to overnight.

Alternatively, when $R_7$ is $C_{1-4}$alkyl, Step 7 may be carried out using conditions suitable for a reductive amination reaction. For example, in the presence of a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.
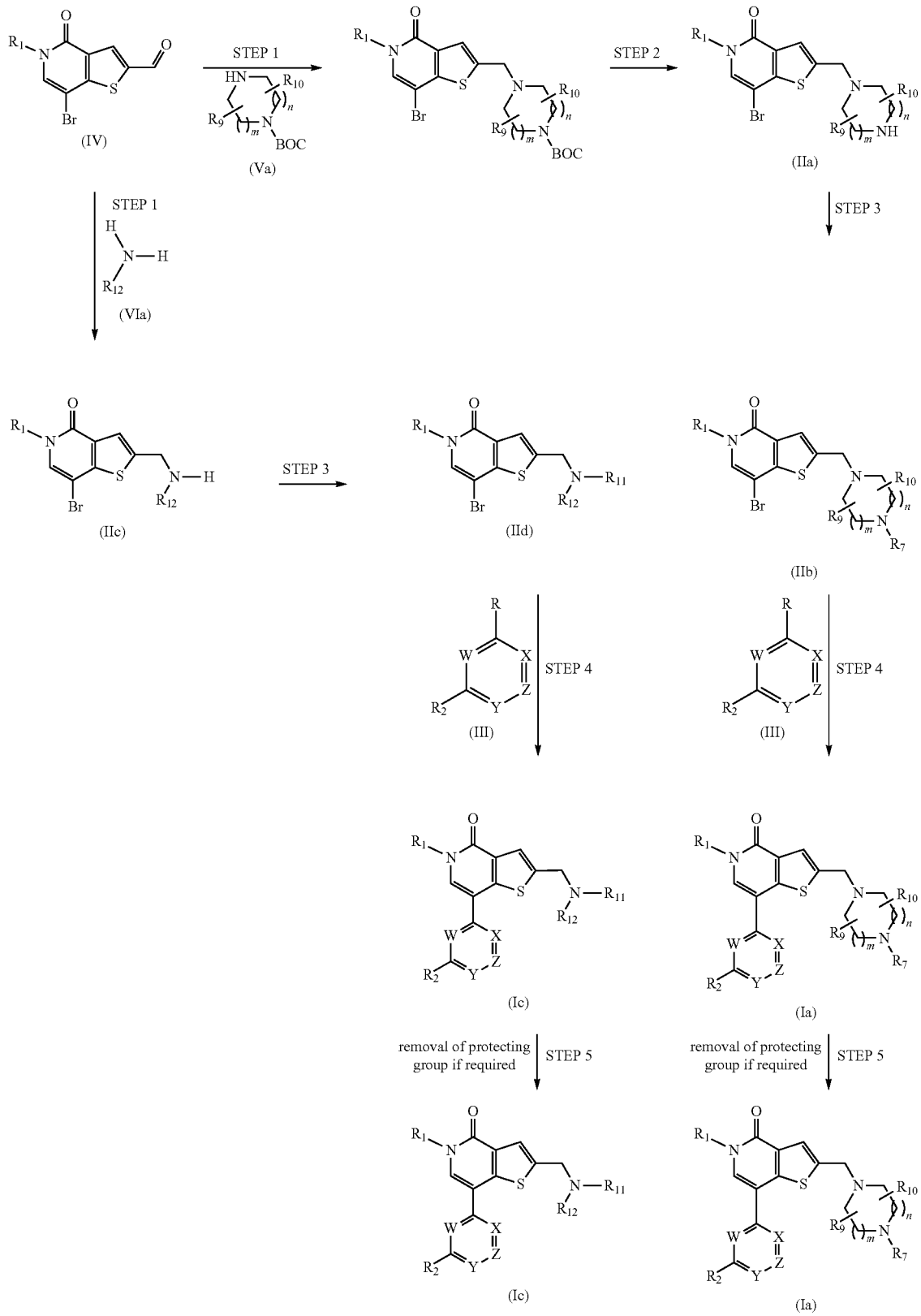
Scheme 2 wherein m, n, $R_1$, $R_2$, $R_7$, $R_9$, $R_{10}$, $R_{11}$, $R_{12}$, W, X, Y and Z are as defined for a compound of formula (I); and R is selected from —B(OH)$_2$, —BF$_3$K,

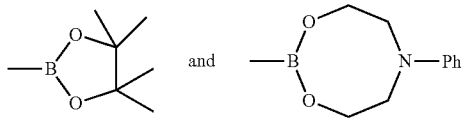

In respect of steps shown in Scheme 2 the following reactions conditions may be utilised.

Step 1 may be carried out with a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

Step 2 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

When $R_7$ is —SO$_2$C$_{1-4}$alkyl, Step 3 may be carried out by treatment with a suitable sulfonylating agent, such as a sulfonyl chloride, in the presence of suitable base, such as pyridine, in a suitable solvent, such as DCM, at a suitable temperature and for a suitable time period, for example 4 hr to overnight.

Step 4 may be carried out with a suitable palladium catalyst, such as PdCl$_2$(PPh$_3$)$_2$, Pd$_2$(dba)$_3$, PdCl$_2$(dppf). DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, s$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

When the protecting group is BOC, Step 5 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Scheme 3

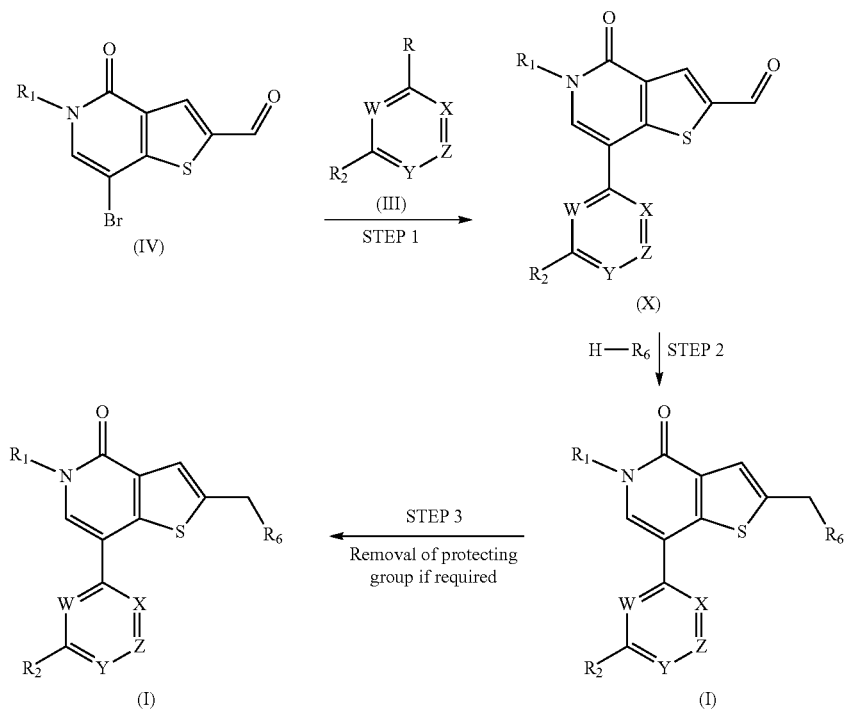

wherein $R_1$, $R_2$, $R_6$, W, X, Y and Z are as defined for a compound of formula (I); and R is selected from —B(OH)$_2$, —BF$_3$K

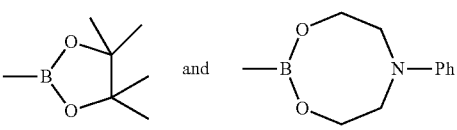

H—R$_6$ is a compound of formula (V) or a compound of formula (VI)

HNHR₁₁R₁₂ (VI)

In respect of steps shown in Scheme 3 the following reactions conditions may be utilised.

Step 1 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, Cs$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

Step 2 may be carried out with a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

wherein R$_1$, R$_2$, R$_6$, W, X, Y and Z are as defined for a compound of formula (I); and R is selected from —B(OH)$_2$, —BF$_3$K,

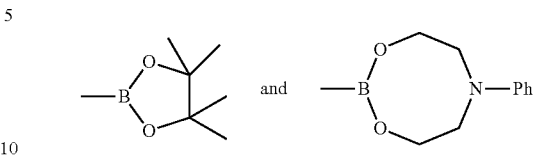

H—R$_6$ is a compound of formula (V) or a compound of formula (VI)

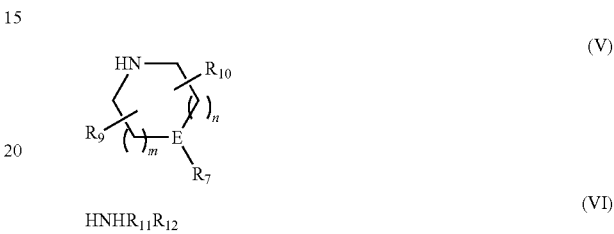

In respect of steps shown in Scheme 4 the following reactions conditions may be utilised.

Step 1 may be carried out by treatment with a suitable reducing agent, such as sodium borohydride, in a suitable solvent, such as ethanol, at a suitable temperature, such as room temperature and for a suitable time period, for example 1 hr.

Scheme 4

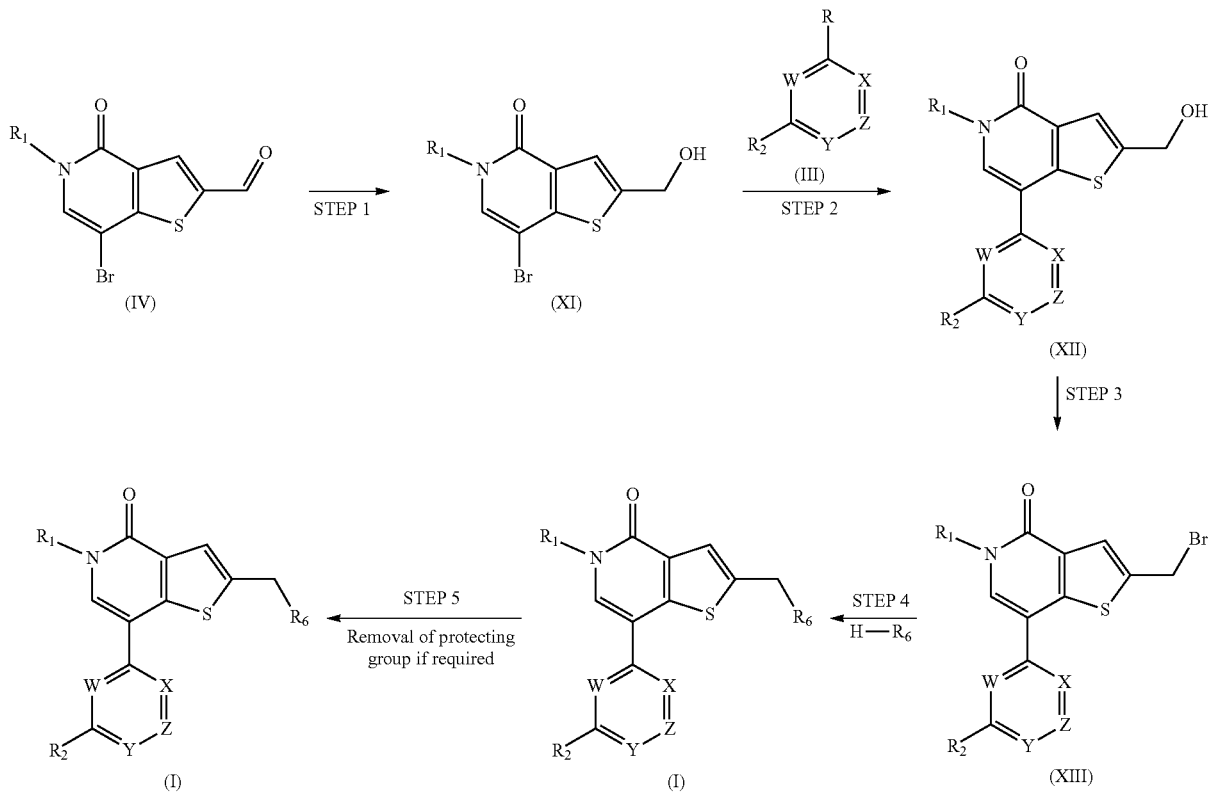

Step 2 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, s$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

Step 3 may be carried out by treatment with a suitable brominating agent, such as PBr$_3$, in a suitable solvent, such as 1,4-dioxane, at a suitable temperature, such as 40-60° C. and for a suitable time period, for example 2 hr to overnight.

Step 4 may be carried out in the presence of a suitable base, such as K$_2$CO$_3$ or DIPEA, in a suitable solvent, such as DMSO or DMF, at a suitable temperature, such as 110° C. in a microwave reactor and for a suitable time period, for example 30 min.

When the protecting group is BOC, Step 5 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Scheme 5

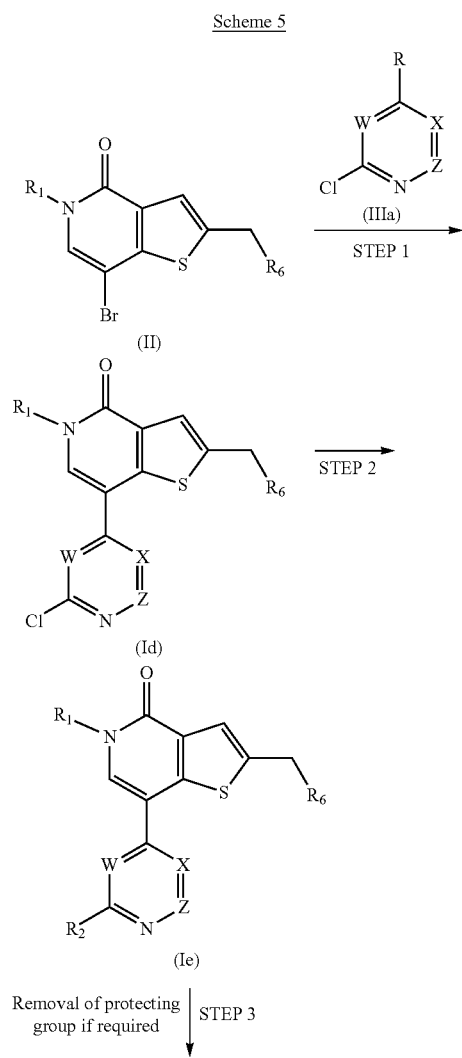

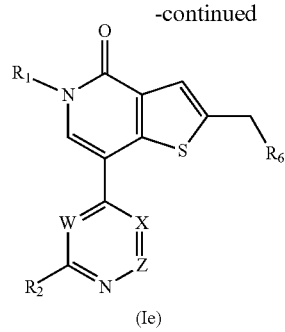

wherein R$_1$, R$_2$, R$_6$, W, X, and Z are as defined for a compound of formula (I); and R is selected from —B(OH)$_2$, —BF$_3$K,

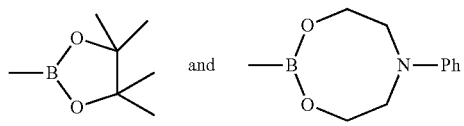

In respect of steps shown in Scheme 5 the following reactions conditions may be utilised.

Step 1 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, s$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

When R$_2$ is —NHCH(CH$_3$)CH$_2$OCH$_3$, —N(CH$_3$)CH$_2$CH$_2$OCH$_3$ or -G-CH(R$_3$)(R$_4$), wherein G is NH or N(CH$_3$) and R$_3$ and R$_4$ are as defined for a compound of formula (I), Step 2 may be carried out by treatment with a suitable amine, in a suitable solvent, such as NMP and at a suitable temperature, such as 250° C. in a microwave reactor and for a suitable time period, such as 30 min. Alternatively the reaction may be carried out by treatment with a suitable amine, in the presence of a suitable catalyst and ligand system, such as Pd$_2$(dba)$_3$/BINAP, in a suitable solvent, such as THF and at a suitable temperature, such as 80° C. and for a suitable time period, for example 4 hr.

Alternatively when R$_2$ is —NHC(O)C$_{1-4}$alkyl or —NHC(O)C$_{3-6}$cycloalkyl, Step 2 may be carried out, in the presence of a suitable catalyst and ligand system, such as Pd$_2$(dba)$_3$/Xantphos, in the presence of a suitable base, such as Cs$_2$CO$_3$, in a suitable solvent, such as 1,4-dioxane and at a suitable temperature, such as 100-160° C., optionally in a microwave reactor and for a suitable time period, for example 2 hr to 2 days.

When the protecting group is BOC, Step 3 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Scheme 6
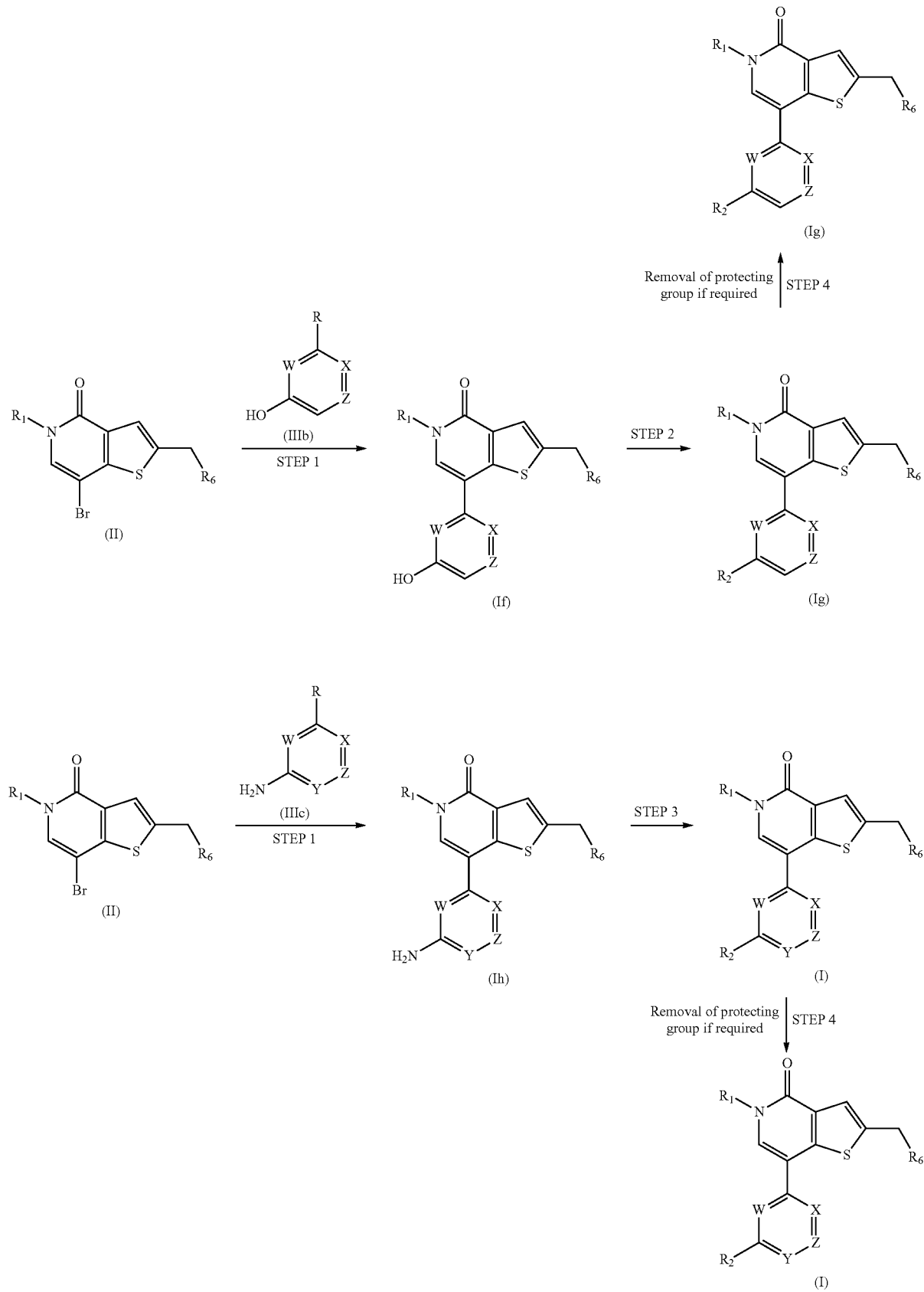

wherein $R_1$, $R_2$, $R_6$, W, X, Y and Z are as defined for a compound of formula (I); and R is selected from —B(OH)$_2$, —BF$_3$K,

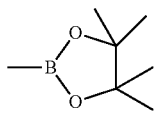 and 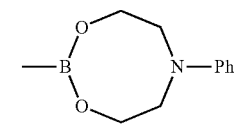

In respect of steps shown in Scheme 6 the following reactions conditions may be utilised.

Step 1 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, s$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

When $R_2$ is —OCH$_2$CH$_2$OCH$_3$, —OCH$_2$CH$_2$CH$_2$OH, or -G-CH($R_3$)($R_4$), wherein G is O and $R_3$ and $R_4$ are as defined for a compound of formula (I), Step 2 may be carried out by treatment with a suitable alkylating agent, such as an alkyl bromide, in the presence of a suitable base, such as K$_2$CO$_3$, in a suitable solvent, such as DMF and at a suitable temperature, such as 100° C. and for a suitable time period, for example 3-24 hr.

When Y is CH and $R_2$ is -G-CH($R_3$)($R_4$), wherein G is NH and $R_3$ and $R_4$ are as defined for a compound of formula (I), Step 3 may be carried out using conditions suitable for a reductive amination: For example by treatment with a suitable aldehyde, in the presence of a suitable reducing agent, such as sodium borohydride or titanium (IV) isopropoxide, in a suitable solvent, such as 2,2,2-trifluoroethanol, optionally in the presence of a suitable acid, such as acetic acid, at a suitable temperature, such as 40° C. to reflux, for a total reaction period of 1-3 days which includes a period of 80-180 min before addition of the reducing agent.

Alternatively when Y is N and $R_2$ is —NHC(O)C$_{1-4}$alkyl, Step 3 may be carried out using conditions suitable for an acylation: For example by treatment with a suitable acyl anhydride or acyl chloride, in the presence of a suitable base, such as pyridine or DIPEA, in a suitable solvent, such as DCM or 1,2-DCE at a suitable temperature, such as room temperature, for a time period, for example 4 hr.

When the protecting group is BOC, Step 4 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

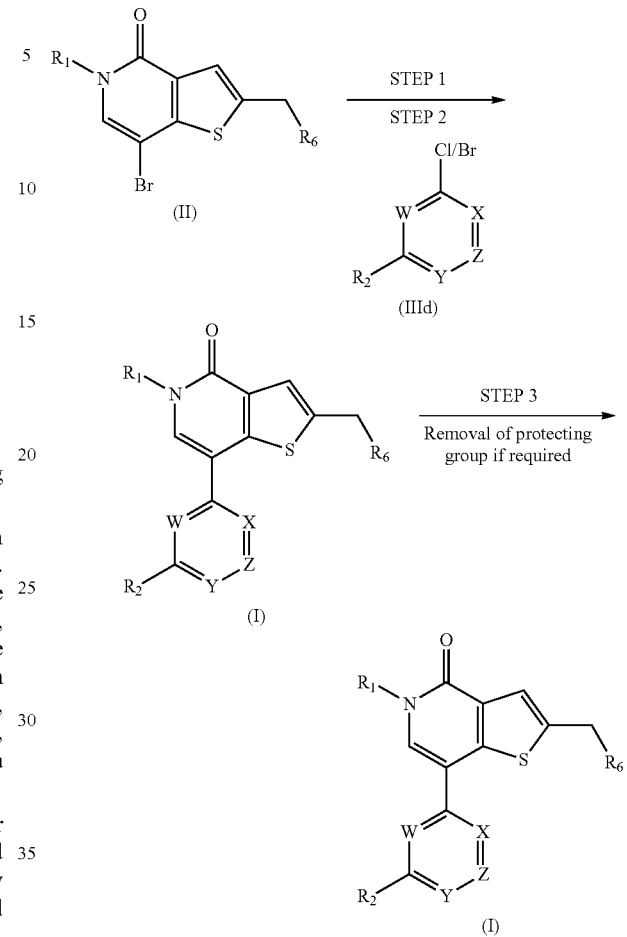

Scheme 7 wherein $R_1$, $R_2$, $R_6$, W, X, Y and Z are as defined for a compound of formula (I).

In respect of steps shown in Scheme 7 the following reactions conditions may be utilised.

Step 1 may be carried out by treatment with bis(pinacolato)diboron in the presence of a suitable catalyst, for example PdCl$_2$(dppf), in the presence of a suitable base, for example KOAc, in suitable solvent, such as 1,4-dioxane, at a suitable temperature, such as 110° C. in a microwave reactor, for a suitable period, such as 30 min.

Step 2 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable base, such as NaOtBu, KOtBu, Na$_2$CO$_3$, Cs$_2$CO$_3$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

When the protecting group is BOC, Step 3 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Scheme 8
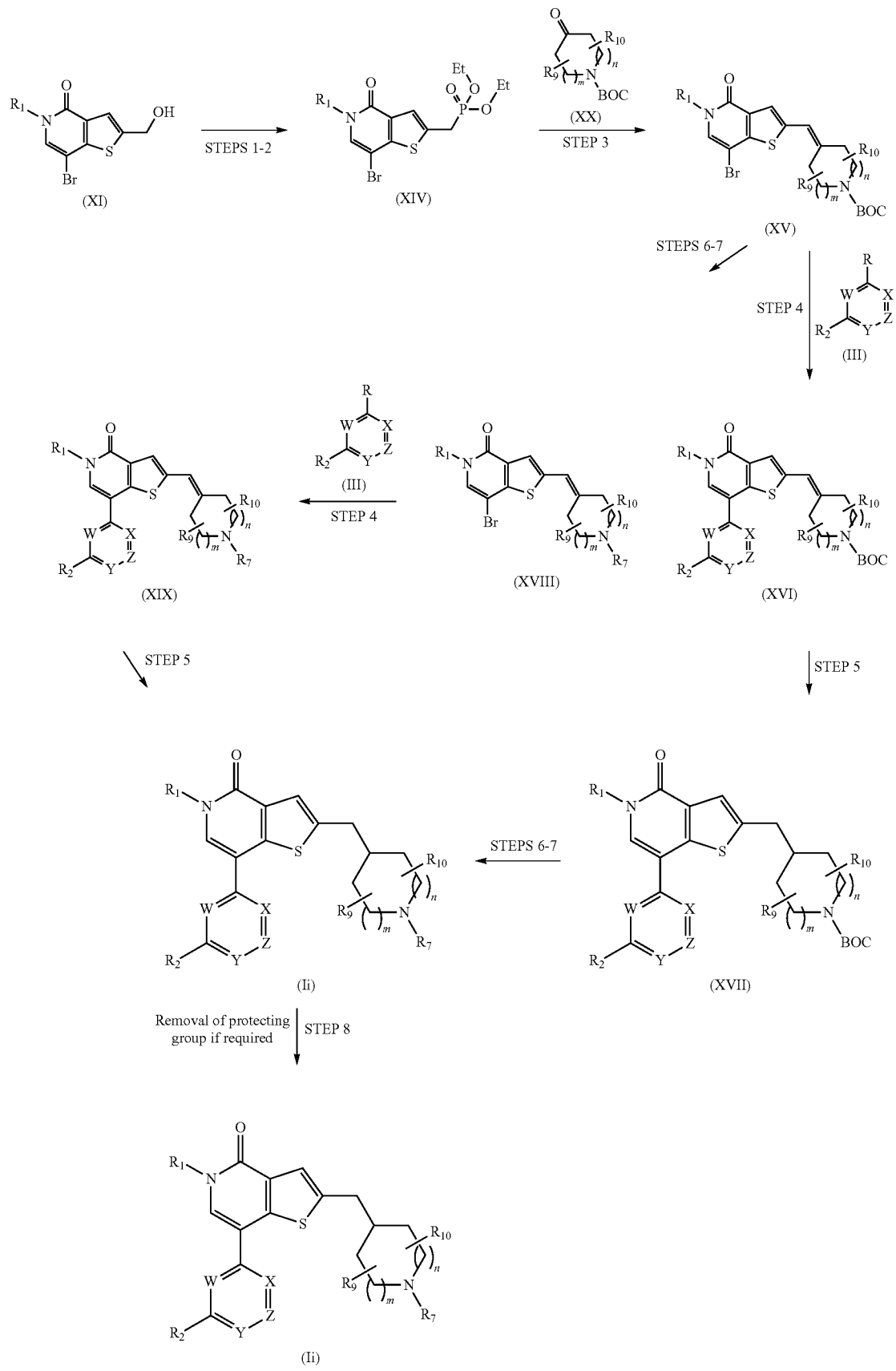

wherein m, n, R$_1$, R$_2$, R$_7$, R$_9$, R$_{10}$ W, X, and Z are as defined for a compound of formula (I); and R is selected from —B(OH)$_2$, —BF$_3$K,

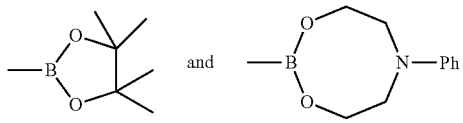

In respect of steps shown in Scheme 8 the following reactions conditions may be utilised.

Step 6 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

When R$_7$ is —SO$_2$C$_{1-4}$alkyl, Step 7 may be carried out by treatment with a suitable sulfonylating agent, such as a sulfonyl chloride, in the presence of suitable base, such as pyridine, in a suitable solvent, such as DCM, at a suitable temperature, such as room temperature and for a suitable period of, for example 1 hr to overnight.

Scheme 9

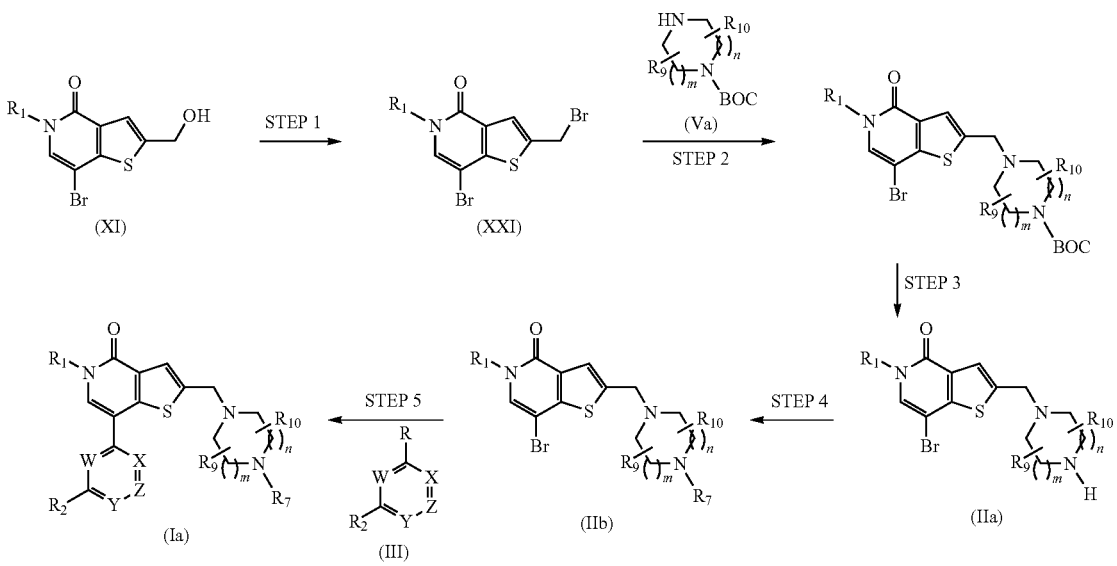

Step 1 may be carried out by treatment with a suitable brominating agent, such as PBr$_3$, in a suitable solvent, such as 1,4-dioxane, at a suitable temperature, such as 40-60° C. and for a suitable time period, for example 2 hr to overnight.

Step 2 may be carried out by treatment with a suitable trialkyl phosphite, such as P(OEt)$_3$, in a suitable solvent, such as toluene, at a suitable temperature, such as 120° C. and for a suitable time period, for example overnight.

Step 3 may be carried out by treatment with a suitable base, such as LDA, in a suitable solvent, such as THF, under suitable reaction conditions, for example for 45 min at −78° C. under an inert atmosphere prior to addition of the ketone, then warming to room temperature overnight.

Step 4 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ or PEPPSI, a suitable additive if required, such as CuI, a suitable base, such as NaO$^t$Bu, KO$^t$Bu, Na$_2$CO$_3$, Cs$_2$CO$_3$, K$_3$PO$_4$ or K$_2$CO$_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

Step 5 may be carried out by treatment with ammonium formate in the presence of a suitable catalyst, such as 10% Pd/C, in a suitable solvent, such as ethanol, under suitable conditions, for example heating at reflux for 2 hr.

wherein m, n, R$_1$, R$_2$, R$_7$, R$_9$, R$_{10}$ W, X, Y, and Z are as defined for a compound of formula (I); and R is selected from —B(OH)$_2$, —BF$_3$K,

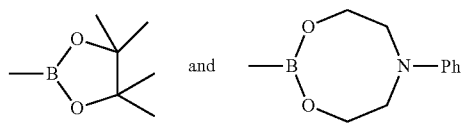

In respect of steps shown in Scheme 9 the following reactions conditions may be utilised.

Step 1 may be carried out by treatment with a suitable brominating agent, such as PBr$_3$, in a suitable solvent, such as 1,4-dioxane, at a suitable temperature, such as 40-60° C. and for a suitable time period, for example 2 hr to overnight.

Step 2 may be carried out in the presence of a suitable base such as potassium carbonate or sodium hydride in a suitable solvent, such as THF or DMF, at a suitable temperature, such as room temperature.

Step 3 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Step 4 may be carried out by treatment with a suitable sulfonylating or acylating agent, such as a sulfonyl chloride, an acyl chloride, or an acyl anhydride, in the presence of a suitable base, such as pyridine, pyridine/DMAP, or triethylamine, in a suitable solvent, such as DCM, acetonitrile or 1,2-DCE, at a suitable temperature, such as room temperature or 40° C. and for a suitable time period, such as 1 hr to overnight.

Alternatively, when $R_7$ is $C_{1-4}$alkyl, Step 4 may be carried out using conditions suitable for a reductive amination reaction. For example, in the presence of a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

Step 5 may be carried out with a suitable palladium catalyst, such as $PdCl_2(PPh_3)_2$, $Pd_2(dba)_3$, $PdCl_2(dppf)$.DCM, $Pd(OAc)_2$, $Pd(PPh_3)_4$ or PEPPSI, a suitable additive if required, such as CuI, a suitable base, such as NaO$^t$Bu, KO$^t$Bu, $Na_2CO_3$, $s_2CO_3$, $K_3PO_4$ or $K_2CO_3$, in a suitable solvent, such as 1,2-DME, aqueous 1,2-DME, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 hr.

Thus, in one embodiment the invention provides a process for preparing a compound of formula (I) comprising reacting a compound of formula (II)

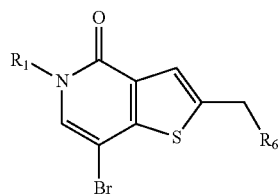
(II)

wherein $R_1$ and $R_6$ are as defined above, with a compound of formula (III)

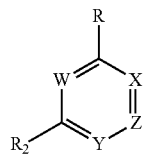
(III)

wherein $R_2$, W, X, Y and Z are as defined above, and R is selected from $B(OH)_2$, $BF_3K$,

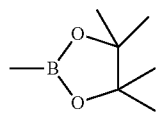 and 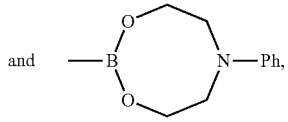

optionally followed by a deprotection step if required.

In another embodiment the invention provides a process for preparing a compound of formula (II) comprising reacting a compound of formula (IV)

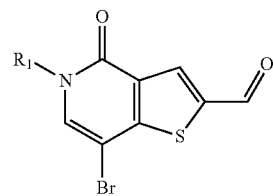
(IV)

wherein $R_1$ is as defined above, with an amine of formula (V) or formula (VI)

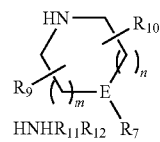
(V)

(VI)

wherein m, n, $R_7$, $R_9$, $R_{10}$, $R_{11}$, $R_{12}$, and E are as defined above, and if $R_{12}$ is $C_{1-4}$alkyleneNHR$_{13}$ then $R_{12}$ is protected by a suitable protecting group, such as BOC.

In another embodiment the invention provides a process for preparing a compound of formula (IV) comprising reacting a compound of formula (VII)

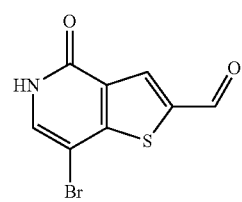
(VII)

with $R_1$I, wherein $R_1$ is as defined above.

In another embodiment the invention provides a process for preparing a compound of formula (VII) comprising reacting a compound of formula (VIII)

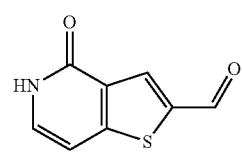
(VIII)

with a brominating agent, for example n-bromosuccinimide.

In another embodiment the invention provides a process for preparing a compound of formula (VIII) comprising reacting a compound of formula (IX)

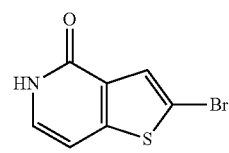
(IX)

with an organometallic, for example n-butyllithium followed by addition of N,N-dimethylformamide.

In a further embodiment the invention provides a process for preparing a compound of formula (Ia) comprising reacting a compound of formula (I) wherein $R_1$, $R_2$, W, X, Y and Z are as defined above, and $R_6$ is

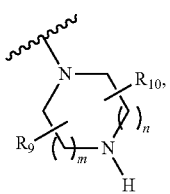

wherein m, n, $R_9$ and $R_{10}$ are as defined above, with a suitable sulfonylating agent, for example methanesulfonyl chloride, a suitable acylating agent, for example benzoyl chloride, or under conditions suitable for a reductive amination, for example with an aldehyde in the presence of suitable reducing agent such as sodium cyanoborohydride.

In another embodiment the invention provides a process for preparing a compound of formula (Ib) comprising reacting a compound of formula (I) wherein $R_1$, $R_2$, W, X, Y and Z are as defined above, and $R_6$ is

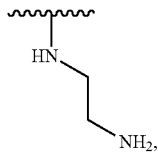

with a suitable sulfonylating agent, for example methanesulfonyl chloride.

In a further embodiment the invention provides a process for preparing a compound of formula (Ia) comprising reacting a compound of formula (IIb)

(IIb)

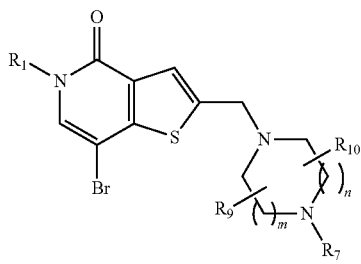

wherein m, n, $R_1$, $R_7$, $R_9$ and $R_{10}$ are as defined above, with a compound of formula (III)

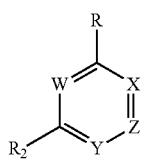

wherein $R_2$, W, X, Y and Z are as defined above, and R is selected from $B(OH)_2$, $BF_3K$,

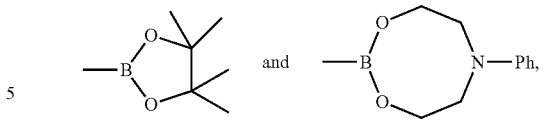

optionally followed by a deprotection step if required.

In another embodiment the invention provides a process for preparing a compound of formula (IIb) comprising reacting a compound of formula (IIa)

(IIa)

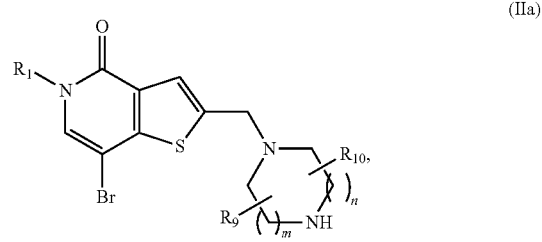

wherein m, n, $R_1$, $R_9$ and $R_{10}$ are as defined above, with a suitable sulfonylating agent or acylating agent, for example methanesulfonyl chloride or acetic anhydride.

In another embodiment the invention provides a process for preparing a compound of formula (IIa) comprising reacting a compound of formula (IV)

(IV)

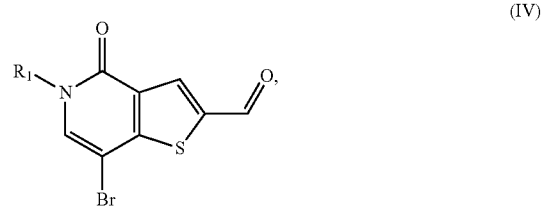

wherein $R_1$ is as defined above, with a compound of formula (Va)

(Va)

wherein m, n, $R_9$ and $R_{10}$ are as defined above, under conditions suitable for a reductive amination reaction, followed by removal of the BOC protecting group.

In a further embodiment the invention provides a process for preparing a compound of formula (Ic) comprising reacting a compound of formula (IId)

(IId)

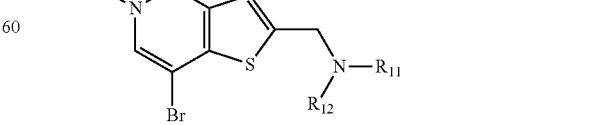

wherein $R_1$, $R_{11}$ and $R_{12}$ are as defined above, with a compound of formula (III)

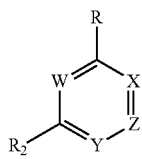

(III)

wherein R, W, X, Y and Z are as defined above, and R is selected from B(OH)$_2$, BF$_3$K,

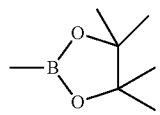 and 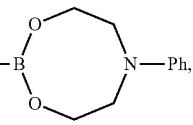

optionally followed by a deprotection step if required.

In another embodiment the invention provides a process for preparing a compound of formula (IId) comprising reacting a compound of formula (IIc)

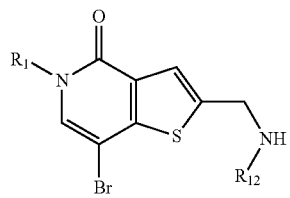

(IIc)

wherein R$_1$ and R$_{12}$ is as defined above, with a suitable sulfonylating agent, for example methanesulfonyl chloride.

In another embodiment the invention provides a process for preparing a compound of formula (IIc) comprising reacting a compound of formula (IV)

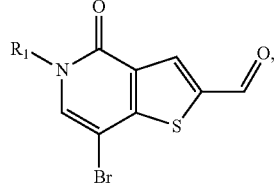

(IV)

wherein R$_1$ is as defined above, with a compound of formula (VIa)

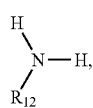

(VIa)

wherein R$_{12}$ is C$_{1-4}$alkyl or C$_{1-4}$alkyleneNHR$_{13}$, under conditions suitable for a reductive amination reaction, followed by removal of any protecting group as required.

In another embodiment the invention provides a process for preparing a compound of formula (I) comprising reacting a compound of formula (X)

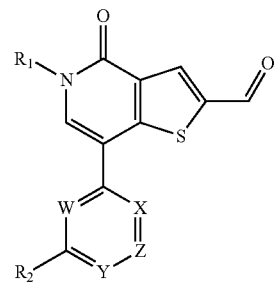

(X)

wherein R$_1$, R$_2$, W, X, Y and Z are as defined above, with an amine of formula (V) or formula (VI)

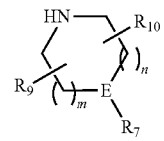

(V)

HNHR$_{11}$R$_{12}$ (VI)

wherein m, n, R$_7$, R$_9$, R$_{10}$, R$_{11}$, R$_{12}$ and E are as defined above, and if R$_{12}$ is C$_{1-4}$alkyleneNHR$_{13}$ then R$_{12}$ is protected by a suitable protecting group, such as BOC. Should a protecting group be required the reaction is followed by a deprotection step.

In a further embodiment the invention provides a process for preparing a compound of formula (X) comprising reacting a compound of formula (IV)

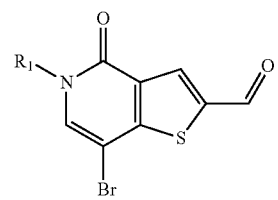

(IV)

wherein R$_1$ is as defined above, with a compound of formula (III)

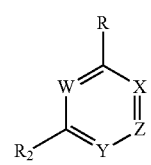

(III)

wherein R$_2$, W, X, Y and Z are as defined above, and R is selected from B(OH)$_2$, BF$_3$K,

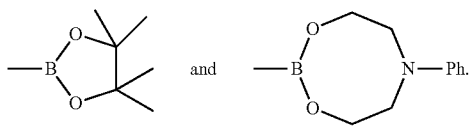

In a further embodiment the invention provides a process for preparing a compound of formula (I) comprising reacting a compound of formula (XIII)

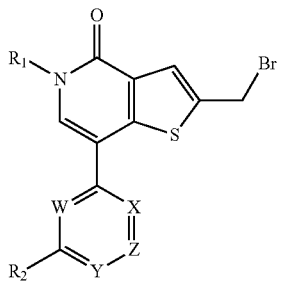

(XIII)

wherein $R_1$, $R_2$, W, X, Y and Z are as defined above, with a compound of formula (V) or formula (VI)

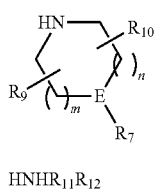

(V)

HNHR$_{11}$R$_{12}$ (VI)

wherein m, n, $R_7$, $R_9$, $R_{10}$, $R_{11}$, $R_{12}$ and E are as defined above, and if $R_{12}$ is $C_{1-4}$alkyleneNHR$_{13}$ then $R_{12}$ is protected by a suitable protecting group, such as BOC. Should a protecting group be required the reaction is followed by a deprotection step.

In a further embodiment the invention provides a process for preparing a compound of formula (XIII) comprising reacting a compound of formula (XII)

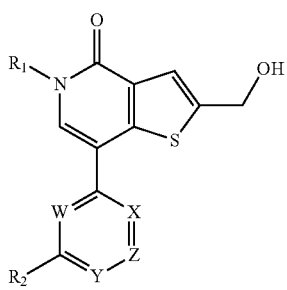

(XII)

wherein $R_1$, $R_2$, W, X, Y and Z are as defined above, with a suitable brominating agent such as tribromophosphine.

In a further embodiment the invention provides a process for preparing a compound of formula (XII) comprising reacting a compound of formula (XI)

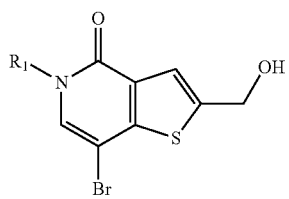

(XI)

wherein $R_1$ is as defined above, with a with a compound of formula (III)

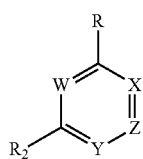

(III)

wherein $R_2$, W, X, Y and Z are as defined above, and R is selected from B(OH)$_2$, BF$_3$K,

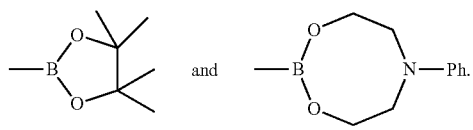

In a further embodiment the invention provides a process for preparing a compound of formula (XI) comprising reacting a compound of formula (IV)

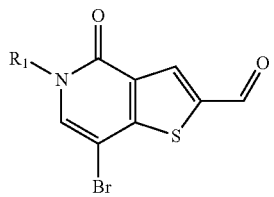

(IV)

wherein $R_1$ is as defined above, with a with a suitable reducing agent such as sodium borohydride.

In a further embodiment the invention provides a process for preparing a compound of formula (Ie) comprising reacting a compound of formula (Id)

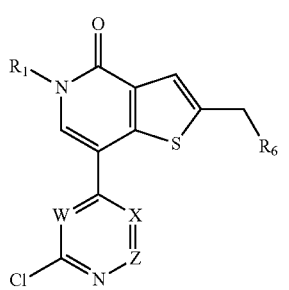

(Id)

wherein R$_1$, R$_6$, W, X and Z are as defined above, with a suitable nucleophile, optionally in the presence of a suitable catalyst/ligand system, for example Pd$_2$(dba)$_3$/BINAP or Pd$_2$(dba)$_3$/Xantphos and optionally in the presence of a suitable base, for example, caesium carbonate, optionally followed by a deprotection step if required.

In another embodiment the invention provides a process for preparing a compound of formula (Id) comprising reacting a compound of formula (II)

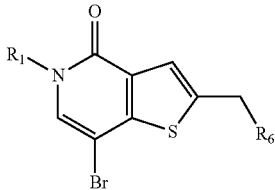
(II)

wherein R$_1$ is as defined above, with a with a compound of formula (IIIa)

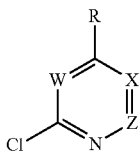
(IIIa)

wherein W, X and Z are as defined above, and R is selected from B(OH)$_2$, BF$_3$K,

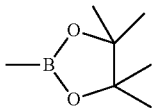 and 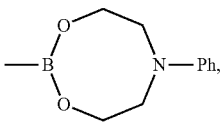

optionally followed by a deprotection step if required.

In a further embodiment the invention provides a process for preparing a compound of formula (Ig) comprising reacting a compound of formula (If)

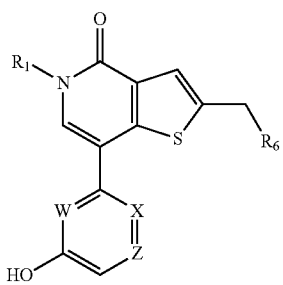
(If)

wherein R$_1$, R$_6$, W, X and Z are as defined above, with a suitable alkylating agent, for example and alkyl bromide, in the presence of a suitable base, for example potassium carbonate, optionally followed by a deprotection step if required.

In another embodiment the invention provides a process for preparing a compound of formula (If) comprising reacting a compound of formula (II)

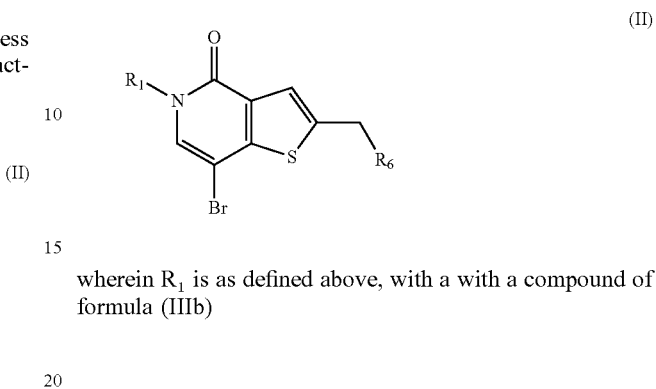
(II)

wherein R$_1$ is as defined above, with a with a compound of formula (IIIb)

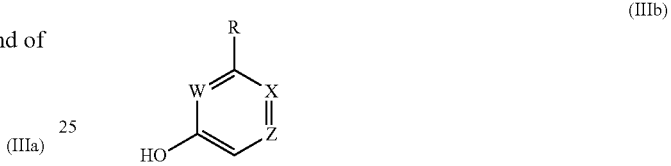
(IIIb)

wherein W, X and Z are as defined above, and R is selected from B(OH)$_2$, BF$_3$K,

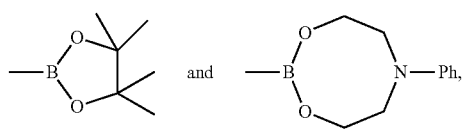 and ...Ph, optionally followed by a deprotection step if required.

In another embodiment the invention provides a process for preparing a compound of formula (I) comprising reacting a compound of formula (Ih)

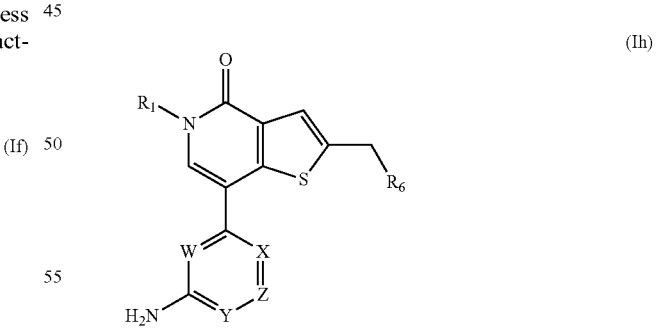
(Ih)

wherein R$_1$, R$_6$, W, X, Y and Z are as defined above, with a suitable acylating agent such a an acyl chloride or and acyl anhydride in the presence of a suitable base, for example pyridine, optionally followed by a deprotection step if required.

In a further embodiment the invention provides a process for preparing a compound of formula (I) comprising reacting a compound of formula (Ih)

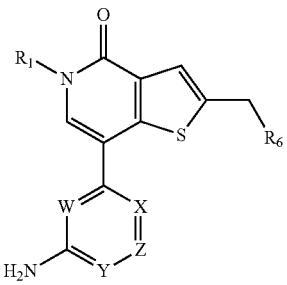

(Ih)

wherein $R_1$, $R_6$, W, X, Y and Z are as defined above, using conditions suitable for a reductive amination, for example reacting with an aldehyde in the presence of a suitable reducing agent such as sodium triacetoxyborohydride or a combination of sodium borohydride and titanium (IV) isopropoxide, optionally followed by a deprotection step if required.

In another embodiment the invention provides a process for preparing a compound of formula (Ih) comprising reacting a compound of formula (II)

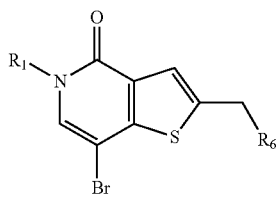

(II)

wherein $R_1$ and $R_6$ are as defined above, with a with a compound of formula (IIIc)

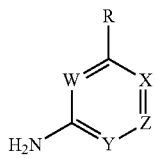

(IIIc)

wherein W, X, Y and Z are as defined above, and R is selected from $B(OH)_2$, $BF_3K$,

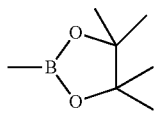 and 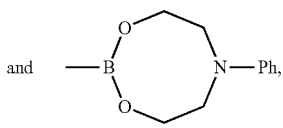, optionally followed by a deprotection step if required.

In another embodiment the invention provides a process for preparing a compound of formula (I) comprising reacting a compound of formula (II)

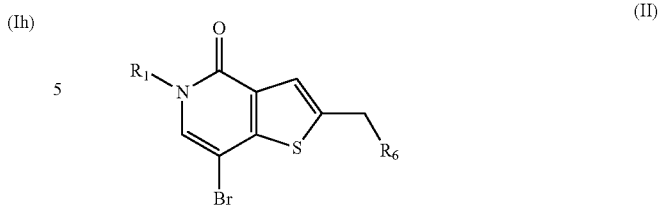

(II)

wherein R, and $R_6$ are as defined above, with bis(pinacolato) boron in the presence of a suitable palladium catalyst and base, to give the pinacol boronate ester, which is then reacted with a compound of formula (IIId)

(IIId)

wherein W, X, Y and Z are as defined above, optionally followed by a deprotection step if required.

In another embodiment the invention provides a process for preparing a compound of formula (Ii) comprising reacting a compound of formula (XVII)

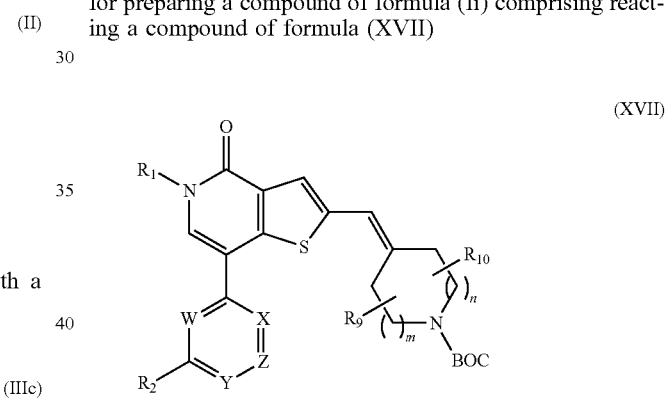

(XVII)

wherein m, n, $R_1$, $R_2$, $R_9$, $R_{10}$, W, X, Y and Z are as defined above, under conditions suitable for removal of a BOC protecting group, for example treatment with hydrochloric acid or trifluoroacetic acid, followed by treatment with a suitable sulfonylating agent such as methanesulfonyl chloride in the presence of a suitable base, for example pyridine, optionally followed by a deprotection step if required.

In a further embodiment the invention provides a process for preparing a compound of formula (XVII) comprising reacting a compound of formula (XVI)

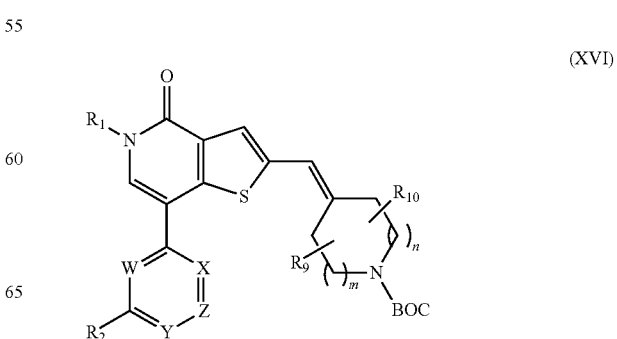

(XVI)

wherein m, n, R$_1$, R$_2$, R$_9$, R$_{10}$, W, X, Y and Z are as defined above, under conditions suitable for a hydrogenation, for example treatment with ammonium formate in the presence of a suitable catalyst such as 10% palladium on carbon.

In a further embodiment the invention provides a process for preparing a compound of formula (XVI) comprising reacting a compound of formula (XV)

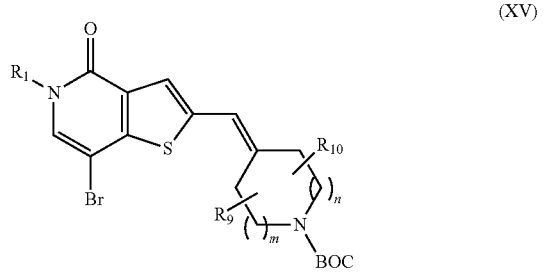

(XV)

wherein m, n, R$_1$, R$_2$, R$_9$ and R$_{10}$ are as defined above, with a compound of formula (III)

(III)

wherein R$_2$, W, X, Y and Z are as defined above, and R is selected from B(OH)$_2$, BF$_3$K,

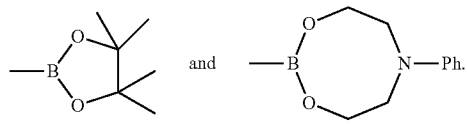

In a further embodiment the invention provides a process for preparing a compound of formula (XV) comprising reacting a compound of formula (XIV)

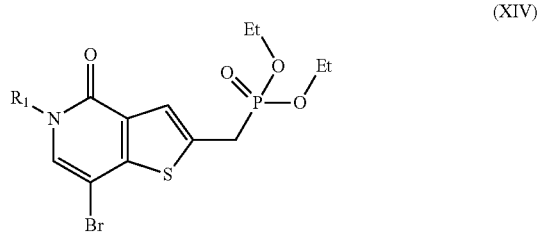

(XIV)

wherein R$_1$ is as defined above, with a compound of formula (XX)

(XX)

wherein, m, n, R$_9$ and R$_{10}$ are as defined above, in the presence of a suitable base such as lithium diisopropylamide.

In a further embodiment the invention provides a process for preparing a compound of formula (XIV) comprising reacting a compound of formula (XI)

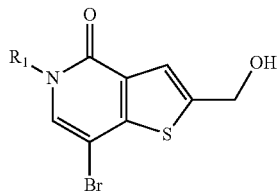

(XI)

wherein R$_1$ is as defined above, with a suitable brominating agent such as tribromophosphine to give the corresponding alkyl bromide which is then followed by treatment with triethylphosphite.

In another embodiment the invention provides a process for preparing a compound of formula (Ii) comprising reacting a compound of formula (XIX)

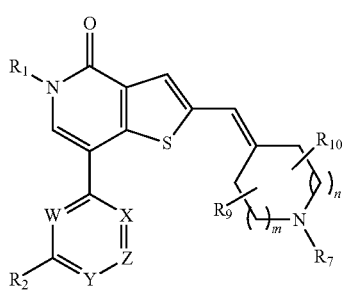

(XIX)

wherein m, n, R$_1$, R$_2$, R$_9$, R$_{10}$, W, X, Y and Z are as defined above, under conditions suitable for a hydrogenation, for example treatment with ammonium formate in the presence of a suitable catalyst such as 10% palladium on carbon, optionally followed by a deprotection step if required.

In a further embodiment the invention provides a process for preparing a compound of formula (XIX) comprising reacting a compound of formula (XVIII)

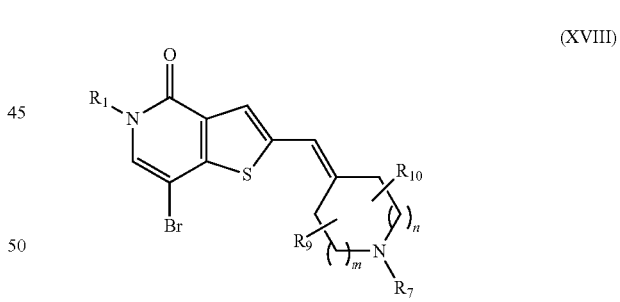

(XVIII)

wherein m, n, R$_1$, R$_2$, R$_7$, R$_9$ and R$_{10}$ are as defined above, with a compound of formula (III)

(III)

wherein R$_2$, W, X, Y and Z are as defined above, and R is selected from B(OH)$_2$, BF$_3$K,

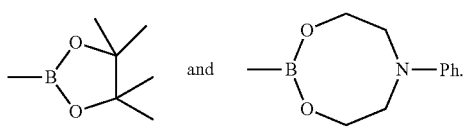

In a further embodiment the invention provides a process for preparing a compound of formula (XVIII) comprising reacting a compound of formula (XV)

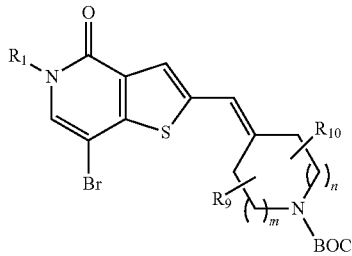

(XV)

wherein m, n, $R_1$, $R_2$, $R_9$ and $R_{10}$ are as defined above, under conditions suitable for removal of a BOC protecting group, for example treatment with hydrochloric acid or trifluoroacetic acid, followed by treatment with a suitable sulfonylating agent such as methanesulfonyl chloride in the presence of a suitable base, for example pyridine.

In a further embodiment the invention provides a process for preparing a compound of formula (IIa)

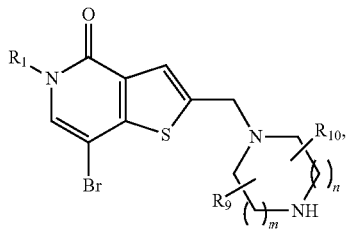

(IIa)

wherein m, n, $R_1$, $R_9$ and $R_{10}$ are as defined above, comprising reacting a compound of formula (XXI)

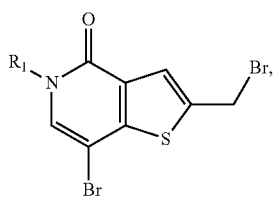

(XXI)

wherein $R_1$ is as defined above, with a compound of formula (Va)

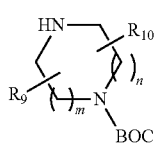

(Va)

wherein m, n, $R_9$ and $R_{10}$ are as defined above, under conditions suitable for an alkylation reaction, followed by removal of the BOC protecting group.

In another embodiment the invention provides a process for preparing a compound of formula (XXI) comprising reacting a compound of formula (XI)

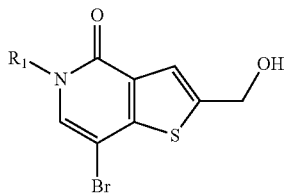

(XI)

wherein $R_1$ is as defined above, with a suitable brominating agent sucas tribromophosphine.

Compounds of formulae (IX), (V), (VI), (XX) and (III) are commercially available or can be readily synthesised by known methods, for example as reported by Suzuki in Chem.Rev., 1995, vol. 95, p2457-2483.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in 1,4-dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In one embodiment there is provided a compound of formula (I) or a pharmaceutically acceptable salt thereof for use in the treatment of acute or chronic auto-immune and/or inflammatory conditions. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of viral infections. In a further embodiment there is provided a compound of formula (I) or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In another embodiment there is provided the use a compound of formula (I) or a pharmaceutically acceptable salt thereof in the manufacture of a medicament for in the treatment of diseases or conditions which involve inflammatory responses to infections with bacteria, viruses, fungi, parasites or their toxins. In another embodiment there is provided the use a compound of formula (I) or a pharmaceutically acceptable salt thereof in the manufacture of a medicament for in the treatment of viral infections. In another embodiment there is provided the use a compound of formula (I) or a pharmaceutically acceptable salt thereof in the manufacture of a medicament for in the treatment of cancer.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In further embodiment there is provided a method of treating cancer in a subject in need thereof which comprises administering a therapeutically effective amount of a compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, or subject (e.g. a human) that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and Ulcerative colitis).

In another embodiment the acute or chronic autoimmune and/or inflammatory condition is multiple sclerosis.

In a further embodiment the acute or chronic autoimmune and/or inflammatory condition is Type I diabetes.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment the viral infection is a HPV infection of skin or cervical epithelia. In another embodiment the viral infection is a latent HIV infection.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multiorgan dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

As used herein the reference to the "treatment" of a particular disease or condition includes the prevention or prophylaxis of such a disease or condition.

The term "diseases or conditions for which a bromodomain inhibitor is indicated", is intended to include each of or all of the above diseases or conditions.

The invention further provides for a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of formula (I) and pharmaceutically acceptable salts are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient.

Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents.

The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

GENERAL EXPERIMENTAL DETAILS

All temperatures referred to are in ° C.
The names of the following compounds have been obtained using the compound naming programme "ACD Name Pro 6.02" or ChemDraw Ultra 12.0.

Abbreviations
1,2-DCE 1,2-dichloroethane
AcOH acetic acid
BINAP 2,2'-bis(diphenylphosphino)-1, 1'-binaphthyl
BOC tert-butyloxycarbonyl
$(Boc)_2O$ di-tert-butyl dicarbonate
nBuLi n-butyllithium
$CDCl_3$ deuterochloroform
$CHCl_3$ chloroform
$Cs_2CO_3$ caesium carbonate
DMSO-$d_6$ deuterated dimethylsulfoxide
1,2-DCE 1,2-dichloroethane
DCM dichloromethane
DIAD diisopropyl azodicarboxylate
DIPEA diisopropylamine
DMAP 4-dimethylaminopyridine
1,2-DME 1,2-dimethoxyethane
DMF N,N-dimethylformamide
DMSO dimethylsulfoxide
DPPA diphenylphosphoryl azide
e.e. enantiomeric excess
$Et_3N$ triethylamine
EtOAc ethyl acetate
EtOH ethanol
hr hour(s)
HATU O-(7-azabenzotriazol-1-yl)-N,N,N',N'-tetramethyluronium hexafluorophosphate
HCl hydrochloric acid/hydrogen chloride
HPLC high performance liquid chromatography
i-PrOAc isopropylacetate
i-$Pr_2O$ diisopropyl ether
$K_2CO_3$ potassium carbonate
LCMS liquid chromatography-mass spectrometry
LiOH lithium hydroxide
M molar (concentration)
M mass (mass spectrometry)
MDAP mass-directed autopreparative chromatography/ mass directed autoprep
MeCN acetonitrile
MeOH methanol
$MgSO_4$ magnesium sulfate
min minute(s)
MP-NCO polymer bound isocyanate scavenger resin
M/Z mass/charge ratio (mass spectrometry)
N normal (concentration)
$NaCNBH_3$ sodium cyanoborohydride
$Na_2CO_3$ sodium carbonate
NaH sodium hydride
$NaHCO_3$ sodium hydrogen carbonate
NaOH sodium hydroxide
$Na_2SO_4$ sodium sulfate
NBS N-bromosuccinimide
$NH_2$-SPE aminopropyl solid phase extraction
$NH_3$ ammonia
$NH_4Cl$ ammonium chloride
NMP N-methyl-2-pyrrolidinone
NMR nuclear magnetic resonance
PEPPSI/PEPPSI-IPr pyridine-enhanced precatalyst preparation stabilization and initiation
Pd/C palladium on carbon
$PdCl_2(dppf)$ dichloro[1,1'-bis(diphenylphosphino)ferrocene]palladium (II)
$PdCl_2(PPh_3)_2$ bis(triphenylphosphine)palladium(II) dichloride
$Pd_2(dba)_3$ tris(dibenzylideneacetone)dipalladium(0)
$Pd(PPh_3)_4$ tetrakis(triphenylphosphine) palladium (0)
Rt retention time
rt room temperature
SCX strong cation exchange
TBME tert-butyl methyl ether
Temp temperature
TFA trifluoroacetic acid
THF tetrahydrofuran
UPLC ultra performance liquid chromatograpy
Xantphos 4,5-bis(diphenylphosphino)-9,9-dimethylxanthene LCMS Methodology
Formic Acid Method
LC Conditions
The UPLC analysis was conducted on an Acquity UPLC BEH C18 column (50 mm×2.1 mm, i.d. 1.7 μm packing diameter) at 40° C.
The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was a summed signal from wavelength of 210 nm to 350 nm.
MS: conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC conditions
The UPLC analysis was conducted on an Acquity UPLC BEH C18 column (50 mm×2.1 mm, i.d. 1.7 μm packing diameter) at 40° C.
The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS: conditions
MS: Waters ZQ
Ionisation mode: Alternate-scan positive and negative electrospray
Scan range: 100 to 1000 AMU
Scan time: 0.27 sec
Inter scan delay: 0.10 sec
NMR
Spectra were run on a 400 MHz NMR machine at either 302 K or for VT spectra at 392-393 K.

Intermediate 1

4-oxo-4,5-dihydrothieno[3,2-c]pyridine-2-carbaldehyde

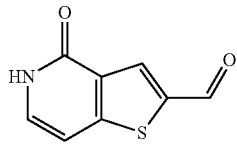

A suspension of 2-bromothieno[3,2-c]pyridin-4(5H)-one (16.7 g, 72.7 mmol) in dry THF (250 mL) was cooled to −78° C., with stirring under nitrogen. n-Butyllithium, 1.6 M in hexanes, (100 mL, 160 mmol) was added dropwise over 30 minutes (internal temp <−60° C.). After complete addition the mixture was stirred at <−60° C. (internal) for 2 hours. A solution of dry N,N-dimethylformamide (10.49 g, 11.11 mL, 143 mmol) in dry THF (20 mL) was added dropwise at <−60° C. The reaction mixture was allowed to stand at room temperature for 1 hour. Water (250 mL) was added carefully. The tetrahydrofuran was evaporated. The residue was diluted with water (100 mL). The solution was acidified (pH~4) with 2M hydrochloric acid. The precipitated solid was filtered off and dried to give the product, 4-oxo-4,5-dihydrothieno[3,2-c]pyridine-2-carbaldehyde (10.9 g, 60.8 mmol, 84% yield) as a light brown solid.

LCMS (2 min, Formic Acid): Rt=0.50 min, MH$^+$=180.

Intermediate 2

7-bromo-4-oxo-4,5-dihydrothieno[3,2-c]pyridine-2-carbaldehyde

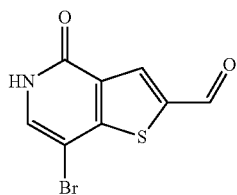

N-Bromosuccinimide (12.9 g, 72.3 mmol) was added portionwise to a stirred suspension of 4-oxo-4,5-dihydrothieno[3,2-c]pyridine-2-carbaldehyde (for a preparation see Intermediate 1, 10.8 g, 60.3 mmol) in THF (200 mL) over 5 minutes. The reaction mixture was stirred at room temperature for 24 hours. The reaction mixture was filtered. The solid was washed with a small amount of tetrahydrofuran, then diethyl ether. This was dried to give the product, 7-bromo-4-oxo-4,5-dihydrothieno[3,2-c]pyridine-2-carbaldehyde (10.3 g, 39.9 mmol, 66% yield) as a light brown solid.

LCMS (2 min, Formic Acid): Rt=0.69 min, (M−H+)=256/258.

Intermediate 3

7-bromo-5-methyl-4-oxo-4,5-dihydrothieno[3,2-c]pyridine-2-carbaldehyde

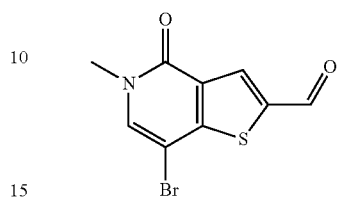

Caesium carbonate (37.9 g, 116 mmol) was added portionwise to a stirred suspension of 7-bromo-4-oxo-4,5-dihydrothieno[3,2-c]pyridine-2-carbaldehyde (for a preparation see Intermediate 2, 10.0 g, 38.7 mmol) in dry THF (250 mL). The reaction mixture was stirred for 20 minutes at room temperature then treated with iodomethane (11.0 g, 4.85 mL, 77 mmol). The reaction mixture was stirred at room temperature overnight. The solvent was evaporated. Water (250 mL) was added to the residue and the mixture stirred for 30 minutes. The suspension was filtered the solid was washed with water and dried to give the product, 7-bromo-5-methyl-4-oxo-4,5-dihydrothieno[3,2-c]pyridine-2-carbaldehyde (9.92 g, 36.5 mmol, 94% yield), as a light brown solid.

LCMS (2 min, High pH): Rt=0.80 min, MH$^+$=272/274.

Intermediate 4

3-bromo-5-(1-phenylethoxy)pyridine

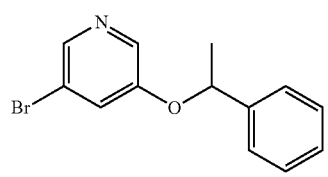 [SMILES: CC(Oc1cncc(Br)c1)c1ccccc1]

Potassium carbonate (1.59 g, 11.5 mmol) was added to a stirred solution of 5-bromopyridin-3-ol (1.0 g, 5.75 mmol) in DMF (10 mL). The reaction mixture was stirred at 60° C. for 30 minutes, then (1-bromoethyl)benzyl bromide (1.12 g, 824 μL, 6.05 mmol) was added. The reaction mixture was stirred at 60° C. for 2 hours. The reaction mixture was cooled to room temperature and partitioned between ethyl acetate (50 mL) and water (25 mL). The organic phase was separated, washed with water and brine, dried and evaporated. The residue was purified by chromatography on silica gel eluting with dichloromethane to give 3-bromo-5-(1-phenylethoxy)pyridine (890 mg, 3.20 mmol, 55.7% yield) as a yellow oil.

LCMS (2 min, Formic Acid): Rt=1.18 min, MH$^+$=278/280.

Intermediate 5

(5-(1-phenylethoxy)pyridin-3-yl)boronic acid

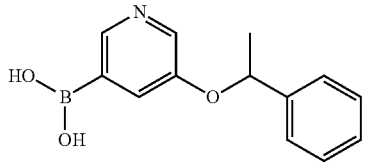 [SMILES: CC(Oc1cncc(B(O)O)c1)c1ccccc1]

A mixture of 3-bromo-5-(1-phenylethoxy)pyridine (for a preparation see Intermediate 4, 100 mg, 0.38 mmol), potassium acetate (149 mg, 1.51 mmol), bis(pinacolato)diboron (481 mg, 1.89 mmol) and 1,1'-bis(diphenylphosphino)ferrocene-palladium(II) dichloride (28 mg, 10 mol %) in 1,4-dioxane (4 mL) was heated in a microwave at 110° C. for 30 minutes. The cooled reaction mixture was diluted with ethyl acetate (15 mL). The suspension was dried over sodium sulphate and the solvent was evaporated. The residue was used in the next step without further purification. (5-(1-phenylethoxy)pyridin-3-yl)boronic acid (91 mg, 0.374 mmol, 100% yield) Quantitative yield assumed.

LCMS (2 min, Formic Acid): Rt=0.63 min, MH$^+$=244.

Intermediate 6

(±)-3-bromo-5-(1-(pyridin-2-yl)ethoxy)pyridine

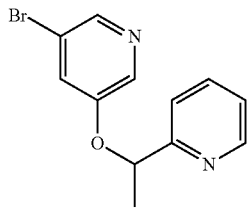 [SMILES: CC(Oc1cncc(Br)c1)c1ccccn1]

A mixture of (±)-1-(pyridin-2-yl)ethanol (100.5 mg, 0.816 mmol), 5-bromopyridin-3-ol (283.2 mg, 1.628 mmol) and 2-(tributylphosphoranylidene)acetonitrile (595.0 mg, 2.465 mmol) in toluene (3 mL) were heated with stirring in a sealed vial in a microwave reactor at 120° C. for 60 min. The mixture was concentrated under a stream of nitrogen and the residue was purified by column chromatography on silica gel eluting with a gradient of 0-50% ethyl acetate in cyclohexane. The required fractions were combined and evaporated in vacuo to give the desired product but contaminated with some of the starting 5-bromopyridin-3-ol. This residue was repurified by chromatography on silica gel eluting with a gradient of 0-8% (2M ammonia in methanol solution) in dichloromethane. The required fractions were combined and the solvent evaporated under a stream of nitrogen to give the desired product (±)-3-bromo-5-(1-(pyridin-2-yl)ethoxy)pyridine (118.9 mg, 0.426 mmol, 52.2% yield) as a brown oil.

LCMS (2 min, Formic Acid): Rt=0.83 min, MH$^+$=279/281.

Intermediate 6 Alternative preparation (±)-3-bromo-5-(1-(pyridin-2-yl)ethoxy)pyridine To a stirred solution of 5-bromopyridin-3-ol (293 mg, 1.686 mmol) in N,N-Dimethylformamide (DMF) (5 mL) was added potassium carbonate (777 mg, 5.62 mmol) followed by (±)-2-(1-bromoethyl)pyridine hydrobromide (500 mg, 1.873 mmol). The reaction was stirred at room temperature under nitrogen for 6 hours. The reaction was quenched with water (30 mL). The product was extracted from the aqueous phase with ethyl acetate (3×25 mL). The organic fractions were combined and washed with brine (30 mL). The organic phase was dried over magnesium sulphate and concentrated under reduced pressure to give a yellow oil. The crude material was loaded on to a 12 g silica gel column and was eluted in 0-50% ethyl acetate in cyclohexane to give (±)-3-bromo-5-(1-(pyridin-2-yl)ethoxy)pyridine as a clear, nearly colourless oil, (415 mg, 1.487 mmol, 79% yield).

LCMS (2 min, Formic Acid): Rt=0.83 min, MH$^+$=279/281

Intermediate 7

(±)-(5-(1-(pyridin-2-yl)ethoxy)pyridin-3-yl)boronic acid

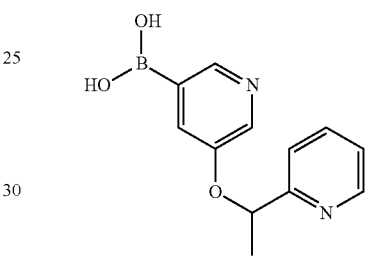

To a microwave vial was added (±)-3-bromo-5-(1-(pyridin-2-yl)ethoxy)pyridine (for a preparation see Intermediate 6, 514.9 mg, 1.845 mmol), potassium acetate (736 mg, 7.50 mmol), bis(pinacolato)diboron (2373 mg, 9.34 mmol), dichloro[1,1'-bis(diphenylphosphino)ferrocene]palladium(II) dichloromethane adduct (138.2 mg, 0.189 mmol) and 1,4-dioxane (15 mL). The vial was sealed and heated with stirring at 110° C. for 30 minutes in a microwave reactor. The mixture was diluted with ethyl acetate (80 mL), dried over magnesium sulphate and filtered through a 10 g Celite cartridge. The filtrate was evaporated in vacuo to give the required product, (±)-(5-(1-(pyridin-2-yl)ethoxy)pyridin-3-yl)boronic acid as a brown solid, (theoretical yield=450 mg assumed). The material was used crude in the next stage without further purification.

LCMS (2 min, Formic Acid): Rt=0.40 min, MH$^+$=245.

Intermediate 7

Alternative preparation (±)-(5-(1-(pyridin-2-yl)ethoxy)pyridin-3-yl)boronic acid To a microwave vial was added (±)-3-bromo-5-(1-(pyridin-2-yl)ethoxy)pyridine (for a preparation see Intermediate 6, 272.7 mg, 0.977 mmol), potassium acetate (383.9 mg, 3.91 mmol), bis(pinacolato)boron (1.2435 g, 4.90 mmol) and 1,4-dioxane (10 mL) followed by PdCl$_2$(dppf) (74.3 mg, 0.102 mmol). The vial was sealed and heated at 110° C. for 30 minutes in a microwave reactor. The mixture was diluted with ethyl acetate (50 mL), dried over magnesium sulphate and filtered. The filtrate was evaporated in vacuo to give a brown residue which was used in the subsequent reaction without further purification.

LCMS (2 min, Formic Acid): Rt=0.41 min, MH$^+$=245

Intermediate 8

3-(benzyloxy)-5-bromopyridine

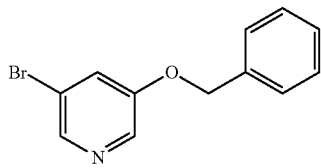 [SMILES: Brc1cncc(OCc2ccccc2)c1]

Caesium carbonate (6.52 g, 20.0 mmol) was added to a stirred solution of 5-bromopyridin-3-ol (1.74 g, 10 mmol) in DMF (25 mL). The reaction mixture was stirred at 60° C. for 30 minutes, then benzyl bromide (2.05 g, 1.43 mL, 12 mmol) was added. The reaction mixture was stirred at 60° C. for 2 hours. The reaction mixture was cooled to room temperature and partitioned between diethyl ether (100 mL) and water (50 mL). The organic phase was separated, dried and evaporated. The residue was purified by chromatography on silica gel eluting with dichloromethane to give 3-(benzyloxy)-5-bromopyridine (1.17 g, 4.43 mmol, 44.3% yield) as an orange solid.

LCMS (2 min, Formic Acid): Rt=1.15 min, MH$^+$=264/266

Intermediate 9

(5-(benzyloxy)pyridin-3-yl)boronic acid

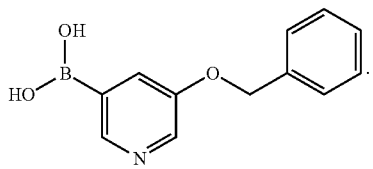 [SMILES: OB(O)c1cncc(OCc2ccccc2)c1]

A mixture of 3-(benzyloxy)-5-bromopyridine (for a preparation see Intermediate 8, 400 mg, 1.51 mmol), potassium acetate (595 mg, 6.06 mmol), bis(pinacolato)diboron (1.92 g, 7.57 mmol) and 1,1'-bis(diphenylphosphino)ferrocene-palladium(II) dichloride (111 mg, 10 mol %) in 1,4-dioxane (4 mL) was heated in a microwave at 110° C. for 30 minutes. The cooled reaction mixture was diluted with ethyl acetate (20 mL). The solution was filtered through Celite. The filtrate was dried and evaporated. The residue was used without further purification. (5-(benzyloxy)pyridin-3-yl)boronic acid (347 mg, 1.514 mmol, 100% yield) quantitative yield assumed.

LCMS (2 min, Formic Acid): Rt=0.56 min, MH$^+$=230.

Intermediate 10

4-bromo-2-((tetrahydro-2H-pyran-4-yl)methoxy)pyridine

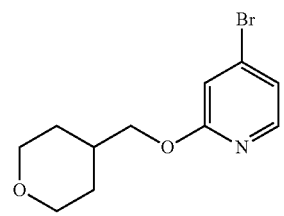 [SMILES: Brc1ccnc(OCC2CCOCC2)c1]

Sodium hydride, 60% suspension in mineral oil, (1.613 g, 40.3 mmol) was added portionwise over 5 minutes to a stirred solution of (tetrahydro-2H-pyran-4-yl)methanol (3.75 g, 3.74 mL, 32.3 mmol) in dry tetrahydrofuran (100 mL), under nitrogen. After complete addition the mixture was stirred at room temperature for 20 minutes. A solution of 4-bromo-2-chloropyridine (4.14 g, 2.39 mL, 21.5 mmol) in dry tetrahydrofuran (10 mL) was added slowly. After complete addition the reaction mixture was stirred at 40° C. for 2 hours. The reaction mixture was cooled to room temperature. The reaction mixture was concentrated to ~¼ volume and diluted with diethyl ether (50 mL). The solution was washed with water (25 mL) and brine (25 mL). The organic phase was dried and evaporated. The residue was dissolved in hexanes and purified by column chromatography on silica gel eluting with 0-20% ethyl acetate in hexanes to give 4-bromo-2-((tetrahydro-2H-pyran-4-yl)methoxy)pyridine (3.7 g, 13.60 mmol, 63.2% yield) as a colourless oil.

LCMS (2 min, High pH): Rt=1.13 min, MH$^+$=272/274.

Intermediate 11

2-((tetrahydro-2H-pyran-4-yl)methoxy)-4-(4,4,5,5-tetramethyl-1,3,2-dioxaborolan-2-yl)pyridine hydrochloride

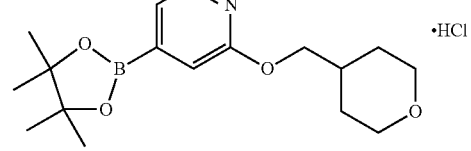

A mixture of 4-bromo-2-((tetrahydro-2H-pyran-4-yl)methoxy)pyridine (for a preparation see Intermediate 10, 400 mg, 1.47 mmol), potassium acetate (577 mg, 5.88 mmol), bis(pinacolato)diboron (1.87 g, 7.36 mmol) and 1,1'-bis(diphenylphosphino)ferrocene-palladium(II) dichloride (108 mg, 10 mol %) in 1,4-dioxane (10 mL) was heated in a microwave at 110° C. for 30 minutes. The cooled reaction mixture was diluted with ethyl acetate (50 mL). The suspension was dried over sodium sulphate, and evaporated. The residue was dissolved in diethyl ether (25 mL) and filtered. The filtrate was treated with 1.0M hydrogen chloride in diethyl ether (1.5 mL, slight excess). The mixture was allowed to stand at room temperature for 1 hour then the solid was filtered off, washed with ether and dried to give 2-((tetrahydro-2H-pyran-4-yl)methoxy)-4-(4,4,5,5-tetramethyl-1,3,2-dioxaborolan-2-yl)pyridine hydrochloride (386 mg, 1.085 mmol, 73.8% yield) as light brown solid.

LCMS (2 min, Formic Acid): Rt=0.52 min, MH+=238 (observed mass ion corresponds to the boronic acid)

NMR is consistent with title compound.

Intermediate 12

3-bromo-5-((tetrahydro-2H-pyran-4-yl)methoxy)pyridine

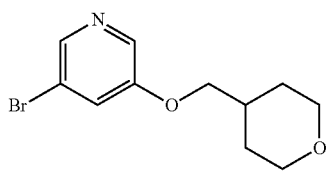

Potassium carbonate (794 mg, 5.75 mmol) was added to a stirred solution of 5-bromopyridin-3-ol (500 mg, 2.87 mmol) in DMF (5 mL). The reaction mixture was stirred at 60° C. for 30 minutes, then 4-(bromomethyl)tetrahydro-2H-pyran (566 mg, 416 µL, 3.16 mmol) was added. The reaction mixture was stirred at 60° C. for 2 hours, then allowed to stand at room temperature overnight. A further portion of 4-(bromomethyl)tetrahydro-2H-pyran (566 mg, 416 µL, 3.16 mmol) was added. and the reaction mixture was stirred at 60° C. for 2 hours. The reaction mixture was cooled to room temperature then partitioned between ethyl acetate (50 mL) and water (25 mL). The organic phase was separated, washed with water and brine, dried and evaporated to give a colourless solid 3-bromo-5-((tetrahydro-2H-pyran-4-yl)methoxy)pyridine (326 mg, 1.198 mmol, 41.7% yield).

LCMS (2 min, Formic Acid): Rt=0.93 min, MH+=272/274.

Intermediate 13

(5-((tetrahydro-2H-pyran-4-yl)methoxy)pyridin-3-yl)boronic acid

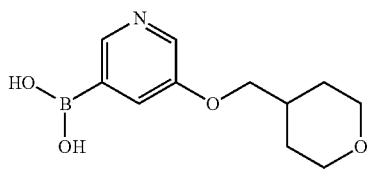 [SMILES: OB(O)c1cncc(OCC2CCOCC2)c1]

To a microwave reaction vial was added 3-bromo-5-((tetrahydro-2H-pyran-4-yl)methoxy)pyridine (for a preparation see Intermediate 12, 0.102 g, 0.375 mmol) followed by potassium acetate (0.147 g, 1.500 mmol), bis(pinacolato)diboron (0.476 g, 1.875 mmol) and [1,1'-bis(diphenylphosphino)ferrocene]dichloropalladium(II) (0.027 g, 0.038 mmol) in a solution of 1,4-dioxane (4 mL). The reaction vessel was sealed and heated to 110° C. for 30 minutes in a microwave. The reaction was diluted with ethyl acetate (30 mL), and dried over magnesium sulphate. The filtrate was collected and concentrated to give a dark brown residue, (5-((tetrahydro-2H-pyran-4-yl)methoxy)pyridin-3-yl)boronic acid (89 mg, 0.375 mmol, 100%). The crude material was used in subsequent steps without further purification. The yield was assumed to be 100%.

LCMS (2 min, Formic Acid): Rt=0.41 min, MH+=238.

Intermediates 14

4-bromo-2-(1-(pyridin-2-yl)ethoxy)pyridine and Intermediate 15

4-bromo-1-(1-(pyridin-2-yl)ethyl)pyridin-2(1H)-one

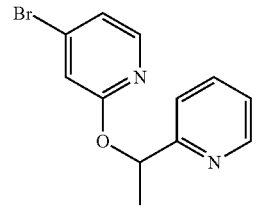

14

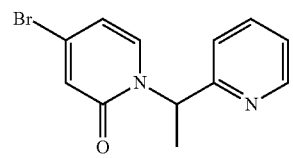

15

To a stirred solution of 4-bromopyridin-2-ol (326 mg, 1.873 mmol) in N,N-dimethylformamide (5 mL) was added potassium carbonate (777 mg, 5.62 mmol) followed by 2-(1-bromoethyl)pyridine hydrobromide (500 mg, 1.873 mmol). The reaction was stirred at room temperature under nitrogen for 6 hours. The reaction was quenched with water (30 mL) and transferred to a separating funnel. The aqueous phase was extracted with ethyl acetate (3×25 mL). The organic fractions were combined and washed with brine (30 mL). The organic phase was collected, dried over magnesium sulphate, and concentrated under reduced pressure to give a pale yellow oil. The crude material was purified by chromatography on silica gel eluting with 0-50% ethyl acetate in cyclohexane to give two products.

Intermediate 14: 4-bromo-2-(1-(pyridin-2-yl)ethoxy)pyridine (352 mg, 1.261 mmol, 67.3% yield) a colourless oil.

LCMS (2 min, Formic Acid): Rt=0.72 min, MH+=279/281.

Intermediate 15: 4-bromo-1-(1-(pyridin-2-yl)ethyl)pyridin-2(1H)-one (86 mg, 0.308 mmol, 16.45% yield) a colourless oil.

LCMS (2 min, Formic Acid): Rt=0.90 min, MH+=279/281.

Intermediate 16

(2-(1-(pyridin-2-yl)ethoxy)pyridin-4-yl)boronic acid

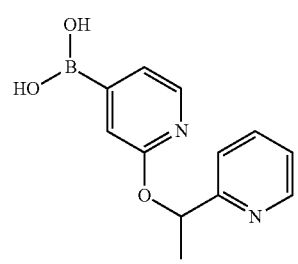 [SMILES: CC(Oc1cc(B(O)O)ccn1)c1ccccn1]

To a microwave reaction vial was added 4-bromo-2-(1-(pyridin-2-yl)ethoxy)pyridine (for a preparation see Intermediate 14, 105 mg, 0.376 mmol) followed by potassium acetate (148 mg, 1.505 mmol), bis(pinacolato)diboron (478 mg, 1.881 mmol), and [1,1'-bis(diphenylphosphino)ferrocene]dichloropalladium(II) (27.5 mg, 0.038 mmol) catalyst in a solution of 1,4-dioxane (4 mL). The reaction vessel was sealed and heated to 110° C. for 30 minutes in a microwave. The reaction mixture was filtered through a Celite frit. The filtrate was transferred to a large microwave reaction vial and treated with potassium acetate (148 mg, 1.505 mmol), bis(pinacolato)diboron (478 mg, 1.881 mmol), and [1,1'-bis(diphenylphosphino)ferrocene]dichloropalladium(II) (27.5 mg, 0.038 mmol). The reaction vessel was sealed and heated to 110° C. for 30 minutes in a microwave. The reaction mixture was diluted with ethyl acetate (20 mL) and dried over magnesium sulphate. The filtrate was concentrated in vacuo to give a brown residue, (2-(1-(pyridin-2-yl)ethoxy)pyridin-4-yl)boronic acid (92 mg, 0.376 mmol, 100%). The material was used in subsequent steps without further purification. 100% yield assumed.

LCMS (2 min, Formic Acid): Rt=0.42 min, MH+=245.

Intermediate 17

3-bromo-5-((1-methoxypropan-2-yl)oxy)pyridine

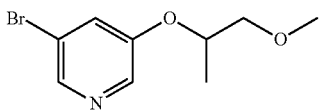

Caesium carbonate (1873 mg, 5.75 mmol) was added to a stirred solution of 5-bromopyridin-3-ol (500 mg, 2.87 mmol) in N,N-dimethylformamide (25 mL). The reaction mixture was stirred at 60° C. for 30 minutes, then 2-bromo-1-methoxypropane (0.367 mL, 3.45 mmol) was added. The reaction mixture was stirred at 60° C. for a further 2 hours, was then cooled to room temperature and partitioned between diethyl ether and water. The organic phase was separated, dried over magnesium sulphate and concentrated in vacuo. Purification of the residue by chromatography on silica gel eluting with 0-5% methanol in dichloromethane gave 3-bromo-5-((1-methoxypropan-2-yl)oxy)pyridine (499 mg, 2.028 mmol, 71%) as a brown oil.

LCMS (2 min, Formic Acid): Rt=0.87 min, MH+=246/248 (weak).

Intermediate 18

(5-((1-methoxypropan-2-yl)oxy)pyridin-3-yl)boronic acid

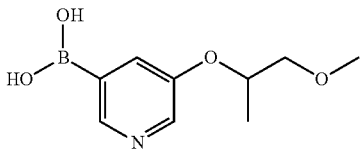

A mixture of 3-bromo-5-((1-methoxypropan-2-yl)oxy)pyridine (for a preparation see Intermediate 17, 77 mg, 0.313 mmol), potassium acetate (123 mg, 1.252 mmol), bis(pinacolato)diboron (397 mg, 1.564 mmol) and [1,1'-bis(diphenylphosphino)ferrocene]dichloropalladium(II) (22.89 mg, 0.031 mmol) in 1,4-dioxane (3 mL) was heated in a microwave at 110° C. for 30 minutes. The cooled reaction mixture was diluted with ethyl acetate (20 mL) and the solution was filtered through Celite. The filtrate was then evaporated in vacuo to give a sticky black oil, (5-((1-methoxypropan-2-yl)oxy)pyridin-3-yl)boronic acid (66 mg, 0.313 mmol, 100%) a quantitative yield was assumed and the crude product was used in the next step without further purification.

LCMS (2 min, Formic Acid): Rt=0.36 min, MH+=212 (weak).

Intermediate 19

(R)-tert-butyl 4-((7-bromo-5-methyl-4-oxo-4,5-dihydrothieno[3,2-c]pyridin-2-yl)methyl)-3-methylpiperazine-1-carboxylate

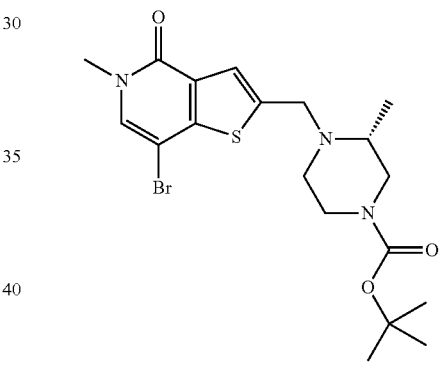

(R)-Tert-butyl 3-methylpiperazine-1-carboxylate (1.77 g, 8.82 mmol) and glacial acetic acid (530 mg, 505 µL, 8.82 mmol) were added to a stirred solution of 7-bromo-5-methyl-4-oxo-4,5-dihydrothieno[3,2-c]pyridine-2-carbaldehyde (for a preparation see Intermediate 3, 2.0 g, 7.35 mmol) in dichloromethane (50 mL). The reaction mixture was stirred at room temperature for 30 minutes then treated with sodium triacetoxyborohydride (7.79 g, 36.7 mmol). The reaction mixture was stirred at room temperature for 8 hours then allowed to stand overnight. Saturated sodium bicarbonate solution (75 mL) was added and the mixture stirred for 10 minutes. The organic phase was separated and the aqueous phase extracted with dichloromethane (2×50 mL). The combined organics were dried and evaporated. The residue was purified by chromatography on silica gel eluting with 3% methanol in dichloromethane, followed by trituration with diethyl ether gave (R)-tert-butyl 4-((7-bromo-5-methyl-4-oxo-4,5-dihydrothieno[3,2-c]pyridin-2-yl)methyl)-3-methylpiperazine-1-carboxylate (3.1 g, 6.79 mmol, 92% yield) as a yellow solid.

LCMS (2 min, Formic Acid): Rt=0.77 min, MH+=456/458.

Intermediate 20

(R)-7-bromo-5-methyl-2-((2-methylpiperazin-1-yl)methyl)thieno[3,2-c]pyridin-4(5H)-one dihydrochloride

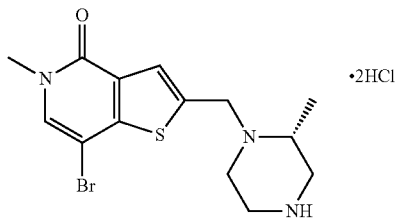

4M Hydrogen chloride in 1,4-dioxane (10 mL, 40 mmol) was added to a stirred solution of (R)-tert-butyl 4-((7-bromo-5-methyl-4-oxo-4,5-dihydrothieno[3,2-c]pyridin-2-yl)methyl)-3-methylpiperazine-1-carboxylate (for a preparation see Intermediate 19, 3.1 g, 6.79 mmol) in 1,4-dioxane (10 mL). The reaction mixture was stirred at room temperature for 24 hours. The solid was filtered off, washed with a small amount of dioxan, then diethyl ether and dried to give (R)-7-bromo-5-methyl-2-((2-methylpiperazin-1-yl)methyl)thieno[3,2-c]pyridin-4(5H)-one dihydrochloride (2.5 g, 5.82 mmol, 86% yield) as a pale yellow solid.

LCMS (2 min, Formic Acid): Rt=0.57 min, MH$^+$=356/358.

Intermediate 21

(R)-7-bromo-5-methyl-2-((2-methyl-4-(methylsulphonyl)piperazin-1-yl)methyl)thieno[3,2-c]pyridin-4(5H)-one

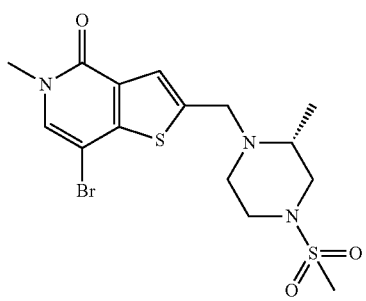 [SMILES: C[C@@H]1CN(S(C)(=O)=O)CCN1Cc1cc2c(=O)n(C)cc(Br)c2s1]

Methanesulphonyl chloride (834 mg, 567 μL, 7.28 mmol) was added to a stirred solution of (R)-7-bromo-5-methyl-2-((2-methylpiperazin-1-yl)methyl)thieno[3,2-c]pyridin-4(5H)-one dihydrochloride (for a preparation see Intermediate 20, 2.5 g, 5.82 mmol) in dichloromethane (20 mL) and pyridine (10 mL). The reaction mixture was stirred at room temperature for 2 hours. A further portion of methanesulphonyl chloride (834 mg, 567 μL, 7.28 mmol) was added and the reaction mixture stirred at room temperature for 2 hours. The solvent was evaporated. The residue was dissolved in ethyl acetate (50 mL) and washed with saturated sodium bicarbonate solution, water (x2) and brine. The organic phase was dried and evaporated. The residue was purified by chromatography on silica gel eluting with 3% methanol in dichloromethane to give the product (R)-7-bromo-5-methyl-2-((2-methyl-4-(methylsulphonyl)piperazin-1-yl)methyl)thieno[3,2-c]pyridin-4(5H)-one (1.9 g, 4.37 mmol, 75% yield) as a light brown solid.

LCMS (2 min, Formic Acid): Rt=0.62 min, MH$^+$=434/436.

Intermediate 22

7-(2-chloropyridin-4-yl)-5-methyl-2-((4-(methylsulphonyl)piperazin-1-yl)methyl)thieno[3,2-c]pyridin-4(5H)-one

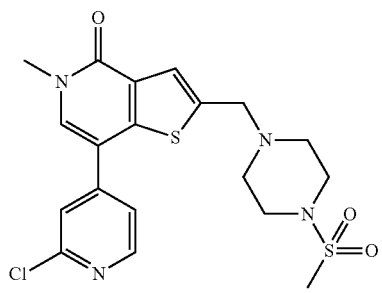 [SMILES: Cn1cc(-c2ccnc(Cl)c2)c2sc(CN3CCN(S(C)(=O)=O)CC3)cc2c1=O]

To a solution of 7-bromo-5-methyl-2-((4-(methylsulphonyl)piperazin-1-yl)methyl)thieno[3,2-c]pyridin-4(5H)-one (for a preparation see Intermediate 69, 371 mg, 0.883 mmol) and (2-chloropyridin-4-yl)boronic acid (208 mg, 1.324 mmol) in tetrahydrofuran (30 mL) were successively added sodium carbonate (2M in water) (1.545 mL, 3.09 mmol) and 1,1'-bis(diphenylphosphino)ferrocene-palladium(II) dichloride-dichloromethane complex (72.1 mg, 0.088 mmol). The reaction mixture was refluxed for 2 hours, whereupon it was allowed to cool to room temperature. The reaction mixture was concentrated in vacuo, and the residue was partitioned between ethyl acetate and water. The aqueous phase was extracted three times with ethyl acetate and the combined organic layers were washed with brine, dried over magnesium sulphate, filtered and concentrated in vacuo. The crude residue was purified by chromatography on silica gel eluting with 2-10% methanol in dichloromethane. The appropriate fractions were combined and concentrated in vacuo to give 7-(2-chloropyridin-4-yl)-5-methyl-2-((4-(methylsulphonyl)piperazin-1-yl)methyl)thieno[3,2-c]pyridin-4(5H)-one (265 mg, 0.585 mmol, 66%) as a dark brown solid.

LCMS (2 min, Formic Acid): Rt=0.77 min, MH$^+$=453/455

Intermediate 23

7-bromo-2-((4-ethylpiperazin-1-yl)methyl)-5-methylthieno[3,2-c]pyridin-4(5H)-one

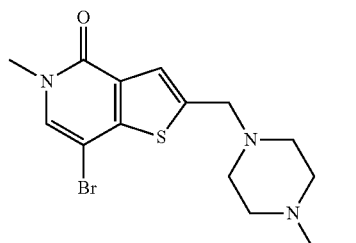

To a stirred solution of 7-bromo-5-methyl-4-oxo-4,5-dihydrothieno[3,2-c]pyridine-2-carbaldehyde (for a preparation see Intermediate 3, 200 mg, 0.735 mmol) in DCM (10 mL) was added 1-ethylpiperazine (0.112 mL, 0.882 mmol) followed by acetic acid (0.042 mL, 0.735 mmol). The reaction was heated to 40° C. and stirred under nitrogen for 15 minutes and was then treated with sodium triacetoxyborohydride (467 mg, 2.205 mmol). The reaction was stirred for 90 minutes and then cooled to room temperature, quenched with saturated sodium bicarbonate solution (25 mL) and stirred under nitrogen for 30 minutes.

The reaction was transferred to a separating funnel and the organic layer was collected. The aqueous phase was extracted with DCM (3×20 mL). The organic fractions were combined and washed with brine (approx. 25 mL). The organic layer was collected, dried over magnesium sulphate, and concentrated under reduced pressure to give a yellow oil.

The crude material was loaded on to a 12 g silica gel column and was eluted in 0-10% MeOH in DCM over 25 column volumes to give 7-bromo-2-((4-ethylpiperazin-1-yl)methyl)-5-methylthieno[3,2-c]pyridin-4(5H)-one as a yellow oil (180 mg, 0.486 mmol, 66.1% yield).

LCMS (2 min, Formic Acid): Rt=0.53 min, MH$^+$=370/372.

Intermediate 24

7-bromo-2-((4-isopropylpiperazin-1-yl)methyl)-5-methylthieno[3,2-c]pyridin-4(5H)-one

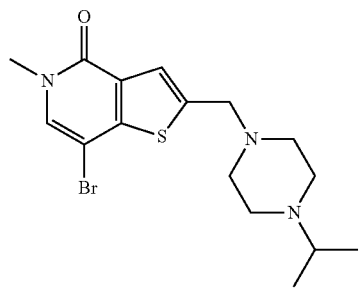 [SMILES: CC(C)N1CCN(Cc2cc3c(=O)n(C)cc(Br)c3s2)CC1]

To a stirred solution of 7-bromo-5-methyl-4-oxo-4,5-dihydrothieno[3,2-c]pyridine-2-carbaldehyde (for a preparation see Intermediate 3, 200 mg, 0.735 mmol) in DCM (10 mL) was added 1-isopropylpiperazine (0.126 mL, 0.882 mmol) followed by acetic acid (0.042 mL, 0.735 mmol). The reaction was heated to 40° C. and stirred under nitrogen for 15 minutes and then treated with sodium triacetoxyborohydride (467 mg, 2.205 mmol). The reaction was stirred for 90 minutes at which point the reaction was cooled to room temperature, quenched with saturated sodium bicarbonate solution (25 mL) and stirred under nitrogen for 15 minutes.

The reaction was transferred to a separating funnel and the organic layer was collected. The aqueous phase was extracted with DCM (3×20 mL). The organic fractions were combined and washed with brine (approx. 25 mL). The organic layer was collected, dried over magnesium sulphate, and concentrated under reduced pressure to give a yellow oil.

The crude material was loaded on to a 12 g silica gel column and was eluted in 0-10% MeOH in DCM over 25 column volumes to give a yellow oil which was the desired product 7-bromo-2-((4-isopropylpiperazin-1-yl)methyl)-5-methylthieno[3,2-c]pyridin-4(5H)-one (152 mg, 0.395 mmol, 53.8% yield).

LCMS (2 min, Formic Acid): Rt=0.59 min, MH$^+$=384/386.

Intermediate 25

7-(3,4-dimethoxyphenyl)-5-methyl-4-oxo-4,5-dihydrothieno[3,2-c]pyridine-2-carbaldehyde

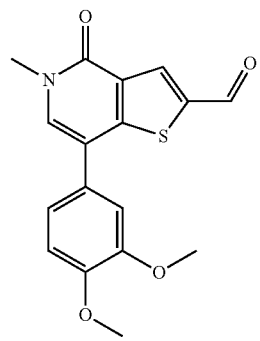 [SMILES: COc1ccc(-c2cn(C)c(=O)c3cc(C=O)sc23)cc1OC]

A mixture of 7-bromo-5-methyl-4-oxo-4,5-dihydrothieno[3,2-c]pyridine-2-carbaldehyde (for a preparation see Intermediate 3, 800 mg, 2.94 mmol), (3,4-dimethoxyphenyl)boronic acid (428 mg, 2.35 mmol), potassium carbonate (1.22 g, 8.82 mmol) and bis(triphenylphosphine)palladium (II) chloride (103 mg, 5 mol %) in 1,2-dimethoxyethane (9 mL) and water (3 mL) was heated in a microwave at 120° C. for 30 minutes. The reaction mixture was cooled and diluted with ethyl acetate (50 mL). The mixture was washed with water (2×15 mL) and the organic phase was dried and evaporated. The residue was purified by chromatography on silica gel eluting with 0-2% methanol in DCM to give 7-(3,4-dimethoxyphenyl)-5-methyl-4-oxo-4,5-dihydrothieno[3,2-c]pyridine-2-carbaldehyde (240 mg, 25% yield) as a yellow solid.

LCMS (2 min, Formic Acid): Rt=0.85 min, MH$^+$=330

Intermediate 26 tert-butyl 4-((7-(3,4-dimethoxyphenyl)-5-methyl-4-oxo-4,5-dihydrothieno[3,2-c]pyridin-2-yl)methyl)piperazine-1-carboxylate

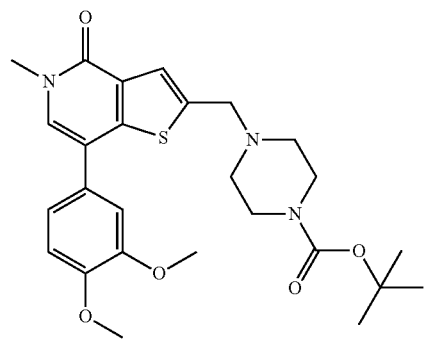 [SMILES: COc1ccc(-c2cn(C)c(=O)c3cc(CN4CCN(C(=O)OC(C)(C)C)CC4)sc23)cc1OC]

To 7-(3,4-dimethoxyphenyl)-5-methyl-4-oxo-4, 5-dihydrothieno[3,2-c]pyridine-2-carbaldehyde (for a preparation see Intermediate 25, 180 mg, 0.546 mmol) in DCM (7 mL) was added tert-butyl piperazine-1-carboxylate (153 mg, 0.820 mmol) and acetic acid (0.047 mL, 0.820 mmol). The reaction mixture was stirred at room temperature for approximately 30 minutes, whereupon sodium triacetoxyborohydride (579 mg, 2.73 mmol) was added and the reaction was refluxed under nitrogen overnight.

The reaction mixture was hydrolyzed by using a saturated aqueous solution of sodium bicarbonate (approx. 20 mL) and the layers were separated. The aqueous phase was extracted with DCM (3×10 mL) and the combined organic layers were washed with brine (approx. 20 mL), dried over magnesium sulphate, filtered and concentrated in vacuo to give a light brown oil.

The residue was dissolved in a small volume of MeOH with a drop of DCM and transferred to a 1 g SCX column. The product was allowed to elute with gravity. The column was then flushed with MeOH (3 column volumes) to remove impurities. The product was collected by flushing the column with 2.0M ammonia in MeOH (3 column volumes). The material was then purified by chromatography on silica gel eluting with 0 to 10% MeOH in DCM. The appropriate fractions were collected and concentrated in vacuo to give tert-butyl 4-((7-(3,4-dimethoxyphenyl)-5-methyl-4-oxo-4, 5-dihydrothieno[3,2-c]pyridin-2-yl)methyl)piperazine-1-carboxylate (88.9 mg, 33% yield) as a yellow oil.

LCMS (2 min, Formic Acid): Rt=0.81 min, MH$^+$=500

Alternative Preparation

To a stirred solution of 7-(3,4-dimethoxyphenyl)-5-methyl-4-oxo-4,5-dihydrothieno[3,2-c]pyridine-2-carbaldehyde (for a preparation see Intermediate 25, 400 mg, 1.214 mmol) in DCM (15 mL) was added tert-butyl piperazine-1-carboxylate (339 mg, 1.822 mmol) and acetic acid (0.104 mL, 1.822 mmol). The reaction was stirred for 10 minutes and then to the reaction was added sodium triacetoxyborohydride (1030 mg, 4.86 mmol). The reaction was heated at 40° C. for one hour.

The reaction was cooled to room temperature and was diluted with saturated sodium bicarbonate solution (20 mL) and stirred for 10 minutes. The reaction mixture was transferred to a 100 mL separating funnel and the organic layer was collected. The aqueous layer was extracted with DCM (3×15 mL). The organic layers were combined and washed with brine (approx. 30 mL). The organic layer was collected and dried over magnesium sulphate and concentrated under reduced pressure to give a brown oil.

The crude material was loaded onto a 40 g silica gel column and eluted in 0-5% MeOH in DCM to give the desired product, a yellow crystalline solid, tert-butyl 4-((7-(3,4-dimethoxyphenyl)-5-methyl-4-oxo-4,5-dihydrothieno[3,2-c]pyridin-2-yl)methyl)piperazine-1-carboxylate (375 mg, 0.751 mmol, 61.8% yield).

LCMS (2 min, Formic Acid): Rt=0.80 min, MH$^+$=500.

Intermediate 28

N-(3-(2-formyl-5-methyl-4-oxo-4,5-dihydrothieno[3,2-c]pyridin-7-yl)phenyl)acetamide

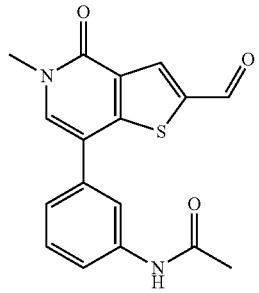 [SMILES: CC(=O)Nc1cccc(-c2cn(C)c(=O)c3cc(C=O)sc23)c1]

A mixture of 7-bromo-5-methyl-4-oxo-4,5-dihydrothieno[3,2-c]pyridine-2-carbaldehyde (for a preparation see Intermediate 3, 272 mg, 1.0 mmol), (3-acetamidophenyl)boronic acid (215 mg, 1.2 mmol), potassium carbonate (414 mg, 3.0 mmol) and bis(triphenylphosphine)palladium(II) chloride (35 mg, 5 mol %) in 1,2-dimethoxyethane (3 mL) and water (0.5 mL) was heated at 120° C. in a microwave for 20 minutes.

The cooled reaction mixture was diluted with ethyl acetate (25 mL). The mixture was filtered through Celite and the filtrate was dried and evaporated to give a green solid N-(3-(2-formyl-5-methyl-4-oxo-4,5-dihydrothieno[3,2-c]pyridin-7-yl)phenyl)acetamide (320 mg, 0.980 mmol, 98% yield).

A 120 mg portion of the material was purified by column chromatography [5-10% methanol/dichloromethane] to give the title compound (100 mg).

LCMS (2 min, Formic Acid): Rt=0.54 min, MH$^+$=411.

Intermediate 29

5-methyl-4-oxo-7-phenyl-4,5-dihydrothieno[3,2-c]pyridine-2-carbaldehyde

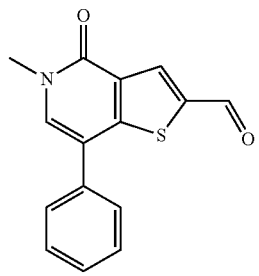 [SMILES: Cn1cc(-c2ccccc2)c2sc(C=O)cc2c1=O]

To a 5 mL microwave vessel was added 7-bromo-5-methyl-4-oxo-4,5-dihydrothieno[3,2-c]pyridine-2-carbaldehyde (for a preparation see Intermediate 3, 272 mg, 1 mmol), phenylboronic acid (146 mg, 1.20 mmol), potassium carbonate (332 mg, 2.40 mmol), and PEPPSI (34.0 mg, 0.050 mmol) in a solution of isopropanol (3 mL) and water (1.00 mL). The reaction mixture was heated at 130° C. for 30 minutes.

The reaction was quenched with 20 mL ammonium chloride solution and transferred to a 100 mL separating funnel and the aqueous layer was extracted with DCM (3×10 mL). The organic layers were combined and dried over magnesium sulphate, filtered, and evaporated to give an orange solid. The residue was washed with MeOH (3×5 mL) and dried to give a red solid. The filtrate appeared to contain more product so was combined again with the solid and concentrated.

The residue was purified by column chromatography (40-80% ethyl acetate in cyclohexane) to give a bright yellow solid, 5-methyl-4-oxo-7-phenyl-4,5-dihydrothieno[3,2-c]pyridine-2-carbaldehyde (50.3 mg, 0.187 mmol, 18.68% yield). The column was flushed with 0-10% MeOH in DCM to give further title compound as an orange solid (134.2 mg) which was slightly less pure.

LCMS (2 min, Formic Acid): Rt=0.94 min, MH$^+$=270.

Intermediate 30

7-bromo-5-ethyl-4-oxo-4,5-dihydrothieno[3,2-c]pyridine-2-carbaldehyde

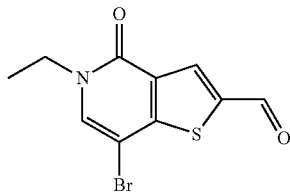

In a 100 mL round bottom flask under nitrogen 7-bromo-4-oxo-4,5-dihydrothieno[3,2-c]pyridine-2-carbaldehyde (for a preparation see Intermediate 2, Ig, 3.87 mmol) was dissolved in THF (30 mL) to produce a light brown suspension. To the reaction mixture was added caesium carbonate (3.79 g, 11.62 mmol) and the reaction was stirred for approx. 30 minutes, becoming a mustard yellow suspension. The reaction was left stirring under nitrogen at room temperature over the weekend. Another portion of iodoethane (0.626 mL, 7.75 mmol) was added to the reaction and it was heated at 60° C. overnight.

The reaction was quenched with ethyl acetate (approx. 40 mL) and transferred to a separating funnel and washed with water. The aqueous layer was extracted with ethyl acetate (2×10 mL). The organic layers were combined and concentrated under reduced pressure to give a brown solid. The residue was purified by column chromatography (20-60% ethyl acetate in cyclohexane) to give a yellow solid 7-bromo-5-ethyl-4-oxo-4,5-dihydrothieno[3,2-c]pyridine-2-carbaldehyde (556.7 mg, 1.946 mmol, 50.2% yield).

LCMS (2 min, Formic Acid): Rt=0.87 min, MH$^+$=286/288.

Intermediate 31

5-ethyl-4-oxo-7-phenyl-4,5-dihydrothieno[3,2-c]pyridine-2-carbaldehyde

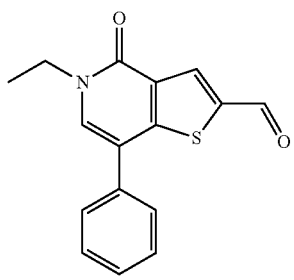 [SMILES: CCn1cc(-c2ccccc2)c2sc(C=O)cc2c1=O]

To a microwave vessel was added 7-bromo-5-ethyl-4-oxo-4,5-dihydrothieno[3,2-c]pyridine-2-carbaldehyde (for a preparation see Intermediate 30, 278 mg, 0.972 mmol), phenylboronic acid (142 mg, 1.166 mmol), potassium carbonate (322 mg, 2.332 mmol), and PEPPSI (34.0 mg, 0.05 mmol) in a solution of isopropanol (3 mL) and water (1 mL). The reaction vessel was sealed and heated in Biotage Initiator microwave reactor to 130° C. for 30 minutes.

The reaction was quenched with ammonium chloride solution (25 mL) and transferred to a separating funnel. The product was extracted with DCM (3×15 mL). The organic layers were combined, dried over magnesium sulphate, filtered, and the solvent was evaporated under reduced pressure to yield an orange solid.

The crude product was added to a 12 g silica gel column and was eluted with 20-50% ethyl acetate in cyclohexane to give a yellow solid, 5-ethyl-4-oxo-7-phenyl-4,5-dihydrothieno[3,2-c]pyridine-2-carbaldehyde (190 mg, 0.671 mmol, 69.0% yield).

LCMS (2 min, Formic Acid): Rt=1.02 min, MH$^+$=284.

Intermediate 32

7-(3,4-dimethoxyphenyl)-5-ethyl-4-oxo-4,5-dihydrothieno[3,2-c]pyridine-2-carbaldehyde

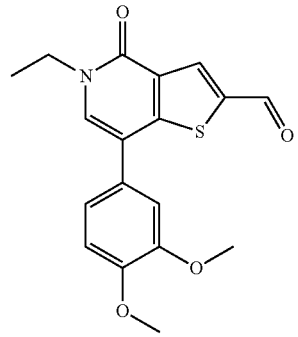 [SMILES: CCn1cc(-c2ccc(OC)c(OC)c2)c2sc(C=O)cc2c1=O]

To a microwave reaction vessel was added 7-bromo-5-ethyl-4-oxo-4,5-dihydrothieno[3,2-c]pyridine-2-carbaldehyde (for a preparation see Intermediate 30, 260 mg, 0.909 mmol), (3,4-dimethoxyphenyl)boronic acid (198 mg, 1.09 mmol), potassium carbonate (301 mg, 2.181 mmol), and PEPPSI (34.0 mg, 0.05 mmol) (last) in a solution of isopropanol (3 mL) and water (1 mL). The reaction vessel was sealed and heated in Biotage Initiator microwave reactor to 130° C. for 30 minutes.

The reaction was diluted with ammonium chloride solution (25 mL) and transferred to a separating funnel. The product was extracted with DCM (3×15 mL). The organic layers were combined and dried over magnesium sulphate. The magnesium sulphate was filtered off and the filtrate was collected and the solvent was removed under reduced pressure to yield an orange solid.

The crude material was purified by column chromatography using a 25 g silica gel column and was eluted with 20-100% ethyl acetate in cyclohexane to yield a yellow solid 7-(3,4-dimethoxyphenyl)-5-ethyl-4-oxo-4,5-dihydrothieno[3,2-c]pyridine-2-carbaldehyde (172.4 mg, 0.502 mmol, 55.3% yield).

LCMS (2 min, Formic Acid): Rt=0.93 min, MH$^+$=344.

Intermediate 33 tert-butyl 4-((7-(3,4-dimethoxyphenyl)-5-methyl-4-oxo-4,5-dihydrothieno[3,2-c]pyridin-2-yl)methyl)-2,6-dimethylpiperazine-1-carboxylate

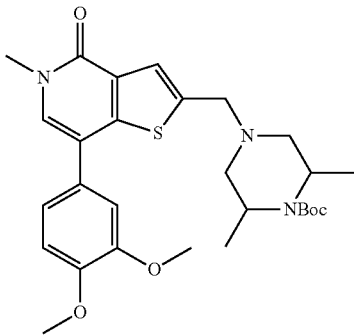

To a solution of 7-(3,4-dimethoxyphenyl)-5-methyl-4-oxo-4,5-dihydrothieno[3,2-c]pyridine-2-carbaldehyde (for a preparation see Intermediate 25, 50 mg, 0.152 mmol) and tert-butyl 2,6-dimethylpiperazine (65.1 mg, 0.304 mmol) in dichloromethane (5 mL) were successively added sodium triacetoxyborohydride (129 mg, 0.607 mmol) and acetic acid (0.013 mL, 0.228 mmol). The reaction mixture was stirred at 40° C. for 3 hours, whereupon a saturated aqueous solution of NaHCO$_3$ was added. The layers were separated and the aqueous layer was extracted three times with DCM. The combined organic layers were washed with brine, dried over MgSO$_4$, filtered and concentrated in vacuo. The crude residue was purified via flash chromatography on silica gel, eluting with 2-10% MeOH in DCM to give tert-butyl 4-((7-(3,4-dimethoxyphenyl)-5-methyl-4-oxo-4,5-dihydrothieno[3,2-c]pyridin-2-yl)methyl)-2,6-dimethylpiperazine-1-carboxylate (35 mg, 44% yield) as viscous yellow oil LCMS (2 min, Formic Acid): Rt=1.10 min, MH$^+$=528

Intermediate 34

7-bromo-5-methyl-2-((methylamino)methyl)thieno[3,2-c]pyridin-4(5H)-one

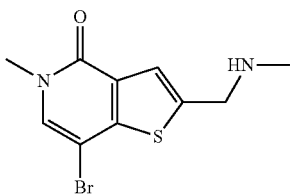

A mixture of 7-bromo-5-methyl-4-oxo-4,5-dihydrothieno[3,2-c]pyridine-2-carbaldehyde (for a preparation see Intermediate 3, 300 mg, 1.10 mmol), and methylamine hydrochloride (744 mg, 11.02 mmol) in dichloromethane (10 mL) was stirred at room temperature for 30 minutes. Sodium triacetoxyborohydride (701 mg, 3.31 mmol) was added and stirring at room temperature continued for 2 hours. A saturated aqueous solution of NaHCO$_3$ (20 mL) was added and the mixture was stirred for 20 minutes. The layers were separated and the aqueous phase was extracted with dichloromethane (2×10 mL). The combined organic layers were dried and evaporated in vacuo.

The residue was purified by chromatography on silica gel eluting with 0-10% methanol in dichloromethane to give 7-bromo-5-methyl-2-((methylamino)methyl)thieno[3,2-c]pyridin-4(5H)-one (116 mg, 37% yield) as a white solid.

LCMS (2 min, Formic Acid): Rt=0.45 min, MH$^+$=287/289

Intermediate 35

N-((7-bromo-5-methyl-4-oxo-4,5-dihydrothieno[3,2-c]pyridin-2-yl)methyl)-N-methylmethanesulphonamide

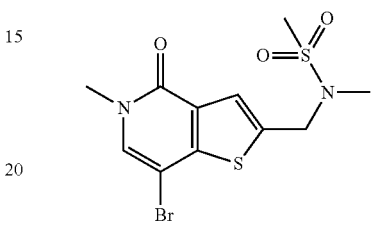

Methanesulphonyl chloride (132 mg, 90 μL, 1.15 mmol) was added to a stirred solution of 7-bromo-5-methyl-2-((methylamino)methyl)thieno[3,2-c]pyridin-4(5H)-one (for a preparation see Intermediate 34, 110 mg, 0.38 mmol) in dichloromethane (3 mL) and pyridine (1 mL). The reaction mixture was stirred at room temperature for 2 hours. The solvent was evaporated and the residue purified by chromatography on silica gel eluting with 0-5% methanol in dichloromethane to give N-((7-bromo-5-methyl-4-oxo-4,5-dihydrothieno[3,2-c]pyridin-2-yl)methyl)-N-methylmethanesulphonamide (130 mg, 93% yield) as a colourless solid.

LCMS (2 min, Formic Acid): Rt=0.77 min, MH$^+$=365/367

Intermediate 36

7-bromo-5-methyl-2-(pyrrolidin-1-ylmethyl)thieno[3,2-c]pyridin-4(5H)-one

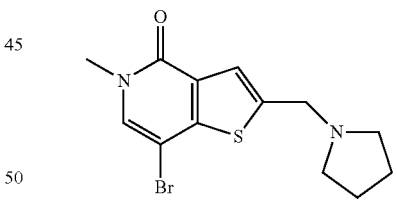

A mixture of 7-bromo-5-methyl-4-oxo-4,5-dihydrothieno[3,2-c]pyridine-2-carbaldehyde (400 mg, 1.47 mmol), pyrrolidine (for a preparation see Intermediate 3, 209 mg, 245 μL, 2.94 mmol) and acetic acid (177 mg, 168 μL, 2.94 mmol) in dichloromethane (10 mL) was stirred at room temperature for 1 hour. Sodium triacetoxyborohydride (1.56 g, 7.36 mmol) was added portionwise and the reaction mixture stirred at room temperature overnight. A saturated aqueous solution of NaHCO$_3$ (15 mL) was added and the reaction mixture was stirred for 20 minutes. The organic phase was separated and the aqueous phase extracted with dichloromethane (2×10 mL). The combined organic layers were dried and evaporated in vacuo. The residue was purified by chromatography on silica gel eluting with 0-5% methanol in dichloromethane to give 7-bromo-5-methyl-2-

Intermediate 37

7-bromo-5-methyl-2-(piperidin-1-ylmethyl)thieno[3,2-c]pyridin-4(5H)-one

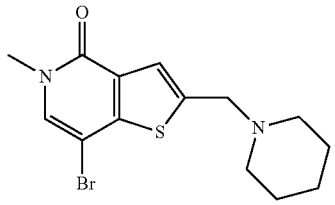 [SMILES: Cn1cc(Br)c2sc(CN3CCCCC3)cc2c1=O]

A mixture of 7-bromo-5-methyl-4-oxo-4,5-dihydrothieno[3,2-c]pyridine-2-carbaldehyde (for a preparation see Intermediate 3, 400 mg, 1.47 mmol), piperidine (250 mg, 290 μL, 2.94 mmol) and acetic acid (177 mg, 168 μL, 2.94 mmol) in dichloromethane (10 mL) was stirred at room temperature for 1 hour. Sodium triacetoxyborohydride (1.56 g, 7.36 mmol) was added portionwise and the reaction mixture stirred at room temperature overnight. A saturated aqueous solution of NaHCO$_3$ (15 mL) was added and the reaction mixture stirred for 20 minutes. The organic phase was separated and the aqueous phase extracted with dichloromethane (2×10 mL). The combined organic layers were dried and evaporated in vacuo. The residue was purified via chromatography on silica gel 0-5% methanol in dichloromethane to give 7-bromo-5-methyl-2-(piperidin-1-ylmethyl)thieno[3,2-c]pyridin-4(5H)-one (340 mg, 68% yield) as an off-white solid.

LCMS (2 min, Formic Acid): Rt=0.51 min, MH$^+$=341/343

Intermediate 38

7-bromo-5-methyl-2-((3-methylmorpholino)methyl)thieno[3,2-c]pyridin-4(5H)-one

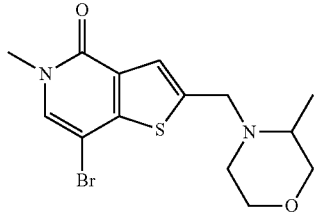

A stirred suspension of 7-bromo-5-methyl-4-oxo-4,5-dihydrothieno[3,2-c]pyridine-2-carbaldehyde (for a preparation see Intermediate 3, 500 mg, 1.837 mmol) in dichloromethane (20 mL) was treated with acetic acid (0.126 mL, 2.205 mmol) followed by 3-methylmorpholine (0.313 mL, 2.76 mmol). The reaction mixture was stirred at room temperature under nitrogen for 15 minutes and was then treated with sodium triacetoxyborohydride (1.56 g, 7.35 mmol). The reaction mixture was stirred for 72 hours, whereupon it was hydrolyzed by adding a saturated aqueous solution of sodium bicarbonate (30 mL). The resulting mixture was stirred for 20 minutes and the layers were separated. The aqueous layer was extracted with DCM (3×30 mL) and the combined organic layers were dried over magnesium sulphate, filtered and concentrated under reduced pressure to give the crude residue. The latter was purified by chromatography on silica gel eluting with 0-5% MeOH in DCM to give 7-bromo-5-methyl-2-((3-methylmorpholino)methyl)thieno[3,2-c]pyridin-4(5H)-one (411 mg, 63% yield) as a thick yellow oil.

LCMS (2 min, Formic Acid): Rt=0.49 min, MH$^+$=357/359

Intermediate 39

(S)-7-bromo-5-methyl-2-((3-methylmorpholino)methyl)thieno[3,2-c]pyridin-4(5H)-one

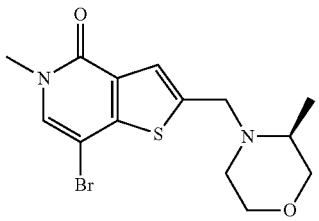

To a stirred solution of 7-bromo-5-methyl-4-oxo-4,5-dihydrothieno[3,2-c]pyridine-2-carbaldehyde (for a preparation see Intermediate 3, 500 mg, 1.837 mmol) in dichloromethane (20 mL) was added (S)-3-methylmorpholine (0.313 mL, 2.76 mmol) followed by acetic acid (0.158 mL, 2.76 mmol). The reaction mixture was heated to 40° C. and stirred for 30 minutes. The reaction mixture was then treated with sodium triacetoxyborohydride (1.56 g, 7.35 mmol) and stirred at 40° C. for two hours. The reaction mixture was hydrolyzed by adding a saturated aqueous solution of sodium bicarbonate (50 mL) and stirred under nitrogen for 10 minutes. The layers were separated and the aqueous phase was extracted with DCM (3×25 mL). The organic layers were combined, dried over magnesium sulphate, filtered and concentrated under reduced pressure to give the crude product as a light orange solid. The latter was purified by chromatography on silica gel eluting with 0-5% MeOH in DCM. The appropriate fractions were combined and concentrated in vacuo to give (S)-7-bromo-5-methyl-2-((3-methylmorpholino)methyl)thieno[3,2-c]pyridin-4(5H)-one (511 mg, 78% yield) as a yellow oil.

LCMS (2 min, Formic Acid): Rt=0.51 min, MH$^+$=357/359

Intermediate 40

7-bromo-2-((4-hydroxypiperidin-1-yl)methyl)-5-methylthieno[3,2-c]pyridin-4(51H)-one

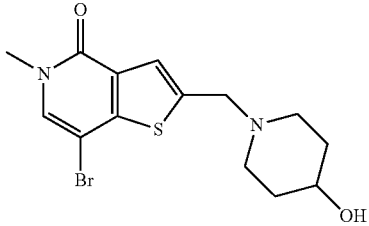 [SMILES: Cn1cc(Br)c2sc(CN3CCC(O)CC3)cc2c1=O]

A mixture of 7-bromo-5-methyl-4-oxo-4,5-dihydrothieno[3,2-c]pyridine-2-carbaldehyde (for a preparation see Intermediate 3, 400 mg, 1.47 mmol), 4-hydroxypiperidine (297 mg, 2.94 mmol) and acetic acid (177 mg, 168 μL, 2.94 mmol) in dichloromethane (10 mL) was stirred at room temperature for 1 hour. Sodium triacetoxyborohydride (1.56 g, 7.36 mmol) was added portionwise and the reaction mixture was stirred at room temperature overnight. A saturated aqueous solution of NaHCO₃ (15 mL) was added and the reaction mixture stirred for 20 minutes. The layers were separated and the aqueous phase extracted with dichloromethane (2×10 mL). The combined organic layers were dried and evaporated in vacuo. The residue was purified by chromatography on silica gel eluting with 0-10% methanol in dichloromethane. The appropriate fractions were concentrated and combined to give 7-bromo-2-((4-hydroxypiperidin-1-yl)methyl)-5-methylthieno[3,2-c]pyridin-4(5H)-one (363 mg, 69% yield) as an off-white solid.

LCMS (2 min, Formic Acid): Rt=0.46 min, MH⁺=357/359

Intermediate 41

(R)-7-bromo-5-methyl-2-((3-methylmorpholino)methyl)thieno[3,2-c]pyridin-4(5H)-one

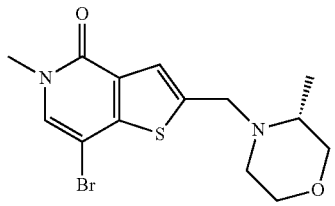 [SMILES: C[C@@H]1COCCN1Cc1cc2c(=O)n(C)cc(Br)c2s1]

To a stirred suspension of 7-bromo-5-methyl-4-oxo-4,5-dihydrothieno[3,2-c]pyridine-2-carbaldehyde (for a preparation see Intermediate 3, 300 mg, 1.102 mmol) in dichloromethane (15 mL) was added acetic acid (0.095 mL, 1.654 mmol) followed by (R)-3-methylmorpholine (0.188 mL, 1.654 mmol). The reaction mixture was stirred at room temperature under nitrogen for 30 minutes and was then treated with sodium triacetoxyborohydride (935 mg, 4.41 mmol). The reaction mixture was stirred for 5 hours, whereupon it was hydrolyzed by adding a saturated aqueous solution of sodium bicarbonate. The mixture was stirred for 20 minutes and the layers were separated. The aqueous phase was extracted with DCM (3×30 mL) and the combined organic layers were dried over magnesium sulphate, filtered and concentrated under reduced pressure to give a yellow oil. The crude material was purified via chromatography on silica gel eluting with 0-5% MeOH in DCM to give (R)-7-bromo-5-methyl-2-((3-methylmorpholino)methyl)thieno[3,2-c]pyridin-4(5H)-one (256 mg, 65% yield) as a thick yellow oil.

LCMS (2 min, Formic Acid): Rt=0.51 min, MH⁺=357/359

Intermediate 42

2-((1,4-oxazepan-4-yl)methyl)-7-bromo-5-methylthieno[3,2-c]pyridin-4(5H)-one

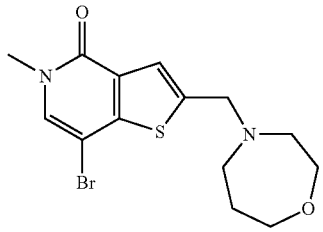 [SMILES: Cn1cc(Br)c2sc(CN3CCCOCC3)cc2c1=O]

To a solution of 7-bromo-5-methyl-4-oxo-4,5-dihydrothieno[3,2-c]pyridine-2-carbaldehyde (for a preparation see Intermediate 3, 200 mg, 0.735 mmol) and 1,4-oxazepane (149 mg, 1.470 mmol) in DCM (10 mL) were successively added sodium triacetoxyborohydride (623 mg, 2.94 mmol) and acetic acid (8.41 µL, 0.147 mmol). The reaction mixture was stirred at 40° C. for 1 hour, whereupon the reaction mixture was hydrolyzed by adding a saturated aqueous solution of sodium carbonate. The aqueous phase was extracted 3 times with DCM and the combined organic layers were washed with brine, dried over MgSO₄, filtered and concentrated in vacuo. The residue was purified by flash chromatography on silica gel eluting with 5 to 60% EtOAc in cyclohexane. The appropriate fractions were combined and concentrated in vacuo to give 2-((1,4-oxazepan-4-yl)methyl)-7-bromo-5-methylthieno[3,2-c]pyridin-4(5H)-one (22 mg, 85%) as a viscous yellow oil.

LCMS (2 min, Formic Acid): Rt=0.46 min, MH⁺=357/359

Intermediate 43

7-bromo-2-(hydroxymethyl)-5-methylthieno[3,2-c]pyridin-4(5H)-one

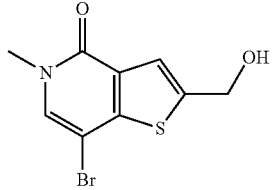

A stirred solution of 7-bromo-5-methyl-4-oxo-4,5-dihydrothieno[3,2-c]pyridine-2-carbaldehyde (for a preparation see Intermediate 3, 1 g, 3.67 mmol) in EtOH (25 mL) was treated with sodium borohydride (0.556 g, 14.70 mmol). The resulting mixture was stirred under nitrogen at room temperature for one hour, whereupon the reaction mixture was treated with acetic acid (5 mL) and stirred for 20 minutes under nitrogen. The mixture was filtered to give a cream coloured solid. The isolated material was suspected to contain sodium acetate due to an initial yield of 128%. The product was stirred in water for 30 minutes and filtered through a glass filter funnel then washed with copious amounts of water. The product was oven dried overnight to give 7-bromo-2-(hydroxymethyl)-5-methylthieno[3,2-c]pyridin-4(5H)-one (724 mg, 2.64 mmol, 71.9% yield).

LCMS (2 min, Formic Acid): Rt=0.65 min, MH⁺=274/276

Intermediate 44 tert-butyl (2-(((7-bromo-5-methyl-4-oxo-4,5-dihydrothieno[3,2-c]pyridin-2-yl)methyl)amino)ethyl)carbamate

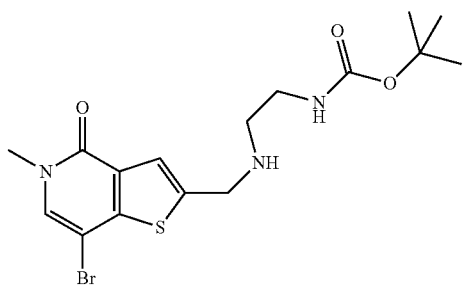 [SMILES: Cn1cc(Br)c2sc(CNCCNC(=O)OC(C)(C)C)cc2c1=O]

Tert-butyl (2-aminoethyl)carbamate (265 mg, 262 µL, 1.65 mmol) and glacial acetic acid (99 mg, 95 µL, 1.65 mmol) were added to a stirred solution of 7-bromo-5-methyl-4-oxo-4,5-dihydrothieno[3,2-c]pyridine-2-carbaldehyde (for a preparation see Intermediate 3, 300 mg, 1.1 mmol) in dichloromethane (5 mL). The reaction mixture was stirred at room temperature for 30 minutes then treated with sodium triacetoxyborohydride (701 mg, 3.31 mmol). The reaction mixture was stirred at room temperature for 24 hours. A saturated aqueous solution of sodium bicarbonate (10 mL) was added and the mixture stirred for 10 minutes. The organic phase was separated and the aqueous phase extracted with dichloromethane (2×50 mL). The combined organics were dried and evaporated. The residue was purified by chromatography on silica gel eluting with 0 to 4% methanol in dichloromethane to give tert-butyl (2-(((7-bromo-5-methyl-4-oxo-4,5-dihydrothieno[3,2-c]pyridin-2-yl)methyl)amino)ethyl)carbamate (360 mg, 78% yield) as a colourless oil.

LCMS (2 min, Formic Acid): Rt=0.65 min, MH$^+$=416/418

Intermediate 45 tert-butyl (2-(((7-(3,4-dimethoxyphenyl)-5-methyl-4-oxo-4,5-dihydrothieno[3,2-c]pyridin-2-yl)methyl)amino)ethyl)carbamate

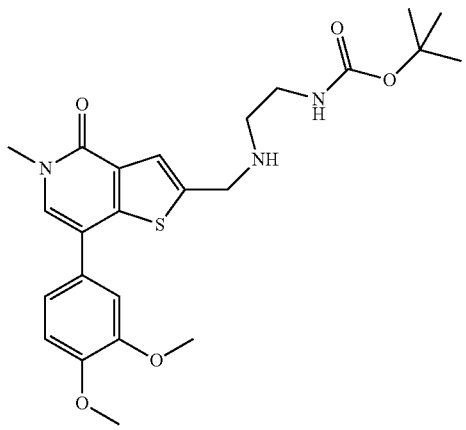 [SMILES: COc1ccc(-c2cn(C)c(=O)c3cc(CNCCNC(=O)OC(C)(C)C)sc23)cc1OC]

A mixture of tert-butyl (2-(((7-bromo-5-methyl-4-oxo-4,5-dihydrothieno[3,2-c]pyridin-2-yl)methyl)amino)ethyl)carbamate (for a preparation see Intermediate 44, 180 mg, 0.43 mmol), 3,4-dimethoxyphenylboronic acid (118 mg, 0.65 mmol), potassium carbonate (179 mg, 1.29 mmol) and bis(triphenylphosphine)palladium(II) chloride (30 mg, 10 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried over sodium sulphate and evaporated. The residue was purified by chromatography on silica gel eluting with 0 to 5% methanol in dichloromethane to give tert-butyl (2-(((7-(3,4-dimethoxyphenyl)-5-methyl-4-oxo-4,5-dihydrothieno[3,2-c]pyridin-2-yl)methyl)amino)ethyl)carbamate (155 mg, 76% yield) as a brown gum.

LCMS (2 min, Formic Acid): Rt=0.70 min, MH$^+$=474

Intermediate 46 tert-butyl (3-(((7-bromo-5-methyl-4-oxo-4,5-dihydrothieno[3,2-c]pyridin-2-yl)methyl)amino)propyl)carbamate

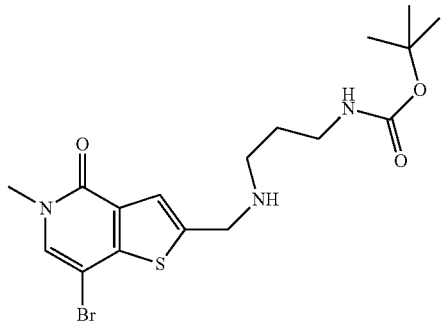 [SMILES: Cn1cc(Br)c2sc(CNCCCNC(=O)OC(C)(C)C)cc2c1=O]

Tert-butyl (3-aminopropyl)carbamate (288 mg, 289 µL, 1.65 mmol) and glacial acetic acid (99 mg, 95 µL, 1.65 mmol) were added to a stirred solution of 7-bromo-5-methyl-4-oxo-4,5-dihydrothieno[3,2-c]pyridine-2-carbaldehyde (for a preparation see Intermediate 3, 300 mg, 1.1 mmol) in dichloromethane (10 mL). The reaction mixture was stirred at room temperature for 30 minutes then treated with sodium triacetoxyborohydride (701 mg, 3.31 mmol). The reaction mixture was stirred at room temperature for 24 hours. A saturated aqueous solution of sodium bicarbonate (10 mL) was added and the mixture stirred for 10 minutes. The organic phase was separated and the aqueous phase extracted with dichloromethane (2×50 mL). The combined organics were dried and evaporated and the residue was purified via chromatography on silica gel eluting with 0 to 4% methanol in dichloromethane to give tert-butyl (3-(((7-bromo-5-methyl-4-oxo-4,5-dihydrothieno[3,2-c]pyridin-2-yl)methyl)amino)propyl)carbamate (303 mg, 64% yield) as a colourless oil.

LCMS (2 min, Formic Acid): Rt=0.67 min, MH$^+$=430/432

Intermediate 47 tert-butyl (3-(((7-(3-(benzyloxy)phenyl)-5-methyl-4-oxo-4,5-dihydrothieno[3,2-c]pyridin-2-yl)methyl)amino)propyl)carbamate

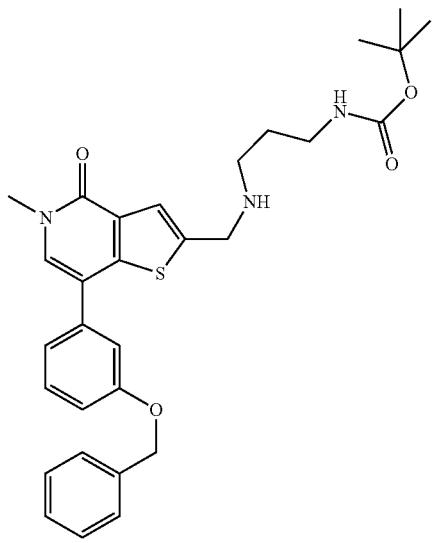 [SMILES: Cn1cc(-c2cccc(OCc3ccccc3)c2)c2sc(CNCCCNC(=O)OC(C)(C)C)cc2c1=O]

A mixture of tert-butyl (3-(((7-bromo-5-methyl-4-oxo-4,5-dihydrothieno[3,2-c]pyridin-2-yl)methyl)amino)propyl)carbamate (for a preparation see Intermediate 46, 150 mg, 0.35 mmol), 3-benzyloxyphenylboronic acid (119 mg, 0.52 mmol), potassium carbonate (145 mg, 1.05 mmol) and bis(triphenylphosphine)palladium(II) chloride (25 mg, 10 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried over sodium sulphate and evaporated. The residue was purified via flash chromatography on silica gel eluting with 0 to 5% methanol in dichloromethane to give tert-butyl (3-(((7-(3-(benzyloxy)phenyl)-5-methyl-4-oxo-4,5-dihydrothieno[3,2-c]pyridin-2-yl)methyl)amino)propyl)carbamate (100 mg, 54% yield) as a brown gum.

LCMS (2 min, Formic Acid): Rt=0.92 min, MH+=534

Intermediate 48

7-bromo-5-methyl-2-((4-(methylsulphonyl)piperidin-1-yl)methyl)thieno[3,2-c]pyridin-4(5H)-one

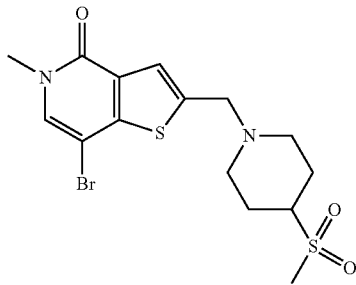 [SMILES: Cn1cc(Br)c2sc(CN3CCC(S(C)(=O)=O)CC3)cc2c1=O]

To a solution of 7-bromo-5-methyl-4-oxo-4,5-dihydrothieno[3,2-c]pyridine-2-carbaldehyde (for a preparation see Intermediate 3, 25 mg, 0.092 mmol) and 4-(methylsulphonyl)piperidine, trifluoroacetic acid salt (50 mg, 0.180 mmol) in DCM (10 mL) were successively added sodium triacetoxyborohydride (78 mg, 0.367 mmol) and acetic acid (7.89 µL, 0.138 mmol). The reaction mixture was stirred at 40° C. for 1 hour, whereupon the reaction mixture was hydrolyzed by adding a saturated aqueous solution of sodium carbonate. The aqueous phase was extracted 3 times with DCM and the combined organic layers were washed with brine, dried over MgSO4, filtered and concentrated in vacuo. The residue was purified by chromatography on silica gel eluting with 0 to 60% EtOAc in cyclohexane to give 7-bromo-5-methyl-2-((4-(methylsulphonyl)piperidin-1-yl)methyl)thieno[3,2-c]pyridin-4(5H)-one (16 mg, 42%) as a viscous yellow oil.

LCMS (2 min, Formic Acid): Rt=0.48 min, MH+=419/421

Intermediate 49

N-(3-(2-formyl-5-methyl-4-oxo-4,5-dihydrothieno[3,2-c]pyridin-7-yl)phenyl)acetamide

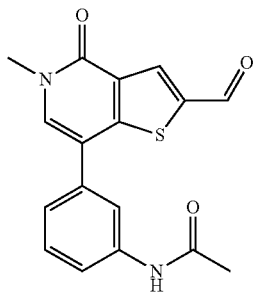 [SMILES: CC(=O)Nc1cccc(-c2cn(C)c(=O)c3cc(C=O)sc23)c1]

A mixture of 7-bromo-5-methyl-4-oxo-4,5-dihydrothieno[3,2-c]pyridine-2-carbaldehyde (for a preparation see Intermediate 3, 272 mg, 1.0 mmol), (3-acetamidophenyl)boronic acid (215 mg, 1.2 mmol), potassium carbonate (414 mg, 3.0 mmol) and bis(triphenylphosphine)palladium(II) chloride (35 mg, 5 mol %) in 1,2-dimethoxyethane (3 mL) and water (0.5 mL) was heated at 120° C. in a microwave for 20 minutes. The cooled reaction mixture was diluted with ethyl acetate (25 mL). The mixture was filtered through Celite and the filtrate was dried and evaporated to give a green solid N-(3-(2-formyl-5-methyl-4-oxo-4,5-dihydrothieno[3,2-c]pyridin-7-yl)phenyl)acetamide (320 mg, 98% yield). A 120 mg portion of the latter was purified by chromatpgraphy on silica gel eluting with 5 to 10% methanol in dichloromethane to give N-(3-(2-formyl-5-methyl-4-oxo-4,5-dihydrothieno[3,2-c]pyridin-7-yl)phenyl)acetamide (100 mg, 31%) as a green solid.

LCMS (2 min, Formic Acid): Rt=0.72 min, MH+=327

Intermediate 50 tert-butyl (2-(((7-(3-(benzyloxy)phenyl)-5-methyl-4-oxo-4,5-dihydrothieno[3,2-c]pyridin-2-yl)methyl)amino)ethyl)carbamate

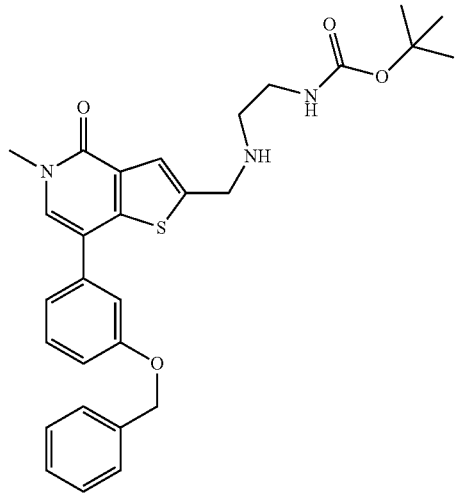 [SMILES: Cn1cc(-c2cccc(OCc3ccccc3)c2)c2sc(CNCCNC(=O)OC(C)(C)C)cc2c1=O]

A mixture of tert-butyl (2-(((7-bromo-5-methyl-4-oxo-4,5-dihydrothieno[3,2-c]pyridin-2-yl)methyl)amino)ethyl)carbamate (for a preparation see Intermediate 44, 180 mg, 0.43 mmol),3-benzyloxyphenylboronic acid (148 mg, 0.65 mmol), potassium carbonate (179 mg, 1.29 mmol) and bis(triphenylphosphine)palladium(II) chloride (30 mg, 10 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried over sodium sulphate and evaporated. The residue was purified by chromatography on silica gel eluting with 0 to 5% methanol in dichloromethane to give tert-butyl (2-(((7-(3-(benzyloxy)phenyl)-5-methyl-4-oxo-4,5-dihydrothieno[3,2-c]pyridin-2-yl)methyl)amino)ethyl)carbamate (107 mg, 48% yield) as a brown gum.

LCMS (2 min, Formic Acid): Rt=0.97 min, MH+=520

Intermediate 52 tert-butyl (3-(((7-(3,4-dimethoxyphenyl)-5-methyl-4-oxo-4,5-dihydrothieno[3,2-c]pyridin-2-yl)methyl)amino)propyl)carbamate

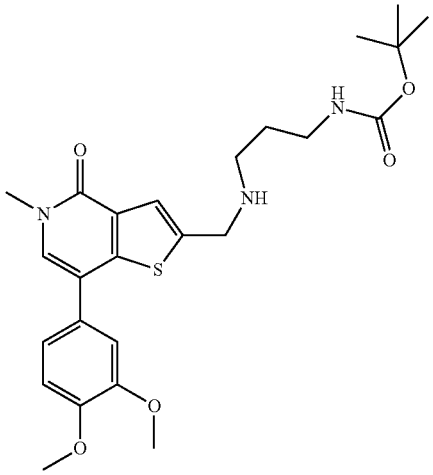 [SMILES: COc1ccc(-c2cn(C)c(=O)c3cc(CNCCCNC(=O)OC(C)(C)C)sc23)cc1OC]

A mixture of tert-butyl (3-(((7-bromo-5-methyl-4-oxo-4,5-dihydrothieno[3,2-c]pyridin-2-yl)methyl)amino)propyl)carbamate (for a preparation see Intermediate 46, 150 mg, 0.35 mmol), 3,4-dimethoxyphenylboronic acid (95 mg, 0.52 mmol), potassium carbonate (145 mg, 1.05 mmol) and bis(triphenylphosphine)palladium(II) chloride (25 mg, 10 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried over sodium sulphate and evaporated. The residue was purified by chromatography on silica gel eluting with 0 to 5% methanol in dichloromethane to give tert-butyl (3-(((7-(3,4-dimethoxyphenyl)-5-methyl-4-oxo-4,5-dihydrothieno[3,2-c]pyridin-2-yl)methyl)amino)propyl)carbamate (143 mg, 84% yield) as a brown gum.

LCMS (2 min, Formic Acid): Rt=0.72 min, MH+=488

Intermediate 53

7-bromo-2-(bromomethyl)-5-methylthieno[3,2-c]pyridin-4(5H)-one

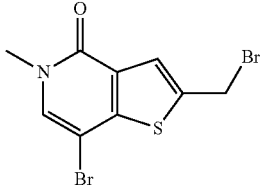

A stirred solution of 7-bromo-2-(hydroxymethyl)-5-methylthieno[3,2-c]pyridin-4(5H)-one (for a preparation see Intermediate 43, 50 mg, 0.182 mmol) in 1,4-dioxane (7 mL) under nitrogen was warmed to 40° C. and then treated with tribromophosphine (0.912 mL, 0.912 mmol). The reaction was stirred under these conditions for 2 hours, whereupon the reaction was cooled to room temperature and concentrated under reduced pressure.

The crude material was not purified and deemed of sufficient quality to use in subsequent reactions.

The yield was assumed to be 100%.

$^1$H NMR (400 MHz, CDCl$_3$) δ-ppm 3.99 (s, 3H), 4.79 (s, 2H), 7.71 (s, 1H), 8.92 (s, 1H)

Intermediate 56 tert-butyl 4-((7-(3,4-dimethoxyphenyl)-5-methyl-4-oxo-4,5-dihydrothieno[3,2-c]pyridin-2-yl)methyl)-2-methylpiperazine-1-carboxylate

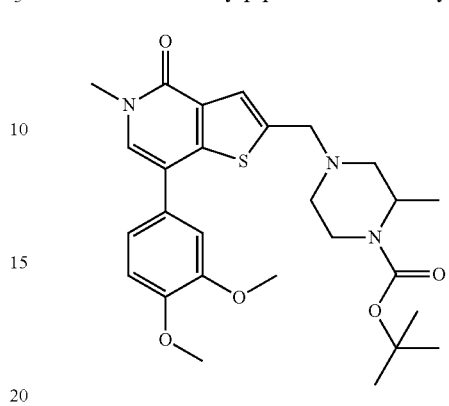

To a solution of 7-(3,4-dimethoxyphenyl)-5-methyl-4-oxo-4,5-dihydrothieno[3,2-c]pyridine-2-carbaldehyde (for a preparation see Intermediate 25, 100 mg, 0.304 mmol) in DCM (5 mL) was added acetic acid (0.026 mL, 0.455 mmol) and tert-butyl 2-methylpiperazine-1-carboxylate (0.073 mL, 0.364 mmol) and the reaction mixture was stirred under nitrogen at room temperature for one hour. Sodium triacetoxyborohydride (322 mg, 1.518 mmol) was then added and the reaction was refluxed under nitrogen overnight. The reaction mixture was allowed to cool to room temperature and was then hydrolyzed with a saturated aqueous solution of sodium bicarbonate (20 mL). The layers were separated and the aqueous phase was extracted with DCM (3×10 mL). The combined organic layers were washed with a saturated aqueous solution of sodium chloride solution (approx. 20 mL), dried over magnesium sulphate, filtered and concentrated under vacuum to give a light brown residue. The residue was purified by chromatography on silica gel eluting with 0 to 5% MeOH in DCM. The appropriate fractions were combined to give an impure light brown residue. The product was therefore loaded onto a 2 g SCX column and was flushed with MeOH (3 column volumes). The product was eluted in 2.0M ammonia in MeOH (3 column volumes) and concentrated to give tert-butyl 4-((7-(3,4-dimethoxyphenyl)-5-methyl-4-oxo-4,5-dihydrothieno[3,2-c]pyridin-2-yl)methyl)-2-methylpiperazine-1-carboxylate (110 mg, 71% yield) as a yellow oil.

LCMS (2 min, Formic Acid): Rt=0.90 min, MH+=514

Intermediate 57 tert-butyl 4-((7-(3,4-dimethoxyphenyl)-5-methyl-4-oxo-4,5-dihydrothieno[3,2-c]pyridin-2-yl)methyl)-1,4-diazepane-1-carboxylate

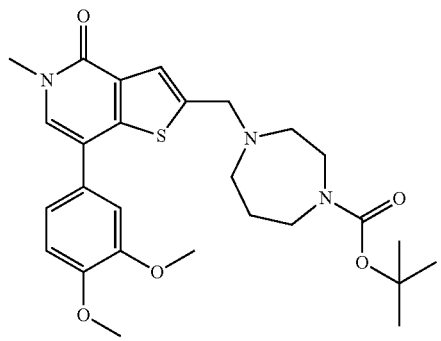 [SMILES: COc1ccc(-c2cn(C)c(=O)c3cc(CN4CCCN(C(=O)OC(C)(C)C)CC4)sc23)cc1OC]

To a solution of 7-(3,4-dimethoxyphenyl)-5-methyl-4-oxo-4,5-dihydrothieno[3,2-c]pyridine-2-carbaldehyde (for a preparation see Intermediate 25, 100 mg, 0.304 mmol) in DCM (5 mL) was added acetic acid (0.026 mL, 0.455 mmol) and tert-butyl 1,4-diazepane-1-carboxylate (0.072 mL, 0.364 mmol) and the reaction was stirred under nitrogen at room temperature for one hour. Sodium triacetoxyborohydride (322 mg, 1.518 mmol) was then added and the reaction mixture was refluxed overnight.

The reaction mixture was allowed to cool to room temperature and was hydrolyzed by using a saturated aqueous solution of sodium bicarbonate (20 mL). The layers were separated and the aqueous phase was extracted with DCM (3×10 mL). The combined organic layers were washed with a brine (approx. 20 mL), dried over magnesium sulphate, filtered and concentrated under reduced pressure to give a pale brown solid.

The residue was purified by chromatography on silica gel eluting with 0 to 5% MeOH in DCM. The purest fractions were combined, concentrated, and dried overnight in a vacuum oven to give tert-butyl 4-((7-(3,4-dimethoxyphenyl)-5-methyl-4-oxo-4,5-dihydrothieno[3,2-c]pyridin-2-yl)methyl)-1,4-diazepane-1-carboxylate (6 mg, 3.9% yield) as a yellow oil. The remaining impure fractions were combined and concentrated. The residue was loaded on a 2 g SCX column and it was flushed with MeOH (3 column volumes). The product was eluted with 2.0M ammonia in MeOH (3 column volumes) and concentrated under reduced pressure to give tert-butyl 4-((7-(3,4-dimethoxyphenyl)-5-methyl-4-oxo-4,5-dihydrothieno[3,2-c]pyridin-2-yl)methyl)-1,4-diazepane-1-carboxylate (79.3 mg, 51% yield) as a yellow oil.

LCMS (2 min, Formic Acid): Rt=0.77 min, MH$^+$=514

Intermediate 58 diethyl ((7-bromo-5-methyl-4-oxo-4,5-dihydrothieno[3,2-c]pyridin-2-yl)methyl)phosphonate

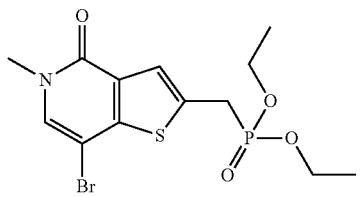 [SMILES: CCOP(=O)(Cc1cc2c(=O)n(C)cc(Br)c2s1)OCC]

A suspension of 7-bromo-2-(bromomethyl)-5-methylthieno[3,2-c]pyridin-4(5H)-one (for a preparation see Intermediate 53, 2.460 g, 7.3 mmol) in toluene (50 mL) and triethylphospite (70 mL) was heated to 120° C. and refluxed overnight under an atmosphere of nitrogen. The reaction mixture was cooled to room temperature and the solvent was removed under reduced pressure to give a thick orange suspension. The reaction mixture was dissolved in DCM (100 mL) and washed with 2.0 M HCl (75 mL). The organic layer was collected and the aqueous phase was extracted with DCM (2×50 mL). The organic fractions were combined and washed with water (100 mL) and brine (100 mL). The organic phase contained a suspension and was filtered through Celite. The organic phase was again washed with water, then collected, dried over magnesium sulphate, and concentrated under reduced pressure to give a yellow oil. The crude material was purified by chromatography on silica gel eluting with 0 to 5% MeOH in DCM. The appropriate fractions were combined and concentrated in vacuo to give diethyl ((7-bromo-5-methyl-4-oxo-4,5-dihydrothieno[3,2-c]pyridin-2-yl)methyl)phosphonate (1.635 g, 57% yield), as a yellow oil. Upon cooling, the product began to precipitate to a yellow solid and cyclohexane was added to the oil to encourage precipitation. The excess solvent was decanted and the product was dried under vacuum to give a pale yellow solid.

LCMS (2 min, Formic Acid): Rt=0.82 min, MH$^+$=394/396

Intermediate 59 tert-butyl 4-((7-bromo-5-methyl-4-oxo-4,5-dihydrothieno[3,2-c]pyridin-2-yl)methylene)piperidine-1-carboxylate

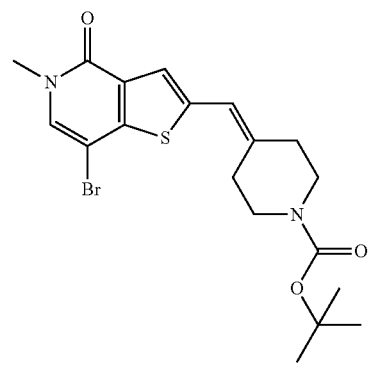 [SMILES: Cn1cc(Br)c2sc(C=C3CCN(C(=O)OC(C)(C)C)CC3)cc2c1=O]

Dry diisopropylamine (0.723 mL, 5.07 mmol) under an atmosphere of nitrogen was cooled to −78 OC and treated with a 1.6 M solution of n-butyllithium (3.17 mL, 5.07 mmol) in hexanes. The mixture was stirred for 5 minutes and then diluted with THF (5 mL). The reaction mixture was then treated dropwise with a solution of diethyl ((7-bromo-5-methyl-4-oxo-4,5-dihydrothieno[3,2-c]pyridin-2-yl)methyl)phosphonate (for a preparation see Intermediate 58, 1 g, 2.54 mmol) in THF (12 mL). The resulting mixture was stirred for 45 minutes and was then treated dropwise with a solution of tert-butyl 4-oxopiperidine-1-carboxylate (0.758 g, 3.80 mmol) in THF (12 mL). The reaction was warmed to room temperature and stirred under an atmosphere of nitrogen overnight. The reaction was quenched with water (50 mL) and the aqueous phase was extracted with ethyl acetate (3×30 mL). The combined organic fractions were washed with brine (50 mL). The organic fraction was collected and the brine was back extracted with a further portion of ethyl acetate (20 mL). The combined organic layers were dried over magnesium sulphate, filtered and concentrated under reduced pressure to give tert-butyl 4-((7-bromo-5-methyl-4-oxo-4,5-dihydrothieno[3,2-c]pyridin-2-yl)methylene)piperidine-1-carboxylate as a brown solid. The product contained unreacted tert-butyl 4-oxopiperidine-1-carboxylate which was visible by $^1$H NMR but was deemed of sufficient quality to be used in subsequent reactions (1.316 g, 118% yield)

LCMS (2 min, Formic Acid): Rt=1.26 min, MH$^+$=439/441

Intermediate 60

7-bromo-5-methyl-2-(piperidin-4-ylidenemethyl)thieno[3,2-c]pyridin-4(5H)-one, Hydrochloride

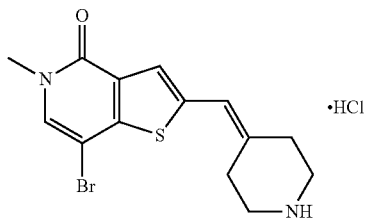 [SMILES: Cn1cc(Br)c2sc(C=C3CCNCC3)cc2c1=O ; Cl]

A solution of tert-butyl 4-((7-bromo-5-methyl-4-oxo-4,5-dihydrothieno[3,2-c]pyridin-2-yl)methylene)piperidine-1-carboxylate (for a preparation see Intermediate 59, 1.316 g, 3.00 mmol) in 1,4-dioxane (5 mL) was treated with a 4.0 M solution of hydrogen chloride (10 mL, 40.0 mmol) in 1,4-dioxane. The reaction mixture was stirred at room temperature under an atmosphere of nitrogen overnight. Diethyl ether (20 mL) was added and the reaction mixture was stirred for 5 minutes. The reaction was allowed to settle and the excess solvent was decanted. This process was repeated again and then any residual solvent was removed under reduced pressure to give an orange solid. The product was oven dried for three hours to give 7-bromo-5-methyl-2-(piperidin-4-ylidenemethyl)thieno[3,2-c]pyridin-4(5H)-one, hydrochloride (1.116 g, 99% yield) as an orange solid.

LCMS (2 min, Formic Acid): Rt=0.61 min, MH$^+$=339, 341

Intermediate 61

7-bromo-5-methyl-2-((1-(methylsulphonyl)piperidin-4-ylidene)methyl)thieno[3,2-c]pyridin-4(5H)-one

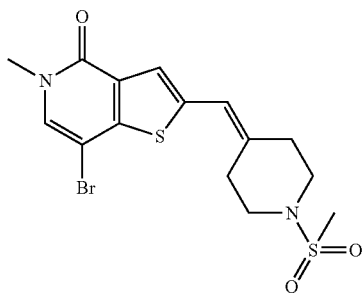 [SMILES: Cn1cc(Br)c2sc(C=C3CCN(S(C)(=O)=O)CC3)cc2c1=O]

To a suspension of 7-bromo-5-methyl-2-(piperidin-4-ylidenemethyl)thieno[3,2-c]pyridin-4(5H)-one, hydrochloride (for a preparation see Intermediate 60, 1.127 g, 3 mmol) in DCM (20 mL) and pyridine (10 mL) was added methanesulphonyl chloride (468 µL, 6.01 mmol). The reaction mixture was stirred at room temperature under an atmosphere of nitrogen for 1 hour. The reaction was treated with a further 2 equivalents of methanesulphonyl chloride (468 µL, 6.01 mmol) and the reaction was stirred under the conditions described for 16 hours.

The reaction was concentrated under reduced pressure to give a dark brown residue. The crude product was dissolved in a small volume of DCM (15 mL) and toluene (30 mL) and the reaction was reconcentrated to remove residual pyridine (x2). The crude product was purified by chromatography on silica gel elution 0 to 5% MeOH in DCM give 7-bromo-5-methyl-2-((1-(methylsulphonyl)piperidin-4-ylidene)methyl)thieno[3,2-c]pyridin-4(5H)-one (1.13 g, 90%) as a yellow solid.

LCMS (2 min, Formic Acid): Rt=0.94 min, MH$^+$=417/419

Intermediate 62

N-(4-(5-methyl-2-((1-(methylsulphonyl)piperidin-4-ylidene)methyl)-4-oxo-4,5-dihydrothieno[3,2-c]pyridin-7-yl)pyridin-2-yl)acetamide

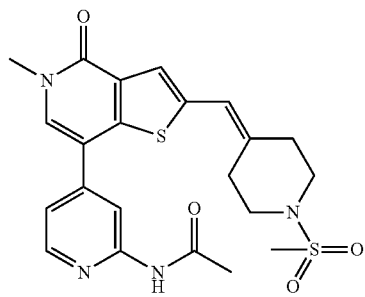 [SMILES: CC(=O)Nc1cc(-c2cn(C)c(=O)c3cc(C=C4CCN(S(C)(=O)=O)CC4)sc23)ccn1]

To a suspension of 7-bromo-5-methyl-2-((1-(methylsulphonyl)piperidin-4-ylidene)methyl)thieno[3,2-c]pyridin-4(5H)-one (for a preparation see Intermediate 61, 200 mg, 0.479 mmol) followed by N-(4-(4,4,5,5-tetramethyl-1,3,2-dioxaborolan-2-yl)pyridin-2-yl)acetamide (251 mg, 0.958 mmol) and potassium carbonate (265 mg, 1.917 mmol) in isopropanol (4 mL) and water (3 mL) was added PEPPSI (32.6 mg, 0.048 mmol) catalyst. The reaction mixture was heated to 130° C. for 30 minutes in the microwave. The reaction was hydrolyzed using a saturated aqueous solution of ammonium chloride (30 mL). The layers were separated and the aqueous phase was extracted with DCM (3×30 mL). The combined organic fractions were dried over magnesium sulphate, filtered and concentrated in vacuo to give a dark brown oil.

The crude material was purified by chromatography on silica gel eluting with 0 to 5% methanol in dichloromethane. The desired product co-eluted with various impurities. The appropriate fractions were concentrated, redissolved in 1:1 DMSO/MeOH, and filtered through a bond elute cartridge to remove insoluble impurities. The material was then repurified by MDAP in three portions to give N-(4-(5-methyl-2-((1-(methylsulphonyl)piperidin-4-ylidene)methyl)-4-oxo-4,5-dihydrothieno[3,2-c]pyridin-7-yl)pyridin-2-yl)acetamide (10 mg, 4.4% yield) as a white solid.

LCMS (2 min, Formic Acid): Rt=0.74 min, MH$^+$=473

Intermediate 63 tert-butyl 4-((7-(3,4-dimethoxyphenyl)-5-methyl-4-oxo-4,5-dihydrothieno[3,2-c]pyridin-2-yl)methylene)piperidine-1-carboxylate

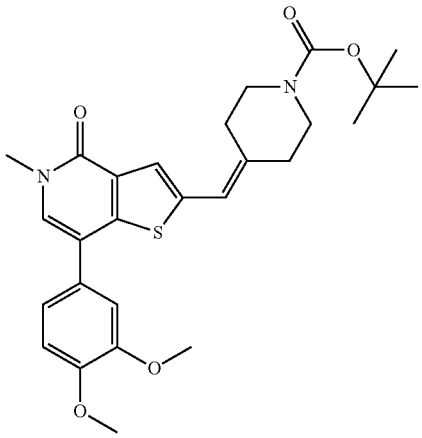 [SMILES: COc1ccc(-c2cn(C)c(=O)c3cc(C=C4CCN(C(=O)OC(C)(C)C)CC4)sc23)cc1OC]

To a suspension of tert-butyl 4-((7-bromo-5-methyl-4-oxo-4,5-dihydrothieno[3,2-c]pyridin-2-yl)methylene)piperidine-1-carboxylate (for a preparation see Intermediate 59, 27 mg, 0.061 mmol), (3,4-dimethoxyphenyl)boronic acid (16.77 mg, 0.092 mmol) and potassium carbonate (25.5 mg, 0.184 mmol) in isopropanol (2 mL) and water (1 mL) was added PEPPSI (4.18 mg, 6.15 μmol) catalyst. The reaction mixture was heated to 130° C. in the microwave for 30 minutes. The reaction was quenched with a saturated aqueous solution of ammonium chloride (15 mL) and the aqueous phase was extracted with DCM (3×15 mL). The combined organic fractions were dried over magnesium sulphate, filtered and concentrated under reduced pressure to give a dark green oil. The crude material was purified by chromatography on silica gel eluting with 0 to 50% ethyl acetate in cyclohexane then 5% MeOH in DCM to give the product as a yellow oil. The material was re-dissolved in diethyl ether and re-concentrated to give tert-butyl 4-((7-(3,4-dimethoxyphenyl)-5-methyl-4-oxo-4,5-dihydrothieno[3,2-c]pyridin-2-yl)methylene)piperidine-1-carboxylate (24 mg, 0.048 mmol, 79% yield) as a light yellow solid.

LCMS (2 min, Formic Acid): Rt=1.22 min, MH$^+$=497

Intermediate 64 tert-butyl 4-((7-(3,4-dimethoxyphenyl)-5-methyl-4-oxo-4,5-dihydrothieno[3,2-c]pyridin-2-yl)methyl)piperidine-1-carboxylate

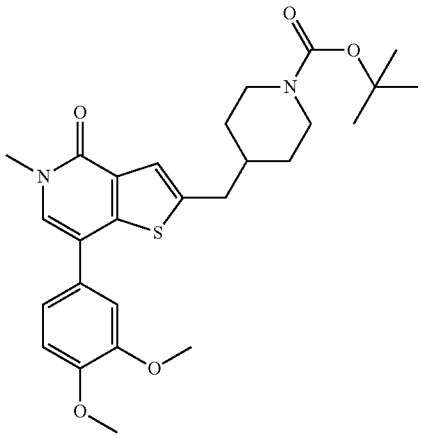 [SMILES: COc1ccc(-c2cn(C)c(=O)c3cc(CC4CCN(C(=O)OC(C)(C)C)CC4)sc23)cc1OC]

A stirred solution of tert-butyl 4-((7-(3,4-dimethoxyphenyl)-5-methyl-4-oxo-4,5-dihydrothieno[3,2-c]pyridin-2-yl)methylene)piperidine-1-carboxylate (for a preparation see Intermediate 63, 22 mg, 0.044 mmol) in ethanol (2 mL) was treated with ammonium formate (13.97 mg, 0.221 mmol) followed by 10% palladium on carbon (50% water paste, 3.6 mg, 20% wt). The resulting suspension was heated to 90° C. and refluxed under an atmosphere of nitrogen for two hours. The reaction was cooled to room temperature and passed through a 2.5 g Celite frit to remove the palladium catalyst. The filtrate was concentrated under reduced pressure to give a white residue. The material was re-dissolved in toluene and re-concentrated (×2) to remove residual ammonium formate impurities, to give tert-butyl 4-((7-(3,4-dimethoxyphenyl)-5-methyl-4-oxo-4,5-dihydrothieno[3,2-c]pyridin-2-yl)methyl)piperidine-1-carboxylate (22.09 mg, 100% yield) a white solid containing traces of ammonium formate.

LCMS (2 min, Formic Acid): Rt=1.21 min, MH$^+$=499

Intermediate 65

7-(3,4-dimethoxyphenyl)-5-methyl-2-(piperidin-4-ylmethyl)thieno[3,2-c]pyridin-4(5H)-one, Hydrochloride

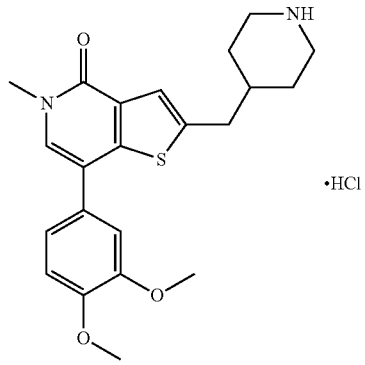 [SMILES: COc1ccc(-c2cn(C)c(=O)c3cc(CC4CCNCC4)sc23)cc1OC ; Cl]

A stirred solution of tert-butyl 4-((7-(3,4-dimethoxyphenyl)-5-methyl-4-oxo-4,5-dihydrothieno[3,2-c]pyridin-2-yl)methyl)piperidine-1-carboxylate (for a preparation see Intermediate 64, 22 mg, 0.044 mmol) in 1,4-dioxane (2 mL) under an atmosphere of nitrogen was treated with 4.0 M HCl in 1,4-dioxane (500 μL). The reaction mixture was stirred for 2 hours. The reaction mixture was treated with a further portion of 4.0 M HCl in 1,4-dioxane (1 mL) and stirred described for another 3 hours. Diethyl ether (3 mL) was added and the reaction mixture stirred for 5 minutes. The solvent was decanted and a fresh portion of diethyl ether (2 mL) was added to the product. The solvent was again decanted and the product was concentrated under reduced pressure to give 7-(3,4-dimethoxyphenyl)-5-methyl-2-(piperidin-4-ylmethyl)thieno[3,2-c]pyridin-4(5H)-one, hydrochloride (18 mg, 94% yield) as a white solid.

LCMS (2 min, Formic Acid): Rt=0.67 min, MH$^+$=477

Intermediate 66

N-(3-(5-methyl-2-((1-(methylsulphonyl)piperidin-4-ylidene)methyl)-4-oxo-4,5-dihydrothieno[3,2-c]pyridin-7-yl)phenyl)acetamide

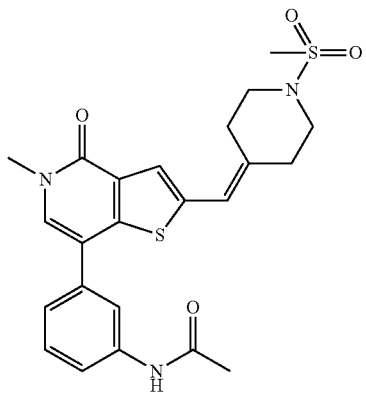 [SMILES: CC(=O)Nc1cccc(-c2cn(C)c(=O)c3cc(C=C4CCN(S(C)(=O)=O)CC4)sc23)c1]

To a suspension of 7-bromo-5-methyl-2-((1-(methylsulphonyl)piperidin-4-ylidene)methyl)thieno[3,2-c]pyridin-4(5H)-one (for a preparation see Intermediate 61, 100 mg, 0.240 mmol), (3-acetamidophenyl)boronic acid (64.3 mg, 0.359 mmol) and potassium carbonate (99 mg, 0.719 mmol) in isopropanol (2 mL) and water (2 mL) was added PEPPSI (16.28 mg, 0.024 mmol) catalyst. The reaction mixture was heated to 130° C. in the microwave for 30 minutes. The reaction mixture was hydrolyzed with a saturated aqueous solution of ammonium chloride (25 mL). The aqueous phase was extracted with DCM (3×15 mL) and the combined organic layers were dried over magnesium sulphate, filtered and concentrated under reduced pressure to give a light yellow solid.

The crude material failed to dissolve in a small volume of DCM and it was therefore not possible to load onto a silica gel column. The mixture was reconcentrated and the crude product was then triturated with diethyl ether to give the product as a yellow solid (85% pure by LCMS). An attempt was made to dissolve the product in THF for column purification but again it was insoluble. The product (120 mg, 1065 yield) was deemed of sufficient quality to be reduced in the subsequent reaction.

LCMS (2 min, Formic Acid): Rt=0.83 min, MH$^+$=472

Intermediate 67

7-bromo-5-methyl-2-((4-methyl-1,4-diazepan-1-yl)methyl)thieno[3,2-c]pyridin-4(5H)-one

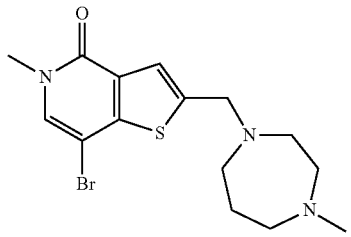

To a stirred solution of 7-bromo-5-methyl-4-oxo-4,5-dihydrothieno[3,2-c]pyridine-2-carbaldehyde (for a preparation see Intermediate 3, 200 mg, 0.735 mmol) in dichloromethane (10 mL) was added 1-methyl-1,4-diazepane (0.110 mL, 0.882 mmol) followed by acetic acid (0.042 mL, 0.735 mmol). The reaction mixture was heated to 40° C. and stirred for 15 minutes. The reaction was treated with sodium triacetoxyborohydride (467 mg, 2.205 mmol) and stirred under nitrogen at 40° C. for one hour whereupon the reaction mixture was cooled to room temperature, quenched with a saturated aqueous solution of bicarbonate (25 mL) and stirred under nitrogen for 15 minutes. The reaction mixture was transferred to a separating funnel and the organic layer was collected. The aqueous phase was extracted with DCM (3×25 mL) and the combined organic fractions were washed with brine dried over magnesium sulphate, filtered and concentrated under reduced pressure to give yellow oil. The crude material was purified by chromatography on silica gel eluting with 0 to 10% [ammonia in MeOH] in DCM to give 7-bromo-5-methyl-2-((4-methyl-1,4-diazepan-1-yl)methyl)thieno[3,2-c]pyridin-4(5H)-one (204 mg, 75% yield) as a yellow oil.

LCMS (2 min, Formic Acid): Rt=0.49 min, MH$^+$=370/372

Intermediate 68

(S)-tert-butyl-4-((7-(3-(benzyloxy)-4-methoxyphenyl)-5-methyl-4-oxo-4,5-dihydrothieno[3,2-c]pyridin-2-yl)methyl)-3-methylpiperazine-1-carboxylate

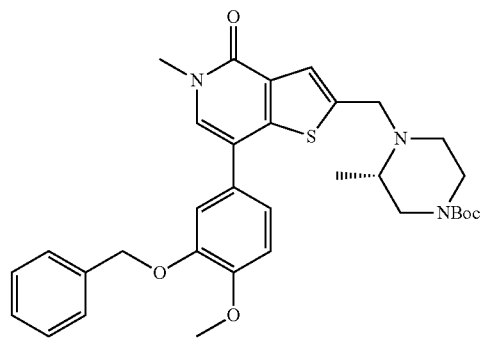 [SMILES: COc1ccc(-c2cn(C)c(=O)c3cc(CN4CCN(C(=O)OC(C)(C)C)C[C@@H]4C)sc23)cc1OCc1ccccc1]

To a solution of (S)-tert-butyl 4-((7-bromo-5-methyl-4-oxo-4,5-dihydrothieno[3,2-c]pyridin-2-yl)methyl)-3-methylpiperazine-1-carboxylate (for a preparation see Intermediate 84, 22 mg, 0.048 mmol) and (3-(benzyloxy)-4-methoxyphenyl)boronic acid (18.66 mg, 0.072 mmol) in isopropanol (2 mL) were successively added potassium carbonate (0.121 mL, 0.241 mmol) and PEPPSI (3.28 mg, 4.82 µmol). The reaction mixture was heated in a microwave reactor at 110° C. for 20 min and was then concentrated in vacuo and the residue partitioned between ethyl acetate and water. The aqueous phase was extracted three times with ethyl acetate and the combined organic layers were washed with brine, dried over magnesium sulphate, filtered and concentrated in vacuo. The residue was diluted in a 1:1 MeOH/DMSO mixture (1 mL) and purified via MDAP. The appropriate fractions were combined and concentrated in vacuo to give a residue which was diluted in a 1:1 MeOH/DMSO mixture (1 mL) and further purified via MDAP. The appropriate fractions were collected and concentrated in vacuo to give (S)-tert-butyl-4-((7-(3-(benzyloxy)-4-methoxyphenyl)-5-methyl-4-oxo-4,5-dihydrothieno[3,2-c]pyridin-2-yl)methyl)-3-methylpiperazine-1-carboxylate (3.2 mg) as a viscous yellow oil.

LCMS (2 min, High pH): Rt=1.40 min, MH$^+$=590

Intermediate 69

7-bromo-5-methyl-2-((4-(methylsulphonyl)piper-azin-1-yl)methyl)thieno[3,2-c]pyridin-4(5H)-one

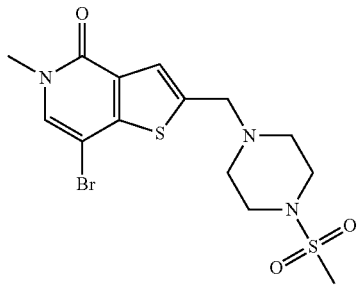 [SMILES: Cn1cc(Br)c2sc(CN3CCN(S(C)(=O)=O)CC3)cc2c1=O]

A solution of 7-bromo-5-methyl-4-oxo-4,5-dihydrothieno[3,2-c]pyridine-2-carbaldehyde (for a preparation see Intermediate 3, 15.0 g, 55.1 mmol) in methanol (340 mL) and glacial acetic acid (40 mL) was treated with 1-(methylsulphonyl)piperazine (13.6 g, 83 mmol) and stirred at room temperature for 15 minutes. 2-Picoline borane complex (6.49 g, 60.6 mmol) was added portionwise over 5 minutes. After complete addition, the reaction mixture was stirred at 50° C. for 1 hour. The reaction mixture was then cooled to room temperature and the solvent evaporated. A saturated aqueous solution of NaHCO$_3$ (50 mL) was added to the residue (gas evolved) and the mixture made basic by the careful addition of solid sodium bicarbonate (more gas evolved). The mixture was extracted with dichloromethane (3×200 mL) and the combined extracts were dried and evaporated in vacuo.

The residue was purified by flash chromatography on silica gel eluting with 0-5% methanol in dichloromethane. The product was triturated with diethyl ether, filtered off and dried to give 7-bromo-5-methyl-2-((4-(methylsulphonyl)piperazin-1-yl)methyl)thieno[3,2-c]pyridin-4(5H)-one (15.58 g, 37.1 mmol, 67.2% yield) as an off-white solid.

LCMS (2 min, Formic Acid): Rt=0.58 min, MH$^+$=420, 422

Intermediate 70

7-bromo-2-((2,4-dimethylpiperazin-1-yl)methyl)-5-methylthieno[3,2-c]pyridin-4(5H)-one

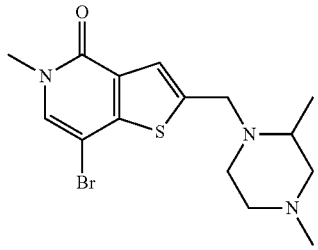

To a suspension of 1,3-dimethylpiperazine dihydrochloride (870 mg, 4.65 mmol) in DCM (10 mL) was added 7-bromo-5-methyl-4-oxo-4,5-dihydrothieno[3,2-c]pyridine-2-carbaldehyde (for a preparation see Intermediate 3, 250 mg, 0.919 mmol) followed by acetic acid (0.063 mL, 1.102 mmol). The resulting mixture was stirred under nitrogen at room temperature for 30 minutes and was then treated with sodium triacetoxyborohydride (974 mg, 4.59 mmol). The reaction was stirred under nitrogen at room temperature for 90 minutes at which point LCMS analysis showed some of the desired product had formed, however a significant amount of the starting material had been reduced to the alcohol by-product and some starting material still remained. The reaction was left under the same conditions overnight. The reaction was quenched with a saturated aqueous solution of bicarbonate (25 mL) and stirred under nitrogen for 20 minutes. The reaction was transferred to a separating funnel and the product was extracted with DCM (3×30 mL). The organic phase was washed with brine (25 mL) and then dried over magnesium sulphate. The filtrate was concentrated under reduced pressure to give a yellow solid. The crude material was purified by MDAP in four portions to give 7-bromo-2-((2,4-dimethylpiperazin-1-yl)methyl)-5-methylthieno[3,2-c]pyridin-4(5H)-one (34 mg, 10% yield) an orange solid.

LCMS (2 min, Formic Acid): Rt=0.58 min, MH$^+$=370/372

Intermediates 71-82

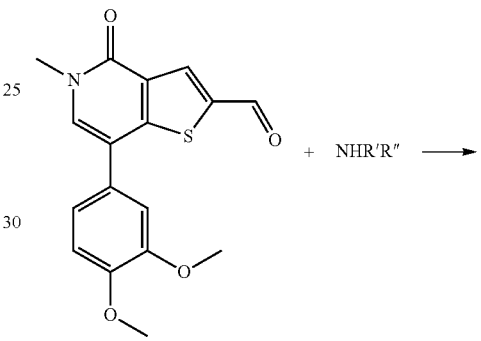

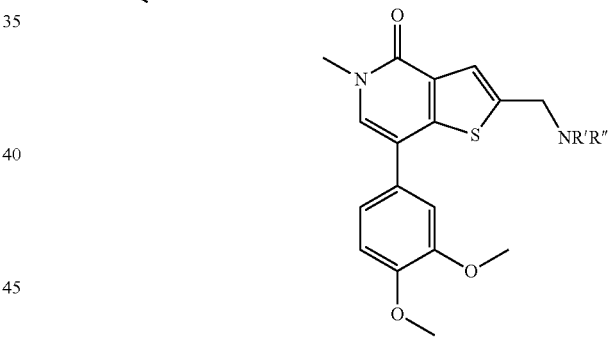

A solution of 7-(3,4-dimethoxyphenyl)-5-methyl-4-oxo-4,5-dihydrothieno[3,2-c]pyridine-2-carbaldehyde (for a preparation see Intermediate 25, 1.36 g, 4.13 mmol) in DCM (32 mL) was dispensed evenly (2 mL) to 16× amines (0.514-0.518 mmol, ~2 eq). The mixtures were treated with acetic acid (0.02 mL, 0.349 mmol), stirred for 5 min then sodium triacetoxyborohydride (4 eq, 1.04 mmol, 220 mg) added. The reaction mixtures were stirred vigorously at rt under nitrogen for 16 hr. The reactions were quenched by the addition of sat. NaHCO$_3$ (aq) (2 mL) and stirred for 10 min. The organic layers were dried through hydrophobic frits and the solvent removed under a stream of nitrogen. The residues were purified by MDAP on Xbridge C18 column using a gradient of solvents 10 mM ammonium carbonate in water adjusted to pH10 with ammonia solution and acetonitrile. The appropriate fractions were combined and the solvent evaporated in a vacuum centrifuge to give the reductive amination products (Intermediates 71-82) which were all used in the next stage.

| | Intermediate | NHR'R" | mmoles of NHR'R" | Supplier of NHR'R" |
|---|---|---|---|---|
| 71 | (R)-tert-butyl 4-((7-(3,4-dimethoxyphenyl)-5-methyl-4-oxo-4,5-dihydrothieno[3,2-c]pyridin-2-yl)methyl)-3-methylpiperazine-1-carboxylate | (R)-tert-butyl 3-methylpiperazine-1-carboxylate | 0.514 | Aldrich |
| 72 | (R)-tert-butyl 3-carbamoyl-4-((7-(3,4-dimethoxyphenyl)-5-methyl-4-oxo-4,5-dihydrothieno[3,2-c]pyridin-2-yl)methyl)piperazine-1-carboxylate | (R)-tert-butyl 3-carbamoylpiperazine-1-carboxylate | 0.515 | Ennona Med Chem Group |
| 73 | (S)-tert-butyl 4-((7-(3,4-dimethoxyphenyl)-5-methyl-4-oxo-4,5-dihydrothieno[3,2-c]pyridin-2-yl)methyl)-2-methylpiperazine-1-carboxylate | (S)-tert-butyl 2-methylpiperazine-1-carboxylate | 0.514 | Insight Chem |
| 74 | 1-tert-butyl 3-methyl 4-((7-(3,4-dimethoxyphenyl)-5-methyl-4-oxo-4,5-dihydrothieno[3,2-c]pyridin-2-yl)methyl)piperazine-1,3-dicarboxylate | 1-tert-butyl 3-methyl piperazine-1,3-dicarboxylate | 0.516 | AstaTech |

| | Intermediate | NHR'R" | mmoles of NHR'R" | Supplier of NHR'R" |
|---|---|---|---|---|
| 75 | (3R,5S)-tert-butyl 4-((7-(3,4-dimethoxyphenyl)-5-methyl-4-oxo-4,5-dihydrothieno[3,2-c]pyridin-2-yl)methyl)-3,5-dimethylpiperazine-1-carboxylate | cis-tert-butyl 3,5-dimethylpiperazine-1-carboxylate | 0.518 | Manchester Organic |
| 76 | (R)-tert-butyl 2-butyl-4-((7-(3,4-dimethoxyphenyl)-5-methyl-4-oxo-4,5-dihydrothieno[3,2-c]pyridin-2-yl)methyl)piperazine-1-carboxylate | (R)-tert-butyl 2-butylpiperazine-1-carboxylate | 0.516 | Activate |
| 77 | (S)-tert-butyl 4-((7-(3,4-dimethoxyphenyl)-5-methyl-4-oxo-4,5-dihydrothieno[3,2-c]pyridin-2-yl)methyl)-2-ethylpiperazine-1-carboxylate | (S)-tert-butyl 2-ethylpiperazine-1-carboxylate | 0.518 | Atlantic |

| | Intermediate | NHR'R" | mmoles of NHR'R" | Supplier of NHR'R" |
|---|---|---|---|---|
| 78 | tert-butyl 4-(((7-(3,4-dimethoxyphenyl)-5-methyl-4-oxo-4,5-dihydrothieno[3,2-c]pyridin-2-yl)methyl)amino)piperidine-1-carboxylate | tert-butyl 4-aminopiperidine-1-carboxylate | 0.514 | Aldrich |
| 79 | (S)-tert-butyl 4-((7-(3,4-dimethoxyphenyl)-5-methyl-4-oxo-4,5-dihydrothieno[3,2-c]pyridin-2-yl)methyl)-3-methylpiperazine-1-carboxylate | (S)-tert-butyl 3-methylpiperazine-1-carboxylate | 0.514 | CNH Technologies |
| 80 | tert-butyl (1-((7-(3,4-dimethoxyphenyl)-5-methyl-4-oxo-4,5-dihydrothieno[3,2-c]pyridin-2-yl)methyl)pyrrolidin-3-yl)carbamate | tert-butyl pyrrolidin-3-ylcarbamate | 0.515 | Tokyo Chemical Industry Co. Ltd |
| 81 | tert-butyl (1-((7-(3,4-dimethoxyphenyl)-5-methyl-4-oxo-4,5-dihydrothieno[3,2-c]pyridin-2-yl)methyl)piperidin-4-yl)carbamate | tert-butyl piperidin-4-ylcarbamate | 0.514 | Aldrich |

| | Intermediate | NHR'R" | mmoles of NHR'R" | Supplier of NHR'R" |
|---|---|---|---|---|
| 82 | tert-butyl (2-(((7-(3,4-dimethoxyphenyl)-5-methyl-4-oxo-4,5-dihydrothieno[3,2-c]pyridin-2-yl)methyl)(methyl)amino)ethyl)carbamate | tert-butyl (2-(methylamino)ethyl)carbamate | 0.517 | KaironKem |

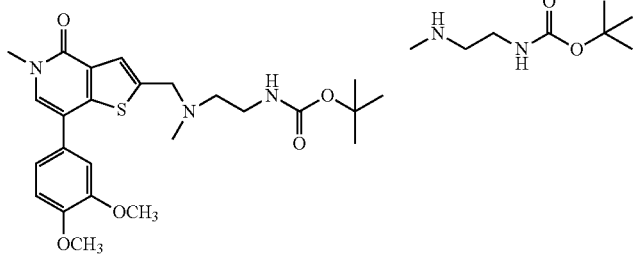

Intermediate 83

4-oxo-7-phenyl-4,5-dihydrothieno[3,2-c]pyridine-2-carbaldehyde

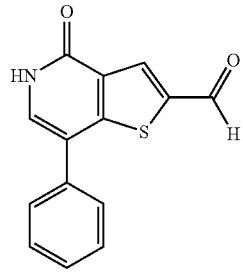 [SMILES: O=Cc1cc2c(=O)[nH]cc(-c3ccccc3)c2s1]

To a suspension of 7-bromo-4-oxo-4,5-dihydrothieno[3,2-c]pyridine-2-carbaldehyde (for a preparation see Intermediate 2, 191 mg, 0.740 mmol) and phenylboronic acid (135 mg, 1.110 mmol) in isopropanol (3.5 mL) in a microwave vial were successively added potassium carbonate (1.850 mL, 3.70 mmol) and PEPPSI (50.3 mg, 0.074 mmol). The reaction mixture was heated at 110° C. in the microwave for 30 min, whereupon the solvents were evaporated. The residue was partitioned between EtOAc and a saturated aqueous solution of sodium bicarbonate. The phases were separated and the aqueous phase was extracted three times with EtOAc. The combined organic layers were washed with brine, dried over MgSO4, filtered and concentrated in vacuo. The crude residue was taken up in MeOH and the precipitate was filtered to give 4-oxo-7-phenyl-4,5-dihydrothieno[3,2-c]pyridine-2-carbaldehyde (160 mg, 85%) as a brown solid.

LCMS (2 min, Formic Acid): Rt=0.84 min, MH+=256

Intermediate 84

(S)-tert-butyl-4-((7-bromo-5-methyl-4-oxo-4,5-dihydrothieno[3,2-c]pyridin-2-yl)methyl)-3-methylpiperazine-1-carboxylate

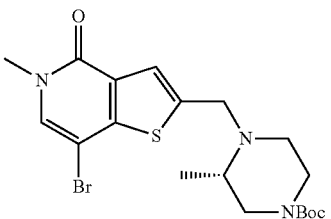 [SMILES: C[C@H]1CN(C(=O)OC(C)(C)C)CCN1Cc1cc2c(=O)n(C)cc(Br)c2s1]

To a solution of 7-bromo-5-methyl-4-oxo-4,5-dihydrothieno[3,2-c]pyridine-2-carbaldehyde (for a preparation see Intermediate 3, 136 mg, 0.500 mmol) and (S)-tert-butyl 3-methylpiperazine-1-carboxylate (200 mg, 1.000 mmol) in DCM (5 mL) were successively added sodium triacetoxyborohydride (424 mg, 1.999 mmol) and acetic acid (5.72 µL, 0.100 mmol). The reaction mixture was stirred at 40° C. for 1 hour, whereupon the reaction mixture was hydrolyzed by adding a saturated aqueous solution of sodium carbonate. The aqueous phase was extracted three times with dichloromethane and the combined organic layers were washed with brine, dried over magnesium sulphate, filtered and concentrated in vacuo. The residue was purified by MDAP and the appropriate fractions were combined and concentrated in vacuo to give (S)-tert-butyl-4-((7-bromo-5-methyl-4-oxo-4,5-dihydrothieno[3,2-c]pyridin-2-yl)methyl)-3-methylpiperazine-1-carboxylate (47 mg) as a viscous yellow oil.

LCMS (2 min, Formic Acid): Rt=0.77 min, MH+=456/458

123

Intermediate 85 tert-butyl 4-(5-methyl-2-((4-(methylsulphonyl)piperazin-1-yl)methyl)-4-oxo-4,5-dihydrothieno[3,2-c]pyridin-7-yl)benzylcarbamate

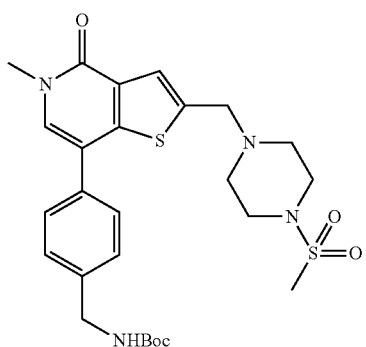 [SMILES: Cn1cc(-c2ccc(CNC(=O)OC(C)(C)C)cc2)c2sc(CN3CCN(S(C)(=O)=O)CC3)cc2c1=O]

To a solution of 7-bromo-5-methyl-2-((4-(methylsulphonyl)piperazin-1-yl)methyl)thieno[3,2-c]pyridin-4(5H)-one (for a preparation see Intermediate 69, 106 mg, 0.252 mmol) and (4-(((tert-butoxycarbonyl)amino)methyl)phenyl)boronic acid (95 mg, 0.378 mmol) in isopropanol (5 mL) were successively added potassium carbonate (0.630 mL, 1.261 mmol) and PEPPSI (17.13 mg, 0.025 mmol). The resulting mixture was heated at 110° C. in the microwave for 1 hour. The reaction mixture was concentrated in vacuo and the crude residue was partitioned between EtOAc and a saturated aqueous solution of sodium bicarbonate. The phases were separated, the aqueous phase was extracted 3 times with EtOAc and the combined organic layers were washed with brine, dried over MgSO$_4$, filtered and concentrated in vacuo. The residue purified via flash chromatography on silica gel using a Biotage SP4 apparatus (25 G column), eluting with 10 to 60% MeOH in DCM. The appropriate fractions were combined and concentrated in vacuo to give tert-butyl 4-(5-methyl-2-((4-(methylsulphonyl)piperazin-1-yl)methyl)-4-oxo-4,5-dihydrothieno[3,2-c]pyridin-7-yl)benzylcarbamate (124 mg, 90%) as a viscous yellow oil.

LCMS (2 min, Formic Acid): Rt=0.83 min, MH$^+$=547

Intermediate 86

2-chloro-N-(2-methoxyethyl)-N-methylpyridin-4-amine

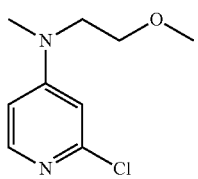

A mixture of 4-bromo-2-chloropyridine (4.35 g, 2.5 mL, 22.6 mmol) and 2-methoxy-N-methylethanamine (6.09 g, 7.5 mL, 68.3 mmol) was heated in a microwave at 150° C. for 1 hour. The reaction mixture was cooled to room temperature. The solution was diluted with toluene (20 mL), the solvent evaporated and then re-evaporated from toluene (x2). The residue was chromatographed [20-50% ethyl acetate/hexane] to give: 2-chloro-N-(2-methoxyethyl)-N-methylpyridin-4-amine (3.25 g, 72% yield) as a colourless oil.

LCMS (2 min, Formic Acid): Rt=0.41 min, MH$^+$=201/203.

Intermediate 87

(S)-3-methyl-1-(methylsulphonyl)piperazine hydrochloride

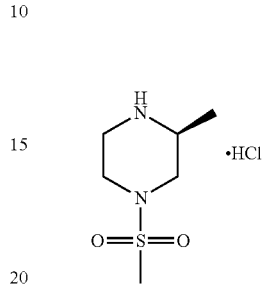

Methanesulphonyl chloride (467 µL, 5.99 mmol) was added to a stirred solution of (S)-tert-butyl 2-methylpiperazine-1-carboxylate (1.0 g, 4.99 mmol) in dichloromethane (20 mL) and pyridine (2 mL).

The reaction mixture was stirred at room temperature overnight. The solvent was evaporated. The residue was dissolved in diethyl ether (50 mL) and washed with 1M hydrochloric acid (25 mL) followed by water (25 mL) and brine (25 mL). The organic phase was dried and evaporated. The product was dissolved in diethyl ether (20 mL) and treated with 4M hydrogen chloride in 1,4-dioxane (4 mL) and allowed to stand at room temperature overnight. The solvent was evaporated. The residue was triturated with diethyl ether, was filtered off, washed with diethyl ether and dried to give (S)-3-methyl-1-(methylsulphonyl)piperazine hydrochloride (457 mg, 2.128 mmol, 42.6% yield) as a colourless solid.

$^1$H NMR (400 MHz, CDCl$_3$) δ-ppm 3.78-3.60 (m, 2H); 3.08 (dt, J=12 Hz and J=4 Hz, 1H); 2.95 (J=12 Hz and J=4 Hz, 1H); 2.95-2.86 (m, 2H); 2.77 (s, 3H); 2.70 (td, J=8 Hz and J=4 Hz, 1H); 2.31 (dd, J=12 Hz and J=12 Hz, 1H); 1.09 (d, J=8 Hz, 3H).

Intermediate 88

(S)-7-bromo-5-methyl-2-((2-methyl-4-(methylsulphonyl)piperazin-1-yl)methyl)thieno[3,2-c]pyridin-4(5H)-one

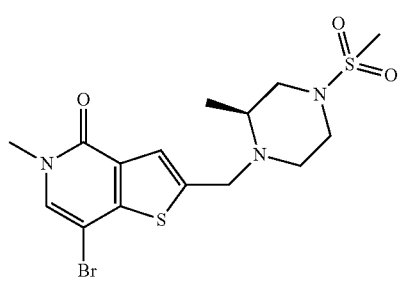 [SMILES: C[C@H]1CN(S(C)(=O)=O)CCN1Cc1cc2c(=O)n(C)cc(Br)c2s1]

(S)-3-methyl-1-(methylsulphonyl)piperazine hydrochloride (for a preparation see Intermediate 87, 1.1 g, 5.12 mmol) and glacial acetic acid (292 µL, 5.11 mmol) were added to a stirred solution of 7-bromo-5-methyl-4-oxo-4,5-dihydrothieno[3,2-c]pyridine-2-carbaldehyde (for a preparation see Intermediate 3, 1.39 g, 5.11 mmol) in dichloromethane (50 mL). The reaction mixture was stirred at room temperature for 30 minutes then treated with sodium triacetoxyborohydride (5.41 g, 25.5 mmol). The reaction mixture was refluxed for 4 hours then cooled to room temperature. Saturated sodium bicarbonate (50 mL) was added and the mixture stirred for 10 minutes. The organic phase was separated and the aqueous phase extracted with dichloromethane (2×50 mL). The combined organics were dried and evaporated. Chromatography [2% methanol/dichloromethane] of the residue gave (S)-7-bromo-5-methyl-2-((2-methyl-4-(methylsulphonyl)piperazin-1-yl)methyl)thieno[3,2-c]pyridin-4(5H)-one as a pale orange solid (1.47 g, 3.38 mmol, 66.3% yield).

LCMS (2 min, Formic Acid): Rt=0.62 min, MH$^+$=434/436

Intermediate 89

(S)-3-bromo-5-(1-(pyridin-2-yl)ethoxy)pyridine

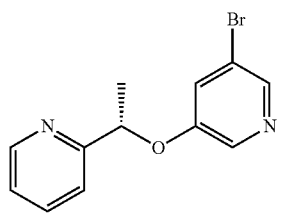 [SMILES: C[C@H](Oc1cncc(Br)c1)c1ccccn1]

A mixture of (R)-1-(pyridin-2-yl)ethanol (107.3 mg, 0.871 mmol), 5-bromopyridin-3-ol (120.9 mg, 0.695 mmol) and 2-(tributylphosphoranylidene)acetonitrile (501.2 mg, 2.077 mmol) in toluene (3 mL) was heated with stirring in a sealed vial in a microwave reactor at 120° C. for 40 min. The mixture was concentrated under a stream of nitrogen and the residue was re-dissolved in DCM (~3 mL) and was purified by Biotage SP4 flash column chromatography (10 g silica SNAP cartridge) eluting with a gradient of 0-8% (2M ammonia in MeOH solution) in DCM. The required fractions were combined and the solvent evaporated under a stream of nitrogen to give the crude desired product which was further purified by Biotage SP4 flash column chromatography (10 g silica SNAP cartridge) eluting with a gradient of 0-50% EtOAc in cyclohexane. The required fractions were combined and the solvent evaporated in vacuo to give the title compound as an orange oil (154.6 mg, 0.554 mmol, 80% yield)

LCMS (2 min, Formic Acid): Rt=0.83 min, MH$^+$=279/281

Enantiomeric purity by chiral HPLC=>86% e.e.

Intermediate 90

(S)-(5-(1-(pyridin-2-yl)ethoxy)pyridin-3-yl)boronic acid

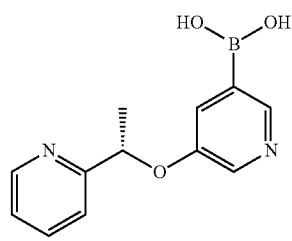 [SMILES: C[C@H](Oc1cncc(B(O)O)c1)c1ccccn1]

To a microwave vial was added (S)-3-bromo-5-(1-(pyridin-2-yl)ethoxy)pyridine (Intermediate 89) (149.3 mg, 0.535 mmol), potassium acetate (211.8 mg, 2.158 mmol), bis(pinacolato)diboron (679.8 mg, 2.68 mmol), dichloro[1,1'-bis(diphenylphosphino)ferrocene]palladium (II) dichloromethane complex (40.7 mg, 0.056 mmol) and 1,4-dioxane (5 mL). The vial was sealed and heated with stirring at 110° C. for 30 min in a microwave reactor. The mixture was diluted with EtOAc (20 mL), dried over magnesium sulphate and filtered through a 2.5 g Celite cartridge. The filtrate was evaporated in vacuo to give the crude title compound as a brown solid, yield=662.4 mg (theoretical yield=131 mg). LCMS and mass recovery together indicated that the product was c.a. 20% pure, and the material was used crude in the next stage without further purification.

LCMS (2 min, Formic Acid): Rt=0.41 min, MH$^+$=245.

Intermediate 91

(R)-1-(ethylsulfonyl)-3-methylpiperazine

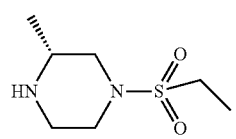

(2R)-2-Methylpiperazine (401 mg, 4 mmol) was dissolved in THF (15 mL). The stirred solution was cooled in an ice-water bath, and treated with 2M aqueous sodium hydroxide (6.0 mL, 12.00 mmol). A solution of ethanesulfonyl chloride (0.4 mL, 4.22 mmol) in THF (2 mL) was added dropwise using further THF (3 mL) to wash in. The reaction mixture was stirred cold, being allowed to warm up slowly. After 2 hr the reaction mixture was partitioned between water (50 mL) and DCM (50 mL). The layers were separated and the aqueous was extracted with further DCM (2×25 mL). The combined organic extracts were concentrated in vacuo. The residue was re-dissolved in DCM (50 mL) and the product extracted into 1M HCl (50 mL). The layers were separated and the aqueous was washed with further DCM (2×25 mL). The aqueous was then treated with 2N aqueous NaOH (27 mL) to give pH~13. This was extracted with DCM (50 mL, 2×25 mL). The combined DCM extracts were concentrated in vacuo to give the title compound (599 mg, 3.12 mmol, 78% yield) as a colourless oil.

LCMS (2 min, High pH): Rt=0.49 min, MH$^+$=193

Intermediate 92

(R)-7-bromo-2-((4-(ethylsulfonyl)-2-methylpiper-azin-1-yl)methyl)-5-methylthieno[3,2-c]pyridin-4(5H)-one

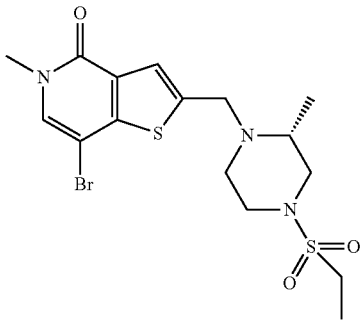 [SMILES: CCS(=O)(=O)N1CCN(Cc2cc3c(=O)n(C)cc(Br)c3s2)[C@H](C)C1]

A suspension of 7-bromo-5-methyl-4-oxo-4,5-dihydrothieno[3,2-c]pyridine-2-carbaldehyde (Intermediate 3) (116 mg, 0.426 mmol) in MeOH (4 mL) and acetic acid (500 μL) was treated with (R)-1-(ethylsulfonyl)-3-methylpiperazine (Intermediate 91) (98.5 mg, 0.512 mmol). The reaction mixture was stirred at rt under nitrogen for 15 min and was then treated with 2-picoline-borane complex (50.1 mg, 0.469 mmol). The reaction mixture was heated to 50° C. and stirred under nitrogen for 1 hr. The reaction was left under the conditions described overnight (16 hours). The reaction was treated with a further portion of 2-picoline-borane complex (50.1 mg, 0.469 mmol) and stirred under the conditions described for a further 2.5 hr. The reaction was cooled to room temperature and concentrated under reduced pressure to give a light orange oil. The oil was taken up in DCM (20 mL) and washed with saturated sodium bicarbonate solution (25 mL). The organic phase was collected and the aqueous phase was back extracted with DCM (2×20 mL). The organic portions were combined, dried over magnesium sulfate, and concentrated under reduced pressure to give an orange oil. The crude material was loaded on to a 12 g silica gel column and was eluted with 0-80% ethyl acetate in cyclohexane over 20 column volumes then with 0-5% MeOH in DCM to give the title compound (102 mg, 0.227 mmol, 53.4% yield), as a pale yellow solid.

LCMS (2 min, Formic Acid): Rt=0.66 min, MH+=448/450.

Intermediate 93

N-(4-(2-(hydroxymethyl)-5-methyl-4-oxo-4,5-dihydrothieno[3,2-c]pyridin-7-yl)pyridin-2-yl)acetamide

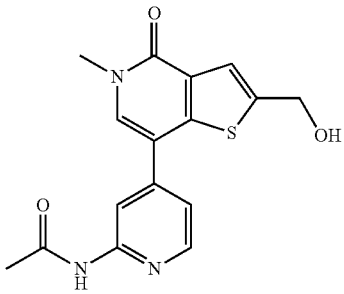 [SMILES: CC(=O)Nc1cc(-c2cn(C)c(=O)c3cc(CO)sc23)ccn1]

A suspension of 7-bromo-2-(hydroxymethyl)-5-methylthieno[3,2-c]pyridin-4(5H)-one (Intermediate 43) (1 g, 3.65 mmol) in isopropanol (25 mL) and water (25 mL) was treated with N-(4-(4,4,5,5-tetramethyl-1,3,2-dioxaborolan-2-yl)pyridin-2-yl)acetamide (1.912 g, 7.30 mmol) followed by potassium carbonate (2.017 g, 14.59 mmol), and lastly the PEPPSI catalyst (0.248 g, 0.365 mmol).

The reaction was warmed to 60° C. and stirred under nitrogen overnight. The reaction mixture was treated with a fresh portion of the PEPPSI (0.248 g, 0.365 mmol) catalyst and heated to 100° C. for 4.5 hours. The reaction was cooled to room temperature, diluted with EtOAc (50 mL), and filtered through a 10 g Celite frit to remove inorganic impurities. The filtrated was concentrated under reduced pressure to give a yellow solid. The material was triturated with diethyl ether to give a yellow solid which was suspended in MeOH and heated to 100° C. The mixture was refluxed for 20 minutes and allowed to cool to room temperature overnight. The solids were collected in a glass filter funnel and washed with cold MeOH (approx. 25 mL). The product was dried under vacuum for 20 minutes and transferred to a vacuum oven to dry for several hours to give the title compound (1.38 g, 4.19 mmol, 115% yield), as a cream coloured solid. $^1$H NMR (400 MHz, DMSO-d$_6$) δ-ppm 10.6 (1H, s), 8.58 (1H, s), 8.50 (1H, s), 8.40 (1H, d), 7.94 (1H, s), 7.40 (1H, s), 7.33 (1H, d), 4.71 (2H, s), 3.60 (3H, s), 2.12 (3H, s).

Intermediate 94

N-(4-(2-(bromomethyl)-5-methyl-4-oxo-4,5-dihydrothieno[3,2-c]pyridin-7-yl)pyridin-2-yl)acetamide

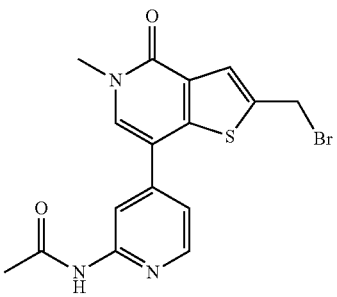 [SMILES: CC(=O)Nc1cc(-c2cn(C)c(=O)c3cc(CBr)sc23)ccn1]

N-(4-(2-(Hydroxymethyl)-5-methyl-4-oxo-4,5-dihydrothieno[3,2-c]pyridin-7-yl)pyridin-2-yl)acetamide (Intermediate 93) (1.38 g, 4.19 mmol) was suspended in 1,4-dioxane (40 mL) and heated to 60° C. The reaction was slowly treated with a 1 M solution of tribromophosphine (20.95 mL, 20.95 mmol) in DCM. The reaction mixture was stirred under an atmosphere of nitrogen at 60° C. overnight (18 hr). The reaction was cooled to room temperature and concentrated under reduced pressure to give a bright yellow solid. The material was taken up in diethyl ether to quench and remove residual tribromophosphine. The solids were collected in a glass filter funnel and washed with fresh ether and dried under vacuum to give the title compound (1.644 g, 4.19 mmol, 100% yield) as a yellow solid. The material was analysed by $^1$H NMR which confirmed formation of the alkyl bromide by the change in chemical shift in the adjacent CH$_2$ in the spectrum of the starting material (δ 4.71 ppm) to the product (δ 5.1 ppm). The material was used in subsequent steps without further purification.

Intermediate 95

7-bromo-2-((3,3-difluoropiperidin-1-yl)methyl)-5-methylthieno[3,2-c]pyridin-4(5H)-one

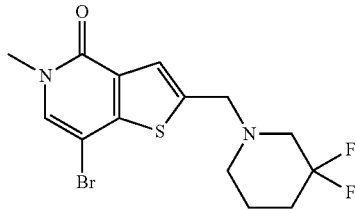 [SMILES: Cn1cc(Br)c2sc(CN3CCCC(F)(F)C3)cc2c1=O]

3,3-Difluoropiperidine hydrochloride (319 mg, 2.02 mmol) was added to a stirred solution of 7-bromo-5-methyl-4-oxo-4,5-dihydrothieno[3,2-c]pyridine-2-carbaldehyde (Intermediate 3) (500 mg, 1.84 mmol) in MeOH (9 mL) and glacial acetic acid (1 mL). The mixture was stirred at room temperature for 15 minutes then 2-picolineborane complex (216 mg, 2.02 mmol) was added. The reaction mixture was stirred at room temperature for 2 hours. The solvent was evaporated. Saturated sodium bicarbonate solution (15 mL) was added. The mixture was extracted with DCM (3×15 mL). The combined extracts were dried and evaporated. The residue was purified by column chromatography on silica gel (2-4% MeOH/DCM) to give the title compound (442 mg, 1.172 mmol, 63.8% yield) as a yellow solid.

LCMS (2 min, Formic Acid): Rt=0.85 min, MH$^+$=377/379

Intermediate 96

7-bromo-2-((3-fluoropiperidin-1-yl)methyl)-5-methylthieno[3,2-c]pyridin-4(5H)-one

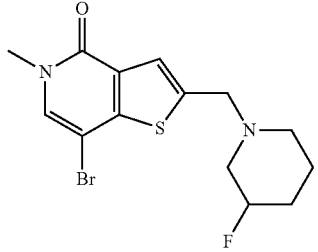 [SMILES: Cn1cc(Br)c2sc(CN3CCCC(F)C3)cc2c1=O]

The title compound was prepared using a method similar to that described for Intermediate 95.

Yellow solid (346 mg, 0.963 mmol, 52.4% yield).

LCMS (2 min, Formic Acid): Rt=0.49 min, MH$^+$=359/361.

Intermediate 97

4-bromo-2-(cyclopropylmethoxy)pyridine

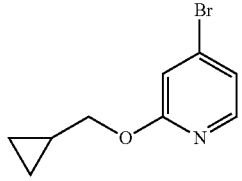 [SMILES: Brc1ccnc(OCC2CC2)c1]

Cyclopropylmethanol (0.247 mL, 3.12 mmol) was dissolved in dry THF (10 mL) and sodium hydride (60% w/w) (125 mg, 3.12 mmol) was added portion-wise, under nitrogen, at rt. After ~30 min, 4-bromo-2-chloropyridine (0.173 mL, 1.559 mmol) was added slowly and the reaction was stirred at rt for 5 days. The reaction was diluted with Et$_2$O (30 mL) and washed with water (20 mL). The organic layer was washed with brine, dried using a hydrophobic frit and evaporated to give a yellow oil (0.432 g). The residue was loaded in DCM and purified on the Biotage SP4 silica (Si) SNAP 25 g column using a 0-20% EtOAc/cyclohexane gradient. Appropriate fractions were combined and evaporated to give a colourless oil (295 mg) This was loaded in cyclohexane and purified by Biotage SP4 SNAP 25 g silica using a gradient of 0-10% EtOAc/cyclohexane gradient. Fractions containing product were combined and evaporated under vacuum to give a colourless oil which was dissolved in 1:1 MeOH:DMSO 1 mL (×3) and purified by MDAP. The solvent was evaporated under vacuum to give a the title compound as a colourless oil (97 mg).

LCMS (2 min, Formic Acid): Rt=1.21 min, MH$^+$=228/230.

Intermediate 98

4-bromo-2-(2-(pyrrolidin-1-yl)ethoxy)pyridine

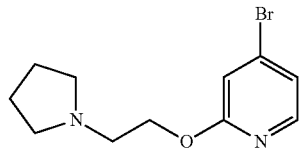 [SMILES: Brc1ccnc(OCCN2CCCC2)c1]

2-(Pyrrolidin-1-yl)ethanol (1.240 mL, 10.39 mmol) was dissolved in THF (30 mL) and sodium hydride (60% w/w) (0.416 g, 10.39 mmol) was added portion-wise under nitrogen. This was left to stir for 15 min at rt before 4-bromo-2-chloropyridine (0.577 mL, 5.20 mmol) was added and left to stir at rt for 3 days. Water was added (40 mL) and the organic product was extracted with EtOAc and washed with brine and separated and dried through a hydrophobic frit and concentrated in vacuo. The residue was purified by silica gel column chromatography [0-5% MeOH/NH$_3$ in DCM] and fractions containing product were combined and concentrated in vacuo to give the title compound.

LCMS (2 min, Formic Acid): Rt=0.54 min, MH$^+$=271/273.

Intermediate 99

4-bromo-2-(2-methoxyethoxy)pyridine

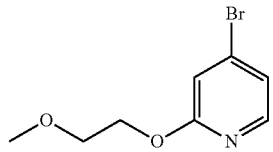

2-Methoxyethanol (0.820 mL, 10.39 mmol) was dissolved in THF (30 mL) and sodium hydride (60% w/w) (0.416 g, 10.39 mmol) was added under nitrogen and left to stir at rt for 15 min. 4-bromo-2-chloropyridine (0.577 mL, 5.20 mmol) was added and the reaction was left stirring at rt overnight. More 2-methoxyethanol (0.410 mL, 5.19 mmol) was dissolved in 1,2-DME (10 mL) and sodium hydride (60% w/w) (0.208 mg, 5.19 mmol) was added. The mixture was stirred under nitrogen at rt for 15 min then added to the reaction which was stirred at rt for 3 days. Water was added (40 mL) and the organic product was extracted with EtOAc and washed with brine, dried through a hydrophobic frit and concentrated in vacuo. The residue was purified by silica gel column chromatography [0-20% EtOAc in cyclohexane] and fractions containing product were concentrated in vacuo to give the title compound as a colourless liquid (314 mg, 1.353 mmol, 26.0% yield).

LCMS (2 min, Formic Acid): Rt=0.93 min, MH$^+$=232/234.

Intermediate 100

4-bromo-3-(cyclopropylmethoxy)pyridine

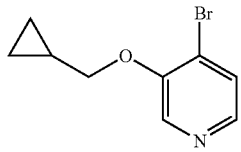 [SMILES: Brc1ccncc1OCC1CC1]

Sodium hydride (60% w/w) (110 mg, 2.76 mmol) was added to 4-bromopyridin-3-ol (400 mg, 2.299 mmol) in DMF (15 mL) at 00° C. and left stirring for 30 minutes. (Bromomethyl)cyclopropane (0.268 mL, 2.76 mmol) was added and the reaction was warmed to rt and stirred overnight. Water was added (40 mL) and the organic product was extracted with EtOAc and washed with brine, dried through a hydrophobic frit and concentrated in vacuo. The residue was purified by silica gel column chromatography [0-5% MeOH/NH$_3$ in DCM] and fractions containing product were combined and concentrated in vacuo to give the title compound as a brown oil (234 mg, 1.026 mmol, 44.6% yield).

LCMS (2 min, Formic Acid): Rt=0.87 min, MH$^+$=228/230.

Intermediate 101

N-(4-bromopyridin-2-yl)propionamide

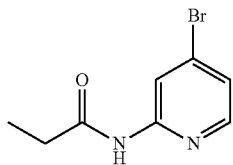

Pyridine (0.374 mL, 4.62 mmol) was added to a solution of 4-bromopyridin-2-amine (400 mg, 2.312 mmol) in DCM (10 mL) and stirred at rt for 20 min. Propionyl chloride (0.232 mL, 2.66 mmol) was added and the solution was stirred at rt overnight. Water was added and the product was extracted with DCM. The organic layer was washed with brine, filtered through a hydrophobic frit, and concentrated in vacuo. The residue was dissolved in MeOH and passed through a 10 g aminopropyl column, eluting with MeOH. The solvent was evaporated of to give the title compound as a white solid (464 mg, 2.026 mmol, 88% yield).

LCMS (2 min, High pH): Rt=0.84 min, MH$^+$=229/231.

Intermediate 102

N-(4-bromopyridin-2-yl)cyclopropanecarboxamide

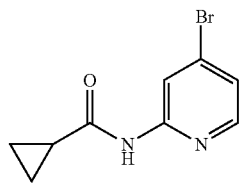 [SMILES: O=C(Nc1cc(Br)ccn1)C1CC1]

Pyridine (0.467 mL, 5.78 mmol) was added to a solution of 4-bromopyridin-2-amine (500 mg, 2.89 mmol) in DCM (10 mL) and stirred at rt for 20 min. Cyclopropanecarbonyl chloride (0.302 mL, 3.32 mmol) was added and the solution was stirred for 4 hr. More cyclopropanecarbonyl chloride (0.302 mL, 3.32 mmol) and pyridine (0.234 mL, 2.89 mmol) were added and the reaction was stirred for 5 hr. Water was added and the product was extracted with DCM. The organic layer was washed with brine, filtered through a hydrophobic frit, and concentrated in vacuo. The residue was dissolved in MeOH and passed through a 10 g aminopropyl column, eluting with MeOH. The solvent was evaporated off to give the title compound as a white solid (610 mg, 2.53 mmol, 88% yield).

LCMS (2 min, Formic Acid): Rt=0.84 min, MH$^+$=241/243.

Intermediate 103

N-(4-bromopyridin-2-yl)acetamide

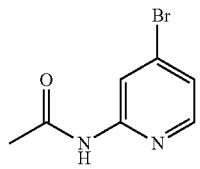

Pyridine (0.374 mL, 4.62 mmol) was added to a solution of 4-bromopyridin-2-amine (400 mg, 2.312 mmol) in DCM (10 mL) and stirred at rt for 20 min. Acetyl chloride (0.190 mL, 2.66 mmol) was added and the solution was stirred at rt overnight. Water was added and the product was extracted with DCM. The organic layer was washed with brine, filtered through a hydrophobic frit, and concentrated in vacuo. The residue was dissolved in MeOH and passed through a 10 g aminopropyl column, eluting with MeOH. The solvent was evaporated give the title compound as a white solid (404 mg, 1.879 mmol, 81% yield).

LCMS (2 min, High pH): Rt=0.65 min, MH$^+$=215/217.

Intermediate 104

N-(4-bromopyridin-2-yl)-N-methylacetamide

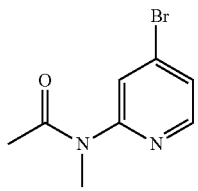

N-(4-Bromopyridin-2-yl)acetamide (Intermediate 103) (406 mg, 1.888 mmol) was dissolved in DMF and cooled to 0° C. Sodium hydride (60% w/w) (91 mg, 2.266 mmol) was added and the mixture was stirred for 15 minutes. Iodomethane (142 µl, 2.266 mmol) was added at rt and the reaction was stirred for 2 hr. Water was added and the product was extracted with diethyl ether (×4). The combined organics were evaporated off to leave a residue which was purified by silica gel column chromatography [50-100% EtOAc/cyclohexane]. Fractions containing product were combined and concentrated in vacuo to give the title compound as a colourless oil (252 mg, 1.100 mmol, 58.3% yield).

LCMS (2 min, High pH): Rt=0.69 min, MH$^+$=229/231.

Intermediate 105

1-(2-((4-bromopyridin-2-yl)oxy)ethyl)pyrrolidin-2-one

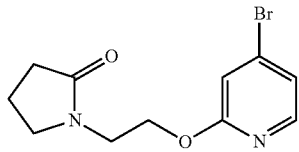 [SMILES: O=C1CCCN1CCOc1cc(Br)ccn1]

A stirred suspension of 1-(2-hydroxyethyl)pyrrolidin-2-one (0.324 mL, 2.87 mmol), triphenylphosphine (904 mg, 3.45 mmol) and 4-bromopyridin-2-ol (500 mg, 2.87 mmol) in THF (10 mL) was flushed with nitrogen and cooled in an ice bath for 15 min before the addition of DIAD (0.670 mL, 3.45 mmol) portion-wise. The mixture was left to stir for 1 hr. The mixture was diluted with EtOAc (20 mL) and water (20 mL). Two layers separated and the aqueous layer was further extracted with EtOAc (2×20 mL). The organic extracts were evaporated to dryness and the remaining yellow solid was dissolved in DCM, loaded onto a SNAP silica cartridge (100 g) and eluted with a gradient of 5% MeOH in EtOAc. Appropriate fractions were combined and reduced in vacuo to give the title compound as a clear oil (490 mg, 59.8%).

LCMS (2 min, Formic Acid): Rt=0.82 min, MH$^+$=285/287.

Intermediate 106

3-bromo-5-(cyclopropylmethoxy)pyridine

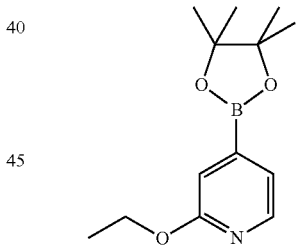

To a stirred suspension of 5-bromopyridin-3-ol (300 mg, 1.724 mmol) in DMF (8 mL) was added, sodium hydride (60% w/w) (83 mg, 2.069 mmol). The mixture was stirred for 30 min and (bromomethyl)cyclopropane (0.201 mL, 2.069 mmol) was added. The mixture was stirred overnight. then heated to 40° C. for 2 hr. The mixture was diluted with water (30 mL), and diethyl ether (30 mL). The layers were separated and the aqueous layer was re-extracted with diethyl ether (3×30 mL). The organics were dried using a hydrophobic frit and concentrated in vacuo to give a yellow oil. This was dissolved in DCM and loaded onto a SNAP silica column (25 g) and eluted with a gradient of 0-30% EtOAc in cyclohexane.

Appropriate fractions were combined and concentrated in vacuo to give the title compound as a clear oil (239 mg, 60.8%).

LCMS (2 min, Formic Acid): Rt=1.03 min, MH$^+$=228/230.

Intermediate 107

2-Ethoxy-4-(4,4,5,5-tetramethyl-1,3,2-dioxaborolan-2-yl)pyridine

A mixture of 4-bromo-2-ethoxypyridine (150 mg, 0.742 mmol), bis(pinacolato)diboron (754 mg, 2.97 mmol), PdCl$_2$(dppf) (54.3 mg, 0.074 mmol) and potassium acetate (291 mg, 2.97 mmol) in 1,4-dioxane (3 mL) was heated in a microwave at 110° C. for 2×30 min. The reaction was diluted with EtOAc and filtered through a Celite column. The filtrate was evaporated to give a brown residue. This crude material was used in subsequent steps without further purification and the yield was assumed to be 100% (0.742 mmol, 185 mg).

LCMS (2 min, Formic Acid): Rt=0.43 min, MH$^+$=168 consistent with hydrolysis to boronic acid under LCMS conditions Intermediates 108-115

The boronate ester intermediates in the following table were prepared in a manner similar to that described for Intermediate 107 and used crude in subsequent steps assuming 100% conversion to the boronate ester product. LCMS using formic acid method shows boronic acid formed under acidic conditions in all cases.

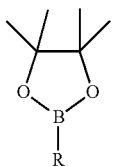

| Intermediate | Starting Material | R | Temp °C. | Time min | LCMS Rt min | MH+ |
|---|---|---|---|---|---|---|
| 108 | Intermediate 97 | 4-(cyclopropylmethoxy)pyridin-2-yl | 110 | 30 | 0.61 | 194 |
| 109 | Intermediate 98 | 2-(2-(pyrrolidin-1-yl)ethoxy)pyridin-4-yl | 100 | 30 | 0.34 | 237 |
| 110 | Intermediate 99 | 2-(2-methoxyethoxy)pyridin-4-yl | 100 | 30 | 0.44 | 198 |
| 111 | Intermediate 100 | 3-(cyclopropylmethoxy)pyridin-4-yl | 100 | 30 | 0.35 | 194 |
| 112 | commercial | 2-methoxypyridin-4-yl | 110 | 30 | 0.35 | 154 |
| 113 | Intermediate 101 | N-(pyridin-2-yl)propionamide-4-yl | 100 | 30 | 0.34 | 195 |
| 114 | Intermediate 103 | N-(pyridin-2-yl)cyclopropanecarboxamide-4-yl | 100 | 30 | 0.37 | 207 |

| Intermediate | Starting Material | R | Temp °C. | Time min | LCMS Rt min | MH+ |
|---|---|---|---|---|---|---|
| 115 | Intermediate 104 | 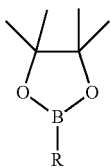 | 100 | 30 | 0.37 | 195 |

Intermediate 116

1-(2-((4-(4,4,5,5-Tetramethyl-1,3,2-dioxaborolan-2-yl)pyridin-2-yl)oxy)ethyl)pyrrolidin-2-one

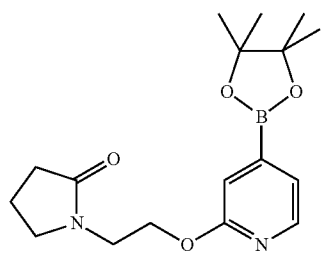 [SMILES: CC1(C)OB(c2ccnc(OCCN3CCCC3=O)c2)OC1(C)C]

To a stirred suspension of 1-(2-((4-bromopyridin-2-yl)oxy)ethyl)pyrrolidin-2-one (Intermediate 105) (490 mg, 1.718 mmol), 4,4,4',4',5,5,5',5'-octamethyl-2,2'-bi(1,3,2-dioxaborolane) (873 mg, 3.44 mmol) and potassium acetate (506 mg, 5.16 mmol) was added PdCl$_2$(dppf) (126 mg, 0.172 mmol). The mixture was placed in a microwave vial and heated in a Biotage Initiator microwave reactor microwave at 100° C. for 1 hr. The mixture was diluted in ethyl acetate and filtered through a Celite cartridge (10 g). The solvent was evaporated to give a brown oil (1.35 g, 4.06 mmol, 236%). This crude material was used in the next step without further purification: 100% conversion assumed therefore maximum purity of crude material is 42%.

LCMS (2 min, Formic Acid): Rt=0.46 min, MH+=251 consistent with hydrolysis to boronic acid under LCMS conditions $^1$H NMR (400 MHz, CDCl$_3$) δ-ppm 8.15 (1H, d), 7.19 (1H, d), 7.12 (1H, s), 4.42 (2H, t), 3.67 (2H, t), 3.53 (2H, t), 2.38 (2H, t), 2.00 (2H, m), 1.34 (12H, s).

Intermediate 117

3-(cyclopropylmethoxy)-5-(4,4,5,5-tetramethyl-1,3,2-dioxaborolan-2-yl)pyridine

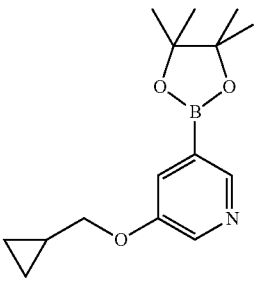 [SMILES: CC1(C)OB(c2cncc(OCC3CC3)c2)OC1(C)C]

The title compound was prepared in crude form from 3-bromo-5-(cyclopropylmethoxy)pyridine (Intermediate 106) using the method described for Intermediate 116.

LCMS (2 min, Formic Acid): Rt=0.43 min, MH+=194 consistent with hydrolysis to boronic acid under LCMS conditions.

Intermediate 118

7-bromo-2-((3-hydroxypiperidin-1-yl)methyl)-5-methylthieno[3,2-c]pyridin-4(5H)-one

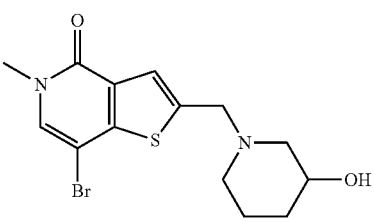 [SMILES: Cn1cc(Br)c2sc(CN3CCCC(O)C3)cc2c1=O]

Piperidin-3-ol hydrochloride (0.759 g, 5.51 mmol) was added to a suspension 7-bromo-5-methyl-4-oxo-4,5-dihydrothieno[3,2-c]pyridine-2-carbaldehyde (Intermediate 3) (1 g, 3.67 mmol) in MeOH (18 mL) and acetic acid (2 mL) and the mixture was stirred for 30 min at rt. 2-Picoline-borane complex (0.590 g, 5.51 mmol) was added and the reaction was stirred o/n. The reaction was heated to 50° C. and stirred for 4 hr. The solvent was evaporated and sodium bicarbonate was added (30 mL). The residue was extracted with DCM (3×20 mL). The extracts were dried by filtration through a hydrophobic frit and then concentrated in vacuo to give the crude product which was purified by silica gel column chromatography [0-5% MeOH in DCM]. Fractions containing pure product were concentrated in vacuo. Fractions containing a mixture of compounds were combined and concentrated in vacuo then purified by silica gel column chromatography [5% MeOH in DCM]. All pure product containing fractions were combined to give the title compound as a yellow solid 7-bromo-2-((3-hydroxypiperidin-1-yl)methyl)-5-methylthieno[3,2-c]pyridin-4(5H)-one (603 mg, 1.688 mmol, 45.9% yield).

LCMS (2 min, Formic Acid): Rt=0.49 min, MH$^+$=357/359.

Intermediate 119

2-chloro-6-(cyclopropylmethoxy)-4-iodopyridine

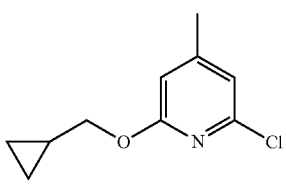

To a stirred suspension of cyclopropylmethanol (0.577 mL, 7.30 mmol) in THF (50 mL) was added sodium hydride (60% w/w) (0.292 g, 7.30 mmol) portion-wise under nitrogen. The mixture was stirred for 30 min then 2,6-dichloro-4-iodopyridine (2 g, 7.30 mmol) was added. The mixture was stirred for 1 hr then evaporated to dryness under reduced pressure. The residue was dissolved in MeOH and silica gel was added. The solvent was removed in vacuo and the material was loaded on to a SNAP 340 g silica gel column as a dry solid and eluted with a gradient of 0-10% DCM in cyclohexane. Appropriate fractions were combined and concentrated in vacuo to give the title compound as a white solid (860 mg, 38%).

LCMS (2 min, Formic Acid): Rt=1.42 min, MH$^+$=310/312

Intermediate 120

2-chloro-6-(cyclopropylmethoxy)-4-(4,4,5,5-tetramethyl-1,3,2-dioxaborolan-2-yl)pyridine

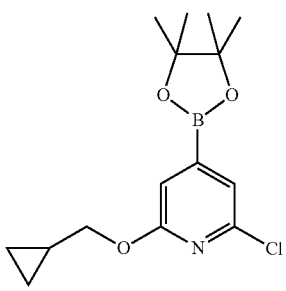 [SMILES: CC1(C)OB(c2cc(Cl)nc(OCC3CC3)c2)OC1(C)C]

To a stirred suspension of 2-chloro-6-(cyclopropylmethoxy)-4-iodopyridine (Intermediate 119) (100 mg, 0.323 mmol) in 1,4-dioxane (8 mL), was added 4,4,4',4',5,5,5',5'-octamethyl-2,2'-bi(1,3,2-dioxaborolane) (164 mg, 0.646 mmol), potassium acetate (95 mg, 0.969 mmol) and PdCl$_2$(dppf) (23.64 mg, 0.032 mmol). This was sealed in a microwave vial, heated to 100° C. in a Biotage microwave for 1 hr then at 120° C. for 2 hr. The mixture was diluted with EtOAc (20 mL) and water (20 mL). Two layers separated and the aqueous layer was further extracted with EtOAc (2×20 mL). The combined organic layers were reduced to give the title compound as a brown oil (160 mg, 0.517 mmol, 160%). This crude material was used in the next step without further purification: 100% conversion assumed therefore maximum purity of crude material is 62.5%.

LCMS (2 min, Formic Acid): Rt=0.95 min, MH$^+$=228/230 consistent with hydrolysis to boronic acid under LCMS conditions.

Intermediate 121: (R)-7-(2-chloro-6-(cyclopropylmethoxy)pyridin-4-yl)-5-methyl-2-((2-methyl-4-(methylsulfonyl)piperazin-1-yl)methyl)thieno[3,2-c]pyridin-4(5H)-one

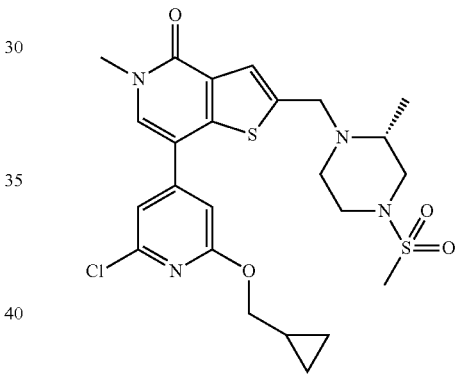

To a stirred suspension of crude 2-chloro-6-(cyclopropylmethoxy)-4-(4,4,5,5-tetramethyl-1,3,2-dioxaborolan-2-yl)pyridine (Intermediate 120) (157 mg, 62.5% w/w, 0.317 mmol) in 1,2-DME (4 mL), was added potassium carbonate (95 mg, 0.691 mmol), (R)-7-bromo-5-methyl-2-((2-methyl-4-(methylsulfonyl)piperazin-1-yl)methyl)thieno[3,2-c]pyridin-4(5H)-one (Intermediate 21) (100 mg, 0.230 mmol) and tetrakis(triphenylphosphine) palladium (0) (11 mg, 9.52 μmol). The contents were sealed in a microwave vial and placed in a Biotage Initiator microwave reactor microwave for 2 hr and heated to 120° C. The mixture was dissolved in EtOAc (20 mL) and water (20 mL). The aqueous layer was further extracted with EtOAc (3×20 mL). The organics were concentrated in vacuo to give a brown oil. This was dissolved in DCM and loaded onto a SNAP silica cartridge (10 g) and eluted with a gradient of 2.5% MeOH in EtOAc. Appropriate fractions were combined and reduced in vacuo to give a brown oil (30 mg, 24.3%).

LCMS (2 min, Formic Acid): Rt=1.02 min, MH$^+$=537/539.

Intermediate 122

7-bromo-5-methyl-2-(morpholinomethyl)thieo[3,2-c]pyridin-4(5H)-one

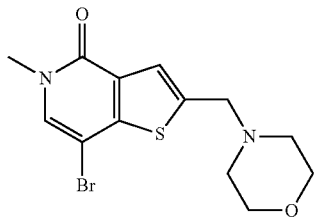

A mixture of 7-bromo-5-methyl-4-oxo-4,5-dihydrothieno[3,2-c]pyridine-2-carbaldehyde (Intermediate 3) (1.0 g, 3.67 mmol) and morpholine (480 mg, 475 µL, 5.51 mmol) in MeOH (19 mL) and glacial acetic acid (1 mL) was stirred at rt for 15 min. The reaction mixture was treated with 2-picoline-borane complex (1.18 g, 11.03 mmol). The reaction mixture was stirred at rt for 24 hours. The solvent was evaporated. Saturated sodium bicarbonate solution (50 mL) was added to the residue. The mixture was extracted with DCM (3×25 9 mL). The combined extracts were washed with brine, dried and evaporated. The residue was by silica gel column chromatography [0-5% MeOH/DCM] to give the title compound (708 mg, 2.063 mmol, 56.1% yield) as a pale yellow solid.

LCMS (2 min, Formic Acid): Rt=0.48 min, MH$^+$=343/345.

Intermediate 123 tert-butyl 4-((7-bromo-5-methyl-4-oxo-4,5-dihydrothieno[3,2-c]pyridin-2-yl)methyl)-1,4-diazepane-1-carboxylate

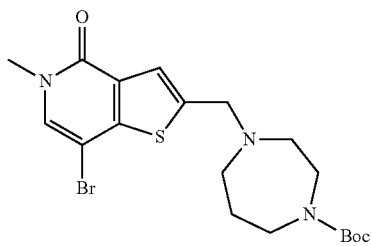 [SMILES: Cn1cc(Br)c2sc(CN3CCCN(C(=O)OC(C)(C)C)CC3)cc2c1=O]

To a solution of 7-bromo-5-methyl-4-oxo-4,5-dihydrothieno[3,2-c]pyridine-2-carbaldehyde (Intermediate 3) (2 g, 7.35 mmol) in MeOH (250 mL) was added acetic acid (1 mL) and tert-butyl 1,4-diazepane-1-carboxylate (2 g, 9.99 mmol). The solution was stirred at rt for 1.5 hr then NaCNBH$_3$ (2.3 g, 36.6 mmol) was added. The solution was stirred at rt overnight then the MeOH (250 mL) was removed in vacuo. The residue was dissolved in DCM (200 mL) and washed with water (3×100 mL). The crude product was purified by silica gel column chromatography eluting with DCM/MeOH (50/1) to give the title compound (1.409 g, 3.09 mmol, 42% yield) as yellow solid.

LCMS: MH$^+$=456/458

Intermediate 124

2-((tetrahydro-2H-pyran-4-yl)methoxy)-4-(4,4,5,5-tetramethyl-1,3,2-dioxaborolan-2-yl)pyridine

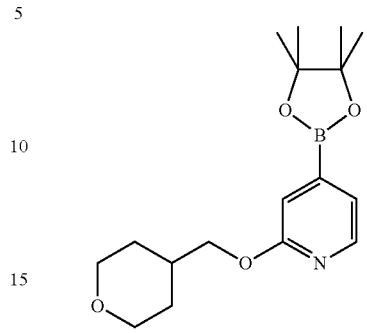

Synthesis and Initial Purification:

To a suspension of 4-bromo-2-((tetrahydro-2H-pyran-4-yl)methoxy)pyridine (Intermediate 10) (11.1 g, 40.8 mmol), 4,4,4',4',5,5,5',5'-octamethyl-2,2'-bi(1,3,2-dioxaborolane) (51.8 g, 204 mmol) and potassium acetate (16.01 g, 163 mmol) in 1,4-dioxane (200 mL) stirred under nitrogen at rt was added solid PdCl$_2$(dppf) (1.492 g, 2.039 mmol) in one charge. The reaction mixture was stirred at 100° C. for 16 hr. The reaction mixture was concentrated and the residue was purified via silica gel column eluting with petroleum ether/EtOAc (5:1) to give the crude title compound (8.7 g, 27.3 mmol, 66.8% yield) as a yellow oil.

LCMS MH$^+$=238 consistent with hydrolysis to boronic acid under LCMS conditions.

1H NMR consistent with desired product but shows significant pinacol related impurities.

Final Purification:

The crude material from the step above was loaded onto a silica gel column (200-300 Mesh Size) and was eluted with petroleum ether/EtOAc (15:1 to 5:1). The appropriate fractions were combined and evaporated in vacuo to give the title compound (5.2 g, 15.96 mmol, 85% yield) as white crystals.

LCMS MH$^+$=238 consistent with hydrolysis to boronic acid under LCMS conditions. $^1$H NMR (400 MHz, DMSO-d$_6$) δ-ppm 8.21 (1H, d), 7.14 (1H, d), 6.98 (1H, s), 4.14 (2H, d), 3.86 (2H, m), 3.29 (2H, m), 2.00 (1H, m), 1.61 (2H, m), 1.27 (12H, s &2H m).

Intermediate 125 tert-butyl 4-((5-methyl-4-oxo-7-(2-((tetrahydro-2H-pyran-4-yl)methoxy)pyridin-4-yl)-4,5-dihydrothieno[3,2-c]pyridin-2-yl)methyl)-1,4-diazepane-1-carboxylate

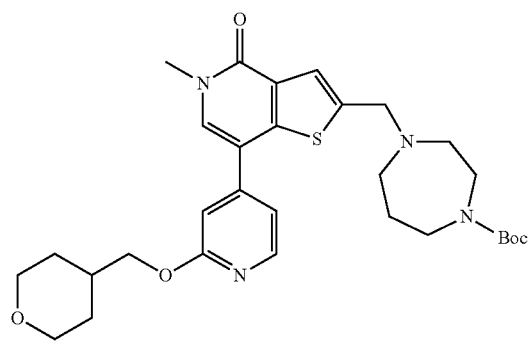 [SMILES: Cn1cc(-c2ccnc(OCC3CCOCC3)c2)c2sc(CN3CCCN(C(=O)OC(C)(C)C)CC3)cc2c1=O]

To a solution of tert-butyl 4-((7-bromo-5-methyl-4-oxo-4,5-dihydrothieno[3,2-c]pyridin-2-yl)methyl)-1,4-diazepane-1-carboxylate (Intermediate 123) (500 mg, 1.096 mmol) in DMF (5 mL) was added 2-((tetrahydro-2H-pyran-4-yl)methoxy)-4-(4,4, 5,5-tetramethyl 1,3,2-dioxaborolan-2-yl)pyridine (Intermediate 124) (350 mg, 1.096 mmol), potassium carbonate (303 mg, 2.191 mmol) and tetrakis (triphenylphosphine) palladium (0) (127 mg, 0.110 mmol). The reaction vessel was sealed and heated in microwave to 120° C. for 30 min under nitrogen. The DMF was removed and the crude product was purified by silica gel column chromatography eluting with DCM/MeOH (20-1) to give the title compound (488 mg, 0.858 mmol, 78% yield) as a light yellow solid.

LCMS: MH$^+$=569, purity 85%.

Intermediate 126

4-bromo-N-(pyridin-2-ylmethyl)pyridin-2-amine

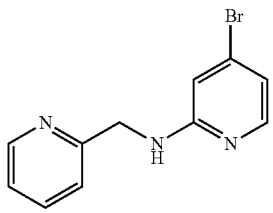 [SMILES: Brc1ccnc(NCc2ccccn2)c1]

To a solution of 4-bromo-2-fluoropyridine (3.58 g, 20.34 mmol) in NMP (17 mL) was added pyridin-2-ylmethanamine (2 g, 18.49 mmol). The reaction mixture was stirred at 100° C. for 1 hr. then cooled to rt and partitioned between DCM (100 mL) and water (100 mL). The organic phase was washed with saturated brine (50 mL), dried over sodium sulphate and concentrated in vacuo to give the title compound (6 g, 3.25 mmol, 17.56% yield) as a yellow oil (containing NMP) that was used without further purification on the next step

LCMS: MH$^+$=264.

Intermediate 127

N-(pyridin-2-ylmethyl)-4-(4,4,5,5-tetramethyl-1,3,2-dioxaborolan-2-yl)pyridin-2-amine

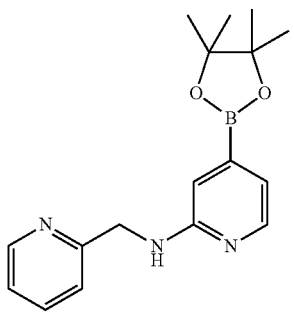 [SMILES: CC1(C)OB(c2ccnc(NCc3ccccn3)c2)OC1(C)C]

To a suspension of crude 4-bromo-N-(pyridin-2-ylmethyl)pyridin-2-amine (Intermediate 126) (5.8 g, 3.07 mmol), 4,4',4',5,5,5',5'-octamethyl-2,2'-bi(1,3,2-dioxaborolane) (3.90 g, 15.37 mmol) and potassium acetate (0.905 g, 9.22 mmol) stirred under nitrogen in 1,4-dioxane (30 mL) at rt, was added 1,1'-bis(diphenylphosphino)ferrocene-palladium(II) dichloride-DCM complex (0.251 g, 0.307 mmol).

The reaction mixture was stirred at 100° C. for 2 hr. The reaction mixture was cooled to rt and filtered. The filtrate was concentrated and the residue was purified by combi-flash chromatography on silica gel (40 g) eluting with EtOAc/petroleum (0-100% over 40 min, 100% over 40 min) to give a crude product as a brown solid. The solid was further purified by re-crystallization with ether/hexane (1:30, 1 mL/30 mL) to give the title compound (700 mg, 2.249 mmol, 73.2% yield) as a brown solid.

LCMS: M/Z 230 indicates hydrolysis of boronate ester under LCMS conditions.

$^1$H NMR (400 MHz, CDCl$_3$) δ-ppm 8.56 (1H, d), 8.14 (1H, d), 7.61 (1H, t), 7.31 (1H, d), 7.17 (1H, t), 6.89 (2H, m), 6.67 (1H, br.s), 4.69 (2H, d), 1.31 (12H, s).

Intermediate 128 tert-butyl 4-((5-methyl-4-oxo-7-(2-((pyridin-2-ylmethyl)amino)pyridin-4-yl)-4,5-dihydrothieno[3,2-c]pyridin-2-yl)methyl)-1,4-diazepane-1-carboxylate

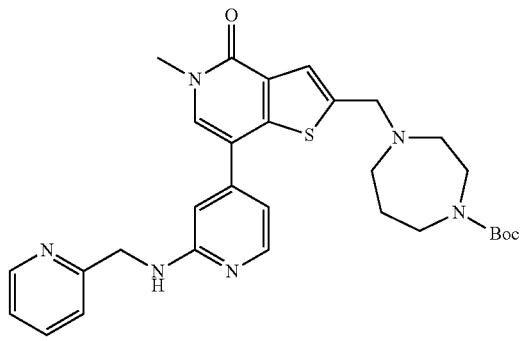 [SMILES: Cn1cc(-c2ccnc(NCc3ccccn3)c2)c2sc(CN3CCCN(C(=O)OC(C)(C)C)CC3)cc2c1=O]

To a suspension of tert-butyl 4-((7-bromo-5-methyl-4-oxo-4,5-dihydrothieno[3,2-c]pyridin-2-yl)methyl)-1,4-diazepane-1-carboxylate (Intermediate 123) (250 mg, 0.548 mmol), N-(pyridin-2-ylmethyl)-4-(4,4,5,5-tetramethyl-1,3,2-dioxaborolan-2-yl)pyridin-2-amine (Intermediate 127) (256 mg, 0.822 mmol) and Cs$_2$CO$_3$ (535 mg, 1.643 mmol) in 1,4-dioxane (20 mL) and water (5 mL) stirred at rt, was added tetrakis(triphenylphosphine)palladium (0) (63.3 mg, 0.055 mmol). The reaction mixture was warmed to 100° C. and stirred for 20 hr under nitrogen. The reaction mixture was cooled to rt and concentrated. DCM (50 mL) was added to the residue which was then filtered. The filtrate was concentrated and the residue was purified by combi-flash chromatography on silica gel (4 g) eluting with MeOH/DCM (0-10% over 20 min, 10% over 10 min) to give the title compound (280 mg, 0.499 mmol, 91% yield) as a brown glass.

LCMS: MH$^+$=561

Intermediate 129

2-((3-bromophenoxy)methyl)pyridine

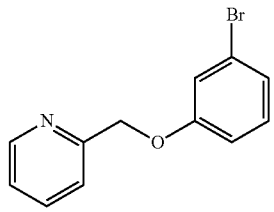 [SMILES: Brc1cccc(OCc2ccccn2)c1]

To a solution of pyridin-2-ylmethanol (5 g, 45.8 mmol) and Et$_3$N (19.16 mL, 137 mmol) in dry DCM (50 mL) stirred under nitrogen at −78° C. was added dropwise, methanesulfonyl chloride (10.50 g, 92 mmol) and then the reaction mixture was stirred at −50° C. for 30 min. The reaction mixture was quenched with water (30 mL) then partitioned between DCM (100 mL) and water (25 mL). The organic phase was washed with saturated brine (50 mL), dried over sodium sulphate and evaporated in vacuo to give pyridin-2-ylmethyl methanesulfonate (8.57 g, theoretical yield: 100%) as an orange oil which was used crude in the next reaction. To a suspension of 3-bromophenol (7.93 g, 45.8 mmol) and K$_2$CO$_3$ (19.00 g, 137 mmol) in MeCN (200 mL) stirred under nitrogen was added dropwise, a solution of pyridin-2-ylmethylmethanesulfonate (8.57 g, 45.8 mmol) in MeCN (30 mL). The reaction mixture was stirred at reflux overnight. The reaction mixture was quenched with water (100 mL) then partitioned between DCM (500 mL) and water (100 mL). The organic phase was washed with saturated brine (3×50 mL), dried over sodium sulphate and evaporated in vacuo. The crude product which was purified by a silica gel column chromatography eluting with EtOAc/petroleum ether (1:2) to give the title compound (9 g, 32.4 mmol, 70.7% yield) as a yellow oil.

LCMS: MH$^+$=264/266

Intermediate 130

2-((3-(4,4,5,5-tetramethyl-1,3,2-dioxaborolan-2-yl)phenoxy)methyl)pyridine

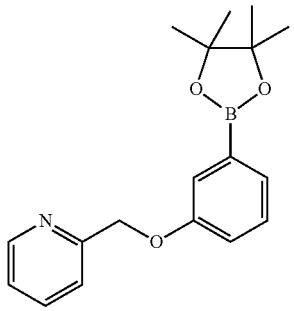 [SMILES: CC1(C)OB(c2cccc(OCc3ccccn3)c2)OC1(C)C]

To a suspension of 2-((3-bromophenoxy)methyl)pyridine (Intermediate 129) (4.0 g, 15.14 mmol), 4,4,4',4',5,5,5',5'-octamethyl-2,2'-bi(1,3,2-dioxaborolane) (19.23 g, 76 mmol) and potassium acetate (4.46 g, 45.4 mmol) in 1,4-dioxane (30 mL) stirred under nitrogen at rt was added 1,1'-bis(diphenylphosphino)ferrocene-palladium(II) dichloride-DCM complex (1.237 g, 1.514 mmol). The reaction mixture was stirred at 100° C. for 2 hr. The reaction mixture was cooled to rt and filtered.

The filtrate was concentrated and the residue was purified by combi-flash chromatography on silica gel (40 g) eluting with EtOAc/petroleum (0-20% over 20 min, 20% over 20 min) to give the title compound (5.2 g, 13.37 mmol, 88% yield, purity: 80% (NMR)) as a yellow oil.

LCMS MH$^+$=312.

$^1$H NMR (400 MHz, CDCl$_3$) δ-ppm 8.60 (1H, d), 7.75 (1H, m), 7.58 (1H, dt), 7.50 (1H, d), 7.45 (1H, d), 7.28 (2H, m), 7.09 (1H, d), 5.25 (2H, s), 1.33 (12H, s).

Intermediate 131 tert-butyl 4-((5-methyl-4-oxo-7-(3-(pyridin-2-ylmethoxy)phenyl)-4,5-dihydrothieno[3,2-c]pyridin-2-yl)methyl)-1,4-diazepane-1-carboxylate

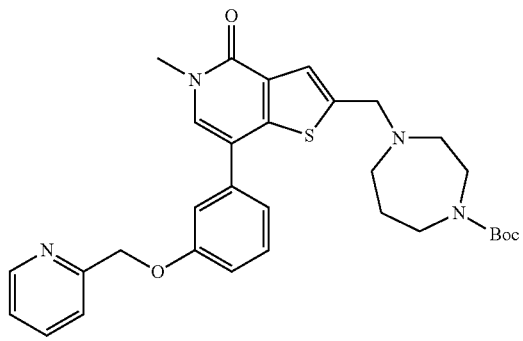 [SMILES: Cn1cc(-c2cccc(OCc3ccccn3)c2)c2sc(CN3CCCN(C(=O)OC(C)(C)C)CC3)cc2c1=O]

The title compound was prepared from Intermediates 123 and 130 using a method similar to that described for intermediate 128. Brown glass (280 mg, 0.499 mmol, 91% yield).

LCMS: MH$^+$=561.

Intermediate 132

4-bromo-2-(pyridin-2-ylmethoxy)pyridine

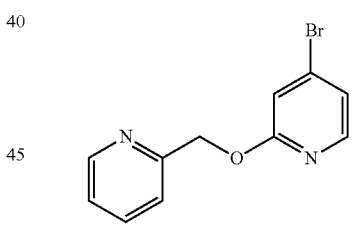

Sodium hydride, 60% suspension in mineral oil, (1.76 g, 44 mmol) was added portion-wise over 5 min to a stirred solution of pyridin-2-ylmethanol (4.37 g, 40.0 mmol) in dry THF (50 mL) under nitrogen. After complete addition the mixture was stirred at rt for 30 min. A solution of 4-bromo-2-chloropyridine (3.85 g, 20 mmol) in dry THF (20 mL) was added slowly. After complete addition the reaction mixture was stirred at rt for 20 hours. The reaction mixture was quenched with aqueous NH$_4$Cl solution (50 mL) and diluted with EtOAc (100 mL). The solution was washed with water (50 mL) and brine (50 mL). The organic phase was dried and evaporated. The residue was purified by combi-flash chromatography on silica gel (40 g) eluting with EtOAc/petroleum (0-50% over 30 min, 50% over 10 min) to give the title compound (1.70 g, 6.41 mmol, 32.1% yield) as a pale yellow oil.

LCMS: MH$^+$=265/267

Intermediate 133

2-(pyridin-2-ylmethoxy)-4-(4,4,5,5-tetramethyl-1,3,2-dioxaborolan-2-yl)pyridine

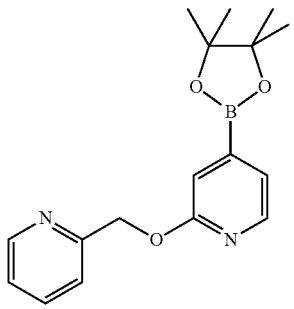 [SMILES: CC1(C)OB(c2ccnc(OCc3ccccn3)c2)OC1(C)C]

The title compound was prepared from Intermediate 132 using a method similar to that described for intermediate 130. Brown oil (2.5 g, 5.61 mmol, 87% yield, purity~70% by $^1$H NMR).

LCMS: M/Z 231 indicates hydrolysis of boronate ester under LCMS conditions. $^1$H NMR (400 MHz, CDCl$_3$) δ-ppm 8.61 (1H, d), 8.17 (1H, d), 7.69 (1H, m), 7.46 (1H, d), 7.25 (3H, m), 5.54 (2H, s), 1.36 (12H, s).

Intermediate 134 tert-butyl 4-((5-methyl-4-oxo-7-(2-(pyridin-2-ylmethoxy)pyridin-4-yl)-4,5-dihydrothieno[3,2-c]pyridin-2-yl)methyl)-1,4-diazepane-1-carboxylate

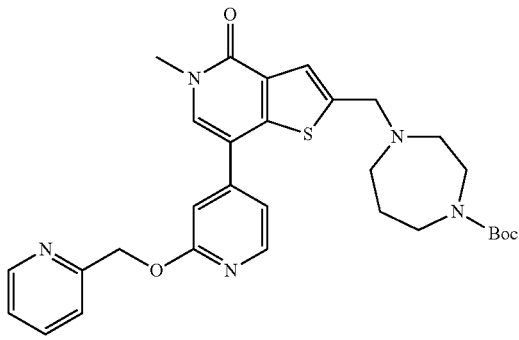

The title compound was prepared from Intermediates 123 and 133 using a method similar to that described for intermediate 128. Brown glass (360 mg, 0.449 mmol, 68% yield, ~70% pure by NMR).
LCMS: MH$^+$=562.

Intermediate 135

2-(benzyloxy)-4-bromopyridine

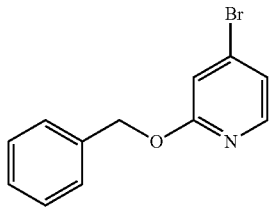 [SMILES: Brc1ccnc(OCc2ccccc2)c1]

To a solution of phenylmethanol (2.248 g, 20.79 mmol) in THF (100 mL), was added NaH (60% w/w) (0.914 g, 22.86 mmol) at 0° C. The reaction mixture was stirred at 0° C. for 4 hr. 4-bromo-2-chloropyridine (2 g, 10.39 mmol) in THF (50 mL) was added dropwise into the reaction mixture at 0° C. The reaction mixture was stirred at 25° C. for overnight. The reaction mixture was partitioned between EtOAc (100 mL) and water (100 mL). The organic phase was washed with saturated brine (100 mL), dried over sodium sulphate and evaporated in vacuo to give the crude product. The crude product was purified by Combi-Flash chromatography on a silica column (24 g) and eluted with EtOAc/petroleum (0~100% over 10 min, 100% over 5 min). Appropriate fractions were evaporated to give the title compound (1.272 g, 4.82 mmol, 46.3% yield) as a white oil.
LCMS: MH$^+$=264/266

Intermediate 136

2-(benzyloxy)-4-(4,4,5,5-tetramethyl-1,3,2-dioxaborolan-2-yl)pyridine

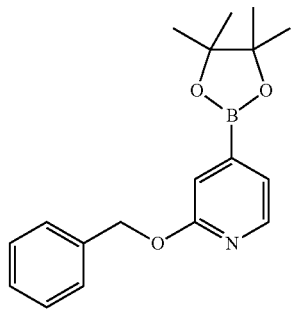 [SMILES: CC1(C)OB(c2ccnc(OCc3ccccc3)c2)OC1(C)C]

The title compound was prepared from Intermediate 135 using a method similar to that described for intermediate 130. Light oil (850 mg, 2.73 mmol, 65.6% yield).
LCMS: M/Z 230 indicates hydrolysis of boronate ester under LCMS conditions. $^1$H NMR (400 MHz, CDCl$_3$) δ-ppm 8.19 (1H, d), 7.45 (2H, d), 7.38 (2H, m), 7.30 (1H, d), 7.20 (2H, m), 5.39 (2H, s), 1.36 (12H, s).

Intermediate 137 tert-butyl 4-((7-(2-(benzyloxy)pyridin-4-yl)-5-methyl-4-oxo-4,5-dihydrothieno[3,2-c]pyridin-2-yl)methyl)-1,4-diazepane-1-carboxylate

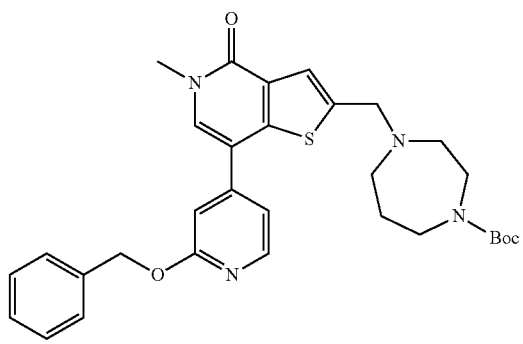 [SMILES: Cn1cc(-c2ccnc(OCc3ccccc3)c2)c2sc(CN3CCCN(C(=O)OC(C)(C)C)CC3)cc2c1=O]

The title compound was prepared from Intermediates 123 and 136 using a method similar to that described for intermediate 128. Brown glass (340 mg, 0.606 mmol, 92% yield).

LCMS: MH⁺=561.

Intermediate 138

7-bromo-2-(((1,1-dioxidotetrahydrothiophen-3-yl)amino)methyl)-5-methylthieno[3,2-c]pyridin-4(5H)-one

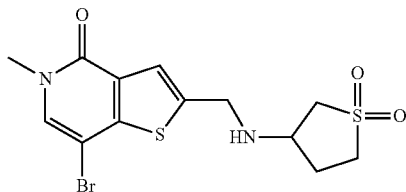 [SMILES: Cn1cc(Br)c2sc(CNC3CCS(=O)(=O)C3)cc2c1=O]

A mixture of 7-bromo-5-methyl-4-oxo-4,5-dihydrothieno[3,2-c]pyridine-2-carbaldehyde (Intermediate 3) (250 mg, 0.919 mmol), 3-aminotetrahydrothiophene 1,1-dioxide (199 mg, 1.470 mmol) in MeOH (3.5 mL) and acetic acid (0.35 mL) was left to stir for 3 hr at 50° C. The 2-picoline-borane complex (108 mg, 1.011 mmol) was added and the reaction mixture was left to stir for a further 4 hr. The solution was allowed to cool to rt and concentrated in vacuo. The residue was diluted with sat. aq. NaHCO₃ (40 mL) and extracted with DCM (3×40 mL). The combined organic layers were passed through a hydrophobic frit and concentrated in vacuo. The resulting residue was purified by silica gel column chromatography eluting with 0-4% MeOH in DCM. The appropriate fractions were combined and evaporated in vacuo to give the title compound (340 mg, 0.87 mmol, 95%) as a pale yellow solid.

LCMS (2 min, Formic Acid): Rt=0.50 min, MH⁺=391/393.

Intermediate 139

7-bromo-2-(((1,1-dioxidotetrahydro-2H-thiopyran-4-yl)amino)methyl)-5-methylthieno[3,2-c]pyridin-4(5H)-one

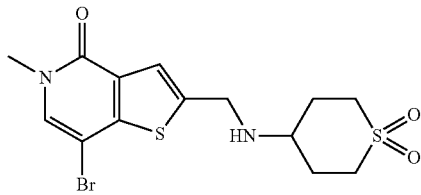 [SMILES: Cn1cc(Br)c2sc(CNC3CCS(=O)(=O)CC3)cc2c1=O]

A mixture of 7-bromo-5-methyl-4-oxo-4,5-dihydrothieno[3,2-c]pyridine-2-carbaldehyde (Intermediate 3) (250 mg, 0.919 mmol) and 4-aminotetrahydro-2H-thiopyran 1,1-dioxide (200 mg, 1.340 mmol) in MeOH (3.5 mL) and acetic acid (0.35 mL) was left to stir at 50° C. for 4 hr. After this time the 2-picoline-borane complex (108 mg, 1.011 mmol) was added and the reaction mixture was left to stir for a further 20 hr. The volatile components were removed in vacuo and the resulting residue was diluted with sat. aq. NaHCO₃ (40 mL). The aqueous layer was extracted with DCM (3×40 mL). The combined organic layers were filtered through a hydrophobic frit and concentrated in vacuo. The resulting residue was purified by silica gel column chromatography eluting with 0-4% MeOH in DCM.

The appropriate fractions were combined and evaporated in vacuo to give the title compound (210 mg, 0.52 mmol, 56%) as a pale yellow solid.

LCMS (2 min, Formic Acid): Rt=0.47 min, MH⁺=405/407.

Intermediate 140

(3-methylpiperidin-3-yl)methanol

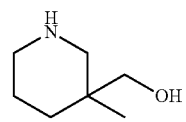

To a solution of 3-methylpiperidine-3-carboxylic acid (600 mg, 4.19 mmol) in THF (30 mL) stirred under nitrogen at 0° C. was added lithium aluminium hydride (318 mg, 8.38 mmol) in THF (30 mL). The reaction mixture was stirred at 60° C. overnight then combined with a separate reaction mixture (carried out on 100 mg scale). The combined mixtures were filtered through a cake of Celite and the filtrate was concentrated to give the title compound (300 mg, 2.090 mmol, 49.9% yield) as a yellow solid.

LCMS: MH⁺=130.

Intermediate 141 tert-butyl 3-(hydroxymethyl)-3-methylpiperidine-1-carboxylate

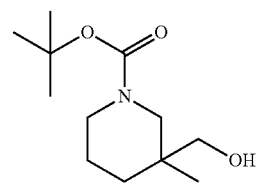 [SMILES: CC1(CO)CCCN(C(=O)OC(C)(C)C)C1]

A solution of (3-methylpiperidin-3-yl)methanol (Intermediate 140) (300 mg, 2.322 mmol), (Boc)₂O (0.647 mL, 2.79 mmol) and triethylamine (0.971 mL, 6.97 mmol) in DCM (20 mL) was stirred under nitrogen at rt overnight. The reaction mixture was quenched with 1M HCl (5 mL). The water phase was extracted by DCM (3×10 mL). The organic layer was evaporated in vacuo to give the crude title compound (300 mg, 1.047 mmol, 45.1% yield) as yellow solid which was used in the next step without further purification.

LCMS: m/z=174 [(M−55)H⁺], consistent with loss of tert-butyl group

Intermediate 142 tert-butyl 3-(methoxymethyl)-3-methylpiperidine-1-carboxylate

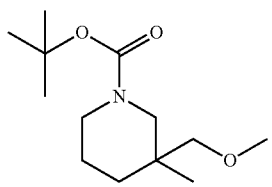 [SMILES: COCC1(C)CCCN(C(=O)OC(C)(C)C)C1]

To a solution of tert-butyl 3-(hydroxymethyl)-3-methylpiperidine-1-carboxylate (Intermediate 141) (300 mg, 1.308 mmol) and NaH (60% w/w) (105 mg, 2.62 mmol) in DMF (5 mL) stirred in the sealed tube at rt for 1 hr, was added methyl iodide (0.818 mL, 13.08 mmol) in DMF (5 mL). The reaction mixture was stirred at rt overnight. The solvent was evaporated in vacuo to give the crude product.

The crude product was partitioned between EtOAc (10 mL) and water (2 mL). The organic layer was evaporated to give the crude title compound (300 mg, 0.986 mmol, 75% yield) as a yellow solid which was used in the next step without further purification.

LCMS: m/z=188 [(M−55)H+], consistent with loss of tert-butyl group.

Intermediate 143

3-(methoxymethyl)-3-methylpiperidine

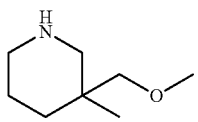

A solution of tert-butyl 3-(methoxymethyl)-3-methylpiperidine-1-carboxylate (Intermediate 142) (300 mg, 1.233 mmol) and TFA (2 mL, 26.0 mmol) in DCM (10 mL) stirred under nitrogen at rt for 1 hr. The solvent was evaporated in vacuo to give the crude title compound (200 mg, 1.117 mmol, 91% yield) as a yellow solid which was used in the next step without further purification.

LCMS: MH+=144.

Intermediate 144 tert-butyl 3-((cyclopropylmethoxy)methyl)-3-methylpiperidine-1-carboxylate

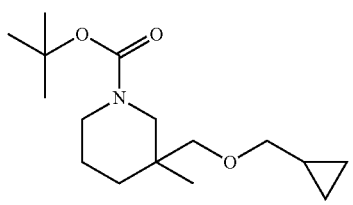 [SMILES: CC1(COCC2CC2)CCCN(C(=O)OC(C)(C)C)C1]

The title compound was prepared from Intermediate 141 and (bromomethyl)cyclopropane using a method similar to that described for Intermediate 142. The crude product was purified by silica gel column chromatography eluting with hexane/EtOAc (5/1) to give the title compound (320 mg, 0.903 mmol, 71.4% yield) as a yellow solid.

LCMS: M/Z=228 [(M−55)H+], consistent with loss of tert-butyl group.

Intermediate 145

3-((cyclopropylmethoxy)methyl)-3-methylpiperidine

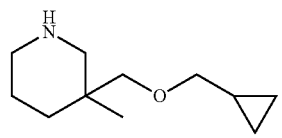

The title compound was prepared from Intermediate 144 using a method similar to that described for Intermediate 143. Crude yellow solid (150 mg, 0.655 mmol, 58% yield).

LCMS: MH+=184.

Intermediate 146

4-bromo-N-(2-methoxyethyl)-N-methylpyridin-2-amine

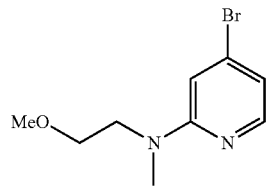

A mixture of 4-bromo-2-chloropyridine (4.35 g, 2.5 ml, 22.6 mmol) and 2-methoxy-N-methylethanamine (6.09 g, 7.5 ml, 68.3 mmol) was heated in a microwave at 150° C. for 1 hr. The reaction mixture was cooled to room temperature. The solution was diluted with toluene (20 mL) and the solvent was evaporated, then re-evaporated from toluene (x2). The residue was chromatographed [20-50% ethyl acetate/hexane] to give the title compound, 4-bromo-N-(2-methoxyethyl)-N-methylpyridin-2-amine (500 mg, 2.040 mmol, 9.02% yield) as a colourless oil. $^1$H NMR (400 MHz, CDCl$_3$) δ-ppm 7.93 (1H, d), 6.64 (2H, m), 3.70 (2H, t), 3.53 (2H, t), 3.32 (3H, s), 3.07 (3H, s).

Also obtained was 2-chloro-N-(2-methoxyethyl)-N-methylpyridin-4-amine (3.25 g, 16.20 mmol, 71.7% yield) as a colourless oil.

$^1$H NMR (400 MHz, CDCl$_3$) δ-ppm 7.95 (1H, d), 6.52 (1H, d), 6.42 (1H, dd), 3.51 (4H, m), 3.32 (3H, s), 3.02 (3H, s).

Intermediate 147

(2-((2-methoxyethyl)(methyl)amino)pyridin-4-yl)boronic acid

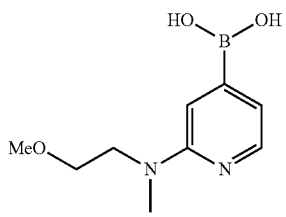

A mixture of 4-bromo-N-(2-methoxyethyl)-N-methylpyridin-2-amine (Intermediate 146) (209 mg, 0.853 mmol), potassium acetate (335 mg, 3.41 mmol), bis(pinacolato)diboron (1083 mg, 4.26 mmol) and PdCl$_2$(dppf) (62.4 mg, 0.085 mmol) in 1,4-dioxane (4 mL) was heated in the microwave at 110° C. for 30 min. The cooled reaction mixture was diluted with ethyl acetate and the solution was filtered through Celite. The filtrate was dried and evaporated in vacuo to give the title compound as a crude black oil. No further purification was attempted and this material was used crude in the following step (quantitative yield assumed).

LCMS (2 min, Formic Acid): Rt=0.34 min, MH$^+$=211.

Intermediate 148 tert-butyl 3-((cyclopropylmethoxy)methyl)-3-methylpyrrolidine-1-carboxylate

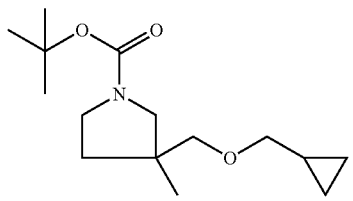 [SMILES: CC1(COCC2CC2)CCN(C(=O)OC(C)(C)C)C1]

The title compound was prepared from tert-butyl 3-((hydroxymethoxy)methyl)-3-methylpyrrolidine-1-carboxylate and (bromomethyl)cyclopropane using a method similar to that described for Intermediate 142 with heating at 60° C. The crude product was purified by silica gel column chromatography eluting with hexane/EtOAc (5/1) to give the title compound (185 mg, 0.687 mmol, 73.9% yield) as a white solid.

LCMS: M/Z=214 [(M−56)H+], consistent with loss of tert-butyl group.

Intermediate 149

3-((cyclopropylmethoxy)methyl)-3-methylpyrrolidine

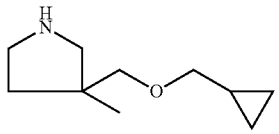

To a solution of tert-butyl 3-((cyclopropylmethoxy)methyl)-3-methylpyrrolidine-1-carboxylate (Intermediate 148) (180 mg, 0.668 mmol) in DCM (10 mL) stirred in air at room temperature was added 2,2,2-trifluoroacetic acid (762 mg, 6.68 mmol) in one charge during 1 min. The reaction mixture was stirred at room temperature for 3 h. The reaction mixture was evaporated and to the residue was partitioned between NaHCO$_3$ (20 mL) and DCM (2×30 mL). The organic phase was dried over sodium sulphate and evaporated in vacuo. The crude product was purified by silica gel column chromatography eluting with DCM/MeOH (20:1) to give the title compound (105 mg, 0.620 mmol, 93% yield) as a light yellow oil.

LCMS: MH$^+$=170.

Intermediate 150

N-(pyridin-2-ylmethyl)-3-(4,4,5,5-tetramethyl-1,3,2-dioxaborolan-2-yl)aniline

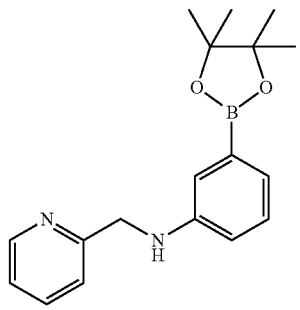 [SMILES: CC1(C)OB(c2cccc(NCc3ccccn3)c2)OC1(C)C]

To 3-(4,4,5,5-tetramethyl-1,3,2-dioxaborolan-2-yl)aniline (3 g, 13.69 mmol) and picolinaldehyde (1.540 g, 14.38 mmol) in MeOH (50 mL) was added AcOH (1 drop) and the mixture was stirred for 20 min. NaCNBH3 (4.30 g, 68.5 mmol) was added and the mixture was stirred at rt overnight. The solvent was removed and the residue was extracted with EtOAc (500 mL) and water (500 mL). The aqueous was re-extracted with EtOAc (300 mL). The combined organics were washed with brine (200 mL) then dried with Na$_2$SO$_4$, filtered and concentrated to yield a crude solid. The crude product was loaded onto a silica gel column and was eluted with Hexane/EtOAc(1/1). Appropriate fractions were combined and concentrated to give the title compound (2.6 g, 7.21 mmol, 52.6% yield) as a colourless oil.

LCMS: MH$^+$=311

Intermediate 151 tert-butyl 4-((5-methyl-4-oxo-7-(3-((pyridin-2-ylmethyl)amino)phenyl)-4,5-dihydrothieno[3,2-c]pyridin-2-yl)methyl)-1,4-diazepane-1-carboxylate

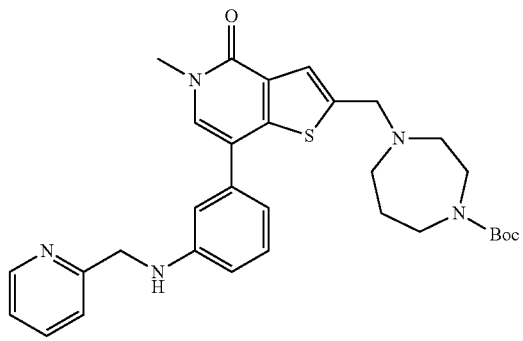

A mixture of N-(pyridin-2-ylmethyl)-3-(4,4,5,5-tetramethyl-1,3,2-dioxaborolan-2-yl)aniline (Intermediate 150) (255 mg, 0.822 mmol), tert-butyl 4-((7-bromo-5-methyl-4-oxo-4,5-dihydrothieno[3,2-c]pyridin-2-yl)methyl)-1,4-diazepane-1-carboxylate (Intermediate 123) (250 mg, 0.548 mmol), and potassium carbonate (151 mg, 1.096 mmol) in a solution of 1,4-dioxane (50 mL) and water (12.50 mL) was degassed with N₂ and tetrakis(triphenylphosphine)palladium (0) (63.3 mg, 0.055 mmol) was added. The reaction was heated to reflux for 3 hr, then concentrated. The residues were partioned between DCM (200 mL) and water (200 mL). The aqueous was re-extracted with DCM (200 mL). The combined organics were washed with brine (200 mL) then dried with Na₂SO₄, filtered and concentrated to yield a crude solid. The crude product was loaded onto a silica gel column and was eluted with DCM/MeOH (10/1). Appropriate fractions were combined and concentrated to give the title compound (320 mg, 0.412 mmol, 75% yield) as a orange solid.

LCMS: MH⁺=560.

Intermediate 152

N-(3-(4,4,5,5-tetramethyl-1,3,2-dioxaborolan-2-yl)phenyl)picolinamide

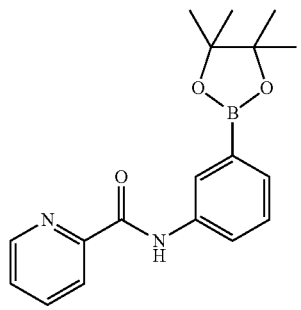 [SMILES: CC1(C)OB(c2cccc(NC(=O)c3ccccn3)c2)OC1(C)C]

A mixture of 3-(4,4,5,5-tetramethyl-1,3,2-dioxaborolan-2-yl)aniline (2 g, 9.13 mmol), picolinic acid (1.349 g, 10.95 mmol), DIPEA (4.78 mL, 27.4 mmol) and HATU (4.51 g, 11.87 mmol) in DMF (20 mL) was stirred overnight at rt. The mixture was extracted with EtOAc (2×200 mL), the combined organics were washed with brine (200 mL), dried with Na2SO₄, filtered and concentrated to yield a crude solid. The crude product was loaded onto a silica gel column and was eluted with Hexane/EtOAc(10/1). Appropriate fractions were combined and concentrated to give the title compound (2.0 g, 6.17 mmol, 67.6% yield) as a white solid. LCMS: MH⁺=325.

Intermediate 153 tert-butyl 4-((5-methyl-4-oxo-7-(3-(picolinamido)phenyl)-4,5-dihydrothieno[3,2-c]pyridin-2-yl)methyl)-1,4-diazepane-1-carboxylate

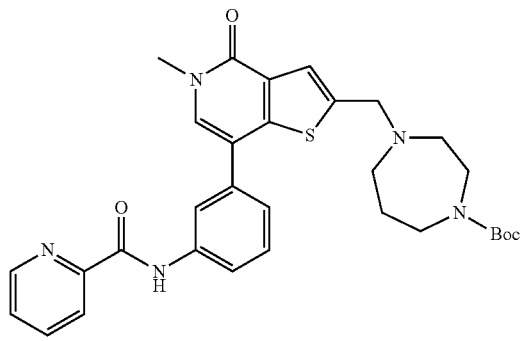 [SMILES: Cn1cc(-c2cccc(NC(=O)c3ccccn3)c2)c2sc(CN3CCCN(C(=O)OC(C)(C)C)CC3)cc2c1=O]

The title compound was prepared from tert-butyl 4-((7-bromo-5-methyl-4-oxo-4,5-dihydrothieno[3,2-c]pyridin-2-yl)methyl)-1,4-diazepane-1-carboxylate (Intermediate 123) and N-(3-(4,4,5,5-tetramethyl-1,3,2-dioxaborolan-2-yl)phenyl)picolinamide (Intermediate 152) using a method similar to that described for Intermediate 151. Orange solid (120 mg, 0.149 mmol, 27.1% yield). LCMS: MH⁺=574.

Intermediate 154 tert-butyl 4-((7-bromo-5-methyl-4-oxo-4,5-dihydrothieno[3,2-c]pyridin-2-yl)methyl)-3-methylpiperazine-1-carboxylate

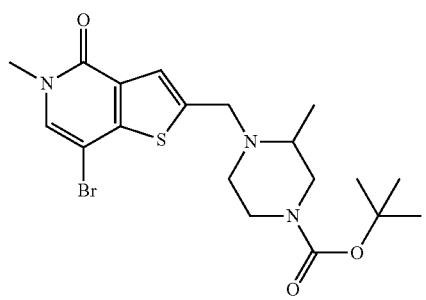 [SMILES: CC1CN(C(=O)OC(C)(C)C)CCN1Cc1cc2c(=O)n(C)cc(Br)c2s1]

A mixture of crude 7-bromo-2-(bromomethyl)-5-methylthieno[3,2-c]pyridin-4(5H)-one (for an example preparation see Intermediate 53) (300 mg, 50% w/w, 0.445 mmol), tert-butyl 3-methylpiperazine-1-carboxylate (178 mg, 0.890 mmol) and potassium carbonate (123 mg, 0.890 mmol) in DMF (10 mL) was stirred for 4 h at rt. The solvent was removed and the crude product was purified by silica gel column chrmoatography eluting with DCM/MeOH to give the crude title compound (400 mg) as a colourless solid which was used in the next step without further purification. LCMS: MH⁺=456/458.

Intermediate 155

7-bromo-5-methyl-2-((2-methylpiperazin-1-yl)methyl)thieno[3,2-c]pyridin-4(5H)-one

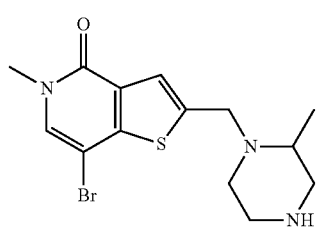

A mixture of crude tert-butyl 4-((7-bromo-5-methyl-4-oxo-4,5-dihydrothieno[3,2-c]pyridin-2-yl)methyl)-3-methylpiperazine-1-carboxylate (Intermediate 154) (400 mg) and TFA (1.5 mL) in DCM was stirred for 16 h. The solvent was removed to give the trifluoroacetic acid salt of the title compound (260 mg, 82% w/w) as an orange oil, which used in the next step without further purification. LCMS: MH⁺=356/358.

Intermediate 156

2-((4-acetyl-2-methylpiperazin-1-yl)methyl)-7-bromo-5-methylthieno[3,2-c]pyridin-4(5H)-one

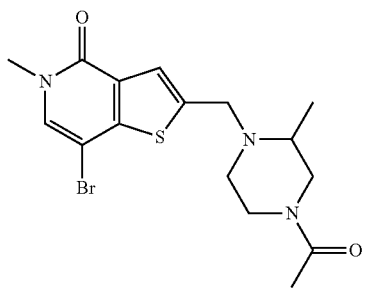 [SMILES: CC(=O)N1CCN(Cc2cc3c(=O)n(C)cc(Br)c3s2)C(C)C1]

To crude 7-bromo-5-methyl-2-((2-methylpiperazin-1-yl)methyl)thieno[3,2-c]pyridin-4(5H)-one (Intermediate 155) (260 mg, 82% w/w, 0.598 mmol) and triethylamine (0.250 mL, 1.795 mmol) in acetonitrile (50 mL) was added acetic anhydride (122 mg, 1.197 mmol) and the mixture was stirred for 4 h. The solvent was removed and the crude product was purified by silica gel column chromatography eluting with DCM/MeOH (20:1) to give the title compound (310 mg, 46% w/w) as a colourless oil, which was used crude in the next step. LCMS: MH+=398/400.

Intermediate 157 tert-butyl 4-((7-bromo-5-methyl-4-oxo-4,5-dihydrothieno[3,2-c]pyridin-2-yl)methyl)-3-oxopiperazine-1-carboxylate

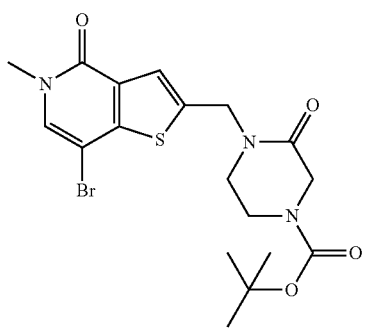 [SMILES: Cn1cc(Br)c2sc(CN3CCN(C(=O)OC(C)(C)C)CC3=O)cc2c1=O]

To a solution of tert-butyl 3-oxopiperazine-1-carboxylate (521 mg, 2.60 mmol) in THF (50 mL) was added sodium hydride (167 mg, 6.94 mmol), the mixture was stirred for 1 h at rt, then crude 7-bromo-2-(bromomethyl)-5-methylthieno[3,2-c]pyridin-4(5H)-one (for an example preparation see Intermedate 53) (900 mg, 65% w/w, 1.736 mmol) was added and the mixture were stirred overnight at rt. The mixture was concentrated and was purified by silica gel column chromatography eluting with DCM/MeOH (50/1) to give the title compound (417 mg, 0.786 mmol, 45.3% yield).

LCMS: M/Z=400/402 [(M−56)H+], consistent with loss of tert-butyl group.

Intermediate 158 tert-butyl 4-((5-methyl-4-oxo-7-(2-((tetrahydro-2H-pyran-4-yl)methoxy)pyridin-4-yl)-4,5-dihydrothieno[3,2-c]pyridin-2-yl)methyl)-3-oxopiperazine-1-carboxylate

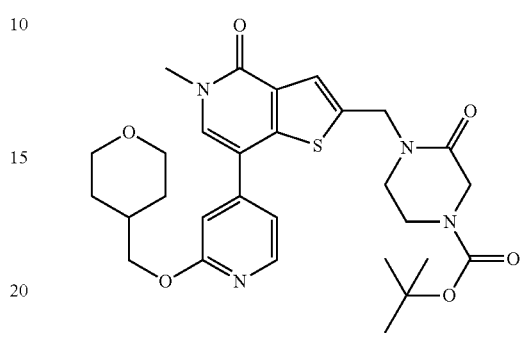

To a solution of tert-butyl 4-((7-bromo-5-methyl-4-oxo-4,5-dihydrothieno[3,2-c]pyridin-2-yl)methyl)-3-oxopiperazine-1-carboxylate (Intermediate 157) (600 mg, 1.315 mmol) in 1,4-dioxane (42 mL) was added 2-((tetrahydro-2H-pyran-4-yl)methoxy)-4-(4,4,5,5-tetramethyl-1,3,2-dioxaborolan-2-yl)pyridine (Intermediate 124) (630 mg, 1.972 mmol) and tetrakis(triphenylphosphine)palladium (0) (76 mg, 0.066 mmol). The reaction was evacuated and purged with nitrogen, followed by addition of cesium carbonate (857 mg, 2.63 mmol) and water (10.50 mL). The mixture was heated to 100° C. overnight. Then the reaction mixture was cooled to rt. The organic layer was removed and the aqueous layer was extracted with EtOAc (3×100 mL), the combined organic extracts were washed with brine (120 mL) and concentrated in vacuo. The crude product was purified by silica gel column chromatography eluting with DCM/MeOH (10:1) to give the title compound (750 mg, 0.791 mmol, 60.2% yield) as a white solid.

LCMS: MH+=569.

Intermediate 159

7-bromo-2-(((2-hydroxyethyl)(methyl)amino)methyl)-5-methylthieno[3,2-c]pyridin-4(5H)-one

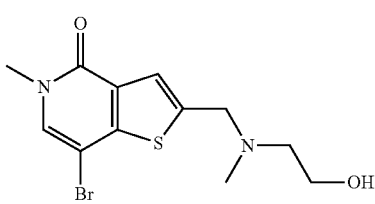 [SMILES: CN(CCO)Cc1cc2c(=O)n(C)cc(Br)c2s1]

A suspension of 7-bromo-5-methyl-4-oxo-4,5-dihydrothieno[3,2-c]pyridine-2-carbaldehyde (Intermediate 3) (1 g, 3.67 mmol) and 2-(methylamino)ethanol (0.590 mL, 7.35 mmol) was heated to 50° C. for 4 h. Picoline borane complex (0.444 g, 4.04 mmol) was added and the reaction mixture was heated for a further 18 h (solvation achieved). The volatile components were removed in vacuo and sat. aq. NaHCO$_3$ (40 mL) was added to the residue (gas evolved). The aqueous layer was extracted with DCM (3×50 mL) and the combined organic layers were passed through a hydrophobic frit and concentrated in vacuo. The resulting residue was purified by silica gel chromatography eluting with 0-4% MeOH/DCM. The appropriate fractions were combined and the solvent was evaporated in vacuo to give the title compound (550 mg, 1.66 mmol, 45%) as a yellow solid. LCMS (2 min, Formic Acid): Rt=0.45 min, MH$^+$=331/333.

Example 1

5-methyl-2-((4-(methylsulphonyl)piperazin-1-yl)methyl)-7-(5-(1-phenylethoxy)pyridin-3-yl)thieno[3,2-c]pyridin-4(5H)-one hydrochloride

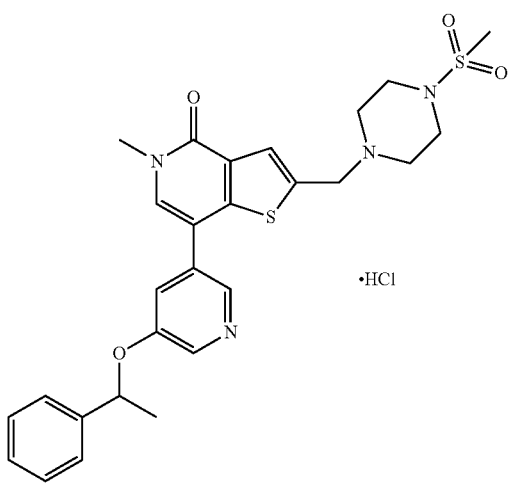 [SMILES: CC(Oc1cncc(-c2cn(C)c(=O)c3cc(CN4CCN(S(C)(=O)=O)CC4)sc23)c1)c1ccccc1 ; Cl]

A mixture of 7-bromo-5-methyl-2-((4-(methylsulphonyl)piperazin-1-yl)methyl)thieno[3,2-c]pyridin-4(5H)-one (for a preparation see Intermediate 69, 105 mg, 0.25 mmol), (5-(1-phenylethoxy)pyridin-3-yl)boronic acid (for a preparation see Intermediate 5, 91 mg, 0.375 mmol), potassium carbonate (104 mg, 0.75 mmol) and bis(triphenylphosphine)palladium(II) chloride (18 mg, 10 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried over sodium sulphate and evaporated. The residue was purified by chromatography on silica gel eluting with 0-5% methanol in dichloromethane. The product was dissolved in ethyl acetate (1 mL) and the solution treated with 1M hydrogen chloride in diethyl ether (0.5 mL). The resulting suspension was diluted with diethyl ether (~10 mL). The solid was filtered off, washed with diethyl ether and dried to give the product 5-methyl-2-((4-(methylsulphonyl)piperazin-1-yl)methyl)-7-(5-(1-phenylethoxy)pyridin-3-yl)thieno[3,2-c]pyridin-4(5H)-one hydrochloride (31 mg, 0.054 mmol, 21.56% yield) as a colourless solid.

LCMS (2 min, Formic Acid): Rt=0.82 min, MH$^+$=539.

Example 2

5-methyl-2-((4-(methylsulphonyl)piperazin-1-yl)methyl)-7-(3-(1-(pyridin-2-yl)ethoxy)phenyl)thieno[3,2-c]pyridin-4(5H)-one

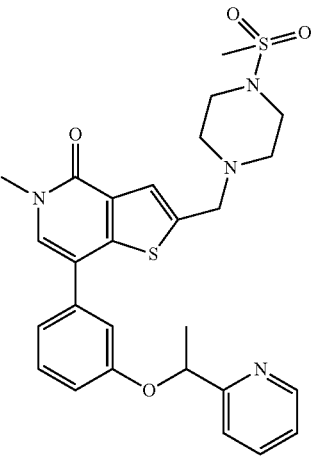 [SMILES: CC(Oc1cccc(-c2cn(C)c(=O)c3cc(CN4CCN(S(C)(=O)=O)CC4)sc23)c1)c1ccccn1]

To a stirred solution of 7-(3-hydroxyphenyl)-5-methyl-2-((4-(methylsulphonyl)piperazin-1-yl)methyl)thieno[3,2-c]pyridin-4(5H)-one (for a preparation see Example 10, 100 mg, 0.231 mmol) in N,N-dimethylformamide (5 mL) was added potassium carbonate (96 mg, 0.692 mmol) followed by 2-(1-bromoethyl)pyridine hydrobromide (73.9 mg, 0.277 mmol). The reaction was heated to 100° C. for 17 hours. The reaction was cooled to room temperature and quenched with water (30 mL). The aqueous layer was extracted with ethyl acetate (3×30 mL). The organic fractions were combined and washed with saturated sodium chloride solution (25 mL). The organic layer was collected, dried over magnesium sulphate and concentrated in vacuo to give a yellow oil. The crude material was purified by chromatography on silica gel eluting with 0-5% methanol in dichloromethane to give a pale yellow oil which was triturated with diethyl ether to give a light yellow solid which was repurified by MDAP to give a clear colourless oil which was triturated with diethyl ether to give an off white solid, 5-methyl-2-((4-(methylsulphonyl)piperazin-1-yl)methyl)-7-(3-(1-(pyridin-2-yl)ethoxy)phenyl)thieno[3,2-c]pyridin-4(5H)-one (24 mg, 0.045 mmol, 19.32% yield).

LCMS (2 min, Formic Acid): Rt=0.75 min, MH$^+$=539

Example 3

(±)-5-methyl-2-((4-(methylsulphonyl)piperazin-1-yl)methyl)-7-(5-(1-(pyridin-2-yl)ethoxy)pyridin-3-yl)thieno[3,2-c]pyridin-4(5H)-one

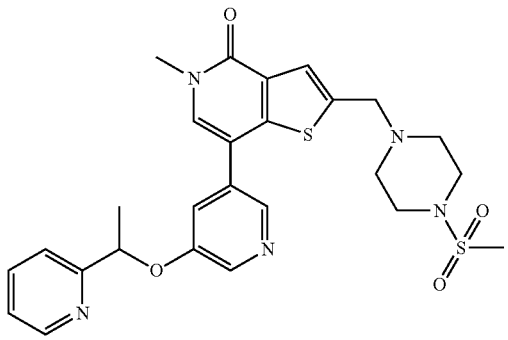 [SMILES: CC(Oc1cncc(-c2cn(C)c(=O)c3cc(CN4CCN(S(C)(=O)=O)CC4)sc23)c1)c1ccccn1]

To a microwave vial was added 7-bromo-5-methyl-2-((4-(methylsulphonyl)piperazin-1-yl)methyl)thieno[3,2-c]pyridin-4(5H)-one (for a preparation see Intermediate 69, 500.0 mg, 1.189 mmol), potassium carbonate (492.7 mg, 3.56 mmol), and PEPPSI-IPr (84.3 mg, 0.124 mmol) followed by (±)-(5-(1-(pyridin-2-yl)ethoxy)pyridin-3-yl)boronic acid (for a preparation see Intermediate 6, 405 mg, 1.659 mmol) in isopropanol (10 mL) and water (4 mL). The vial was sealed and heated with stirring at 110° C. for 30 min in a microwave reactor. The reaction mixture was diluted with saturated aqueous sodium bicarbonate solution (80 mL) and extracted with dichloromethane (3×50 mL). The combined organic layers were back-washed with water (50 mL), filtered through a cartridge fitted with a hydrophobic frit and evaporated in vacuo. The residue was purified by chromatography on silica gel eluting 0-20% methanol in dichloromethane. The required fractions were combined and evaporated in vacuo to give a residue which was still impure. The residue was repurified by chromatography on silica gel eluting with a gradient of 0-70% (20% methanol in dichloromethane solution) in ethyl acetate. The required fractions were combined and evaporated in vacuo to give the desired product (±)-5-methyl-2-((4-(methylsulphonyl)piperazin-1-yl)methyl)-7-(5-(1-(pyridin-2-yl)ethoxy)pyridin-3-yl)thieno[3,2-c]pyridin-4(5H)-one (193.1 mg, 0.358 mmol, 30.1% yield) as a pale yellow foam.

LCMS (2 min, Formic Acid): Rt=0.62 min, MH+=540.

Example 3A (R)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one

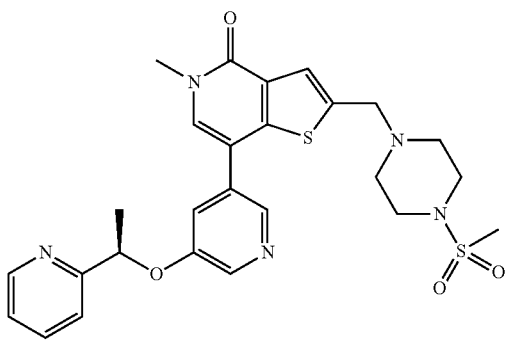 [SMILES: C[C@@H](Oc1cncc(-c2cn(C)c(=O)c3cc(CN4CCN(S(C)(=O)=O)CC4)sc23)c1)c1ccccn1]

and

Example 3B (S)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one

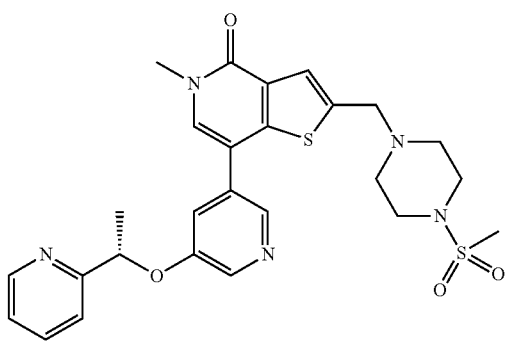 [SMILES: C[C@H](Oc1cncc(-c2cn(C)c(=O)c3cc(CN4CCN(S(C)(=O)=O)CC4)sc23)c1)c1ccccn1]

A sample of 5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one (Example 3) was separated into its enantiomeric components by chiral preparative HPLC to give the title compounds as follows:

190 mg of racemate was dissolved at a rate of 5 mg per 0.5 mL EtOH and 0.5 mL portions were injected onto a 2 cm×25 cm Chiralpak IB column. The column was eluted with 30% EtOH(+0.2% isopropylamine)/Heptane, flow rate=20 mL/min, wavelength 260 nm. Appropriate fractions were combined, concentrated, re-dissolved in DCM and re-concentrated to give the title compounds as white solids.

Example 3A: 72 mg. LCMS (2 min, Formic Acid): Rt=0.64 min, MH+=540. Enantiomeric purity by chiral HPLC=>99% e.e.

Example 3B: 73 mg. LCMS (2 min, Formic Acid): Rt=0.63 min, MH+=540. Enantiomeric purity by chiral HPLC=97% e.e.

Example 3B (S)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one

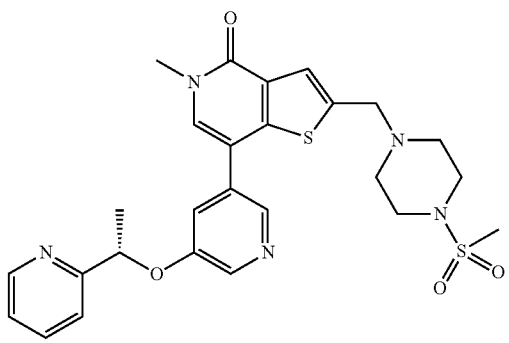 [SMILES: C[C@H](Oc1cncc(-c2cn(C)c(=O)c3cc(CN4CCN(S(C)(=O)=O)CC4)sc23)c1)c1ccccn1]

Alternative Preparation

To a microwave vial was added 7-bromo-5-methyl-2-((4-(methylsulfonyl)piperazin-1-yl)methyl)thieno[3,2-c]pyridin-4(5H)-one (Intermediate 69) (161.5 mg, 0.384 mmol), potassium carbonate (161.2 mg, 1.166 mmol), [1,3-bis(2,6-diisopropylphenyl)-imidazol-2-ylidene](3-chloropyridyl) palladium(II) dichloride (PEPPSI-IPr) (28.4 mg, 0.042 mmol) followed by (S)-(5-(1-(pyridin-2-yl)ethoxy)pyridin-3-yl)boronic acid (Intermediate 90) (131 mg, 0.537 mmol) (662 mg of the crude material theoretically containing a maximum of 131 mg, 0.537 mmol of the required boronic acid) in isopropanol (2.5 mL) and water (1 mL). The vial was sealed and heated with stirring at 110° C. for 30 min in a microwave reactor. The reaction mixture was diluted with saturated aqueous sodium bicarbonate solution (30 mL) and extracted with DCM (3×20 mL). The combined organic phases were filtered through a cartridge fitted with a hydrophobic frit and evaporated in vacuo. The residue was loaded in DCM (~10 mL) onto a 25 g SNAP silica cartridge and was purified by Biotage SP4 flash column chromatography eluting with a gradient of 0-70% (20% MeOH in DCM solution) in EtOAc. The required fractions were combined and evaporated in vacuo to give the desired product but still with a significant impurity. The residue was re-dissolved in dichloromethane (~5 mL), loaded onto a 25 g SNAP silica cartridge and was purified by Biotage SP4 flash column chromatography eluting with a gradient of 0-10% MeOH in DCM. The required fractions were combined and evaporated in vacuo to give the desired product as a yellow gum but still with an impurity present. The residue was dissolved in MeCN (ca. 2 mL) and a solid crystallised out from the solution. The mother liquor was pipetted away from the solid and the solid washed with MeCN (3×0.5 mL). The combined mother liquors were evaporated under a stream of nitrogen to give the title compound (83.4 mg, 0.155 mmol, 40.2% yield)

LCMS (2 min, Formic Acid): Rt=0.63 min, MH$^+$=540
Purity=>95%
Enantiomeric purity by chiral HPLC=>88% e.e.

Example 4

7-(5-(benzylox)pyridin-3-yl)-5-methyl-2-((4-(methylsulphonyl)piperazin-1-yl)methyl)thieno[3,2-c]pyridin-4(5H)-one

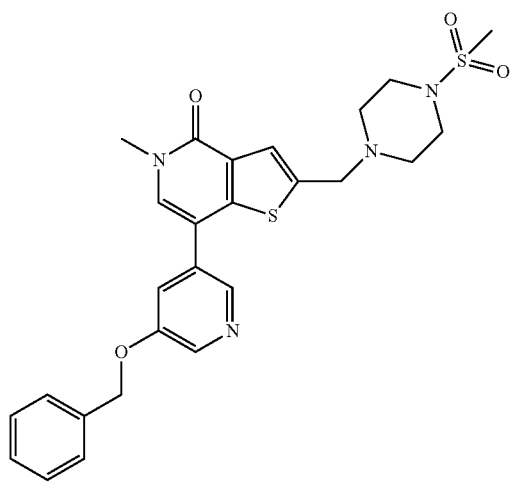 [SMILES: Cn1cc(-c2cncc(OCc3ccccc3)c2)c2sc(CN3CCN(S(C)(=O)=O)CC3)cc2c1=O]

A mixture of 7-bromo-5-methyl-2-((4-(methylsulphonyl)piperazin-1-yl)methyl)thieno[3,2-c]pyridin-4(5H)-one (for a preparation see Intermediate 69, 100 mg, 0.24 mmol), (5-(benzyloxy)pyridin-3-yl)boronic acid (for a preparation see Intermediate 9, 109 mg, 0.48 mmol), potassium carbonate (164 mg, 1.19 mmol) and bis(triphenylphosphine)palladium(II) chloride (17 mg, 6 mol %) in 1,2-dimethoxyethane (3 mL) and water (0.5 mL) was heated in a microwave at 120° C. for 20 minutes. The cooled reaction mixture was diluted with ethyl acetate (50 mL). The solution was dried and evaporated. The residue was purified by chromatography on silica gel eluting with 2-6% methanol in dichloromethane to give 7-(5-(benzyloxy)pyridin-3-yl)-5-methyl-2-((4-(methylsulphonyl)piperazin-1-yl)methyl)thieno[3,2-c]pyridin-4(5H)-one (36 mg, 0.069 mmol, 28.8% yield) as a light brown solid.

LCMS (2 min, Formic Acid): Rt=0.81 min, MH$^+$=525.

Example 5

5-methyl-2-((4-(methylsulphonyl)piperazin-1-yl)methyl)-7-(3-((tetrahydro-2H-pyran-4-yl)methoxy)phenyl)thieno[3,2-c]pyridin-4(5H)-one

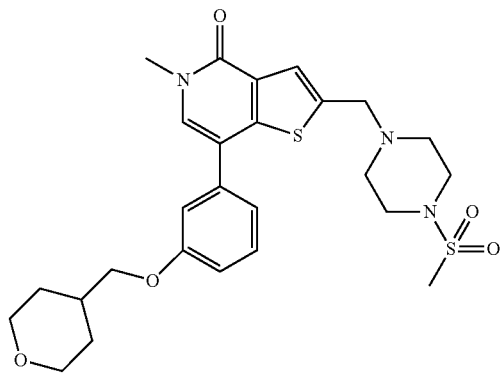 [SMILES: Cn1cc(-c2cccc(OCC3CCOCC3)c2)c2sc(CN3CCN(S(C)(=O)=O)CC3)cc2c1=O]

To a solution of 7-(3-hydroxyphenyl)-5-methyl-2-((4-(methylsulphonyl)piperazin-1-yl)methyl)thieno[3,2-c]pyridin-4(5H)-one (for a preparation see Example 10, 17 mg, 0.039 mmol) and 4-(bromomethyl)tetrahydro-2H-pyran (21.06 mg, 0.118 mmol) in N,N-dimethylformamide (2 mL) was added potassium carbonate (16.26 mg, 0.118 mmol). The resulting mixture was stirred at 100° C. for 3 hours, whereupon it was allowed to cool to room temperature. The reaction mixture was partitioned between ethyl acetate and water. The aqueous phase was extracted 3 times with ethyl acetate and the combined organic layers were washed with brine, dried over magnesium sulphate, filtered and concentrated in vacuo. The residue was purified by chromatography on silica gel eluting with 2-10% methanol in dichloromethane. The appropriate fractions were combined and concentrated in vacuo to give 5-methyl-2-((4-(methylsulphonyl)piperazin-1-yl)methyl)-7-(3-((tetrahydro-2H-pyran-4-yl)methoxy)phenyl)thieno[3,2-c]pyridin-4(5H)-one (13 mg, 0.025 mmol, 65%).

LCMS (2 min, Formic Acid): Rt=0.80 min, MH$^+$=532

Example 6

7-(3-isopropoxyphenyl)-5-methyl-2-((4-(methylsulphonyl)piperazin-1-yl)methyl)thieno[3,2-c]pyridin-4(5H)-one

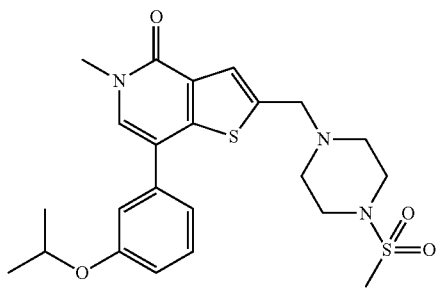 [SMILES: CC(C)Oc1cccc(-c2cn(C)c(=O)c3cc(CN4CCN(S(C)(=O)=O)CC4)sc23)c1]

To a solution of 7-bromo-5-methyl-2-((4-(methylsulphonyl)piperazin-1-yl)methyl)thieno[3,2-c]pyridin-4(5H)-one (for a preparation see Intermediate 69, 100 mg, 0.238 mmol) and (3-isopropoxyphenyl)boronic acid (64.2 mg, 0.357 mmol) in isopropanol (5 mL) were successively added 2M aqueous potassium carbonate solution (0.595 mL, 1.189 mmol) and PEPPSI-IPr (16.16 mg, 0.024 mmol). The resulting mixture was heated at 110° C. in the microwave for 30 minutes, whereupon the reaction mixture was allowed to cool down to room temperature and was concentrated in vacuo. The crude residue was partitioned between ethyl acetate and a saturated aqueous solution of sodium bicarbonate. The phases were separated, the aqueous phase was extracted 3 times with ethyl acetate and the combined organic layers were washed with brine, dried over magnesium sulphate, filtered and concentrated in vacuo. The residue was purified by chromatography on silica gel eluting with 10-60% methanol in dichloromethane. The appropriate fractions were combined and concentrated in vacuo to give 7-(3-isopropoxyphenyl)-5-methyl-2-((4-(methylsulphonyl)piperazin-1-yl)methyl)thieno[3,2-c]pyridin-4(5H)-one (57 mg, 0.12 mmol, 50%) as a colourless oil.

LCMS (2 min, High pH): Rt=1.12 min, MH$^+$=476

Example 7

5-methyl-2-((4-(methylsulphonyl)piperazin-1-yl)methyl)-7-(2-((tetrahydro-2H-pyran-4-yl)methoxy)pyridin-4-yl)thieno[3,2-c]pyridin-4(5H)-one

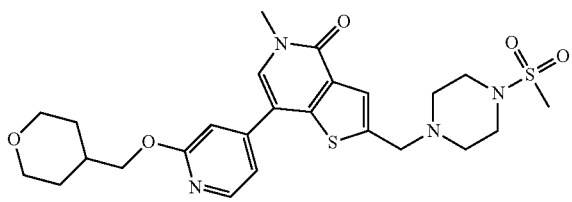 [SMILES: Cn1cc(-c2ccnc(OCC3CCOCC3)c2)c2sc(CN3CCN(S(C)(=O)=O)CC3)cc2c1=O]

A mixture of 7-bromo-5-methyl-2-((4-(methylsulphonyl)piperazin-1-yl)methyl)thieno[3,2-c]pyridin-4(5H)-one (for a preparation see Intermediate 69, 424 mg, 1 mmol), 2-((tetrahydro-2H-pyran-4-yl)methoxy)-4-(4,4,5,5-tetramethyl-1,3,2-dioxaborolan-2-yl)pyridine hydrochloride (for a preparation see Intermediate 11, 359 mg, 1 mmol), and potassium carbonate (697 mg, 5.04 mmol) in toluene (10 mL) and ethanol (10 mL) was degassed and the vessel refilled with nitrogen. Bis(triphenylphosphine)palladium(II) chloride (14 mg, 2 mol %) was added and the mixture stirred at 80° C., under nitrogen, for 2 hours. The reaction mixture was cooled to room temperature and diluted with ethyl acetate (20 mL). The mixture was filtered through Celite. The solvent was evaporated from the filtrate and the residue purified by chromatography on silica gel eluting with 2% methanol in dichloromethane to give impure product which was repurified by MDAP to give 5-methyl-2-((4-(methylsulphonyl)piperazin-1-yl)methyl)-7-(2-((tetrahydro-2H-pyran-4-yl)methoxy)pyridin-4-yl)thieno[3,2-c]pyridin-4(5H)-one (140 mg, 0.263 mmol, 26.1% yield) as a colourless solid.

LCMS (2 min, Formic Acid): Rt=0.71 min, MH$^+$=533

Example 8

7-(3-(2-methoxyethoxy)phenyl)-5-methyl-2-((4-(methylsulphonyl)piperazin-1-yl)methyl)thieno[3,2-c]pyridin-4(5H)-one

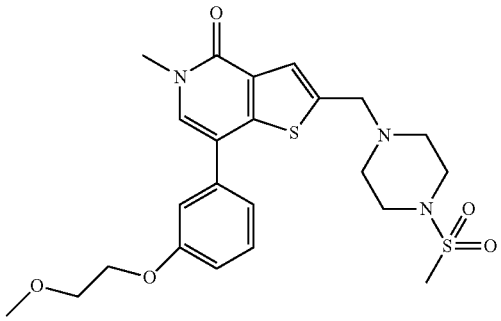 [SMILES: COCCOc1cccc(-c2cn(C)c(=O)c3cc(CN4CCN(S(C)(=O)=O)CC4)sc23)c1]

To a solution of 7-(3-hydroxyphenyl)-5-methyl-2-((4-(methylsulphonyl)piperazin-1-yl)methyl)thieno[3,2-c]pyridin-4(5H)-one (for a preparation see Example 10, 24 mg, 0.055 mmol) and 1-bromo-2-methoxyethane (23.08 mg, 0.166 mmol) in N,N-dimethylformamide (2 mL) was added potassium carbonate (22.95 mg, 0.166 mmol). The resulting mixture was stirred at 100° C. for 12 hours, whereupon it was allowed to cool to room temperature. The residue was partitioned between ethyl acetate and water. The phases were separated and the aqueous phase was extracted with ethyl acetate (5×). The combined organic layers were washed with brine, dried over magnesium sulphate, filtered and concentrated in vacuo. The crude residue was purified via MDAP. The appropriate fractions were collected and concentrated in vacuo to give 7-(3-(2-methoxyethoxy)phenyl)-5-methyl-2-((4-(methylsulphonyl)piperazin-1-yl)methyl)thieno[3,2-c]pyridin-4(5H)-one (22 mg, 0.045 mmol, 81%) as a colourless oil.

LCMS (2 min, Formic Acid): Rt=0.70 min, MH$^+$=492.

Example 9

7-(3-(3-hydroxypropoxy)phenyl)-5-methyl-2-((4-(methylsulphonyl)piperazin-1-yl)methyl)thieno[3,2-c]pyridin-4(5H)-one hydrochloride

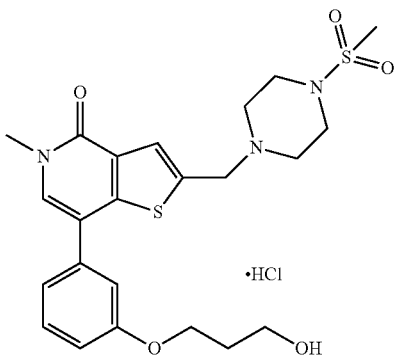 [SMILES: Cn1cc(-c2cccc(OCCCO)c2)c2sc(CN3CCN(S(C)(=O)=O)CC3)cc2c1=O ; Cl]

A mixture of 7-(3-hydroxyphenyl)-5-methyl-2-((4-(methylsulphonyl)piperazin-1-yl)methyl)thieno[3,2-c]pyridin-4(5H)-one (for a preparation see Example 10, 60 mg, 0.14 mmol), potassium carbonate (57 mg, 0.41 mmol) and 3-bromopropan-1-ol (20 mg, 13 µL, 0.14 mmol) in dry DMF (3 mL) was stirred at 60° C. for 24 hours. The reaction mixture was cooled to room temperature then partitioned between water (10 mL) and ethyl acetate (15 mL). The aqueous phase was extracted with ethyl acetate (15 mL). The combined organics were dried and evaporated. The residue was purified by chromatography on silica gel eluting with 0-5% methanol in dichloromethane. The product was repurified by MDAP. The product was dissolved in ethyl acetate (0.5 mL) and treated with 1M hydrogen chloride in diethyl ether (0.25 mL). Diethyl ether (5 mL) was added, the precipitate was filtered off, washed with diethyl ether and dried to give 7-(3-(3-hydroxypropoxy)phenyl)-5-methyl-2-((4-(methylsulphonyl)piperazin-1-yl)methyl)thieno[3,2-c]pyridin-4(5H)-one hydrochloride (11 mg, 0.021 mmol, 15.05% yield) as a colourless solid.

LCMS (2 min, Formic Acid): Rt=0.65 min, MH$^+$=492.

Example 10

7-(3-hydroxyphenyl)-5-methyl-2-((4-(methylsulphonyl)piperazin-1-yl)methyl)thieno[3,2-c]pyridin-4(5H)-one

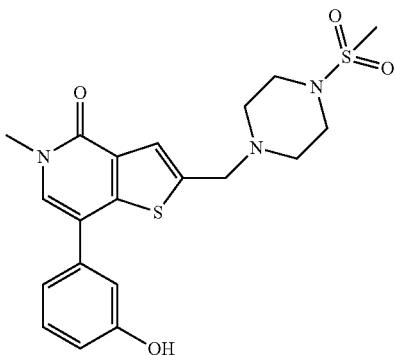 [SMILES: Cn1cc(-c2cccc(O)c2)c2sc(CN3CCN(S(C)(=O)=O)CC3)cc2c1=O]

A mixture of 7-bromo-5-methyl-2-((4-(methylsulphonyl)piperazin-1-yl)methyl)thieno[3,2-c]pyridin-4(5H)-one (for a preparation see Intermediate 69, 400 mg, 1.0 mmol), (3-hydroxyphenyl)boronic acid (166 mg, 1.2 mmol), potassium carbonate (415 mg, 3.0 mmol) and bis(triphenylphosphine)palladium(II) chloride (35 mg, 5 mol %) in 1,2-dimethoxyethane (10 mL) and water (1 mL) was heated in a microwave at 120° C. for 30 minutes. The cooled reaction mixture was diluted with ethyl acetate (50 mL). The solution was dried and evaporated. The residue was purified by chromatography on silica gel eluting with 2-5% methanol in dichloromethane and the product triturated with diethyl ether to give 7-(3-hydroxyphenyl)-5-methyl-2-((4-(methylsulphonyl)piperazin-1-yl)methyl)thieno[3,2-c]pyridin-4(5H)-one (400 mg, 0.923 mmol, 92% yield) as a yellow solid.

LCMS (2 min, Formic Acid): Rt=0.61 min, MH$^+$=434.

Example 11

5-methyl-2-((4-(methylsulphonyl)piperazin-1-yl)methyl)-7-(5-((tetrahydro-2H-pyran-4-yl)methoxy)pyridin-3-yl)thieno[3,2-c]pyridin-4(5H)-one

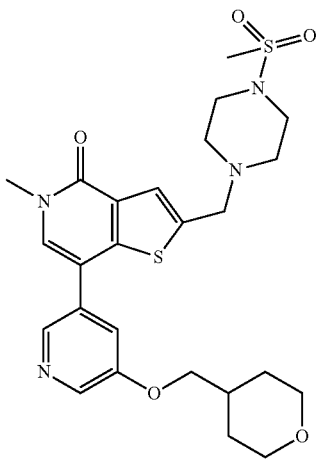 [SMILES: Cn1cc(-c2cncc(OCC3CCOCC3)c2)c2sc(CN3CCN(S(C)(=O)=O)CC3)cc2c1=O]

To a microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 105 mg, 0.25 mmol) followed by potassium carbonate (104 mg, 0.750 mmol), PEPPSI-IPr (16.99 mg, 0.025 mmol), and (5-((tetrahydro-2H-pyran-4-yl)methoxy)pyridin-3-yl)boronic acid (89 mg, 0.375 mmol) in a solution of isopropanol (3 mL) and water (1 mL). The reaction vessel was sealed and heated to 130° C. for 30 minutes in a microwave. The reaction was diluted with dichloromethane (30 mL) and washed with saturated ammonium chloride solution. The organic layer was collected and the aqueous phase was extracted with dichloromethane (2×25 mL). The organic fractions were combined, dried over magnesium sulphate, and concentrated under reduced pressure. The crude material was purified by chromatography on silica gel eluting with 0-5% methanol in dichloromethane to give impure product. The material was repurified my MDAP to give 5-methyl-2-((4-(methylsulphonyl)piperazin-1-yl)methyl)-7-(5-((tetrahydro-2H-pyran-4-yl)methoxy)pyridin-3-yl)thieno[3,2-c]pyridin-4(5H)-one (30.3 mg, 0.057 mmol, 22.75% yield) as an off-white solid.

LCMS (2 min, Formic Acid): Rt=0.61 min, MH$^+$=533.

Example 12

7-(5-hydroxypyridin-3-yl)-5-methyl-2-((4-(methylsulphonyl)piperazin-1-yl)methyl)thieno[3,2-c]pyridin-4(5H)-one

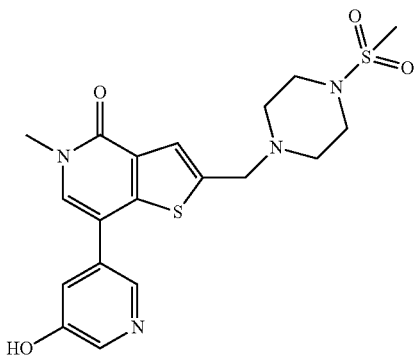 [SMILES: Cn1cc(-c2cncc(O)c2)c2sc(CN3CCN(S(C)(=O)=O)CC3)cc2c1=O]

A mixture of 7-bromo-5-methyl-2-((4-(methylsulphonyl)piperazin-1-yl)methyl)thieno[3,2-c]pyridin-4(5H)-one (for a preparation see Intermediate 69, 170 mg, 0.404 mmol), (5-hydroxypyridin-3-yl)boronic acid (399 mg, 2.87 mmol), potassium carbonate (279 mg, 2.022 mmol) and bis(triphenylphosphine)palladium(II) chloride (17 mg, 0.024 mmol) in 1,2-dimethoxyethane (6 mL) and water (1 mL) was heated in the microwave at 120° C. for 30 minutes. The cooled reaction mixture was diluted with ethyl acetate and an aqueous saturated solution of sodium bicarbonate was added. The phases were separated and the aqueous phase was extracted three times with ethyl acetate. The combined organic layers were washed with brine, dried over magnesium sulphate, filtered and concentrated in vacuo. The crude residue was purified via MDAP. The appropriate fractions were combined and concentrated in vacuo to give 7-(5-hydroxypyridin-3-yl)-5-methyl-2-((4-(methylsulphonyl)piperazin-1-yl)methyl)thieno[3,2-c]pyridin-4(5H)-one (14 mg, 0.032 mmol, 8%) as a white solid.

LCMS (2 min, Formic Acid): Rt=0.42 min, MH$^+$=435.

Example 13

5-methyl-2-((4-(methylsulphonyl)piperazin-1-yl)methyl)-7-(2-(1-(pyridin-2-yl)ethoxy)pyridin-4-yl)thieno[3,2-c]pyridin-4(5H)-one

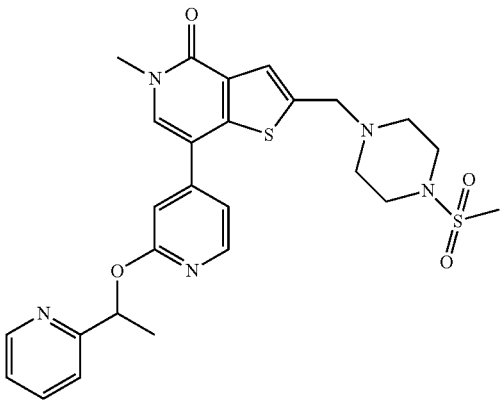 [SMILES: CC(Oc1cc(-c2cn(C)c(=O)c3cc(CN4CCN(S(C)(=O)=O)CC4)sc23)ccn1)c1ccccn1]

To a microwave reaction vial was added 7-bromo-5-methyl-2-((4-(methylsulphonyl)piperazin-1-yl)methyl)thieno[3,2-c]pyridin-4(5H)-one (105 mg, 0.25 mmol) (for a preparation see Intermediate 69, 105 mg, 0.25 mmol), potassium carbonate (104 mg, 0.750 mmol), (2-(1-(pyridin-2-yl)ethoxy)pyridin-4-yl)boronic acid (for a preparation see Intermediate 16, 92 mg, 0.377 mmol), and PEPPSI-IPr (16.99 mg, 0.025 mmol) in a solution of isopropanol (3 mL) and water (1 mL). The reaction vessel was sealed and heated to 130° C. for 30 minutes in a microwave. The reaction was diluted with saturated ammonium chloride solution (30 mL) and the aqueous phase was extracted with dichloromethane (3×30 mL). The organic fractions were combined, dried over magnesium sulphate, and concentrated under reduced pressure to give a dark brown oil. This was purified by chromatography on silica gel eluting with 0-10% methanol in dichloromethane to give a product which was repurified by MDAP. The product was triturated with diethyl ether to give 5-methyl-2-((4-(methylsulphonyl)piperazin-1-yl)methyl)-7-(2-(1-(pyridin-2-yl)ethoxy)pyridin-4-yl)thieno[3,2-c]pyridin-4(5H)-one (15 mg, 0.028 mmol, 11.12% yield) as a white solid.

LCMS (2 min, Formic Acid): Rt=0.57 min, MH$^+$=540.

Example 14

7-(5-((1-methoxypropan-2-yl)oxy)pyridin-3-yl)-5-methyl-2-((4-(methylsulphonyl)piperazin-1-yl)methyl)thieno[3,2-c]pyridin-4(5H)-one

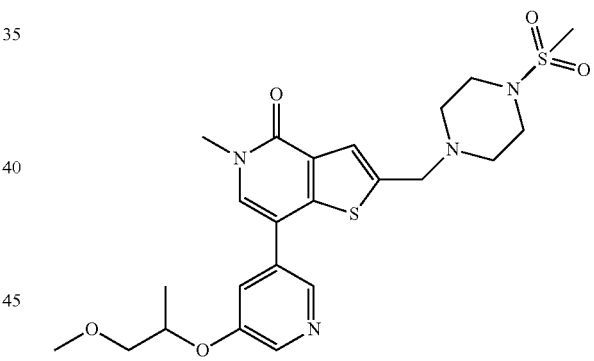

A mixture of 7-bromo-5-methyl-2-((4-(methylsulphonyl)piperazin-1-yl)methyl)thieno[3,2-c]pyridin-4(5H)-one (for a preparation see Intermediate 69, 118 mg, 0.282 mmol), (5-((1-methoxypropan-2-yl)oxy)pyridin-3-yl)boronic acid (for a preparation see Intermediate 18, 66.1 mg, 0.313 mmol), potassium carbonate (130 mg, 0.939 mmol) and bis(triphenylphosphine)palladium(II) chloride (21.97 mg, 0.031 mmol) in 1,2-dimethoxyethane (3 mL) and water (0.5 mL) was heated in a microwave at 120° C. for 20 minutes. The cooled reaction mixture was diluted with ethyl acetate (50 mL) and the solution was dried over magnesium sulphate and evaporated in vacuo. The residue was purified by chromatography on silica gel, eluting with 2-10% methanol in dichloromethane to give 7-(5-((1-methoxypropan-2-yl)oxy)pyridin-3-yl)-5-methyl-2-((4-(methylsulphonyl)piperazin-1-yl)methyl)thieno[3,2-c]pyridin-4(5H)-one (33 mg, 0.065 mmol, 21%) as a light brown solid.

LCMS (2 min, Formic Acid): Rt=0.61 min, MH$^+$=507.

Example 15

7-(3-methoxyphenyl)-5-methyl-2-((4-(methylsulphonyl)piperazin-1-yl)methyl)thieno[3,2-c]pyridin-4(5H)-one

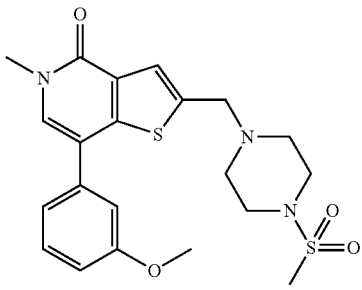 [SMILES: COc1cccc(-c2cn(C)c(=O)c3cc(CN4CCN(S(C)(=O)=O)CC4)sc23)c1]

To a microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), (3-methoxyphenyl)boronic acid (30.4 mg, 0.200 mmol), potassium carbonate (55.2 mg, 0.400 mmol), isopropanol (2 mL), and water (1 mL). PEPPSI-IPr (34 mg, 0.050 mmol) was added to the reaction.

The reaction vessel was sealed and heated in a microwave to 130° C. for 30 minutes. After cooling the reaction was quenched with saturated ammonium chloride solution (15 mL) and dichloromethane (15 mL) and filtered through Celite. The organic layer was collected. The aqueous later was extracted with dichloromethane (3×15 mL). The organic layers were combined and dried over magnesium sulphate. The solvent was removed under reduced pressure. The residue was purified by chromatography on silica gel eluting with 0-10% methanol in dichloromethane to give an orange solid which was repurified by MDAP to give 7-(3-methoxyphenyl)-5-methyl-2-((4-(methylsulphonyl)piperazin-1-yl)methyl)thieno[3,2-c]pyridin-4(5H)-one (5 mg, 0.01 mmol, 6%) as a colourless oil.

LCMS (2 min, Formic Acid): Rt=0.74 min, MH$^+$=448.

Example 16

5-methyl-2-((4-(methylsulphonyl)piperazin-1-yl)methyl)-7-(3-(1-phenylethoxy)phenyl)thieno[3,2-c]pyridin-4(5H)-one

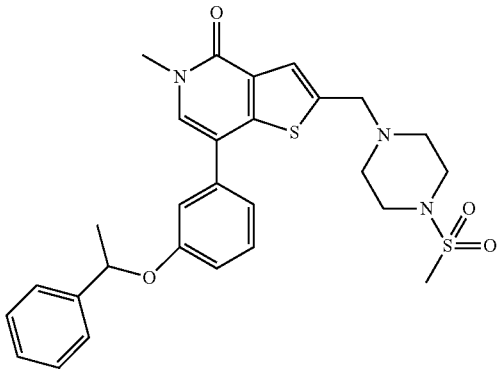 [SMILES: CC(Oc1cccc(-c2cn(C)c(=O)c3cc(CN4CCN(S(C)(=O)=O)CC4)sc23)c1)c1ccccc1]

To a solution of 7-(3-hydroxyphenyl)-5-methyl-2-((4-(methylsulphonyl)piperazin-1-yl)methyl)thieno[3,2-c]pyridin-4(5H)-one (for a preparation see Example 10, 22 mg, 0.051 mmol) and (1-bromoethyl)benzene (28.2 mg, 0.152 mmol) in N,N-dimethylformamide (2 mL) was added potassium carbonate (21.04 mg, 0.152 mmol). The resulting mixture was stirred at 100° C. for 24 hours, whereupon it was allowed to cool to room temperature. The residue was partitioned between ethyl acetate and water. The phases were separated and the aqueous phase was extracted with ethyl acetate (5×). The combined organic layers were washed with brine, dried over magnesium sulphate, filtered and concentrated in vacuo. The crude residue was dissolved in a 1:1 DMSO/MeOH mixture (1 mL) and was purified via MDAP. The appropriate fractions were collected and concentrated in vacuo to give, 5-methyl-2-((4-(methylsulphonyl)piperazin-1-yl)methyl)-7-(3-(1-phenylethoxy)phenyl)thieno[3,2-c]pyridin-4(5H)-one (3.1 mg, 5.8 μmol, 11%) as a yellow oil.

LCMS (2 min, Formic Acid): Rt=0.99 min, MH$^+$=538.

Example 17

5-methyl-2-((4-(methylsulphonyl)piperazin-1-yl)methyl)-7-(3-((1-phenylethyl)amino)phenyl)thieno[3,2-c]pyridin-4(5H)-one

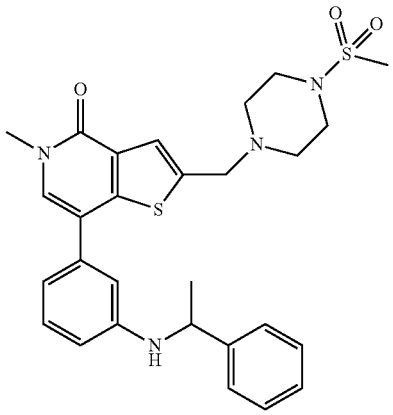

7-(3-Aminophenyl)-5-methyl-2-((4-(methylsulphonyl)piperazin-1-yl)methyl)thieno[3,2-c]pyridin-4(5H)-one (for a preparation see Example 25, 270 mg, 0.624 mmol) and titanium(IV) isopropoxide (266 mg, 277 μL, 0.94 mmol) were added to a stirred solution of acetophenone (112 mg, 109 μL, 0.94 mmol) in 2,2,2-trifluoroethanol (10 mL) at 70° C. The reaction mixture was refluxed for 3 hours, then treated with sodium borohydride (71 mg, 1.88 mmol). The reaction mixture was refluxed overnight. A further portion of sodium borohydride (71 mg, 1.88 mmol) was added and reflux continued for 4 hours. The reaction mixture was cooled and the solvent evaporated. The residue was dissolved in dichloromethane (20 mL). The solution was washed with saturated sodium bicarbonate solution then water. The organic phase was dried and evaporated. The residue was purified by chromatography on silica gel eluting with 2% methanol in dichloromethane to give 5-methyl-2-((4-(methylsulphonyl)piperazin-1-yl)methyl)-7-(3-((1-phenylethyl)amino)phenyl)thieno[3,2-c]pyridin-4(5H)-one (78 mg, 0.145 mmol, 23.28% yield) as an off-white solid.

LCMS (2 min, Formic Acid): Rt=0.94 min, MH$^+$=537

Example 18

(R)-N-(3-(5-methyl-2-((2-methyl-4-(methylsulphonyl)piperazin-1-yl)methyl)-4-oxo-4,5-dihydrothieno[3,2-c]pyridin-7-yl)phenyl)acetamide

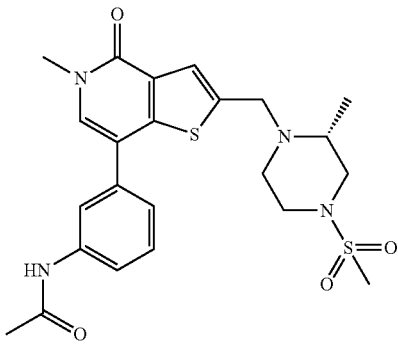 [SMILES: CC(=O)Nc1cccc(-c2cn(C)c(=O)c3cc(CN4CCN(S(C)(=O)=O)C[C@H]4C)sc23)c1]

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.23 mmol), (3-acetamidophenyl)boronic acid (62 mg, 0.35 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate, filtered and the solvent evaporated. The residue was purified by chromatography on silica gel eluting with 2-5% methanol in dichloromethane to give (R)-N-(3-(5-methyl-2-((2-methyl-4-(methylsulphonyl)piperazin-1-yl)methyl)-4-oxo-4,5-dihydrothieno[3,2-c]pyridin-7-yl)phenyl)acetamide (59 mg, 0.121 mmol, 52.4% yield) as a colourless solid.

LCMS (2 min, Formic Acid): Rt=0.60 min, MH$^+$=489

Example 19

5-methyl-2-((4-(methylsulphonyl)piperazin-1-yl)methyl)-7-(3-(((tetrahydro-2H-pyran-4-yl)methyl)amino)phenyl)thieno[3,2-c]pyridin-4(5H)-one

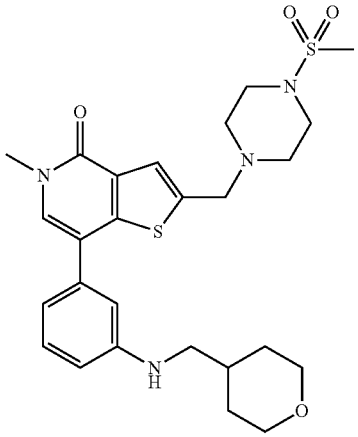

A stirred solution of tetrahydro-2H-pyran-4-carbaldehyde (39.6 mg, 0.347 mmol) in 2,2,2-trifluoroethanol (3 mL) was heated to 40° C. and treated with 7-(3-aminophenyl)-5-methyl-2-((4-(methylsulphonyl)piperazin-1-yl)methyl) thieno[3,2-c]pyridin-4(5H)-one (for a preparation see Example 25, 100 mg, 0.231 mmol) and acetic acid (0.013 mL, 0.231 mmol). The reaction was stirred at 40° C. for 2 hours and then treated with sodium borohydride (10.50 mg, 0.277 mmol). The reaction was left under nitrogen at 40° C. over the weekend. The reaction was cooled to room temperature and then concentrated under reduced pressure to give a pink solid. The material was dissolved in dichloromethane (25 mL) and washed with saturated sodium bicarbonate solution (25 mL). The organic layer was collected and the product was extracted from the aqueous layer with dichloromethane (3×20 mL). The organic fractions were combined, dried over magnesium sulphate, and concentrated under reduced pressure. The crude material was purified by chromatography on silica gel eluting with 0-5% methanol in dichloromethane to give a solid which was repurified by MDAP to give 5-methyl-2-((4-(methylsulphonyl)piperazin-1-yl)methyl)-7-(3-(((tetrahydro-2H-pyran-4-yl)methyl)amino)phenyl)thieno[3,2-c]pyridin-4(5H)-one (11 mg, 0.021 mmol, 9% yield) as a colourless solid.

LCMS (2 min, Formic Acid): Rt=0.77 min, MH$^+$=531

Example 20

N-(3-(5-methyl-2-((4-(methylsulphonyl)piperazin-1-yl)methyl)-4-oxo-4,5-dihydrothieno[3,2-c]pyridin-7-yl)phenyl)acetamide

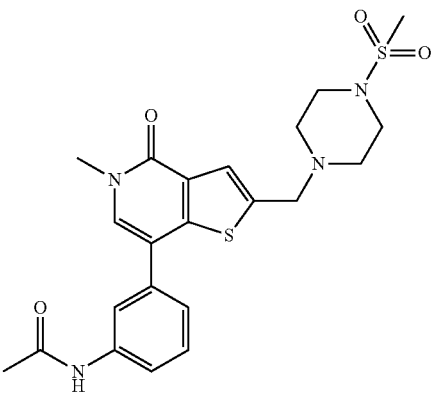 [SMILES: CC(=O)Nc1cccc(-c2cn(C)c(=O)c3cc(CN4CCN(S(C)(=O)=O)CC4)sc23)c1]

A mixture of 7-bromo-5-methyl-2-((4-(methylsulphonyl)piperazin-1-yl)methyl)thieno[3,2-c]pyridin-4(5H)-one (for a preparation see Intermediate 69, 210 mg, 0.5 mmol), N-(3-(4,4,5,5-tetramethyl-1,3,2-dioxaborolan-2-yl)phenyl)acetamide (261 mg, 1.0 mmol), potassium carbonate (346 mg, 2.5 mmol) and bis(triphenylphosphine)palladium(II) chloride (35 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was purified by chromatography on silica gel eluting with 0-5% methanol in dichloromethane (twice) and the product triturated with diethyl ether to give N-(3-(5-methyl-2-((4-(methylsulphonyl)piperazin-1-yl)methyl)-4-oxo-4,5-dihydrothieno[3,2-c]pyridin-7-yl)phenyl)acetamide (71 mg, 0.150 mmol, 30% yield) as a yellow solid.

LCMS (2 min, Formic Acid): Rt=0.57 min, MH$^+$=475.

Example 21

7-(2-((2-methoxyethyl)(methyl)amino)pyridin-4-yl)-5-methyl-2-((4-(methylsulphonyl)piperazin-1-yl)methyl)thieno[3,2-c]pyridin-4(5H)-one, 2 formic acid salt

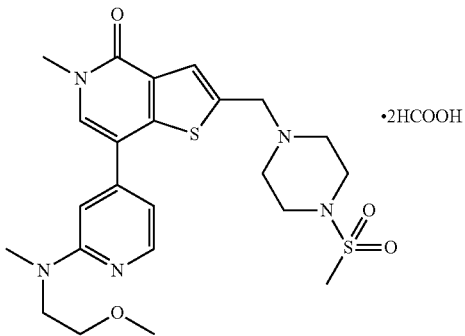 [SMILES: COCCN(C)c1cc(-c2cn(C)c(=O)c3cc(CN4CCN(S(C)(=O)=O)CC4)sc23)ccn1]

To a solution of 7-(2-chloropyridin-4-yl)-5-methyl-2-((4-(methylsulphonyl)piperazin-1-yl)methyl)thieno[3,2-c]pyridin-4(5H)-one (for a preparation see Intermediate 22, 17 mg, 0.038 mmol) in N-methyl-2-pyrrolidone (1 mL) was added 2-methoxy-N-methylethanamine (1004 mg, 11.26 mmol). The reaction mixture was stirred in the microwave for 30 min at 250° C., whereupon it was allowed to cool to room temperature. The excess 2-methoxy-N-methylethanamine was removed in vacuo and the residue was purified by MDAP. The appropriate fractions were combined and concentrated in vacuo to give 7-(2-((2-methoxyethyl)(methyl)amino)pyridin-4-yl)-5-methyl-2-((4-(methylsulphonyl)piperazin-1-yl)methyl)thieno[3,2-c]pyridin-4(5H)-one, 2 formic acid salt. (11 mg, 0.018 mmol, 49%) as a brown oil.

LCMS (2 min, Formic Acid): Rt=0.77 min, MH$^+$=506

Example 22

7-(2-((1-methoxypropan-2-yl)amino)pyridin-4-yl)-5-methyl-2-((4-(methylsulphonyl)piperazin-1-yl)methyl)thieno[3,2-c]pyridin-4(5H)-one 3 formic acid salt

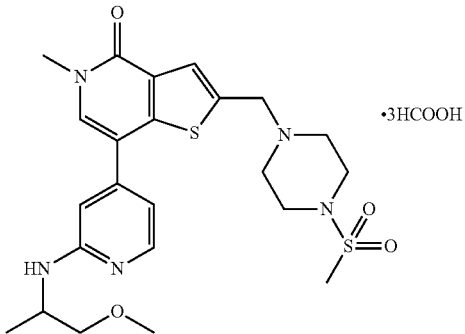 [SMILES: COCC(C)Nc1cc(-c2cn(C)c(=O)c3cc(CN4CCN(S(C)(=O)=O)CC4)sc23)ccn1]

To a solution of 7-(2-chloropyridin-4-yl)-5-methyl-2-((4-(methylsulphonyl)piperazin-1-yl)methyl)thieno[3,2-c]pyridin-4(5H)-one (for a preparation see Intermediate 22, 47 mg, 0.104 mmol) in N-methyl-2-pyrrolidone (1 mL) was added 1-methoxypropan-2-amine (925 mg, 10.38 mmol). The reaction mixture was stirred in the microwave for 30 min at 250° C., whereupon it was allowed to cool to room temperature. The excess 1-methoxypropan-2-amine (925 mg, 10.38 mmol) was removed in vacuo and the residue was purified via MDAP. The appropriate fractions were combined and concentrated in vacuo to give, 7-(2-((1-methoxypropan-2-yl)amino)pyridin-4-yl)-5-methyl-2-((4-(methylsulphonyl)piperazin-1-yl)methyl)thieno[3,2-c]pyridin-4(5H)-one, 3 Formic acid salt (10.9 mg, 0.017 mmol, 16%) as a yellow oil.

LCMS (2 min, Formic Acid): Rt=0.50 min, MH$^+$=506

Example 23

7-(2-((cyclopropylmethyl)amino)pyridin-4-yl)-5-methyl-2-((4-(methylsulphonyl)piperazin-1-yl)methyl)thieno[3,2-c]pyridin-4(5H)-one, 3 Formic acid salt

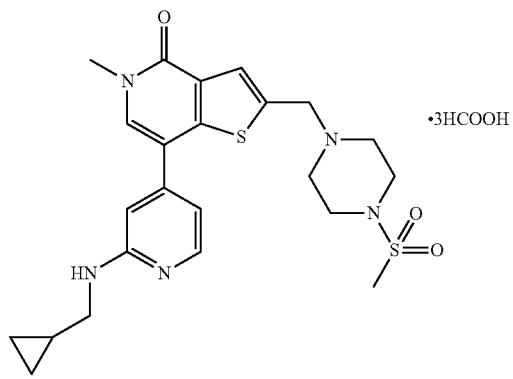 [SMILES: Cn1cc(-c2ccnc(NCC3CC3)c2)c2sc(CN3CCN(S(C)(=O)=O)CC3)cc2c1=O]

To a mixture of 7-(2-chloropyridin-4-yl)-5-methyl-2-((4-(methylsulphonyl)piperazin-1-yl)methyl)thieno[3,2-c]pyridin-4(5H)-one (for a preparation see Intermediate 22, 64 mg, 0.141 mmol) and cyclopropylmethanamine (20.10 mg, 0.283 mmol) in tetrahydrofuran (5 mL) were successively added sodium tert-butoxide (67.9 mg, 0.706 mmol), BINAP (17.60 mg, 0.028 mmol) and tris(dibenzylideneacetone)dipalladium(0) (12.94 mg, 0.014 mmol). The resulting mixture was stirred at 80° C. for 4 hours. The reaction mixture was allowed to cool down to room temperature and was hydrolyzed by adding water. The mixture was diluted with ethyl acetate and the phases were separated. The aqueous phase was extracted 3 times with ethyl acetate and the combined organic layers were washed with brine, dried over magnesium sulphate, filtered and concentrated in vacuo.

The residue was purified via MDAP. The appropriate fractions were collected and concentrated in vacuo to give, 7-(2-((cyclopropylmethyl)amino)pyridin-4-yl)-5-methyl-2-((4-(methylsulphonyl)piperazin-1-yl)methyl)thieno[3,2-c]pyridin-4(5H)-one, 3 Formic acid salt (18 mg, 0.029 mmol, 20%) as a colourless oil.

LCMS (2 min, Formic Acid): Rt=0.49 min, MH$^+$=488

Example 24

N-(3-(5-methyl-2-((4-(methylsulphonyl)piperazin-1-yl)methyl)-4-oxo-4,5-dihydrothieno[3,2-c]pyridin-7-yl)phenyl)formamide

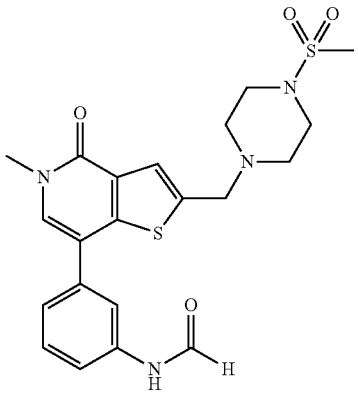

A mixture of 7-bromo-5-methyl-2-((4-(methylsulphonyl)piperazin-1-yl)methyl)thieno[3,2-c]pyridin-4(5H)-one (for a preparation see Intermediate 69, 100 mg, 0.238 mmol), N-(3-(4,4,5,5-tetramethyl-1,3,2-dioxaborolan-2-yl)phenyl)formamide (88 mg, 0.357 mmol), potassium carbonate (164 mg, 1.189 mmol) and bis(triphenylphosphine)palladium(II) chloride (8.35 mg, 0.012 mmol) in ethanol (2 mL) and toluene (2 mL) was heated in a microwave for 20 minutes at 120° C. The reaction mixture was diluted with ethyl acetate (15 mL) the mixture was also dried over magnesium sulphate. The mixture was filtered and the solvent evaporated from the filtrate. The residue was purified by chromatography on silica gel eluting 0-5% methanol in dichloromethane. The product was repurified by MDAP to give N-(3-(5-methyl-2-((4-(methylsulphonyl)piperazin-1-yl)methyl)-4-oxo-4,5-dihydrothieno[3,2-c]pyridin-7-yl)phenyl)formamide (12 mg, 0.026 mmol, 10.95% yield) as a white solid.

LCMS (2 min, Formic Acid): Rt=0.58 min, MH$^+$=461.

Example 25

7-(3-aminophenyl)-5-methyl-2-((4-(methylsulphonyl)piperazin-1-yl)methyl)thieno[3,2-c]pyridin-4(5H)-one

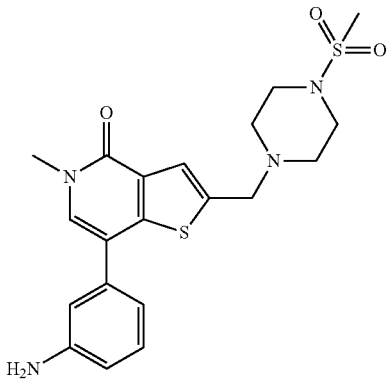 [SMILES: Cn1cc(-c2cccc(N)c2)c2sc(CN3CCN(S(C)(=O)=O)CC3)cc2c1=O]

To a microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol) followed by (3-aminophenyl)boronic acid (23.46 mg, 0.171 mmol), potassium carbonate (47.3 mg, 0.343 mmol), and PEPPSI-IPr (34.0 mg, 0.05 mmol) in a solution of isopropanol (2 mL) and water (1 mL). The reaction vessel was sealed and heated in microwave at 130° C. for 30 minutes. The reaction was diluted with saturated ammonium chloride solution (15 mL) and mixed with dichloromethane (10 mL). The solution was filtered through Celite. The organic layer was collected.

The aqueous phase was extracted with dichloromethane (3×15 mL). The organic fractions were combined and dried over magnesium sulphate. The filtrate was concentrated to give a light brown oil. Which was purified by chromatography on silica gel eluting with 0-5% methanol in dichloromethane to give an oil. The oil was triturated with diethyl ether to give 7-(3-aminophenyl)-5-methyl-2-((4-(methylsulphonyl)piperazin-1-yl)methyl)thieno[3,2-c]pyridin-4(5H)-one (36 mg, 0.083 mmol, 58.3% yield) as an off-white solid.

LCMS (2 min, Formic Acid): Rt=0.52 min, MH$^+$=433

Example 26

7-(3-(benzylamino)phenyl)-5-methyl-2-((4-(methylsulphonyl)piperazin-1-yl)methyl)thieno[3,2-c]pyridin-4(5H)-one hydrochloride

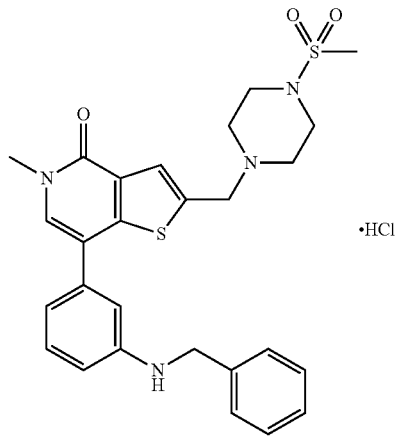

To 2,2,2-trifluoroethanol (3 mL) under nitrogen, was added benzaldehyde (0.023 mL, 0.231 mmol) and the solution was heating to 38° C. The reaction was treated with 7-(3-aminophenyl)-5-methyl-2-((4-(methylsulphonyl)piperazin-1-yl)methyl)thieno[3,2-c]pyridin-4(5H)-one (for a preparation see Example 25, 100 mg, 0.231 mmol) and stirred vigorously for 5 minutes. The reaction was then treated with sodium borohydride (10.50 mg, 0.277 mmol) and stirred at 38° C. for 80 minutes. The reaction was treated with a further portion of sodium borohydride (10.50 mg, 0.277 mmol) and left to stir at 40° C. over the weekend. The reaction was allowed to cool to room temperature. The reaction was filtered and the solid was washed with 2,2,2-trifluoroethanol (5 mL). The filtrate was concentrated under reduced pressure to give a light brown oil. A precipitate formed with the addition of dichloromethane. The mixture was washed with water (15 mL). The aqueous phase was extracted with dichloromethane (3×10 mL). The organic layers were combined, dried over magnesium sulphate, and concentrated under reduced pressure to give a light brown oil. This was purified by chromatography on silica gel eluting with 0-5% methanol in dichloromethane. The product was triturated with diethyl ether to give an off white solid which was re-purified by MDAP to give an oil.

The oil was dissolved in ethyl acetate (1 mL) and treated with 1.0M HCl in diethyl ether (1 mL) to form the hydrochloride salt. The precipitate was triturated with diethyl ether to give 7-(3-(benzylamino)phenyl)-5-methyl-2-((4-(methylsulphonyl)piperazin-1-yl)methyl)thieno[3,2-c]pyridin-4(5H)-one hydrochloride (75.4 mg, 0.135 mmol, 58.3% yield) as an off-white solid.

LCMS (2 min, Formic Acid): Rt=0.90 min, MH+=523

Example 27

5-methyl-2-((4-(methylsulphonyl)piperazin-1-yl)methyl)-7-(2-(((tetrahydrofuran-2-yl)methyl)amino)pyridin-4-yl)thieno[3,2-c]pyridin-4(5H)-one, 3 formic acid salt

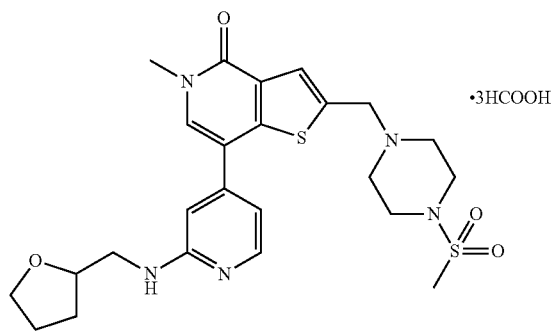 [SMILES: Cn1cc(-c2ccnc(NCC3CCCO3)c2)c2sc(CN3CCN(S(C)(=O)=O)CC3)cc2c1=O]

To a solution of 7-(2-chloropyridin-4-yl)-5-methyl-2-((4-(methylsulphonyl)piperazin-1-yl)methyl)thieno[3,2-c]pyridin-4(5H)-one (for a preparation see Intermediate 22, 50 mg, 0.110 mmol) in N-methyl-2-pyrrolidone (1 mL) was added (tetrahydrofuran-2-yl)methanamine (1116 mg, 11.04 mmol). The reaction mixture was stirred in the microwave for 30 min at 250° C., whereupon it was allowed to cool to room temperature. The excess (tetrahydrofuran-2-yl)methanamine (1116 mg, 11.04 mmol) was removed in vacuo and the residue was purified via MDAP. The appropriate fractions were combined and concentrated in vacuo to give 5-methyl-2-((4-(methylsulphonyl)piperazin-1-yl)methyl)-7-(2-(((tetrahydrofuran-2-yl)methyl)amino)pyridin-4-yl)thieno[3,2-c]pyridin-4(5H)-one, 3 formic acid salt (11 mg, 0.017 mmol, 15%) as a yellow oil.

LCMS (2 min, Formic Acid): Rt=0.49 min, MH+=518

Example 28

7-(3-(benzyloxy)phenyl)-2-((4-ethylpiperazin-1-yl)methyl)-5-methylthieno[3,2-c]pyridin-4(5H)-one

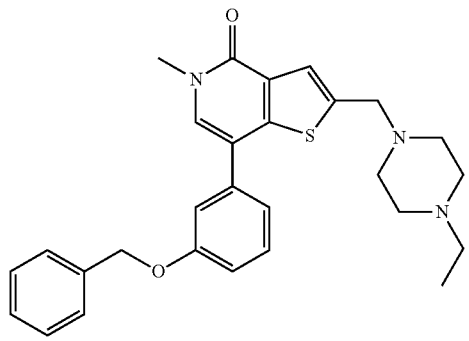 [SMILES: CCN1CCN(Cc2cc3c(=O)n(C)cc(-c4cccc(OCc5ccccc5)c4)c3s2)CC1]

To a microwave reaction vial was added 7-bromo-2-((4-ethylpiperazin-1-yl)methyl)-5-methylthieno[3,2-c]pyridin-4(5H)-one (for a preparation see Intermediate 23, 180 mg, 0.486 mmol) in a solution of isopropanol (2 mL) and water (1 mL). To the reaction was added (3-(benzyloxy)phenyl)boronic acid (166 mg, 0.729 mmol) followed by potassium carbonate (202 mg, 1.458 mmol) and lastly PEPPSI (33.0 mg, 0.049 mmol). The reaction vessel was sealed and heated to 130° C. for 30 minutes in the Biotage Initiator microwave reactor with 10 seconds of pre-stirring.

The reaction was transferred to a separating funnel and diluted with saturated ammonium chloride solution (approx. 30 mL). The aqueous phase was extracted with DCM (3×20 mL). The organic fractions were combined, dried over magnesium sulphate, and concentrated under reduced pressure to give a dark brown oil.

The crude material was loaded on to a 12 g silica gel column and was eluted with 2.0M ammonia in MeOH/DCM (0-10%) over 26 column volumes to give semi-pure product. All fractions containing product were combined, concentrated, and re-purified by MDAP and the collected fractions were evaporated to give a pale yellow oil. This was dissolved in ethyl acetate (1 mL) and treated with 1.0M HCl in diethyl ether (250 μL) to give an off-white solid. The solid was filtered, washed with diethyl ether (×3) and oven dried over night to give 7-(3-(benzyloxy)phenyl)-2-((4-ethylpiperazin-1-yl)methyl)-5-methylthieno[3,2-c]pyridin-4(5H)-one, hydrochloride (127 mg, 0.249 mmol, 51.2% yield).

LCMS (2 min, Formic Acid): Rt=0.92 min, MH+=474

Example 29

7-(3-(benzyloxy)phenyl)-2-((4-isopropylpiperazin-1-yl)methyl)-5-methylthieno[3,2-c]pyridin-4(5H)-one

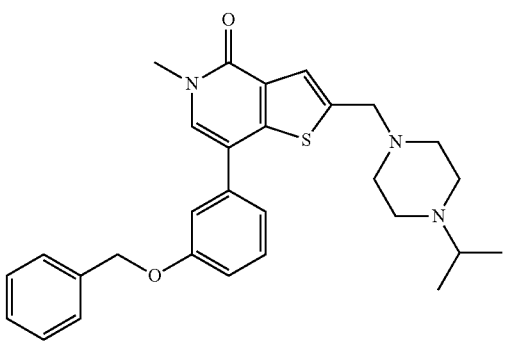 [SMILES: CC(C)N1CCN(Cc2cc3c(=O)n(C)cc(-c4cccc(OCc5ccccc5)c4)c3s2)CC1]

To a microwave reaction vial was added 7-bromo-2-((4-isopropylpiperazin-1-yl)methyl)-5-methylthieno[3,2-c]pyridin-4(5H)-one (for a preparation see Intermediate 24, 150 mg, 0.390 mmol) in a solution of isopropanol (3 mL) and water (1.5 mL) followed by (3-(benzyloxy)phenyl)boronic acid (134 mg, 0.585 mmol), potassium carbonate (162 mg, 1.171 mmol), and lastly PEPPSI (26.5 mg, 0.039 mmol). The reaction vessel was sealed and heated to 130° C. for 30 minutes in a Biotage Initiator microwave reactor with 10 seconds of pre-stirring.

The reaction was transferred to a separating funnel and diluted with saturated ammonium chloride solution (30 mL). The aqueous phase was extracted with DCM (3×25 mL). The organic fractions were combined, dried over magnesium sulphate, and concentrated under reduced pressure to give dark brown residue.

The crude material was loaded on to a 12 g silica gel column and was eluted in 0-10% MeOH in DCM over 25 column volumes to an orange solid, the desired product 7-(3-(benzyloxy)phenyl)-2-((4-isopropylpiperazin-1-yl)methyl)-5-methylthieno[3,2-c]pyridin-4(5H)-one (92 mg, 0.189 mmol, 48.3% yield).

LCMS (2 min, Formic Acid): Rt=0.90 min, MH+=488.

Example 30

2-((4-benzoylpiperazin-1-yl)methyl)-7-(3,4-dimethoxyphenyl)-5-methylthieno[3,2-c]pyridin-4(5H)-one and Example 33

2-((4-(benzylsulphonyl)piperazin-1-yl)methyl)-7-(3,4-dimethoxyphenyl)-5-methylthieno[3,2-c]pyridin-4(5H)-one

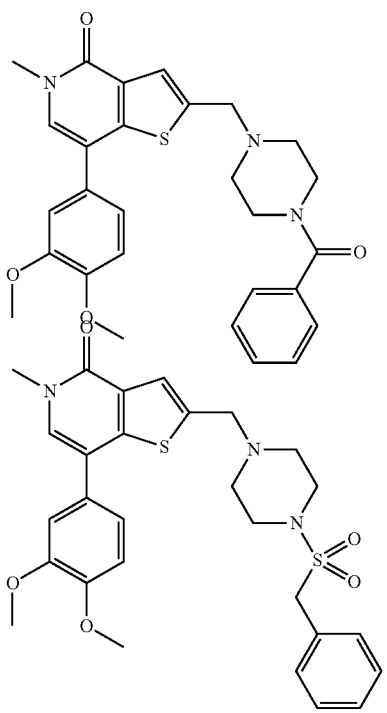

To a stirred solution of 7-(3,4-dimethoxyphenyl)-5-methyl-2-(piperazin-1-ylmethyl)thieno[3,2-c]pyridin-4(5H)-one, 2 hydrochloride (for a preparation see Example 64, 60 mg, 0.127 mmol) in DCM (2 mL) and pyridine (3 mL) was added a catalytic quantity of DMAP (1 mg, 8.19 μmol) followed by phenylmethanesulphonyl chloride (86 mg, 0.451 mmol). The reaction was stirred at room temperature for one hour. To the reaction was added a further portion of DMAP (1 mg, 8.19 μmol) followed by another portion of phenylmethanesulphonyl chloride (86 mg, 0.451 mmol) and the reaction was heated to 40° C. for 18 hours. To the reaction was added 1,2-DCE (1 mL) followed by another portion of DMAP (1 mg, 8.19 μmol) and benzoyl chloride (86 mg, 0.612 mmol). The reaction was heated at 60° C. for 4 hours.

The reaction was cooled to room temperature. The solvent was removed under reduced pressure. The crude material was re-dissolved in toluene (7 mL) and then the solvent was removed under reduced pressure.

The crude material was dissolved in DCM (15 mL) and transferred to a 50 mL separating funnel and washed with saturated bicarbonate solution (10 mL). The organic layer was collected. The aqueous layer was extracted with DCM (3×10 mL). The organic layers were combined and dried over magnesium sulphate. The filtrate was concentrated under reduced pressure to give a dark green oil.

The crude material was loaded onto a 12 g silica gel column and the product was eluted in 0-5% MeOH in DCM over 28 column volumes to give a yellow solid, 2-((4-(benzylsulphonyl)piperazin-1-yl)methyl)-7-(3,4-dimethoxyphenyl)-5-methylthieno[3,2-c]pyridin-4(5H)-one (Example 33) (25 mg, 0.045 mmol, 35.6% yield).

LCMS (2 min, Formic Acid): Rt=0.85 min, MH+=554. A brown oil was also obtained from the column chromatography that was further purified by MDAP (Formic Acid method) to give a light yellow oily residue, 2-((4-benzoylpiperazin-1-yl)methyl)-7-(3,4-dimethoxyphenyl)-5-methylthieno[3,2-c]pyridin-4(5H)-one (Example 30) (8 mg, 0.016 mmol, 12.5% yield).

LCMS (2 min, Formic Acid): Rt=0.74 min, MH+=504.

Example 31

7-(3,4-dimethoxyphenyl)-2-((4-(ethylsulphonyl)piperazin-1-yl)methyl)-5-methylthieno[3,2-c]pyridin-4(5H)-one

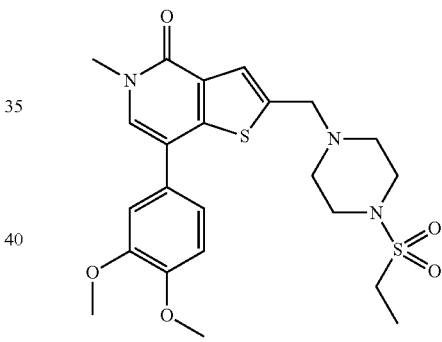

To a stirred solution of 7-(3,4-dimethoxyphenyl)-5-methyl-2-(piperazin-1-ylmethyl)thieno[3,2-c]pyridin4(5H)-one, hydrochloride (for a preparation see Example 64, 45 mg, 0.103 mmol) in DCM (2 mL) and pyridine (1.0 mL) was added ethanesulphonyl chloride (0.02 mL, 0.206 mmol) and the reaction was stirred under nitrogen for two hours. To the reaction was added a further portion of ethanesulphonyl chloride (0.02 mL, 0.206 mmol) and it was stirred overnight. To the reaction was added DMAP (1 mg, 8.19 μmol) and it was stirred for 5 hours.

To the reaction was added a small volume of toluene and the solvent was removed under reduced pressure to give an orange solid.

The residue was loaded onto a 4 g silica gel column and the product was eluted in 0-5% MeOH in DCM. The solvent was removed from the product under reduced pressure and the residue was oven dried overnight to give a light green solid, 7-(3,4-dimethoxyphenyl)-2-((4-(ethylsulphonyl)piperazin-1-yl)methyl)-5-methylthieno[3,2-c]pyridin-4(5H)-one (21.6 mg, 0.044 mmol, 42.6% yield).

LCMS (2 min, Formic Acid): Rt=0.70 min, MH+=492.

Example 32

N-(3-(5-methyl-2-((4-methylpiperazin-1-yl)methyl)-4-oxo-4,5-dihydrothieno[3,2-c]pyridin-7-yl)phenyl)acetamide

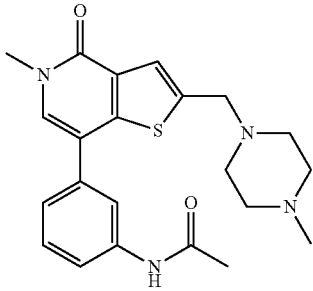

A mixture of N-(3-(2-formyl-5-methyl-4-oxo-4,5-dihydrothieno[3,2-c]pyridin-7-yl)phenyl)acetamide (for a preparation see Intermediate 28, 100 mg, 0.31 mmol), 1-methylpiperazine (46 mg, 0.46 mmol), and acetic acid (28 mg, 27 µL, 0.62 mmol) in dichloromethane (10 mL) was stirred at room temperature for 15 minutes. The reaction mixture was treated with sodium triacetoxyborohydride (260 mg, 1.23 mmol) and stirred at 40° C. for 1 hour.

The cooled reaction mixture was diluted with methanol (10 mL) and the dichloromethane was evaporated. The methanolic solution was loaded onto a 5 g SCX column. The product was eluted with 2M ammonia in methanol. The solvent was evaporated and the residue triturated with diethyl ether to give N-(3-(5-methyl-2-((4-methylpiperazin-1-yl)methyl)-4-oxo-4,5-dihydrothieno[3,2-c]pyridin-7-yl)phenyl)acetamide (88 mg, 0.214 mmol, 70.0% yield) as a light yellow solid.

LCMS (2 min, Formic Acid): Rt=0.54 min, MH$^+$=411.

Example 34

7-(3,4-dimethoxyphenyl)-5-methyl-2-((4-(phenylsulphonyl)piperazin-1-yl)methyl)thieno[3,2-c]pyridin-4(5H)-one

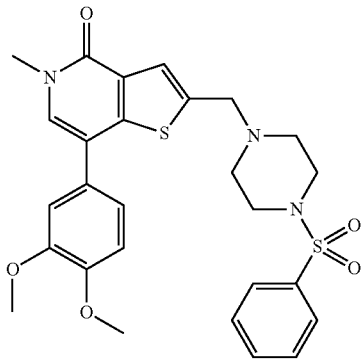 [SMILES: COc1ccc(-c2cn(C)c(=O)c3cc(CN4CCN(S(=O)(=O)c5ccccc5)CC4)sc23)cc1OC]

To a stirred solution of 7-(3,4-dimethoxyphenyl)-5-methyl-2-(piperazin-1-ylmethyl)thieno[3,2-c]pyridin-4(5H)-one, 2 hydrochloride (for a preparation see Example 64, 60 mg, 0.127 mmol) in DCM (2 mL) and pyridine (3 mL) was added a catalytic quantity of DMAP (1 mg, 8.19 µmol), followed by benzenesulphonyl chloride (0.057 mL, 0.447 mmol). The reaction was stirred at room temperature for one hour.

The reaction was concentrated under reduced pressure. The crude material was dissolved in DCM (2 mL) and toluene (10 mL) and again concentrated under reduced pressure to give an orange oil which was oven dried for 4 hours.

The crude material was loaded onto a 12 g silica gel column and eluted in 0-5% MeOH in DCM over 28 column volumes to give a yellow oil. The oil was triturated with diethyl ether to give a bright yellow solid, 7-(3,4-dimethoxyphenyl)-5-methyl-2-((4-(phenylsulphonyl)piperazin-1-yl)methyl)thieno[3,2-c]pyridin-4(5H)-one (11 mg, 0.02 mmol, 16.05% yield).

LCMS (2 min, Formic Acid): Rt=0.87 min, MH$^+$=540.

Example 35

2-((4-acetylpiperazin-1-yl)methyl)-5-methyl-7-phenylthieno[3,2-c]pyridin-4(5H)-one

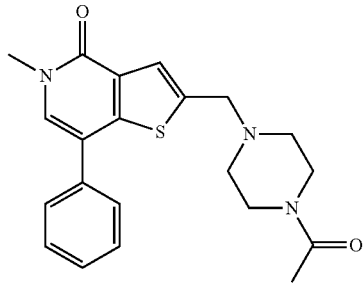 [SMILES: CC(=O)N1CCN(Cc2cc3c(=O)n(C)cc(-c4ccccc4)c3s2)CC1]

To a 25 mL round bottom flask was added 5-methyl-4-oxo-7-phenyl-4,5-dihydrothieno[3,2-c]pyridine-2-carbaldehyde (for a preparation see Intermediate 29, 92.2 mg, 0.342 mmol) dissolved in DCM (5 mL). To the solution was added 1-(piperazin-1-yl)ethanone (65.8 mg, 0.514 mmol) and acetic acid (0.029 mL, 0.514 mmol) and the reaction was stirred at room temperature under nitrogen for approx. 1 hour. Then to the reaction solution was added sodium triacetoxyborohydride (363 mg, 1.712 mmol) and the reaction was heated under reflux under nitrogen for one hour.

The reaction was allowed to cool to room temperature and allowed to stand under nitrogen for ~3 days. The reaction was then diluted with saturated sodium bicarbonate solution and transferred to a separating funnel. The product was extracted with DCM (3×10 mL). The organic layers were combined and washed with brine and then dried over magnesium sulphate. The filtrate was collected in a 150 mL round bottom flask using vacuum filtration and the solvent was removed under reduced pressure to give an orange solid.

The crude material was dissolved in a small volume of MeOH and transferred to a 1 g SCX column. The column was eluted with MeOH (3 column volumes) to remove impurities. The column was then eluted with 2.0M ammonia in MeOH (3 column volumes) and the solvent was removed under reduced pressure to give an orange oil. To the oily residue was added a small volume of diethyl ether and it was triturated resulting in the formation of a solid. The flask was left for approx. 45 minutes and the ether was removed with a pipette. The residue was dried under reduced pressure to yield an orange solid 2-((4-acetylpiperazin-1-yl)methyl)-5-methyl-7-phenylthieno[3,2-c]pyridin-4(5H)-one (119 mg, 0.312 mmol, 91% yield).

LCMS (2 min, Formic Acid): Rt=0.64 min, MH$^+$=382.

Example 36

7-(3,4-dimethoxyphenyl)-2-((4-(isopropylsulphonyl)piperazin-1-yl)methyl)-5-methylthieno[3,2-c]pyridin-4(5H)-one

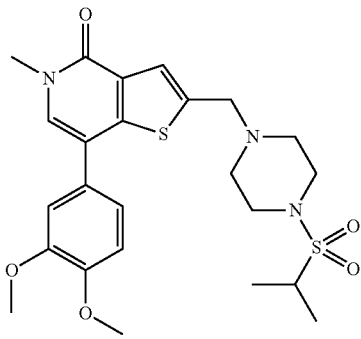 [SMILES: COc1ccc(-c2cn(C)c(=O)c3cc(CN4CCN(S(=O)(=O)C(C)C)CC4)sc23)cc1OC]

To a stirred solution of 7-(3,4-dimethoxyphenyl)-5-methyl-2-(piperazin-1-ylmethyl)thieno[3,2-c]pyridin-4(5H)-one, 2 hydrochloride (for a preparation see Example 64, 60 mg, 0.127 mmol) in DCM (2 mL) was added pyridine (3 mL), propane-2-sulphonyl chloride (0.043 mL, 0.381 mmol) and a catalytic quantity of DMAP (1 mg, 8.19 µmol). The reaction was stirred under nitrogen overnight. To the reaction was added a further portion of propane-2-sulphonyl chloride (0.043 mL, 0.381 mmol) and it was heated at 40° C. for 2 hours. A further portion of propane-2-sulphonyl chloride (0.043 mL, 0.381 mmol) was added and heating was continued for 5 hours.

The reaction was cooled to room temperature and left under nitrogen overnight. The solvent was removed under reduced pressure to yield a brown oil. The oil was re-dissolved in DCM (approx. 3 mL) and mixed with toluene (approx. 10 mL) and the crude material was concentrated under reduced pressure and dried in a vacuum oven for 4 hours. To remove the excess propane-2-sulphonyl chloride the crude material was dissolved in DCM (5 mL) and washed with saturated sodium bicarbonate solution (10 mL). The organic layer was collected and the aqueous layer was extracted with DCM (3×5 mL). The organic layers were combined and dried over magnesium sulphate. The filtrate was collected and concentrated under reduced pressure. The product was purified by MDAP to give a yellow oil. The oil was triturated with diethyl ether to give a yellow oil, 7-(3,4-dimethoxyphenyl)-2-((4-(isopropylsulphonyl)piperazin-1-yl)methyl)-5-methylthieno[3,2-c]pyridin-4(5H)-one (16 mg, 0.032 mmol, 24.9% yield).

LCMS (2 min, Formic Acid): Rt=0.75 min, MH$^+$=506.

Example 37

7-(3,4-dimethoxyphenyl)-5-methyl-2-((4-methylpiperazin-1-yl)methyl)thieno[3,2-c]pyridin-4(5H)-one

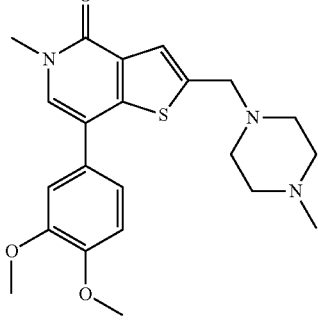

To a suspension of 7-(3,4-dimethoxyphenyl)-5-methyl-4-oxo-4,5-dihydrothieno[3,2-c]pyridine-2-carbaldehyde (for a preparation see Intermediate 25, 16.5 mg, 0.05 mmol) in tetrahydrofuran (2 mL) was added 1-methylpiperazine (22 uL, 0.2 mmol, 4 eq) followed by sodium triacetoxyborohydride (42 mg, 0.2 mmol, 4 eq). The mixture was stirred at room temperature for 2 days.

The material was passed through a 5 g NH$_2$-SPE cartridge eluting with 5:1 dichloromethane/methanol. The solvent was evaporated and the residue was loaded onto a 5 g SCX cartridge, washed with methanol and then eluted with NH$_3$ in methanol. The solvent was removed and the residue was further purified on a 10 g NH$_2$-SPE column eluting with 99:1-90:10 dichloromethane/methanol. Combination and evaporation of the desired fractions gave the product 7-(3,4-dimethoxyphenyl)-5-methyl-2-((4-methylpiperazin-1-yl)methyl)thieno[3,2-c]pyridin-4(5H)-one.

LCMS (2 min, Formic Acid): Rt=0.76 min, MH$^+$=414.

Example 38

4-((7-(3,4-dimethoxyphenyl)-5-methyl-4-oxo-4,5-dihydrothieno[3,2-c]pyridin-2-yl)methyl)-N,N,N-dimethylpiperazine-1-sulphonamide

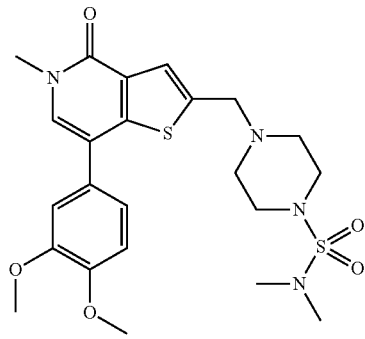 [SMILES: COc1ccc(-c2cn(C)c(=O)c3cc(CN4CCN(S(=O)(=O)N(C)C)CC4)sc23)cc1OC]

To a suspension of 7-(3,4-dimethoxyphenyl)-5-methyl-4-oxo-4,5-dihydrothieno[3,2-c]pyridine-2-carbaldehyde (for a preparation see Intermediate 25, 16.5 mg, 0.05 mmol) in tetrahydrofuran (2 mL) was added N,N-dimethylpiperazine-1-sulphonamide (39 mg, 0.2 mmol) followed by sodium triacetoxyborohydride (42 mg, 0.2 mmol). The mixture was stirred at room temperature overnight. The material was loaded onto a 5 g SCX cartridge, washed with methanol and then eluted with NH$_3$ in methanol. The eluted material was concentrated and then purified on a 10 g NH$_2$-SPE column eluting with 99:1-90:10 dichloromethane/methanol. The eluted material was again concentrated and then purified on a 20 g silica column eluting with 95:5-5:1 dichloromethane/methanol. The concentrated product was dissolved in dichloromethane and MP-NCO was added and the reaction was stirred at room temperature for 2 hr. The material was again purified on a 12 g silica column using a graduating solvent system of 98:2-9:1 dichloromethane/methanol. Evaporation of the solvent gave the product 4-((7-(3,4-dimethoxyphenyl)-5-methyl-4-oxo-4,5-dihydrothieno[3,2-c]pyridin-2-yl)methyl)-N,N-dimethylpiperazine-1-sulphonamide (9.7 mg).

LCMS (2 min, Formic Acid): Rt=0.89 min, MH$^+$=507.

Example 39

2-((4-acetylpiperazin-1-yl)methyl)-7-(3,4-dimethoxyphenyl)-5-methylthieno[3,2-c]pyridin-4(5H)-one

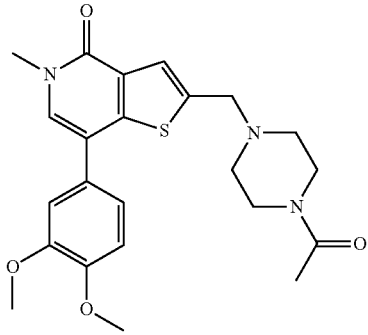 [SMILES: COc1ccc(-c2cn(C)c(=O)c3cc(CN4CCN(C(C)=O)CC4)sc23)cc1OC]

1-Acetylpiperazine (78 mg, 0.61 mmol) and glacial acetic acid (22 mg, 21 µL, 0.37 mmol) were added to a stirred solution of 7-(3,4-dimethoxyphenyl)-5-methyl-4-oxo-4,5-dihydrothieno[3,2-c]pyridine-2-carbaldehyde (for a preparation see Intermediate 25, 100 mg, 0.30 mmol) in dichloromethane (10 mL). The reaction mixture was stirred at room temperature for 30 minutes then treated with sodium triacetoxyborohydride (193 mg, 0.91 mmol). The reaction mixture was heated under reflux for 4 hours then cooled to room temperature.

Saturated sodium bicarbonate (10 mL) was added and the mixture stirred for 10 minutes. The organic phase was separated and the aqueous phase extracted with dichloromethane (2×10 mL). The combined organics were dried and evaporated. Chromatography [2% methanol/dichloromethane] of the residue followed by trituration with diethyl ether gave a yellow gum. The compound was dissolved in the minimum amount of ethyl acetate. 1.0M hydrogen chloride in diethyl ether (0.5 mL) and diethyl ether (10 mL) was added. The solid was filtered off, washed with diethyl ether and dried to give 2-((4-acetylpiperazin-1-yl)methyl)-7-(3,4-dimethoxyphenyl)-5-methylthieno[3,2-c]pyridin-4(5H)-one, hydrochloride (60 mg, 0.126 mmol, 41.3% yield) as a colourless solid.

LCMS (2 min, Formic Acid): Rt=0.58 min, MH$^+$=442.

Example 40

7-(3-(benzyloxy)phenyl)-5-methyl-2-((4-methyl-1,4-diazepan-1-yl)methyl)thieno[3,2-c]pyridin-4(5H)-one, Hydrochloride

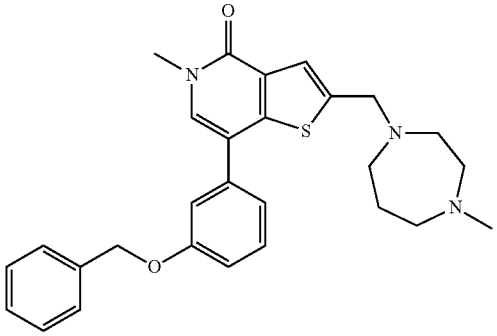 [SMILES: CN1CCCN(Cc2cc3c(=O)n(C)cc(-c4cccc(OCc5ccccc5)c4)c3s2)CC1]

To a suspension of 7-bromo-5-methyl-2-((4-methyl-1,4-diazepan-1-yl)methyl)thieno[3,2-c]pyridin-4(5H)-one (for a preparation see Intermediate 67, 200 mg, 0.540 mmol), 3-(benzyloxy)phenyl)boronic acid (165 mg, 0.724 mmol) and potassium carbonate (202 mg, 1.458 mmol) in isopropanol (3 mL) and water (1.5 mL) was added PEPPSI (36.7 mg, 0.054 mmol) catalyst. The reaction mixture was heated to 130° C. in the microwave for 30 minutes. The reaction mixture was transferred to a separating funnel and diluted with a saturated aqueous solution of ammonium chloride (approx. 30 mL). The aqueous phase was extracted with DCM (4×20 mL) and the combined organic fractions were dried over magnesium sulphate, filtered and concentrated under reduced pressure to give brown oil. The crude material purified by chromatography on silica gel eluting with 0 to 10% [2.0M ammonia in MeOH] in DCM to give an impure pale yellow oil. The latter was repurifed by MDAP to give the product as a pale yellow oil. This material was dissolved in ethyl acetate (1 mL) and treated with 1.0M HCl in diethyl ether (250 µL) to give 7-(3-(benzyloxy)phenyl)-5-methyl-2-((4-methyl-1,4-diazepan-1-yl)methyl)thieno[3,2-c]pyridin-4(5H)-one, hydrochloride (109 mg, 40% yield) as an off white solid, LCMS (2 min, Formic Acid): Rt=0.89 min, MH$^+$=474

Example 41

N-(3-(5-methyl-2-((1-(methylsulphonyl)piperidin-4-yl)methyl)-4-oxo-4,5-dihydrothieno[3,2-c]pyridin-7-yl)phenyl)acetamide

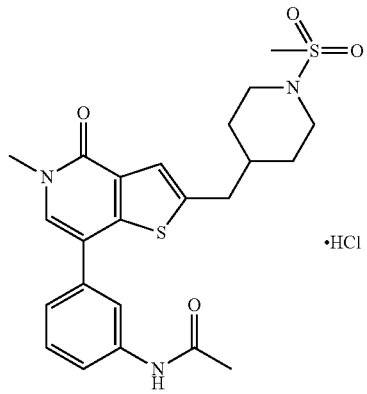 [SMILES: CC(=O)Nc1cccc(-c2cn(C)c(=O)c3cc(CC4CCN(S(C)(=O)=O)CC4)sc23)c1 ; Cl]

N-(3-(5-methyl-2-((1-(methylsulphonyl)piperidin-4-ylidene)methyl)-4-oxo-4,5-dihydrothieno[3,2-c]pyridin-7-yl)phenyl)acetamide (for a preparation see Intermediate 66, 120 mg, 0.254 mmol) in a solution of ethanol (25 mL) was treated with ammonium formate (80 mg, 1.272 mmol) followed by 10% palladium in carbon, (50% water paste, 24 mg). The reaction mixture was heated refluxed under an atmosphere of nitrogen. The reaction was treated with a further 5 equivalents of ammonium formate (80 mg, 1.272 mmol) and another portion of 10% palladium in carbon (50% water paste, 24 mg). The resulting suspension was refluxed for a further three hours, whereupon the reaction mixture was cooled to room temperature and filtered through a 2.5 g Celite frit. The filtrate was concentrated under reduced pressure to give an off white solid. The crude material was triturated with diethyl ether to give a cream coloured solid (66 mg) which was only 77% pure my LCMS. The product was therefore re-purified by MDAP to give N-(3-(5-methyl-2-((1-(methylsulphonyl)piperidin-4- yl)methyl)-4-oxo-4,5-dihydrothieno[3,2-c]pyridin-7-yl)phenyl)acetamide (13 mg, 11% yield) as a white solid, LCMS (2 min, Formic Acid): Rt=0.82 min, MH+=474

Example 42

7-(2,4-difluorophenyl)-5-methyl-2-((4-(methylsulphonyl)piperazin-1-yl)methyl)thieno[3,2-c]pyridin-4(5H)-one

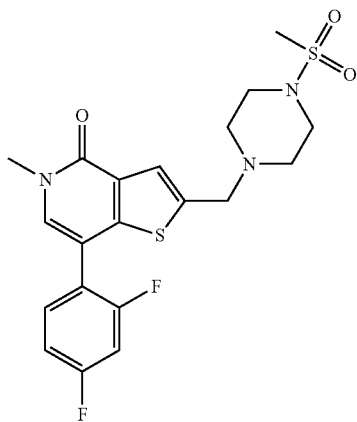 [SMILES: Cn1cc(-c2ccc(F)cc2F)c2sc(CN3CCN(S(C)(=O)=O)CC3)cc2c1=O]

To a 2-5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), (2,4-difluorophenyl) boronic acid (31.6 mg, 0.200 mmol), and potassium carbonate (55.2 mg, 0.400 mmol) in a solution of isopropanol (2 mL) and water (1.000 mL). To the reaction was then added the PEPPSI (34.0 mg, 0.05 mmol). The reaction vessel was sealed and heated in the Biotage Initiator microwave reactor to 130° C. for 30 minutes with 10 seconds of pre-stirring. After cooling, the reaction was diluted with saturated ammonium chloride solution (15 mL) and DCM (10 mL), shaken and filtered through Celite. The filtrate was transferred to a separating funnel and the organic layer was collected. The aqueous layer was extracted with DCM (3×10 mL). The organic layers were combined and dried over MgSO4. The filtrate was collected and concentrated to give a dark yellow solid. The residue was loaded onto a 12 g silica gel column and eluted in 0-5% MeOH in DCM to give a yellow oil. The oil was triturated with diethyl ether and dried under reduced pressure to give 7-(2,4-difluorophenyl)-5-methyl-2-((4-(methylsulphonyl)piperazin-1-yl)methyl)thieno[3,2-c]pyridin-4(5H)-one (58.2 mg, 77% yield) as a pale yellow solid.

LCMS (2 min, Formic Acid): Rt=0.75 min, MH+=454

Example 43

5-methyl-2-((4-(methylsulphonyl)piperazin-1-yl)methyl)-7-(pyridin-2-yl)thieno[3,2-c]pyridin-4(5H)-one

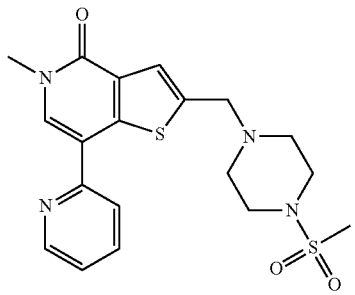

A mixture of 7-bromo-5-methyl-2-((4-(methylsulphonyl)piperazin-1-yl)methyl)thieno[3,2-c]pyridin-4(5H)-one (for a preparation see Intermediate 69, 200 mg, 0.48 mmol), 6-phenyl-2-(pyridin-2-yl)-1,3,6,2-dioxazaborocane (638 mg, 2.38 mmol), potassium orthophosphate (303 mg, 1.43 mmol), copper(I) iodide (45 mg, 0.24 mmol) and bis(triphenylphosphine)palladium(II) chloride (33 mg, 10 mol %) in dry, degassed DMF (8 mL) was heated in the microwave at 150° C. for 45 minutes. The cooled reaction mixture was diluted with ethyl acetate (20 mL) and washed with water (×2) and brine. The organic phase was dried and evaporated. The residue was chromatographed [0-5% methanol/dichloromethane]. The product was triturated with diethyl ether to give impure product, which was repurified by MDAP to give 5-methyl-2-((4-(methylsulphonyl)piperazin-1-yl)methyl)-7-(pyridin-2-yl)thieno[3,2-c]pyridin-4(5H)-one (18 mg, 9%) as a colourless solid.

LCMS (2 min, Formic Acid): Rt=0.59 min, MH+=419.

Example 44

5-methyl-2-((4-(methylsulphonyl)piperazin-1-yl)methyl)-7-phenylthieno[3,2-c]pyridin-4(5H)-one

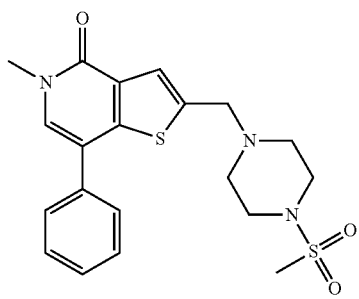 [SMILES: Cn1cc(-c2ccccc2)c2sc(CN3CCN(S(C)(=O)=O)CC3)cc2c1=O]

To a solution of 5-methyl-4-oxo-7-phenyl-4,5-dihydrothieno[3,2-c]pyridine-2-carbaldehyde (for a preparation see Intermediate 29, 75 mg, 0.278 mmol) and 1-(methylsulphonyl)piperazine (91 mg, 0.557 mmol) in DCM (5 mL) were successively added sodium triacetoxyborohydride (236 mg, 1.114 mmol) and acetic acid (0.024 mL, 0.418 mmol). The reaction mixture was stirred at 40° C. for 1 hour, whereupon a saturated aqueous solution of NaHCO3 was added. The layers were separated and the aqueous phase was extracted 3 times with DCM. The combined organic layers were washed with brine, dried over MgSO4, filtered and concentrated in vacuo to give 5-methyl-2-((4-(methylsulphonyl)piperazin-1-yl)methyl)-7-phenylthieno[3,2-c]pyridin-4(5H)-one (59 mg, 51% yield) as a white solid.

LCMS (2 min, Formic Acid): Rt=0.72 min, MH+=418

Example 45

2-((2,4-dimethylpiperazin-1-yl)methyl)-5-methyl-7-(5-((tetrahydro-2H-pyran-4-yl)methoxy)pyridin-3-yl)thieno[3,2-c]pyridin-4(5H)-one, Formic Acid Salt

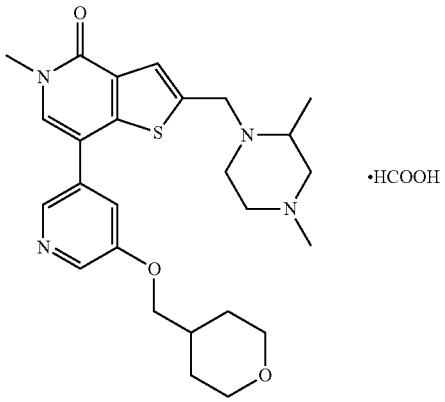

To a suspension of 7-bromo-2-((2,4-dimethylpiperazin-1-yl)methyl)-5-methylthieno[3,2-c]pyridin-4(5H)-one (for a preparation see Intermediate 70, 34 mg, 0.092 mmol), (5-((tetrahydro-2H-pyran-4-yl)methoxy)pyridin-3-yl)boronic acid (for a preparation see Intermediate 13, 32.6 mg, 0.138 mmol) and potassium carbonate (38.1 mg, 0.275 mmol) in isopropanol (3 mL) and water (1 mL) was added PEPPSI (6.24 mg, 9.18 μmol) catalyst. The reaction mixture was heated at 110° C. in the microwave for 30 minutes, whereupon the reaction mixture was hydrolyzed by adding a saturated aqueous solution of ammonium chloride (20 mL). The aqueous phase was extracted with DCM (4×25 mL) and the combined organic fractions were dried over magnesium sulphate, filtered and concentrated under reduced pressure to give a dark brown oil. The crude material was purified by chromatography on silica gel eluting with 0 to 15% MeOH in DCM to give a brown oil which was only 75% pure by LCMS. The product was re-purified by MDAP to give 2-((2,4-dimethylpiperazin-1-yl)methyl)-5-methyl-7-(5-((tetrahydro-2H-pyran-4-yl)methoxy)pyridin-3-yl)thieno[3,2-c]pyridin-4(5H)-one, Formic acid salt (6.5 mg, 13%) as an off white solid.

LCMS (2 min, Formic Acid): Rt=0.61 min, MH+=483

Example 46

2-((1,4-diazepan-1-yl)methyl)-7-(3,4-dimethoxyphenyl)-5-methylthieno[3,2-c]pyridin-4(5H)-one, dihydrochloride

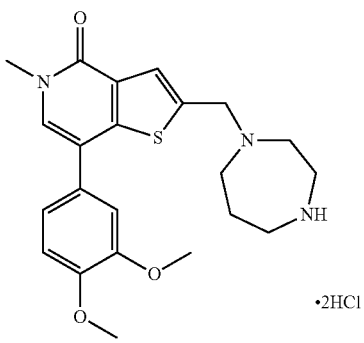 [SMILES: COc1ccc(-c2cn(C)c(=O)c3cc(CN4CCCNCC4)sc23)cc1OC]

Tert-butyl 4-((7-(3,4-dimethoxyphenyl)-5-methyl-4-oxo-4,5-dihydrothieno[3,2-c]pyridin-2-yl)methyl)-1,4-diazepane-1-carboxylate (for a preparation see Intermediate 57, 116 mg, 0.226 mmol) was dissolved in 1,4-dioxane (0.5 mL) and 4M HCl in 1,4-dioxane (0.5 mL) was added to the reaction mixture. The reaction mixture was stirred at room temperature for 3 hr. Diethyl ether (5 mL) was added and the mixture triturated. The supernatant was decanted off. Another portion of diethyl ether (5 mL) was added and the trituration repeated. The solvent was decanted and the residue dried in vacuo to give 2-((1,4-diazepan-1-yl)methyl)-7-(3,4-dimethoxyphenyl)-5-methylthieno[3,2-c]pyridin-4(5H)-one dihydrochloride (71 mg, 0.146 mmol, 64.6% yield) as a white powder.

LCMS (2 min, High pH): Rt=0.84 min, MH+=414

Example 47

2-(((3-aminopropyl)amino)methyl)-7-(3-(benzyloxy)phenyl)-5-methylthieno[3,2-c]pyridin-4(5H)-one, 2 Hydrochloride

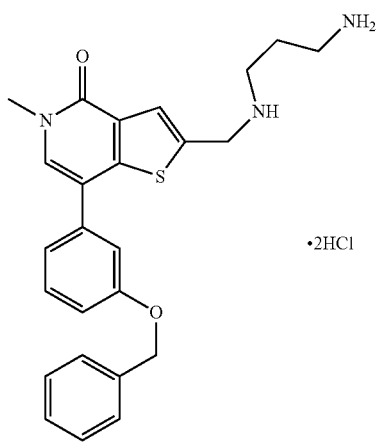 [SMILES: Cn1cc(-c2cccc(OCc3ccccc3)c2)c2sc(CNCCCN)cc2c1=O]

4M Hydrogen chloride in 1,4-dioxane (0.5 mL, 2 mmol) was added to a stirred solution of tert-butyl (3-(((7-(3-(benzyloxy)phenyl)-5-methyl-4-oxo-4,5-dihydrothieno[3,2-c]pyridin-2-yl)methyl)amino)propyl)carbamate (for a preparation see Intermediate 47, 100 mg, 0.29 mmol) in 1,4-dioxane (0.5 mL). The reaction mixture was stirred at room temperature for 4 hours. The reaction mixture was diluted with diethyl ether (5 mL) and stirred at room temperature for 1 hour then allowed to stand overnight. The solid was filtered off, washed with diethyl ether and dried to give 2-(((3-aminopropyl)amino)methyl)-7-(3-(benzyloxy)phenyl)-5-methylthieno[3,2-c]pyridin-4(5H)-one, 2 Hydrochloride (86 mg, 91% yield) as an off-white solid.

LCMS (2 min, Formic Acid): Rt=0.64 min, MH+=434

Example 48

N-(2-(((7-(3-(benzyloxy)phenyl)-5-methyl-4-oxo-4,5-dihydrothieno[3,2-c]pyridin-2-yl)methyl)amino)ethyl)methanesulphonamide And

Example 48A

N-((7-(3-(benzyloxy)phenyl)-5-methyl-4-oxo-4,5-dihydrothieno[3,2-c]pyridin-2-yl)methyl)-N-(2-(methylsulfonamido)ethyl)methanesulfonamide

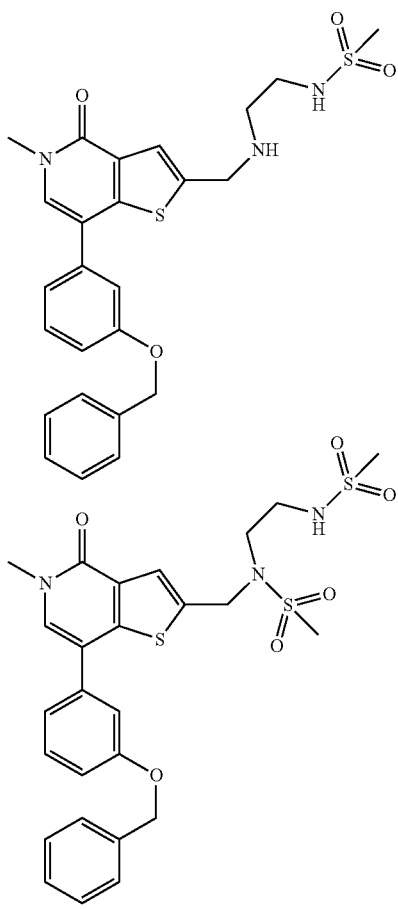

Methanesulphonyl chloride (22 mg, 15 µL, 0.2 mmol) was added to a stirred mixture of 2-(((2-aminoethyl)amino)methyl)-7-(3-(benzyloxy)phenyl)-5-methylthieno[3,2-c]pyridin-4(5H)-one, 2 Hydrochloride (for a preparation see Example 53, 80 mg, 0.16 mmol), pyridine (1 mL) and dichloromethane (2 mL). The reaction mixture was stirred at room temperature for 4 hours. Methanesulphonyl chloride (34 mg, 23 µL, 0.3 mmol) was added and the mixture stirred at room temperature overnight. The mixture was diluted with dichloromethane (10 mL) and then was washed with a saturated aqueous solution of NaHCO$_3$ (10 mL) and water (10 mL). The organic phase was dried and evaporated. The residue was purified by chromatography on silica gel eluting with 0 to 10% methanol in dichloromethane to give N-(2-(((7-(3-(benzyloxy)phenyl)-5-methyl-4-oxo-4,5-dihydrothieno[3,2-c]pyridin-2-yl)methyl)amino)ethyl)methanesulphonamide (Example 48) (14 mg, 17.3% yield) as a colourless oil.

LCMS (2 min, Formic Acid): Rt=0.85 min, MH$^+$=498 and N-((7-(3-(benzyloxy)phenyl)-5-methyl-4-oxo-4, 5-dihydrothieno[3,2-c]pyridin-2-yl)methyl)-N-(2-(methylsulfonamido)ethyl)methanesulfonamide (Example 48A) (10 mg, 10.7% yield) as a colourless oil.

LCMS (2 min, Formic Acid): Rt=1.05 min, MH$^+$=576

Example 49

N-(4-(5-methyl-2-((1-(methylsulphonyl)piperidin-4-yl)methyl)-4-oxo-4,5-dihydrothieno[3,2-c]pyridin-7-yl)pyridin-2-yl)acetamide

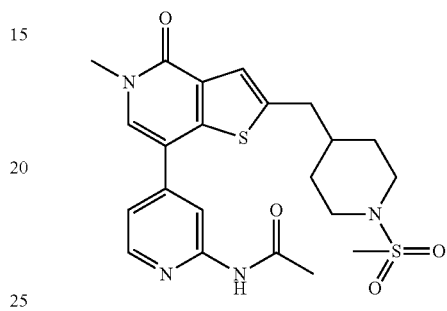

A stirred suspension of N-(4-(5-methyl-2-((1-(methylsulphonyl)piperidin-4-ylidene)methyl)-4-oxo-4,5-dihydrothieno[3,2-c]pyridin-7-yl)pyridin-2-yl)acetamide (for a preparation see Intermediate 62, 10 mg, 0.021 mmol) in ethanol (2 mL) was treated with ammonium formate (6.67 mg, 0.106 mmol) followed by 10% palladium on carbon (50% water paste, 4 mg, 40% wt). The reaction mixture was heated to 90° C. and refluxed under an atmosphere of nitrogen for two hours. The reaction was cooled to room temperature and filtered through a 2.5 g Celite frit. The residue was washed with ethanol (2×5 mL). The filtrated was collected and concentrated under reduced pressure to give N-(4-(5-methyl-2-((1-(methylsulphonyl)piperidin-4-yl)methyl)-4-oxo-4,5-dihydrothieno[3,2-c]pyridin-7-yl)pyridin-2-yl)acetamide (3 mg, 30%) as a white solid.

LCMS (2 min, Formic Acid): Rt=0.72 min, MH$^+$=475

Example 50

N-(3-(5-methyl-2-((4-methyl-1,4-diazepan-1-yl)methyl)-4-oxo-4,5-dihydrothieno[3,2-c]pyridin-7-yl)phenyl)acetamide

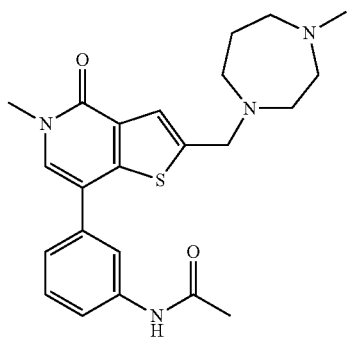

A mixture of N-(3-(2-formyl-5-methyl-4-oxo-4,5-dihydrothieno[3,2-c]pyridin-7-yl)phenyl)acetamide (for a preparation see Intermediate 49, 100 mg, 0.31 mmol), 1-methyl-homopiperazine (70 mg, 0.61 mmol), and acetic acid (37 mg, 35 μL, 0.62 mmol) in dichloromethane (10 mL) was stirred at room temperature for 15 minutes. The reaction mixture was treated with sodium triacetoxyborohydride (260 mg, 1.23 mmol) and stirred at room temperature overnight. A saturated aqueous solution of sodium bicarbonate (10 mL) was added and the mixture stirred for 15 minutes. The organic phase was separated and the aqueous phase extracted with dichloromethane (2×10 mL). The combined organics were dried and evaporated. The residue was purified by chromatography on silica gel eluting 10 to 20% methanol in dichloromethane to give N-(3-(5-methyl-2-((4-methyl-1,4-diazepan-1-yl)methyl)-4-oxo-4,5-dihydrothieno[3,2-c]pyridin-7-yl)phenyl)acetamide (13 mg, 10% yield) as a pale yellow solid.

LCMS (2 min, Formic Acid): Rt=0.51 min, MH$^+$=425

Example 51

7-(3,4-dimethoxyphenyl)-5-methyl-2-((1-(methylsulphonyl)piperidin-4-yl)methyl)thieno[3,2-c]pyridin-4(5H)-one

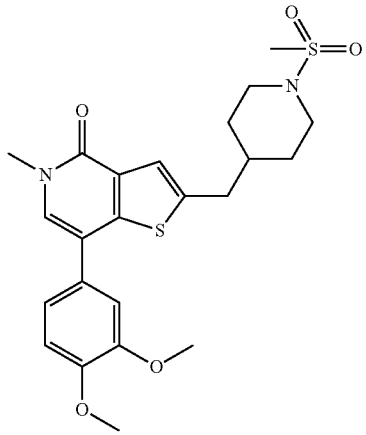 [SMILES: COc1ccc(-c2cn(C)c(=O)c3cc(CC4CCN(S(C)(=O)=O)CC4)sc23)cc1OC]

A stirred solution of 7-(3,4-dimethoxyphenyl)-5-methyl-2-(piperidin-4-ylmethyl)thieno[3,2-c]pyridin-4(5H)-one, hydrochloride (for a preparation see Intermediate 65, 18 mg, 0.041 mmol) in DCM (1 mL) and pyridine (500 μL) was treated with methanesulphonyl chloride (10 μL, 0.128 mmol). The resulting solution was stirred at room temperature under an atmosphere of nitrogen for 2 hours. The reaction was treated with a further 6 equivalents of methane sulphonyl chloride (20 μL, 6.2 mmol) and the reaction was stirred for an additional hour. A small portion of the starting material remained unreacted. The reaction was treated with a further 6 equivalents of methane sulphonyl chloride (20 μL, 6.2 mmol) and was left under the conditions described for 16 hours. The reaction mixture was then diluted with toluene (10 mL) and concentrated under reduced pressure. The reaction mixture was redissolved in toluene and reconcentrated to remove residual pyridine. The crude product was dissolved in DCM and since there were insoluble inorganic impurities, the product was passed through a 2.5 g Celite frit. The filtrate was collected and concentrated under reduced pressure to give a yellow solid. The crude material was purified by chromatography on silica gel eluting with 0 to 5% MeOH in DCM to give 7-(3,4-dimethoxyphenyl)-5-methyl-2-((1-(methylsulphonyl)piperidin-4-yl)methyl)thieno[3,2-c]pyridin-4(5H)-one (14 mg, 71% yield) as an orange oil.

LCMS (2 min, Formic Acid): Rt=0.93 min, MH$^+$=477

Example 52

2-(((3-aminopropyl)amino)methyl)-7-(3,4-dimethoxyphenyl)-5-methylthieno[3,2-c]pyridin-4(5H)-one, 2 hydrochloride

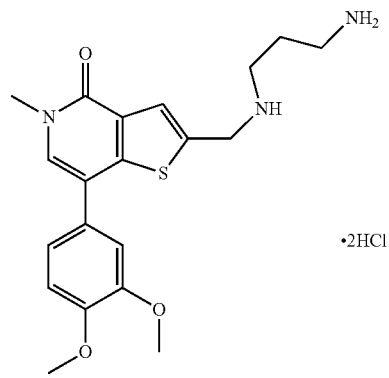 [SMILES: COc1ccc(-c2cn(C)c(=O)c3cc(CNCCCN)sc23)cc1OC]

4M Hydrogen chloride in 1,4-dioxane (0.5 mL, 2 mmol) was added to a stirred solution of tert-butyl (3-(((7-(3,4-dimethoxyphenyl)-5-methyl-4-oxo-4, 5-dihydrothieno[3,2-c]pyridin-2-yl)methyl)amino)propyl)carbamate (for a preparation see Intermediate 52, 143 mg, 0.29 mmol) in 1,4-dioxane (0.5 mL). The reaction mixture was stirred at room temperature for 4 hours. The reaction mixture was diluted with diethyl ether (5 mL) and stirred at room temperature for 1 hour then allowed to stand overnight. The solid was filtered off, washed with diethyl ether and dried to give 2-(((3-aminopropyl)amino)methyl)-7-(3,4-dimethoxyphenyl)-5-methylthieno[3,2-c]pyridin-4(5H)-one, 2 hydrochloride (122 mg, 90% yield) as an off-white solid.

LCMS (2 min, Formic Acid): Rt=0.47 min, MH$^+$=388

Example 53

2-(((2-aminoethyl)amino)methyl)-7-(3-(benzyloxy)phenyl)-5-methylthieno[3,2-c]pyridin-4(5H)-one, 2 hydrochloride

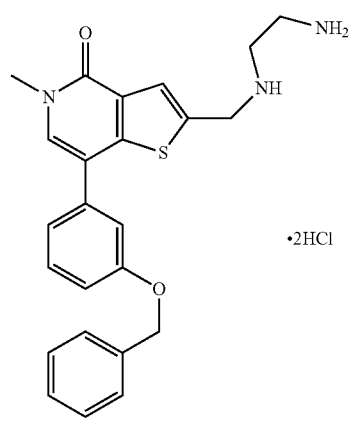 [SMILES: Cn1cc(-c2cccc(OCc3ccccc3)c2)c2sc(CNCCN)cc2c1=O ; "·2HCl"]

4M Hydrogen chloride in 1,4-dioxane (0.5 mL, 2 mmol) was added to a stirred solution of tert-butyl (2-(((7-(3-(benzyloxy)phenyl)-5-methyl-4-oxo-4,5-dihydrothieno[3,2-c]pyridin-2-yl)methyl)amino)ethyl)carbamate (for a preparation see Intermediate 50, 107 mg, 0.21 mmol) in 1,4- dioxane (0.5 mL). The reaction mixture was stirred at room temperature for 4 hours. The reaction mixture was diluted with diethyl ether (5 mL) and stirred at room temperature for 1 hour then allowed to stand overnight. The solid was filtered off, washed with diethyl ether and dried to give 2-(((2-aminoethyl)amino)methyl)-7-(3-(benzyloxy)phenyl)-5-methylthieno[3,2-c]pyridin-4(5H)-one, 2 hydrochloride (87 mg, 86% yield) as an off-white solid.

LCMS (2 min, Formic Acid): Rt=0.67 min, MH$^+$=420

Example 54

5-methyl-2-((4-(methylsulphonyl)Diperazin-1-yl)methyl)-7-(pyridin-4-yl)thieno[3,2c]pyridin-4(5H)-one

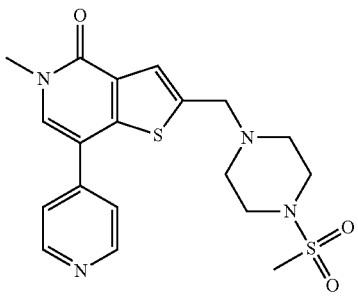

To a solution of 7-bromo-5-methyl-2-((4-(methylsulphonyl)piperazin-1-yl)methyl)thieno[3,2-c]pyridin-4(5H)-one (for a preparation see Intermediate 69, 105 mg, 0.250 mmol) and pyridin-4-ylboronic acid (46.1 mg, 0.375 mmol) in isopropanol (1.5 mL) in a microwave vial were successively added potassium carbonate (0.624 mL, 1.249 mmol) and PEPPSI (16.97 mg, 0.025 mmol). The reaction mixture was stirred at 110° C. in the microwave for 30 minutes. The reaction mixture was concentrated in vacuo and partitioned between water and EtOAc. The phases were separated and the aqueous phase was extracted with EtOAc, The combined organic layers were washed with brine, dried over MgSO4, filtered and concentrated in vacuo. The crude residue was dissolved in a 1:1 MeOH/DMSO mixture and was purified via MDAP using an ammonium bicarbonate modifier. The collected fractions were combined and concentrated in vacuo to give 5-methyl-2-((4-(methylsulphonyl)piperazin-1-yl)methyl)-7-(pyridin-4-yl)thieno[3,2-c]pyridin-4(5H)-one (19 mg, 18% yield) as a yellow solid.

LCMS (2 min, High pH): Rt=0.75 min, MH$^+$=419.

Example 55

7-(3,4-dimethoxyphenyl)-5-methyl-2-((4-(methylsulphonyl)-1,4-diazepan-1-yl)methyl)thieno[3,2-c]pyridin-4(5H)-one

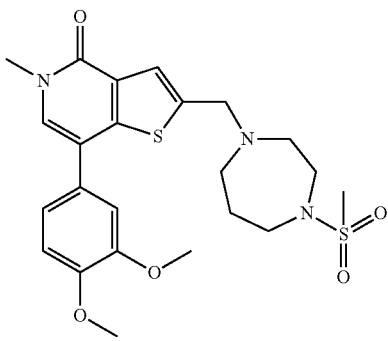 [SMILES: COc1ccc(-c2cn(C)c(=O)c3cc(CN4CCCN(S(C)(=O)=O)CC4)sc23)cc1OC]

To a stirred solution of 2-((1,4-diazepan-1-yl)methyl)-7-(3,4-dimethoxyphenyl)-5-methylthieno[3,2-c]pyridin-4(5H)-one, hydrochloride (for a preparation see Example 46, 67 mg, 0.149 mmol) in dichloromethane (3 mL) and pyridine (1 mL) was added methanesulphonyl chloride (12 μl, 0.154 mmol). The reaction was stirred at room temperature under nitrogen for two hours. A further portion of methanesulphonyl chloride (12 μl, 0.154 mmol) was added and the reaction mixture was stirred for half an hour and then left to sit under nitrogen over the weekend. Two more equivalents of methanesulphonyl chloride were added and it was stirred under nitrogen for another 3 hours. To the reaction was added a small volume of toluene and the solvent was removed under reduced pressure to give a yellow/brown solid. The residue was purified via chromatography on silica gel eluting with 0 to 10% MeOH in DCM to give 7-(3,4-dimethoxyphenyl)-5-methyl-2-((4-(methylsulphonyl)-1,4-diazepan-1-yl)methyl)thieno[3,2-c]pyridin-4(5H)-one (35 mg, 0.071 mmol, 47.8% yield) as a brown crystalline solid.

LCMS (2 min, Formic Acid): Rt=0.64 min, MH$^+$=492

Example 56

7-(3,4-dimethoxyphenyl)-5-methyl-2-((3-methyl-4-(methylsulphonyl)piperazin-1-yl)methyl)thieno[3,2-c]pyridin-4(5H)-one

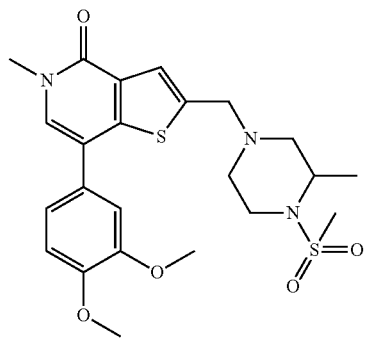

To a stirred solution of 7-(3,4-dimethoxyphenyl)-5-methyl-2-((3-methylpiperazin-1-yl)methyl)thieno[3,2-c]pyridin-4(5H)-one hydrochloride (for a preparation see Example 66, 88 mg, 0.196 mmol) in dichloromethane (2 mL) and pyridine (1 mL) was added methanesulphonyl chloride (0.018 mL, 0.235 mmol). The reaction was stirred under nitrogen at room temperature for several hours and then left sat under nitrogen for the weekend. Another equivalent of methanesulphonyl chloride (0.018 mL, 0.235 mmol) was added and the reaction was stirred under nitrogen for three hours. A small volume of toluene was then added and the solvent was removed under reduced pressure to give a red solid.

The residue purified by chromatography on silica gel eluting with 0 to 5% MeOH in DCM. The appropriate fractions were combined and concentrated under reduced pressure to give 7-(3,4-dimethoxyphenyl)-5-methyl-2-((3-methyl-4-(methylsulphonyl)piperazin-1-yl)methyl)thieno[3,2-c]pyridin-4(5H)-one (75 mg, 78% yield) as a red crystalline solid LCMS (2 min, Formic Acid): Rt=0.76 min, MH$^+$=492

Example 57

7-(3,4-dimethoxyphenyl)-5-methyl-2-((4-(methylsulphonyl)piperazin-1-yl)methyl)thieno[3,2-c]pyridin-4(5H)-one

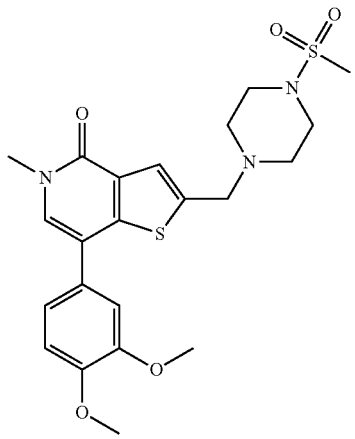

To a microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 200 mg, 0.476 mmol) followed by (3,4-dimethoxyphenyl)boronic acid (130 mg, 0.714 mmol), potassium carbonate (197 mg, 1.427 mmol), and lastly the PEPPSI (32.3 mg, 0.048 mmol) catalyst in a solution of isopropanol (2 mL) and water (2.000 mL). The reaction vessel was sealed and heated to 130° C. for 30 minutes in a microwave with 10 seconds of pre-stirring. The reaction was quenched with saturated ammonium chloride solution (30 mL) and the product was extracted from the aqueous phase with DCM (3×30 mL). The organic fractions were combined, dried over magnesium sulphate, and concentrated under reduced pressure to give a dark brown oil. The crude material was loaded on to a 12 g silica gel column and was eluted in 0-5% MeOH in DCM over 20 column volumes to give 7-(3,4-dimethoxyphenyl)-5-methyl-2-((4-(methylsulphonyl)piperazin-1-yl)methyl)thieno[3,2-c]pyridin-4(5H)-one (154 mg, 68% yield) as a yellow oil. The product was triturated with diethyl ether to give a light yellow solid.

LCMS (2 min, Formic Acid): Rt=0.65 min, MH$^+$=478

Example 58

7-(5-methoxy-2-methylphenyl)-5-methyl-2-((4-(methylsulphonyl)piperazin-1-yl)methyl)thieno[3,2-c]pyridin-4(5H)-one

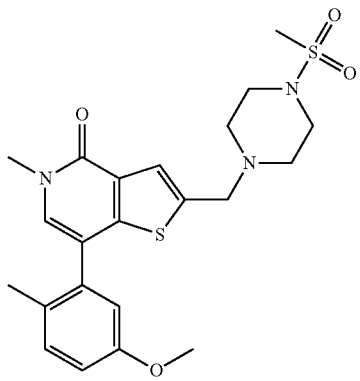 [SMILES: COc1ccc(C)c(-c2cn(C)c(=O)c3cc(CN4CCN(S(C)(=O)=O)CC4)sc23)c1]

To a 2-5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol), (5-methoxy-2-methylphenyl)boronic acid (35.5 mg, 0.214 mmol), potassium carbonate (59.2 mg, 0.428 mmol), and lastly the PEPPSI™-IPr (34.0 mg, 0.05 mmol) in a solution of isopropanol (2 mL) and water (1 mL). The reaction vessel was sealed and heated to 130° C. in the Biotage Initiator microwave reactor for 30 minutes with 10 seconds of pre-stirring. The reaction was quenched with saturated ammonium chloride solution (15 mL) and mixed with DCM (5 mL). The solution was then filtered through Celite to remove the palladium. The filtrate was transferred to a separating funnel and the organic layer was collected. The aqueous layer was extracted with DCM (3×7 mL). The organic layers were combined and dried over magnesium sulphate. The filtrated was collected and concentrated under reduced pressure to give a brown oil. The crude material was loaded onto a 12 g silica gel column and was eluted in 0-5% MeOH in DCM to give a pale yellow oil. The oil was triturated with diethyl ether to give 7-(5-methoxy-2-methylphenyl)-5-methyl-2-((4-(methylsulphonyl)piperazin-1-yl)methyl)thieno[3,2-c]pyridin-4(5H)-one (34.7 mg, 53% yield) as an off white solid.

LCMS (2 min, Formic Acid): Rt=0.76 min, MH$^+$=462

Example 59

7-(3-methoxy-2-methylphenyl)-5-methyl-2-((4-(methylsulphonyl)piperazin-1-yl)methyl)thieno[3,2-c]pyridin-4(5H)-one

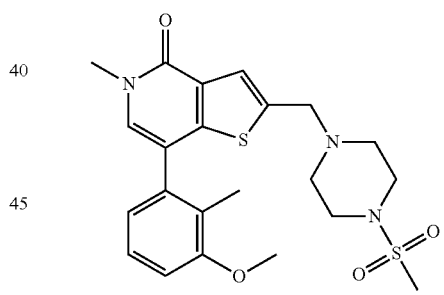

To a microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 100 mg, 0.238 mmol) followed by 2-(3-methoxy-2-methylphenyl)-4,4,5,5-tetramethyl-1,3,2-dioxaborolane (248 mg, 0.999 mmol), potassium carbonate (164 mg, 1.189 mmol) and lastly PEPPSI (34.0 mg, 0.05 mmol) in a solution of isopropanol (2 mL) and water (1 mL). The reaction vessel was sealed and heated to 130° C. in the Biotage Initiator microwave reactor for 30 minutes with 20 seconds of pre-stirring. The reaction was diluted with DCM (20 mL) and passed through Celite. The filtrate was transferred to a separating funnel and washed with saturated ammonium chloride solution (50 mL). The organic layer was collected and the aqueous phase was extracted with DCM (2×30 mL). The organic fractions were combined, dried over MgSO₄ and concentrated under reduced pressure to give a brown oil. The crude material was loaded on to a 25 g silica gel column and was eluted in 0-5% MeOH in DCM over 20 column volumes to give crude product. This was re-purified by MDAP to give a clear oil which was triturated with diethyl ether to give 7-(3-methoxy-2-methylphenyl)-5-methyl-2-((4-(methylsulphonyl)piperazin-1-yl)methyl)thieno[3,2-c]pyridin-4(5H)-one (6 mg, 5% yield) as a white solid.

LCMS (2 min, Formic Acid): Rt=0.77 min, MH⁺=462.

Example 60

7-(2-ethylphenyl)-5-methyl-2-((4-(methylsulphonyl)piperazin-1-yl)methyl)thieno[3,2-c]pyridin-4(5H)-one

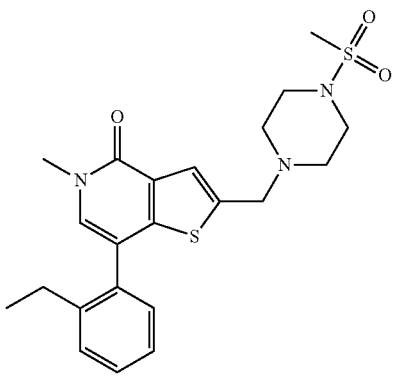 [SMILES: CCc1ccccc1-c1cn(C)c(=O)c2cc(CN3CCN(S(C)(=O)=O)CC3)sc12]

To a 2-5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol), (2-ethylphenyl)boronic acid (25.7 mg, 0.171 mmol), potassium carbonate (47.3 mg, 0.343 mmol), and lastly PEPPSI (34.0 mg, 0.05 mmol) in a solution of isopropanol (2 mL) and water (1 mL). The reaction vessel was sealed and heated in the Biotage Initiator microwave reactor to 130° C. for 30 minutes with 10 seconds of pre-stirring. The reaction was quenched with saturated ammonium chloride solution (15 mL) and mixed with DCM (approx. 5 mL). The solution was passed through Celite to remove the palladium. The filtrate was transferred to a separating funnel and the organic layer was collected. The aqueous layer was extracted with DCM (3×10 mL). The organic layers were combined and dried over MgSO₄. The filtrate was collected and concentrated under reduced pressure to give a light brown oil. The crude product was loaded onto a 12 g silica gel column and eluted in 0-5% MeOH in DCM over 25 column volumes to give a yellow oil. The oil was triturated with diethyl ether to give 7-(2-ethylphenyl)-5-methyl-2-((4-(methylsulphonyl)piperazin-1-yl)methyl)thieno[3,2-c]pyridin-4(5H)-one (54.5 mg, 0.122 mmol, 86% yield) an off white solid.

LCMS (2 min, Formic Acid): Rt=0.83 min, MH⁺=446

Example 61

N-(3-(5-methyl-2-((N-methylmethylsulphonamido)methyl)-4-oxo-4,5-dihydrothieno[3,2-c]pyridin-7-yl)phenyl)acetamide

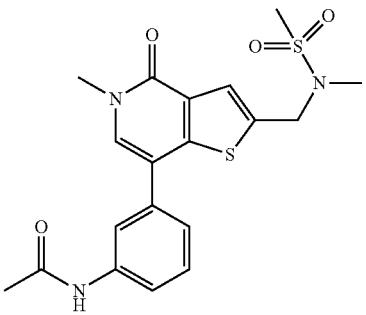 [SMILES: CC(=O)Nc1cccc(-c2cn(C)c(=O)c3cc(CN(C)S(C)(=O)=O)sc23)c1]

A mixture of N-((7-bromo-5-methyl-4-oxo-4,5-dihydrothieno[3,2-c]pyridin-2-yl)methyl)-N-methylmethanesulphonamide (for a preparation see Intermediate 35, 40 mg, 0.11 mmol), (3-acetamidophenyl)boronic acid (25 mg, 0.14 mmol), potassium carbonate (46 mg, 0.33 mmol) and bis(triphenylphosphine)palladium(II) chloride (8 mg, 10 mol %) in 1,2-DME (3 mL) and water (0.5 mL) was heated in a microwave at 120° C. for 20 minutes. The cooled reaction mixture was diluted with ethyl acetate (20 mL), dried over sodium sulphate, filtered and evaporated in vacuo. The residue was purified by chromatography on silica gel 0 to 4% methanol in dichloromethane. The product was repurified by MDAP to give N-(3-(5-methyl-2-((N-methylmethylsulphonamido)methyl)-4-oxo-4,5-dihydrothieno[3,2-c]pyridin-7-yl)phenyl)acetamide (6 mg, 13% yield) as a colourless solid.

LCMS (2 min, Formic Acid): Rt=0.72 min, MH⁺=420

Example 62

7-(4-methoxyphenyl)-5-methyl-2-((4-(methylsulphonyl)piperazin-1-yl)methyl)thieno[3,2-c]pyridin-4(5H)-one

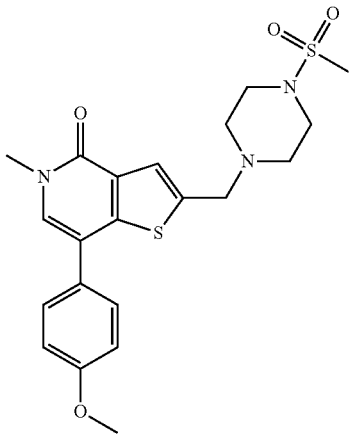

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), (4-methoxyphenyl)boronic acid (30.4 mg, 0.200 mmol), potassium carbonate (55.2 mg, 0.400 mmol) in a solution of isopropanol (2 mL)

and water (1 mL). Lastly to the reaction was added PEPPSI (34 mg, 0.050 mmol). The reaction vessel was sealed and heated in Biotage Initiator microwave reactor to 130° C. for 30 minutes with 10 seconds of pre-stirring. After cooling, to the reaction was added ammonium chloride solution (15 mL) and DCM (15 mL). The mixture was then passed through Celite to remove excess palladium. The filtrate was transferred to a separating funnel and the organic layer collected. The aqueous phase was extracted with DCM (2×15 mL). The organic layers were combined and dried over $MgSO_4$ then filtered and concentrated under reduced pressure to give a light brown oil. The residue was loaded onto a 12 g silica gel column and eluted in 0-5% MeOH in DCM. The purest fractions were combined and the solvent was removed under reduced pressure and the residue was oven dried overnight to give 7-(4-methoxyphenyl)-5-methyl-2-((4-(methylsulphonyl)piperazin-1-yl)methyl)thieno[3,2-c]pyridin-4(5H)-one (42 mg, 56% yield) as a green-brown solid.

LCMS (2 min, Formic Acid): Rt=0.73 min, $MH^+$=448.

A second crop of product was obtained which contained impurities and concentrated under reduced pressure and oven dried overnight to give 7-(4-methoxyphenyl)-5-methyl-2-((4-(methylsulphonyl)piperazin-1-yl)methyl)thieno[3,2-c]pyridin-4(5H)-one (32 mg, 0.071 mmol, 43% yield) as a pale green solid, LCMS (2 min, Formic Acid): Rt=0.73 min, $MH^+$=448.

Example 63

5-methyl-7-(4-(methylsulphonyl)phenyl)-2-((4-(methylsulphonyl)piperazin-1-yl)methyl)thieno[3,2-c]pyridin-4(5H)-one

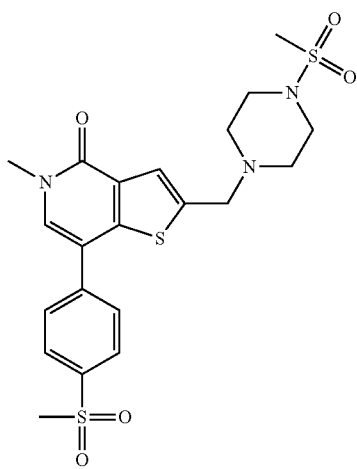 [SMILES: Cn1cc(-c2ccc(S(C)(=O)=O)cc2)c2sc(CN3CCN(S(C)(=O)=O)CC3)cc2c1=O]

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol), (4-(methylsulphonyl)phenyl)boronic acid (34.3 mg, 0.171 mmol), potassium carbonate (47.3 mg, 0.343 mmol), and lastly PEPPSI (34.0 mg, 0.05 mmol) in a solution of isopropanol (2 mL) and water (1 mL). The reaction vessel was sealed and heated in the Biotage Initiator microwave reactor to 130° C. for 30 minutes with 10 seconds of pre-stirring. After cooling, the reaction was quenched with saturated ammonium chloride solution (15 mL) and DCM (5 mL) and mixed. The filtrate was passed through Celite to remove the palladium. The filtrate was transferred to a separating funnel and the organic layer was collected. The aqueous layer was extracted with DCM (3×10 mL). The organic layers were combined and dried over $MgSO_4$. The filtrate was collected and concentrated under reduced pressure to give a yellow oil. The crude material was loaded onto a 12 g silica gel column and eluted in 0-5% MeOH in DCM to give a yellow solid, which contained impurities. The solid was triturated with diethyl ether to give a lighter yellow solid, 5-methyl-7-(4-(methylsulphonyl)phenyl)-2-((4-(methylsulphonyl)piperazin-1-yl)methyl)thieno[3,2-c]pyridin-4(5H)-one (53.6 mg, 76% yield).

LCMS (2 min, Formic Acid): Rt=0.57 min, $MH^+$=496

Example 64

7-(3,4-dimethoxyphenyl)-5-methyl-2-(piperazin-1-ylmethyl)thieno[3,2-c]pyridin-4(5H)-one

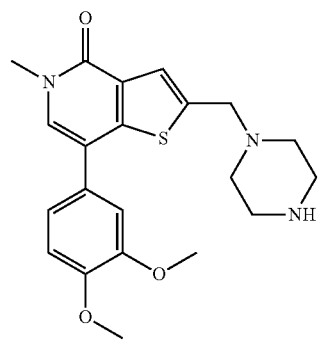 [SMILES: COc1ccc(-c2cn(C)c(=O)c3cc(CN4CCNCC4)sc23)cc1OC]

To a 25 mL round bottom flask under nitrogen was added tert-butyl 4-((7-(3,4-dimethoxyphenyl)-5-methyl-4-oxo-4,5-dihydrothieno[3,2-c]pyridin-2-yl)methyl)piperazine-1-carboxylate (for a preparation see Intermediate 26, 73.9 mg, 0.148 mmol) followed by 1,4-dioxane (1 mL). 4.0M HCl in 1,4-dioxane (1 mL) was added and the reaction mixture was stirred at room temperature for several hours until LCMS showed the reaction had gone to completion. Diethyl ether (approx. 20 mL) was added and the reaction mixture was stirred for 5 minutes. The reaction was allowed to settle and the diethyl ether was decanted. A fresh portion of diethyl ether was added to the precipitate and it was again stirred under nitrogen for 5 minutes, left to settle, and the excess ether was decanted. The remaining solvent was removed under reduced pressure and the product dried in a vacuum over overnight to give the HCl salt of 7-(3,4-dimethoxyphenyl)-5-methyl-2-(piperazin-1-ylmethyl)thieno[3,2-c]pyridin-4(5H)-one (57.4 mg) as an off white solid LCMS (2 min, Formic Acid): Rt=0.61 min, $MH^+$=400

Alternative Preparation

To a stirred solution of tert-butyl 4-((7-(3,4-dimethoxyphenyl)-5-methyl-4-oxo-4,5-dihydrothieno[3,2-c]pyridin-2-yl)methyl)piperazine-1-carboxylate (for a preparation see Intermediate 26, 375 mg, 0.751 mmol) in 1,4-dioxane (2 mL) was added 4.0M HCl in 1,4-dioxane (5 mL). The reaction was stirred at room temperature under nitrogen for two hours.

The reaction was diluted with diethyl ether (approx. 20 mL) and stirred for 5 minutes. The reaction mixture was left to settle and the excess diethyl ether was decanted off. This process was repeated an additional two times. Remaining solvent was removed under reduced pressure and the product was oven dried to give the 2HCl salt of 7-(3,4-dimethoxyphenyl)-5-methyl-2-(piperazin-1-ylmethyl)thieno[3,2- c]pyridin-4(5H)-one, 2 hydrochloride (332 mg) as a yellow solid LCMS (2 min, Formic Acid): Rt=0.63 min, MH+=400.

Example 65

2-(((2-aminoethyl)amino)methyl)-7-(3,4-dimethoxyphenyl)-5-methylthieno[3,2-c]pyridin-4(5H)-one, 2 Hydrochloride

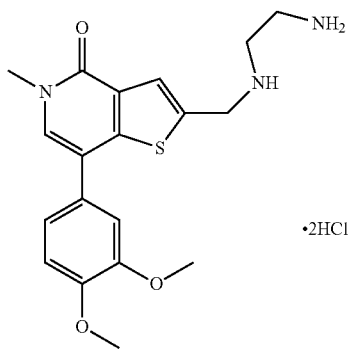 [SMILES: COc1ccc(-c2cn(C)c(=O)c3cc(CNCCN)sc23)cc1OC]

4M Hydrogen chloride in 1,4-dioxane (0.5 mL, 2 mmol) was added to a stirred solution of tert-butyl (2-(((7-(3,4-dimethoxyphenyl)-5-methyl-4-oxo-4, 5-dihydrothieno[3,2-c]pyridin-2-yl)methyl)amino)ethyl)carbamate (for a preparation see Intermediate 45, 155 mg, 0.33 mmol) in 1,4-dioxane (0.5 mL). The reaction mixture was stirred at room temperature for 4 hours. The reaction mixture was diluted with diethyl ether (5 mL) and stirred at room temperature for 1 hour, then allowed to stand overnight. The solid was filtered off, washed with diethyl ether and dried to give 2-(((2-aminoethyl)amino)methyl)-7-(3,4-dimethoxyphenyl)-5-methylthieno[3,2-c]pyridin-4(5H)-one, 2 Hydrochloride (132 mg, 90% yield) as an off-white solid.

LCMS (2 min, Formic Acid): Rt=0.47 min, MH+=374

Example 66

7-(3,4-dimethoxyphenyl)-5-methyl-2-((3-methylpiperazin-1-yl)methyl)thieno[3,2-c]pyridin-4(5H)-one, Hydrochloride

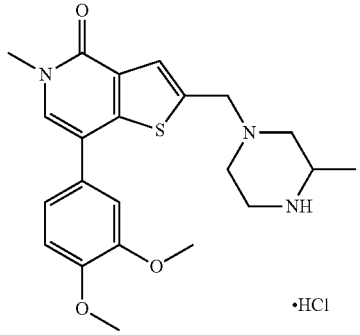

To a solution of tert-butyl 4-((7-(3,4-dimethoxyphenyl)-5-methyl-4-oxo-4,5-dihydrothieno[3,2-c]pyridin-2-yl)methyl)-2-methylpiperazine-1-carboxylate (for a preparation see Intermediate 56, 110 mg, 0.214 mmol) in 1,4-dioxane (1 mL) was added 4.0M HCl in 1,4-dioxane (1 mL) and the reaction was stirred under nitrogen for several hours.

Diethyl ether (20 mL) was added and the reaction mixture was stirred under nitrogen for 5 minutes. The reaction was allowed to settle and was left to stand overnight. The diethyl ether was decanted and a fresh portion of diethyl ether was added. The mixture was stirred for 5 minutes, allowed to settle, and the diethyl ether was decanted. The product was dried under reduced pressure to give 7-(3,4-dimethoxyphenyl)-5-methyl-2-((3-methylpiperazin-1-yl)methyl)thieno[3,2-c]pyridin-4(5H)-one, hydrochloride (112 mg, 116% yield) as an off-white solid contaminated by some remaining diethyl ether.

LCMS (2 min, Formic Acid): Rt=0.85 min, MH+=414

Example 67

N-(2-(((7-(3,4-dimethoxyphenyl)-5-methyl-4-oxo-4,5-dihydrothieno[3,2-c]pyridin-2-yl)methyl)amino)ethyl)methanesulphonamide and Example 67A N-((7-(3,4-dimethoxyphenyl)-5-methyl-4-oxo-4,5-dihydrothieno[3,2-c]pyridin-2-yl)methyl)-N-(2-(methylsulfonamido)ethyl)methanesulfonamide

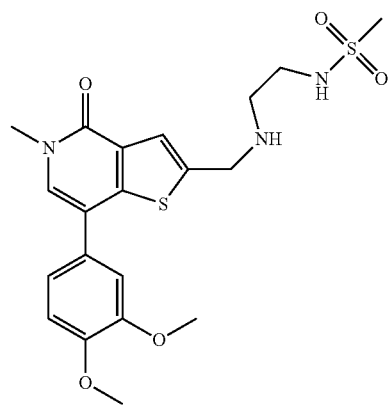

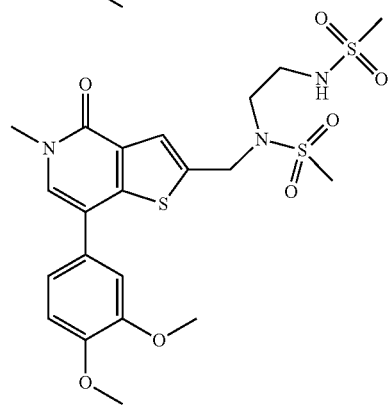

Methanesulphonyl chloride (34 mg, 23 µL, 0.3 mmol) was added to a stirred mixture of 2-(((2-aminoethyl)amino)methyl)-7-(3,4-dimethoxyphenyl)-5-methylthieno[3,2-c]pyridin-4(5H)-one, 2 Hydrochloride (for a preparation see Example 65, 110 mg, 0.25 mmol), pyridine (1 mL) and dichloromethane (2 mL). The reaction mixture was stirred at room temperature for 4 hours. Methanesulphonyl chloride (34 mg, 23 µL, 0.3 mmol) was added and the mixture stirred at room temperature overnight. The mixture was diluted with dichloromethane (10 mL). The reaction mixture was washed with a saturated aqueous solution of NaHCO₃ (10 mL) and water (10 mL). The organic phase was dried and evaporated in vacuo. The residue was purified by chromatography on silica gel eluting with 0 to 10% methanol in dichloromethane. The residue was repurified by MDAP to give N-(2-(((7-(3,4-dimethoxyphenyl)-5-methyl-4-oxo-4,5-dihydrothieno[3,2-c]pyridin-2-yl)methyl)amino)ethyl) methanesulphonamide (Example 67) (9 mg, 0.020 mmol, 8.09% yield) as a colourless oil.

LCMS (2 min, Formic Acid): Rt=0.58 min, MH⁺=452 and

N-((7-(3,4-dimethoxyphenyl)-5-methyl-4-oxo-4,5-dihydrothieno[3,2-c]pyridin-2-yl)methyl)-N-(2-(methylsulfonamido)ethyl)methanesulfonamide (Example 67A) (8 mg, 0.015 mmol, 6.1% yield) as a colourless oil.

LCMS (2 min, Formic Acid): Rt=0.76 min, MH⁺=530

Example 68

5-methyl-2-((4-(methylsulphonyl)piperazin-1-yl) methyl)-7-(m-tolyl)thieno[3,2-c]pyridin-4(5H)-one

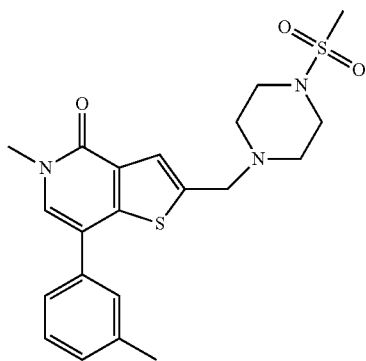 [SMILES: Cc1cccc(-c2cn(C)c(=O)c3cc(CN4CCN(S(C)(=O)=O)CC4)sc23)c1]

To a 2-5 mL microwave reaction vial was added 7-bromo-5-methyl-2-((4-(methylsulphonyl)piperazin-1-yl)methyl) thieno[3,2-c]pyridin-4(5H)-one (for a preparation see Intermediate 69, 70 mg, 0.167 mmol), m-tolylboronic acid (27.2 mg, 0.200 mmol), and potassium carbonate (55.2 mg, 0.400 mmol) in a solution of isopropanol (2 mL) and water (1.000 mL). Lastly to the reaction mixture was added the PEPPSI (34.0 mg, 0.05 mmol). The reaction vessel was sealed and heated in Biotage Initiator microwave reactor to 130° C. for 30 minutes with 10 seconds of pre-stirring. After cooling, the reaction was quenched with saturated ammonium chloride solution (15 mL) and DCM (15 mL) and passed through Celite to remove palladium. The filtrate was transferred to a separating funnel and the organic layer was collected. The aqueous layer was extracted with DCM (2×10 mL). The organic fractions were combined and dried over MgSO4. The filtrate was collected and concentrated under reduced pressure to give a light brown crystalline solid. The residue was loaded onto a 12 g silica gel column and eluted in 0-5% MeOH in DCM. The purest fractions were concentrated under reduced pressure to give a yellow oil. The oil was triturated with diethyl ether to give 5-methyl-2-((4-(methylsulphonyl)piperazin-1-yl)methyl)-7-(m-tolyl)thieno[3,2-c]pyridin-4(5H)-one (59.5 mg, 83% yield) as an off-white solid.

LCMS (2 min, Formic Acid): Rt=0.77 min, MH⁺=432.

Example 69

7-(3,4-dimethoxyphenyl)-2-((1,1-dioxidothiomorpholino)methyl)-5-methylthieno[3,2-c]pyridin-4 (5H)-one

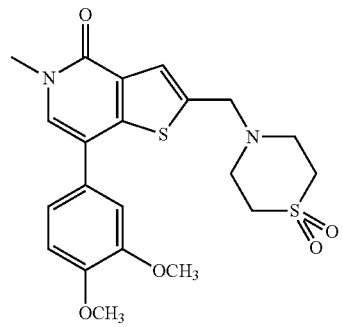 [SMILES: COc1ccc(-c2cn(C)c(=O)c3cc(CN4CCS(=O)(=O)CC4)sc23)cc1OC]

Example 69 was prepared in the array described for Intermediates 71-82, wherein the amine reagent (NHR'R") was thiomorpholine 1,1-dioxide, obtained from Tokyo Chemical Industry Co., Ltd (TCI), to give a yield of 28 mg, 0.062 mmol, 23% yield.

LCMS pH (2 min, High pH): Rt 0.82 min, MH⁺=449.

Example 70

(R)-7-(3,4-dimethoxyphenyl)-5-methyl-2-((3-methyl morpholino)methyl)thieno[3,2-c]pyridin-4(5H)-one

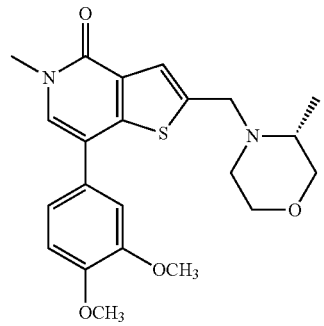

To a suspension of (R)-7-bromo-5-methyl-2-((3-methylmorpholino)methyl)thieno[3,2-c]pyridin-4(5H)-one (for a preparation see Intermediate 41, 256 mg, 0.717 mmol), potassium carbonate (495 mg, 3.58 mmol) and (3,4-dimethoxyphenyl)boronic acid (326 mg, 1.791 mmol) in isopropanol (4 mL) and water (4 mL) was added PEPPSI (48.7 mg, 0.072 mmol). The reaction mixture was heated in the microwave at 130° C. for 30 minutes. The cooled reaction mixture was hydrolyzed with a saturated aqueous solution of ammonium chloride (30 mL) and the layers were separated. The aqueous phase was extracted with DCM (3×30 mL) and the combined organic layers were dried over magnesium sulphate, filtered and concentrated under reduced pressure to give a dark green oil. The crude material purified by chromatography on silica gel eluting with 0-80% ethyl acetate in cyclohexane followed by 0-5% MeOH in DCM. The appropriate fractions were combined and concentrated in vacuo to give (R)-7-(3,4-dimethoxyphenyl)-5-methyl-2-((3-methylmorpholino)methyl)thieno[3,2-c]pyridin-4(5H)-one (288 mg, 97% yield) as a light pink oil.

LCMS (2 min, Formic Acid): Rt=0.60 min, MH⁺=415

Example 71

7-(2-(benzyloxy)phenyl)-5-methyl-2-((4-(methylsulphonyl)piperazin-1-yl)methyl)thieno[3,2-c]pyridin-4(5H)-one

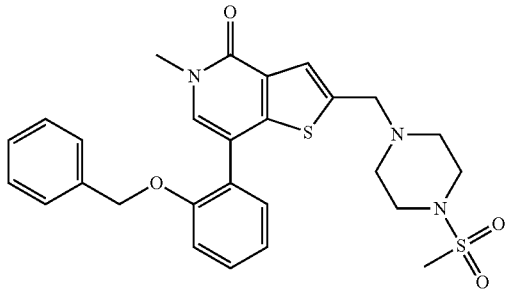 [SMILES: Cn1cc(-c2ccccc2OCc2ccccc2)c2sc(CN3CCN(S(C)(=O)=O)CC3)cc2c1=O]

To a solution of 7-bromo-5-methyl-2-((4-(methylsulphonyl)piperazin-1-yl)methyl)thieno[3,2-c]pyridin-4(5H)-one (for a preparation see Intermediate 69, 150 mg, 0.357 mmol) and 2-(2-(benzyloxy)phenyl)-4,4,5,5-tetramethyl-1,3,2-dioxaborolane (166 mg, 0.535 mmol) in isopropanol (5 mL) were successively added potassium carbonate (0.892 mL, 1.784 mmol) and PEPPSI (24.25 mg, 0.036 mmol). The resulting mixture was heated at 110° C. in the microwave for 30 min, whereupon the reaction mixture was allowed to cool down to rt and was concentrated in vacuo. The crude residue was partitioned between EtOAc and a saturated aqueous solution of sodium bicarbonate. The phases were separated, the aqueous phase was extracted 3 times with EtOAc and the combined organic layers were washed with brine, dried over MgSO$_4$, filtered and concentrated in vacuo. The residue was purified via MDAP. The appropriate fractions were combined and concentrated in vacuo to give 7-(2-(benzyloxy)phenyl)-5-methyl-2-((4-(methylsulphonyl)piperazin-1-yl)methyl)thieno[3,2-c]pyridin-4(5H)-one (85 mg, 46% yield) as a white solid.

LCMS (2 min, Formic Acid): Rt=0.89 min, MH$^+$=524.

Example 72

5-methyl-2-((4-(methylsulphonyl)piperazin-1-yl)methyl)-7-(4-(trifluoromethyl)phenyl)thieno[3,2-c]pyridin-4(5H)-one

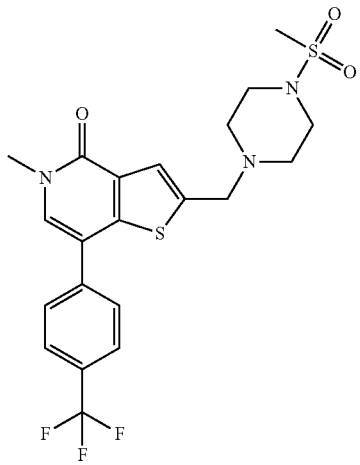 [SMILES: Cn1cc(-c2ccc(C(F)(F)F)cc2)c2sc(CN3CCN(S(C)(=O)=O)CC3)cc2c1=O]

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol), (4-(trifluoromethyl)phenyl)boronic acid (32.5 mg, 0.171 mmol), and potassium carbonate (47.3 mg, 0.343 mmol) in a solution of isopropanol (2 mL) and water (1 mL). To the reaction was then added PEPPSI (34.0 mg, 0.05 mmol). The reaction vessel was sealed and heated in a Biotage Initiator microwave reactor to 130° C. for 30 minutes with 10 seconds of pre-stirring. After cooling the reaction was quenched with saturated ammonium chloride solution (15 mL) and mixed with DCM (10 mL). The solution was passed through Celite to remove the palladium. The filtrate was transferred to a separating funnel and the organic layer was collected. The aqueous layer was extracted with DCM (2×10 mL). The organic layers were combined and dried over MgSO4 and the filtrate was collected using vacuum filtration. The product was concentrated under reduced pressure to give a brown oil.

The residue was loaded onto a 12 g silica gel column and chromatographed in 0-5% MeOH in DCM over 22 column volumes. The purest fractions were combined and concentrated to give a yellow oil.

The oil was triturated with diethyl ether and oven dried overnight to give 5-methyl-2-((4-(methylsulphonyl)piperazin-1-yl)methyl)-7-(4-(trifluoromethyl)phenyl)thieno[3,2-c]pyridin-4(5H)-one (59 mg, 85% yield) as a yellow solid.

LCMS (2 min, Formic Acid): Rt=0.87 min, MH$^+$=486

Example 73

2-((1,4-oxazepan-4-yl)methyl)-7-(2-((2-methoxyethyl)(methyl)amino)pyridin-4-yl)-5-methylthieno[3,2-c]pyridin-4(5H)-one, Formic acid salt

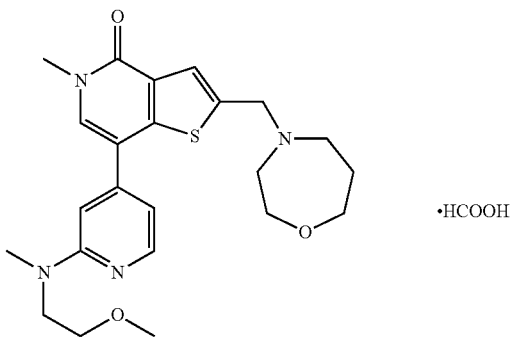 [SMILES: COCCN(C)c1cc(-c2cn(C)c(=O)c3cc(CN4CCCOCC4)sc23)ccn1 ; "·HCOOH"]

·HCOOH

To a solution of 2-((1,4-oxazepan-4-yl)methyl)-7-(2-chloropyridin-4-yl)-5-methylthieno[3,2-c]pyridin-4(5H)-one (for a preparation see Example 85, 102 mg, 0.262 mmol) in NMP (1 mL) was added 2-methoxy-N-methylethanamine (6996 mg, 78 mmol). The reaction mixture was stirred in the microwave for 30 min at 250° C., whereupon it was allowed to cool to rt. The excess 2-methoxy-N-methylethanamine (6996 mg, 78 mmol) was removed in vacuo and the residue (dissolved in NMP) was purified via MDAP. The appropriate fractions were combined and concentrated in vacuo to give 2-((1,4-oxazepan-4-yl)methyl)-7-(2-((2-methoxyethyl)(methyl)amino)pyridin-4-yl)-5-methylthieno[3,2-c]pyridin-4(5H)-one, Formic acid salt (92 mg, 72%) as a viscous yellow oil.

LCMS (2 min, Formic Acid): Rt=0.48 min, MH$^+$=443

Example 74

7-(3,4-dimethoxyphenyl)-2-((4-hydroxypiperidin-1-yl)methyl)-5-methylthieno[3,2-c]pyridin-4(5H)-one, Hydrochloride

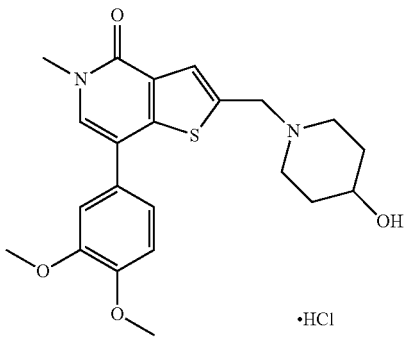 [SMILES: COc1ccc(-c2cn(C)c(=O)c3cc(CN4CCC(O)CC4)sc23)cc1OC ; Cl]

A mixture of 7-bromo-2-((4-hydroxypiperidin-1-yl)methyl)-5-methylthieno[3,2-c]pyridin-4(5H)-one (for a preparation see Intermediate 40, 50 mg, 0.14 mmol), (3,4-dimethoxyphenyl)boronic acid (38 mg, 0.21 mmol), potassium carbonate (58 mg, 0.42 mmol) and bis(triphenylphosphine)palladium(II) chloride (10 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated in vacuo. The residue was purified via chromatography on silica gel eluting with 0-10% methanol in dichloromethane. The resulting product was dissolved in ethyl acetate (0.5 mL) and treated with 1.0M hydrogen chloride in diethyl ether (0.5 mL). Diethyl ether (10 mL) was added and the solid was filtered off and dried to give 7-(3,4-dimethoxyphenyl)-2-((4-hydroxypiperidin-1-yl)methyl)-5-methylthieno[3,2-c]pyridin-4(5H)-one, Hydrochloride (50 mg, 79% yield) as a colourless solid.

LCMS (2 min, Formic Acid): Rt=0.58 min, MH+=415

Example 75

7-(4-methoxy-2-methylphenyl)-5-methyl-2-((4-(methylsulphonyl)piperazin-1-yl)methyl)thieno[3,2-c]pyridin-4(5H)-one

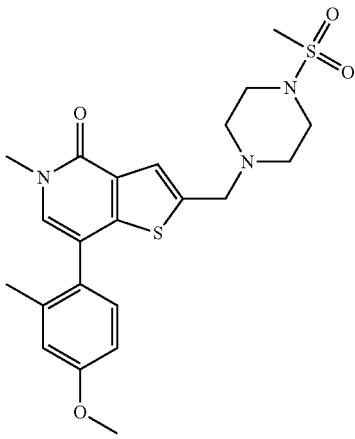 [SMILES: COc1ccc(-c2cn(C)c(=O)c3cc(CN4CCN(S(C)(=O)=O)CC4)sc23)c(C)c1]

To a 2-5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 100 mg, 0.238 mmol) followed by (4-methoxy-2-methylphenyl)boronic acid (47.4 mg, 0.285 mmol), potassium carbonate (79 mg, 0.571 mmol) and lastly PEPPSI (34.0 mg, 0.05 mmol) in a solution of isopropanol (2 mL) and water (1 mL). The reaction vessel was sealed and heated in the Biotage Initiator microwave reactor to 130° C. for 30 minutes with 10 seconds of pre-stirring. The reaction was diluted with saturated sodium bicarbonate solution (20 mL) and shaken with DCM (20 mL). The solution was passed through Celite to remove the palladium. The filtrate was transferred to a separating funnel and the organic layer was collected. The aqueous layer was extracted with DCM (3×20 mL). The organic layers were combined, dried over MgSO4 and concentrated under reduced pressure to give a light brown oil. The crude material was loaded onto a 12 g silica gel column and the product was eluted in 0-5% MeOH in DCM over 25 column volumes to give a yellow oil. The oil was triturated with diethyl ether and oven dried overnight to give 7-(4-methoxy-2-methylphenyl)-5-methyl-2-((4-(methylsulphonyl)piperazin-1-yl)methyl)thieno[3,2-c]pyridin-4(5H)-one (51 mg, 46% yield) as a light orange solid, LCMS (2 min, Formic Acid): Rt=0.75 min, MH+=462.

Example 76

4-(5-methyl-2-((4-(methylsulphonyl)piperazin-1-yl)methyl)-4-oxo-4,5-dihydrothieno[3,2-c]pyridin-7-yl)benzonitrile

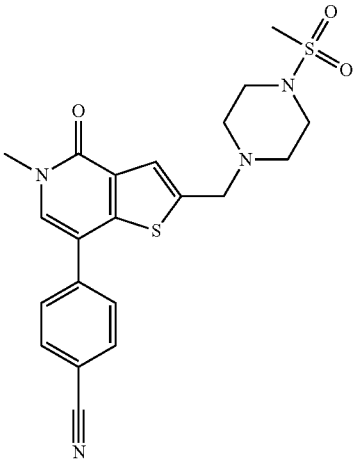 [SMILES: Cn1cc(-c2ccc(C#N)cc2)c2sc(CN3CCN(S(C)(=O)=O)CC3)cc2c1=O]

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol), (4-cyanophenyl)boronic acid (25.2 mg, 0.171 mmol), potassium carbonate (47.3 mg, 0.343 mmol), and lastly PEPPSI (34.0 mg, 0.05 mmol) in a solution of isopropanol (2 mL) and water (1 mL). The reaction vessel was sealed and heated in the Biotage Initiator microwave reactor to 130° C. for 30 minutes with 10 seconds of pre-stirring. After cooling, the reaction was quenched with saturated ammonium chloride solution (15 mL) and mixed with DCM (10 mL). The solution was passed through Celite to remove the palladium catalyst. The filtrate was transferred to a separating funnel and the organic layer was collected. The aqueous layer was extracted with DCM (3×10 mL). The organic layers were combined and dried over MgSO$_4$. The filtrate was collected and concentrated under reduced pressure to give a brown solid. The crude product was loaded onto a 12 g silica gel column and was eluted in 0-5% MeOH in DCM over 25 column volumes to give a yellow oil. The oil was triturated with diethyl ether to give 4-(5-methyl-2-((4-(methylsulphonyl)piperazin-1-yl)methyl)-4-oxo-4,5-dihydrothieno[3,2-c]pyridin-7-yl)benzonitrile (47.4 mg, 75% yield) as a yellow solid, LCMS (2 min, Formic Acid): Rt=0.66 min, MH$^+$=443

Example 77

N-(4-(5-methyl-2-((3-methyl morpholino)methyl)-4-oxo-4,5-dihydrothieno[3,2-c]pyridin-7-yl)pyridin-2-yl)acetamide

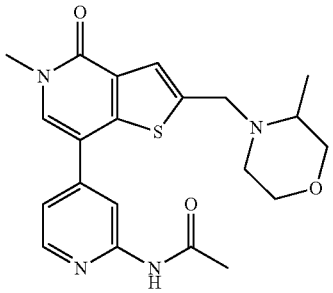 [SMILES: CC(=O)Nc1cc(-c2cn(C)c(=O)c3cc(CN4CCOCC4C)sc23)ccn1]

A stirred suspension of 7-(2-aminopyridin-4-yl)-5-methyl-2-((3-methylmorpholino)methyl)thieno[3,2-c]pyridin-4(5H)-one (for a preparation see Example 86, 100 mg, 0.270 mmol) in DCM (4 mL) and pyridine (4 mL) was treated with acetic anhydride (51 μL, 0.541 mmol). The reaction mixture was stirred at room temperature under an atmosphere of nitrogen for two hours. The reaction was treated with another portion of acetic anhydride (51 μL, 0.541 mmol) and stirred under the conditions described for a further 2 hours.

The reaction mixture was then concentrated under reduced pressure, and the residue was azeotroped with toluene to remove residual pyridine. The material was triturated with diethyl ether to give the desired product as an orange solid. LC/MS showed that there was still some starting material remaining. The product was therefore dissolved in DCM (3 mL) and pyridine (2 mL) and treated with acetic anhydride (102 μL, 1.082 mmol) and the reaction mixture was stirred at room temperature under nitrogen over the weekend.

The reaction was concentrated under reduced pressure. The material was dissolved in DCM (2 mL), treated with toluene (15 mL) and the reaction mixture was concentrated in vacuo to remove residual pyridine. The product was triturated with diethyl ether to give a brown solid which was only 72% pure by LCMS. The residue was purified via MDAP. The appropriate fractions were combined and concentrated in vacuo to give N-(4-(5-methyl-2-((3-methylmorpholino)methyl)-4-oxo-4,5-dihydrothieno[3,2-c]pyridin-7-yl)pyridin-2-yl)acetamide (48 mg, 43% yield) as a yellow solid.

LCMS (2 min, Formic Acid): Rt=0.46 min, MH$^+$=413

Example 78

(S)-7-(3-(benzyloxy)phenyl)-5-methyl-2-((3-methylmorpholino)methyl)thieno[3,2-c]pyridin-4(5H)-one

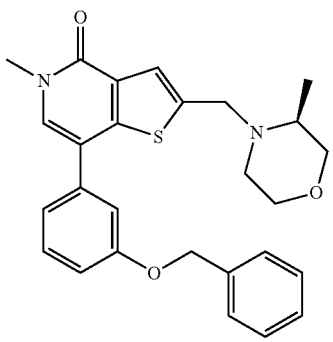 [SMILES: C[C@H]1COCCN1Cc1cc2c(=O)n(C)cc(-c3cccc(OCc4ccccc4)c3)c2s1]

To a stirred solution of (S)-7-(3-hydroxyphenyl)-5-methyl-2-((3-methylmorpholino)methyl)thieno[3,2-c]pyridin-4(5H)-one (for a preparation see Example 81, 90 mg, 0.243 mmol) in DMF (5 mL) was added potassium carbonate (40.3 mg, 0.292 mmol) followed by (bromomethyl)benzene (0.087 mL, 0.729 mmol). The reaction mixture was heated to 100° C. and stirred under nitrogen for 3.5 hours. Another portion of potassium carbonate (40.3 mg, 0.292 mmol) was added and the reaction was stirred for a further 90 minutes. The reaction was cooled to room temperature and left sitting under nitrogen for 48 hours.

The reaction mixture was then diluted with water (30 mL) and transferred to a separating funnel. The layers were separated and the aqueous phase was extracted with ethyl acetate (3×25 mL). The combined organic fractions were washed with brine (30 mL), dried over magnesium sulphate, and concentrated under reduced pressure to give a yellow oil. The crude material was purified via chromatography on silica gel eluting with 0 to 5% MeOH in DCM. The appropriate fractions were combined and concentrated in vacuo to give S)-7-(3-(benzyloxy)phenyl)-5-methyl-2-((3-methylmorpholino)methyl)thieno[3,2-c]pyridin-4(5H)-one (83 mg, 74% yield) as a white solid.

LCMS (2 min, Formic Acid): Rt=0.89 min, MH$^+$=461

Example 79

N-(3-(5-methyl-2-((3-methylmorpholino)methyl)-4-oxo-4,5-dihydrothieno[3,2-c]pyridin-7-yl)phenyl)acetamide

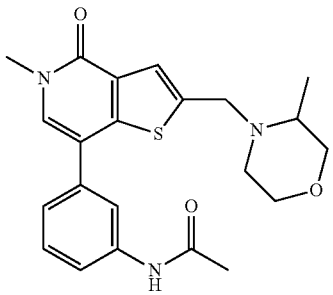 [SMILES: CC(=O)Nc1cccc(-c2cn(C)c(=O)c3cc(CN4CCOCC4C)sc23)c1]

To a suspension of 7-bromo-5-methyl-2-((3-methylmorpholino)methyl)thieno[3,2-c]pyridin-4(5H)-one (for a preparation see Intermediate 38, 70 mg, 0.196 mmol), (3-acetamidophenyl)boronic acid (105 mg, 0.588 mmol) and potassium carbonate (162 mg, 1.176 mmol) in isopropanol (2 mL) and water (2 mL) was added PEPPSI (13.31 mg, 0.020 mmol) catalyst. The reaction mixture was heated at 130° C. for 30 minutes in the microwave, whereupon the reaction was hydrolyzed using an aqueous saturated ammonium chloride solution (25 mL). The aqueous phase was extracted with DCM (3×25 mL) and the combined organic layers were dried over magnesium sulphate, filtered and concentrated under reduced pressure to give a brown solid.

The crude material purified by chromatography on silica gel eluting with 0 to 5% MeOH in DCM to give N-(3-(5-methyl-2-((3-methylmorpholino)methyl)-4-oxo-4,5-dihydrothieno[3,2-c]pyridin-7-yl)phenyl)acetamide (69 mg, 86% yield) as a yellow solid.

LCMS (2 min, Formic Acid): Rt=0.54 min, MH+=412

Example 80

7-(2-((2-methoxyethyl)(methyl)amino)pyridin-4-yl)-5-methyl-2-((4-(methylsulphonyl)piperidin-1-yl)methyl)thieno[3,2-c]pyridin-4(5H)-one

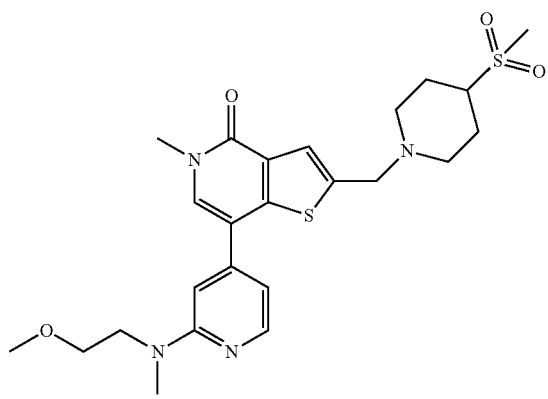 [SMILES: COCCN(C)c1cc(-c2cn(C)c(=O)c3cc(CN4CCC(S(C)(=O)=O)CC4)sc23)ccn1]

A mixture of 7-bromo-5-methyl-2-((4-(methylsulphonyl)piperidin-1-yl)methyl)thieno[3,2-c]pyridin-4(5H)-one (for a preparation see Intermediate 48, 11 mg, 0.026 mmol), (2-((2-methoxyethyl)(methyl)amino)pyridin-4-yl)boronic acid (Intermediate 147) (8.26 mg, 0.039 mmol), potassium carbonate (10.88 mg, 0.079 mmol) and bis(triphenylphosphine)palladium(II) chloride (1.841 mg, 2.62 μmol) in water (0.5 mL) and 1,2-DME (1.5 mL) was heated in a microwave at 120° C. for 20 minutes. The cooled reaction mixture was diluted with ethyl acetate and the solution dried over MgSO4 and evaporated. The residue was diluted in a 1:1 MeOH/DMSO mixture and purified via MDAP to give 7-(2-((2-methoxyethyl)(methyl)amino)pyridin-4-yl)-5-methyl-2-((4-(methylsulphonyl)piperidin-1-yl)methyl)thieno[3,2-c]pyridin-4(5H)-one (5.1 mg, 39%) as a viscous light yellow oil.

LCMS (2 min, Formic Acid): Rt=0.42 min, MH+=505

Example 81

(S)-7-(3-hydroxyphenyl)-5-methyl-2-((3-methylmorpholino)methyl)thieno[3,2-c]pyridin-4(5H)-one

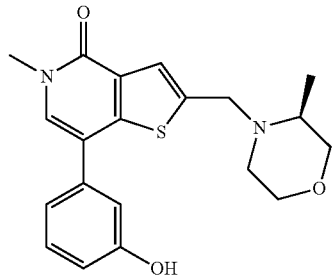 [SMILES: C[C@H]1COCCN1Cc1cc2c(=O)n(C)cc(-c3cccc(O)c3)c2s1]

To a suspension of (S)-7-bromo-5-methyl-2-((3-methylmorpholino)methyl)thieno[3,2-c]pyridin-4(5H)-one (for a preparation see Intermediate 39, 250 mg, 0.700 mmol), (3-hydroxyphenyl)boronic acid (193 mg, 1.400 mmol) and potassium carbonate (484 mg, 3.50 mmol) in isopropanol (2.5 mL) and water (1.5 mL) was added PEPPSI (47.5 mg, 0.070 mmol) catalyst. The reaction mixture was heated at 130° C. in the microwave for 30 minutes. The reaction mixture was then diluted with DCM (30 mL) and transferred to a separating funnel. A saturated ammonium chloride solution (50 mL) was added and the layers were separated. The aqueous phase was extracted with DCM (2×30 mL) and the combined organic fractions were dried over magnesium sulphate and concentrated under reduced pressure to give a light brown oil. The crude material was purified by chromatography on silica gel eluting with 0 to 7% MeOH in DCM. The appropriate fractions were combined and evaporated in vacuo to give (S)-7-(3-hydroxyphenyl)-5-methyl-2-((3-methylmorpholino)methyl)thieno[3,2-c]pyridin-4(5H)-one (192 mg, 74% yield) as a yellow solid.

LCMS (2 min, Formic Acid): Rt=0.55 min, MH+=371

Example 82

(S)-7-(3,4-dimethoxyphenyl)-5-methyl-2-((3-methylmorpholino)methyl)thieno[3,2-c]pyridin-4(5H)-one

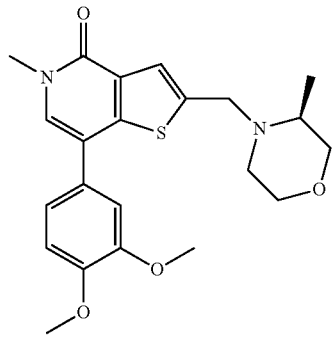 [SMILES: COc1ccc(-c2cn(C)c(=O)c3cc(CN4CCOC[C@@H]4C)sc23)cc1OC]

To a suspension of (S)-7-bromo-5-methyl-2-((3-methylmorpholino)methyl)thieno[3,2-c]pyridin-4(5H)-one (for a preparation see Intermediate 39, 40 mg, 0.112 mmol), (3,4-dimethoxyphenyl)boronic acid (30.6 mg, 0.168 mmol) and potassium carbonate (77 mg, 0.560 mmol) in isopropanol (2 mL) and water (1 mL) was added PEPPSI (34 mg, 0.05 mmol) catalyst. The reaction mixture was heated to 130° C. for 30 minutes in a Biotage Initiator microwave reactor. The cooled reaction mixture was diluted with DCM (5 mL) and water (5 mL), and the mixture was passed through Celite.

The filtrate was washed with a saturated aqueous solution of ammonium chloride (25 mL) and the aqueous phase was extracted with DCM (3×20 mL). The organic layers were combined, dried over magnesium sulphate, filtered and concentrated in vacuo to give the crude product as a dark brown oil. The latter was purified by chromatography on silica gel eluting with 0-5% MeOH in DCM to give (S)-7-(3,4-dimethoxyphenyl)-5-methyl-2-((3-methylmorpholino)methyl)thieno[3,2-c]pyridin-4(5H)-one (34.7 mg, 0.084 mmol, 75% yield) as a green oil.

LCMS (2 min, Formic Acid): Rt=0.62 min, MH⁺=415

Example 83

7-(3,4-dimethoxyphenyl)-5-methyl-2-((3-methylmorpholino)methyl)thieno[3,2-c]pyridin-4(5H)-one

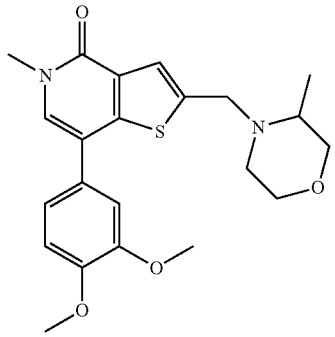 [SMILES: COc1ccc(-c2cn(C)c(=O)c3cc(CN4CCOCC4C)sc23)cc1OC]

To a suspension of 7-bromo-5-methyl-2-((3-methylmorpholino)methyl)thieno[3,2-c]pyridin-4(5H)-one (for a preparation see Intermediate 38, 70 mg, 0.196 mmol), (3,4-dimethoxyphenyl)boronic acid (107 mg, 0.588 mmol) and potassium carbonate (162 mg, 1.176 mmol) in isopropanol (2 mL) and water (2 mL) was added PEPPSI (13 mg, 0.020 mmol) catalyst. The reaction mixture was heated to 130° C. in the microwave for 30 minutes. The cooled reaction mixture was hydrolyzed with a saturated aqueous solution of ammonium chloride (25 mL) and the aqueous phase was extracted with DCM (3×20 mL). The organic layers were combined, dried over magnesium sulphate, filtered and concentrated under reduced pressure to give a dark green oil. The crude material was purified by chromatography on silica gel eluting with 0-5% MeOH in DCM. The resulting residue was triturated with diethyl ether to give 7-(3,4-dimethoxyphenyl)-5-methyl-2-((3-methylmorpholino)methyl)thieno[3,2-c]pyridin-4(5H)-one (56 mg, 69% yield) as an orange solid.

LCMS (2 min, Formic Acid): Rt=0.61 min, MH⁺=415

Example 84

7-(3,4-dimethoxyphenyl)-5-methyl-2-(piperidin-1-ylmethyl)thieno[3,2-c]pyridin-4(5H)-one, Hydrochloride

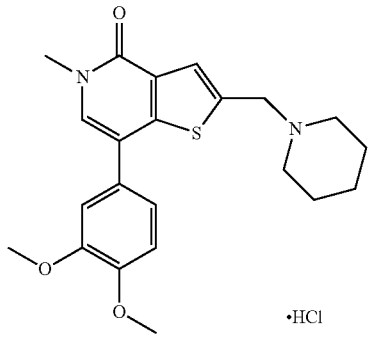 [SMILES: COc1ccc(-c2cn(C)c(=O)c3cc(CN4CCCCC4)sc23)cc1OC ; Cl]

A mixture of 7-bromo-5-methyl-2-(piperidin-1-ylmethyl)thieno[3,2-c]pyridin-4(5H)-one (for a preparation see Intermediate 37, 50 mg, 0.15 mmol), (3,4-dimethoxyphenyl)boronic acid (40 mg, 0.22 mmol), potassium carbonate (61 mg, 0.44 mmol) and bis(triphenylphosphine)palladium(II) chloride (11 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL) and the solution was dried over sodium sulphate then evaporated. The residue was purified by chromatography on silica gel 0-5% methanol in dichloromethane and the resulting product was subsequently dissolved in ethyl acetate (0.5 mL) and treated with 1.0M hydrogen chloride in diethyl ether (0.5 mL). Diethyl ether (10 mL) was added, and the solid was filtered off and dried to give 7-(3,4-dimethoxyphenyl)-5-methyl-2-(piperidin-1-ylmethyl)thieno[3,2-c]pyridin-4(5H)-one, hydrochloride (53 mg, 83% yield) as a white solid.

LCMS (2 min, Formic Acid): Rt=0.64 min, MH⁺=399

Example 85

2-((1,4-oxazepan-4-yl)methyl)-7-(2-chloropyridin-4-yl)-5-methylthieno[3,2-c]pyridin-4(5H)-one

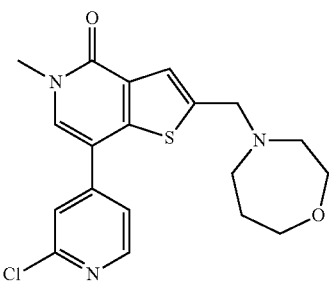 [SMILES: Cn1cc(-c2ccnc(Cl)c2)c2sc(CN3CCCOCC3)cc2c1=O]

To a solution of 2-((1,4-oxazepan-4-yl)methyl)-7-bromo-5-methylthieno[3,2-c]pyridin-4(5H)-one (for a preparation see Intermediate 42, 220 mg, 0.616 mmol) and (2-chloropyridin-4-yl)boronic acid (145 mg, 0.924 mmol) in THF (20 mL) were successively added sodium carbonate (2M in water) (0.924 mL, 1.847 mmol) and PdCl₂(dppf)-DCM adduct (50.3 mg, 0.062 mmol). The reaction mixture was refluxed for 2 hours, whereupon it was allowed to cool to rt. The reaction mixture was concentrated in vacuo, and the residue was partitioned between EtOAc and water. The aqueous phase was extracted three times with EtOAc and the combined organic layers were washed with brine, dried over MgSO₄, filtered and concentrated in vacuo. The crude residue was purified via flash chromatography on silica gel eluting with 2 to 10% MeOH in DCM. The appropriate fractions were combined and concentrated in vacuo to give 2-((1,4-oxazepan-4-yl)methyl)-7-(2-chloropyridin-4-yl)-5-methylthieno[3,2-c]pyridin-4(5H)-one (158 mg, 66%) as a light yellow solid.

LCMS (2 min, Formic Acid): Rt=0.54 min, MH⁺=390

Example 86

7-(2-aminopyridin-4-yl)-5-methyl-2-((3-methylmorpholino)methyl)thieno[3,2-c]pyridin-4(5H)-one hydrochloride

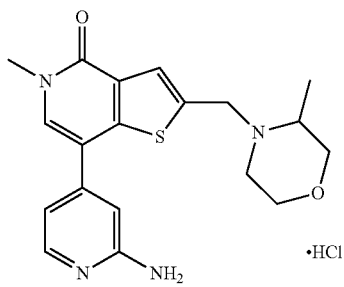 [SMILES: CC1COCCN1Cc1cc2c(=O)n(C)cc(-c3ccnc(N)c3)c2s1 ; Cl]

To a suspension of 7-bromo-5-methyl-2-((3-methylmorpholino)methyl)thieno[3,2-c]pyridin-4(5H)-one (for a preparation see Intermediate 38, 270 mg, 0.756 mmol), 4-(4,4,5,5-tetramethyl-1,3,2-dioxaborolan-2-yl)pyridin-2-amine, Hydrochloride (434 mg, 1.692 mmol) and potassium carbonate (522 mg, 3.78 mmol), in isopropanol (4 mL) and water (4 mL) was added PEPPSI (51.3 mg, 0.076 mmol) catalyst The reaction mixture was heated to 130° C. for 30 minutes in a Biotage Initiator microwave reactor whereupon the reaction was quenched with an aqueous saturated ammonium chloride solution (35 mL). The aqueous phase was extracted with DCM (3×30 mL) and the combined organic layers were dried over magnesium sulphate, filtered and concentrated under reduced pressure to give a light brown oil. The material was loaded onto a 5 g SCX column which was flushed with methanol (2×10 mL) to remove impurities. The product was eluted from the column with 2.0 M ammonia in MeOH (3×10 mL). The solvent was removed under reduced pressure to give the desired product as a light brown residue. The latter was subsequently dissolved in a small volume of THF (approx. 10 mL) and treated with 1.0 M HCl in diethyl ether (2 mL). The material was diluted with diethyl ether (20 mL) and the product was collected by filtration and washed with fresh ether (2×5 mL). The product was oven dried to give 7-(2-aminopyridin-4-yl)-5-methyl-2-((3-methylmorpholino)methyl)thieno[3,2-c]pyridin-4(5H)-one, hydrochloride (316 mg, 94% yield) as a yellow solid.

LCMS (2 min, Formic Acid): Rt=0.34 min, MH$^+$=371

Example 87

5-methyl-2-((methylamino)methyl)-7-(2-((tetrahydro-2H-pyran-4-yl)methoxy)pyridin-4-yl)thieno[3,2-c]pyridin-4(5H)-one

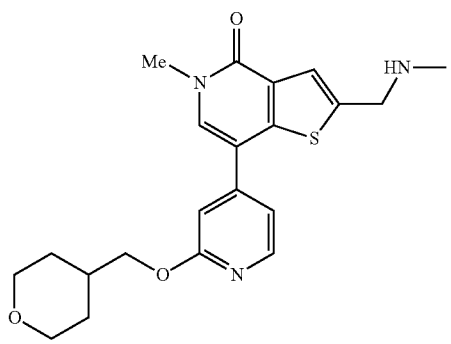 [SMILES: CNCc1cc2c(=O)n(C)cc(-c3ccnc(OCC4CCOCC4)c3)c2s1]

To a suspension of 7-bromo-5-methyl-2-((methylamino)methyl)thieno[3,2-c]pyridin-4(5H)-one (for a preparation see Intermediate 34, 94.5 mg, 0.329 mmol), potassium carbonate (136 mg, 0.987 mmol) and (2-((tetrahydro-2H-pyran-4-yl)methoxy)pyridin-4-yl)boronic acid (117 mg, 0.494 mmol) in isopropanol (3 mL) and water (1 mL) was added PEPPSI (22.36 mg, 0.033 mmol) catalyst. The reaction mixture was heated at 130° C. for 30 minutes in a Biotage Initiator microwave reactor, whereupon it was hydrolyzed using a saturated aqueous solution of ammonium chloride (30 mL). The aqueous phase was extracted with DCM (4×30 mL) and the combined organic layers dried over magnesium sulphate, filtered and concentrated under reduced pressure to give a dark brown oil. The crude material was purified via chromatography on silica gel eluting with 0 to 10% MeOH in DCM and then 20% MeOH in DCM. The appropriate fractions were combined and concentrated in vacuo to give to give 5-methyl-2-((methylamino)methyl)-7-(2-((tetrahydro-2H-pyran-4-yl)methoxy)pyridin-4-yl)thieno[3,2-c]pyridin-4(5H)-one (40 mg, 30% yield) as a brown oil.

LCMS (2 min, Formic Acid): Rt=0.61 min, MH$^+$=400

Example 88

7-(3,4-dimethoxyphenyl)-5-methyl-2-(pyrrolidin-1-ylmethyl)thieno[3,2-c]pyridin-4(5H)-one, Hydrochloride

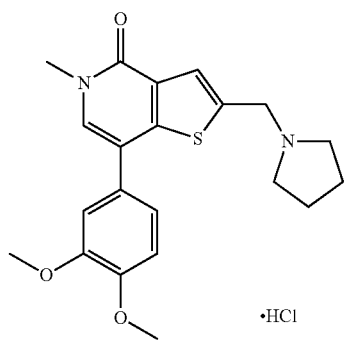 [SMILES: COc1ccc(-c2cn(C)c(=O)c3cc(CN4CCCC4)sc23)cc1OC ; Cl]

A mixture of 7-bromo-5-methyl-2-(pyrrolidin-1-ylmethyl)thieno[3,2-c]pyridin-4(5H)-one (for a preparation see Intermediate 36, 50 mg, 0.15 mmol), (3,4-dimethoxyphenyl)boronic acid (42 mg, 0.23 mmol), potassium carbonate (63 mg, 0.46 mmol) and bis(triphenylphosphine)palladium(II) chloride (11 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL) and the solution was dried over sodium sulphate then evaporated in vacuo. The residue was purified by chromatography on silica gel eluting with 0-5% methanol in dichloromethane. The product was subsequently dissolved in ethyl acetate (0.5 mL) and treated with 1.0M hydrogen chloride in diethyl ether (0.5 mL) and diethyl ether (10 mL) was added. The solid was filtered off and dried to give 7-(3,4-dimethoxyphenyl)-5-methyl-2-(pyrrolidin-1-ylmethyl)thieno[3,2-c]pyridin-4(5H)-one, hydrochloride (51 mg, 79% yield) as a white solid.

LCMS (2 min, Formic Acid): Rt=0.61 min, MH$^+$=385

Example 89

N-((7-(3,4-dimethoxyphenyl)-5-methyl-4-oxo-4,5-dihydrothieno[3,2-c]pyridin-2-yl)methyl)-N-methyl-methanesulphonamide

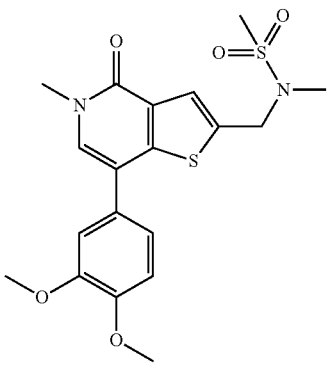

A mixture of N-((7-bromo-5-methyl-4-oxo-4,5-dihydrothieno[3,2-c]pyridin-2-yl)methyl)-N-methylmethanesulphonamide (for a preparation see Intermediate 35, 40 mg, 0.11 mmol), (3,4-dimethoxyphenyl)boronic acid (25 mg, 0.14 mmol), potassium carbonate (46 mg, 0.33 mmol) and bis(triphenylphosphine)palladium(II) chloride (8 mg, 10 mol %) in 1,2-DME (3 mL) and water (0.5 mL) was heated in a microwave at 120° C. for 20 minutes. The cooled reaction mixture was diluted with ethyl acetate (20 mL), dried over sodium sulphate and filtered. The filtrated was evaporated in vacuo and the residue purified by chromatography on silica gel eluting with 0-4% methanol in dichloromethane. The resulting impure product was repurified by MDAP to give N-((7-(3,4-dimethoxyphenyl)-5-methyl-4-oxo-4,5-dihydrothieno[3,2-c]pyridin-2-yl)methyl)-N-methylmethanesulphonamide (41 mg, 89% yield) as a colourless glass.

LCMS (2 min, Formic Acid): Rt=0.82 min, MH$^+$=423

Example 90

7-(3,4-dimethoxyphenyl)-2-((3,5-dimethylpiperazin-1-yl)methyl)-5-methylthieno[3,2-c]pyridin-4(5H)-one

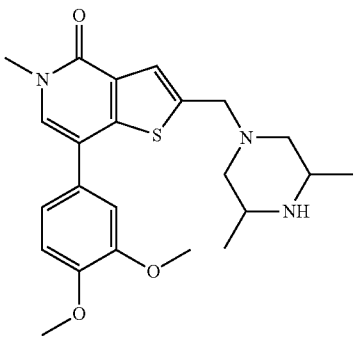

To a solution of tert-butyl 4-((7-(3,4-dimethoxyphenyl)-5-methyl-4-oxo-4,5-dihydrothieno[3,2-c]pyridin-2-yl)methyl)-2,6-dimethylpiperazine-1-carboxylate (for a preparation see Intermediate 33, 26 mg, 0.049 mmol) in 1,4-dioxane (1 mL) was added 2M HCl in 1,4-dioxane (1 mL). The resulting mixture was stirred at rt for 2 hours whereupon it was concentrated in vacuo. The resulting residue was triturated in Et$_2$O, filtered and dried in vacuo to give 7-(3,4-dimethoxyphenyl)-2-((3,5-dimethylpiperazin-1-yl)methyl)-5-methylthieno[3,2-c]pyridin-4(5H)-one hydrochloride (23 mg, 100% yield) as a yellow viscous oil.

LCMS (2 min, Formic Acid): Rt=0.65 min, MH$^+$=428

Example 91

(S)-5-methyl-2-((3-methylmorpholino)methyl)-7-(3-((tetrahydro-2H-pyran-4-yl)methoxy)phenyl)thieno[3,2-c]pyridin-4(5H)-one hydrochloride

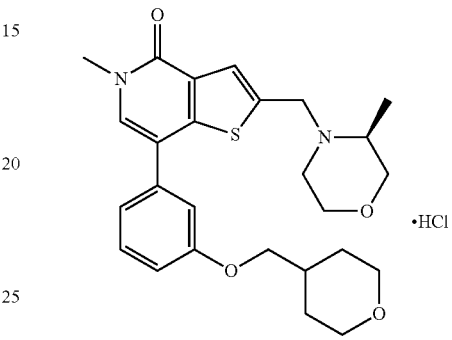

To a stirred solution of (S)-7-(3-hydroxyphenyl)-5-methyl-2-((3-methylmorpholino)methyl)thieno[3,2-c]pyridin-4(5H)-one (for a preparation see Example 81, 90 mg, 0.243 mmol) in N,N-dimethylformamide ((5 mL) was added potassium carbonate (40.3 mg, 0.292 mmol) followed by 4-(bromomethyl)tetrahydro-2H-pyran (0.096 mL, 0.729 mmol). The reaction mixture was heated to 100° C. and stirred under nitrogen for 3.5 hours. Another portion of potassium carbonate (40.3 mg, 0.292 mmol) was added and the reaction was stirred for a further 90 minutes. The reaction was cooled to room temperature and left under nitrogen for 48 hours. The reaction was re-heated to 100° C. and stirred for 90 minutes.

The reaction mixture was then allowed to cool to room temperature, diluted with water (30 mL) and transferred to a separating funnel. The aqueous phase was extracted with ethyl acetate (3×25 mL) and the combined organic layers were washed with brine (30 mL), dried over magnesium sulphate, and concentrated under reduced pressure to give a yellow oil. The crude material was purified via chromatography on silica gel eluting with 0 to 7% MeOH in DCM. The appropriate fractions were combined and concentrated in vacuo to give (S)-5-methyl-2-((3-methylmorpholino)methyl)-7-(3-((tetrahydro-2H-pyran-4-yl)methoxy)phenyl)thieno[3,2-c]pyridin-4(5H)-one as a yellow oil. The product was subsequently dissolved in ethyl acetate (1 mL) and 1.0M HCl in diethyl ether (250 µL) was added to give (S)-5-methyl-2-((3-methylmorpholino)methyl)-7-(3-((tetrahydro-2H-pyran-4-yl)methoxy)phenyl)thieno[3,2-c]pyridin-4(5H)-one, hydrochloride (67 mg, 55% yield) as an off white solid.

LCMS (2 min, Formic Acid): Rt=0.75 min, MH$^+$=469

Examples 92-103

Intermediates 71-82 were dissolved in DCM (0.5 mL) and treated with TFA (0.5 mL). The solutions were allowed to stand, covered, at rt for 2.5 hr. The reaction mixtures were evaporated under a stream of nitrogen overnight and the residues dissolved in MeOH (0.25 mL). The solutions were applied to MeOH preconditioned 1 g SCX-2 cartridges and left for 5 min. The cartridges were washed with MeOH (5 mL) followed by 2 M ammonia in MeOH solution (5 mL). The basic washes were evaporated under a stream of nitrogen to give Examples 92-103 listed in the table below:

| Ex No. | Name | Structure | Mass (mg) | % Yield | MH+ | RT (min) |
|---|---|---|---|---|---|---|
| 92 | (R)-7-(3,4-dimethoxyphenyl)-5-methyl-2-((2-methylpiperazin-1-yl)methyl)thieno[3,2-c]pyridin-4(5H)-one | 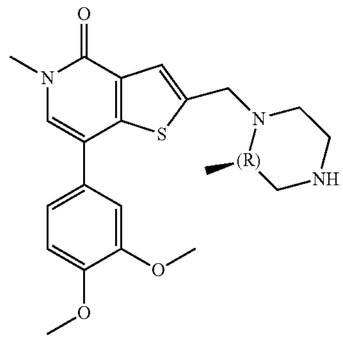 | 28 | 30 | 414 | 0.78 |
| 93 | (R)-1-((7-(3,4-dimethoxyphenyl)-5-methyl-4-oxo-4,5-dihydrothieno[3,2-c]pyridin-2-yl)methyl)piperazine-2-carboxamide | 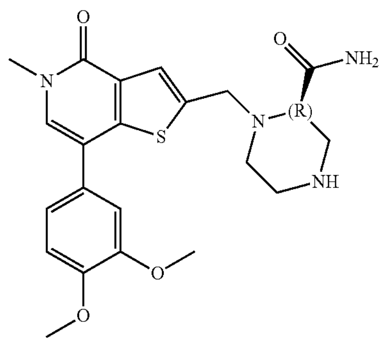 | 29 | 29 | 443 | 0.69 |
| 94 | (S)-7-(3,4-dimethoxyphenyl)-5-methyl-2-((3-methylpiperazin-1-yl)methyl)thieno[3,2-c]pyridin-4(5H)-one | 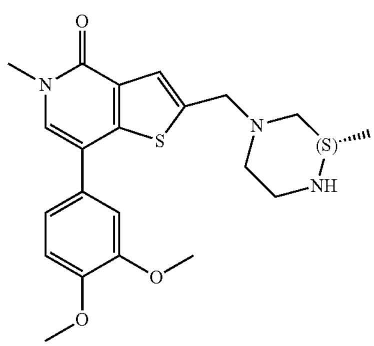 | 37 | 38 | 414 | 0.78 |
| 95 | methyl 1-((7-(3,4-dimethoxyphenyl)-5-methyl-4-oxo-4,5-dihydrothieno[3,2-c]pyridin-2-yl)methyl)piperazine-2-carboxylate | 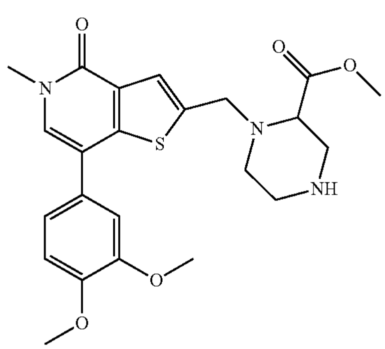 | 24 | 24 | 458 | 0.81 |

| Ex No. | Name | Structure | Mass (mg) | % Yield | MH+ | RT (min) |
|---|---|---|---|---|---|---|
| 96 | 7-(3,4-dimethoxyphenyl)-2-((cis-2,6-dimethylpiperazin-1-yl)methyl)-5-methylthieno[3,2-c]pyridin-4(5H)-one | 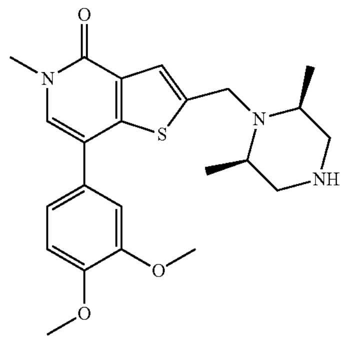 [SMILES: COc1ccc(-c2cn(C)c(=O)c3cc(CN4[C@H](C)CNC[C@@H]4C)sc23)cc1OC] | 11 | 14 | 428 | 0.80 |
| 97* | (R)-2-((3-butylpiperazin-1-yl)methyl)-7-(3,4-dimethoxyphenyl)-5-methylthieno[3,2-c]pyridin-4(5H)-one | 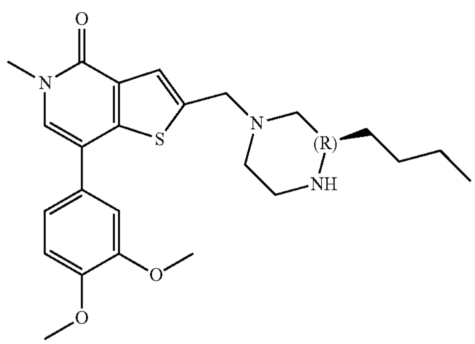 | 32 | 29 | 456 | 0.99 |
| 98 | (S)-7-(3,4-dimethoxyphenyl)-2-((3-ethylpiperazin-1-yl)methyl)-5-methylthieno[3,2-c]pyridin-4(5H)-one | 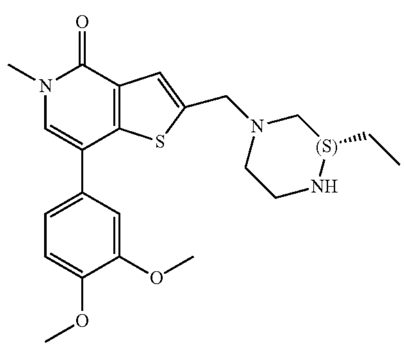 | 38 | 38 | 428 | 0.84 |
| 99 | 7-(3,4-dimethoxyphenyl)-5-methyl-2-((piperidin-4-ylamino)methyl)thieno[3,2-c]pyridin-4(5H)-one | 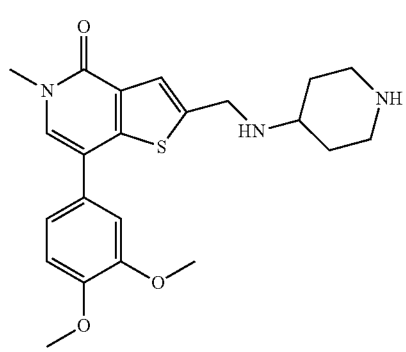 [SMILES: COc1ccc(-c2cn(C)c(=O)c3cc(CNC4CCNCC4)sc23)cc1OC] | 18 | 19 | 414 | 0.72 |

| Ex No. | Name | Structure | Mass (mg) | % Yield | MH+ | RT (min) |
|---|---|---|---|---|---|---|
| 100 | (S)-7-(3,4-dimethoxyphenyl)-5-methyl-2-((2-methylpiperazin-1-yl)methyl)thieno[3,2-c]pyridin-4(5H)-one | 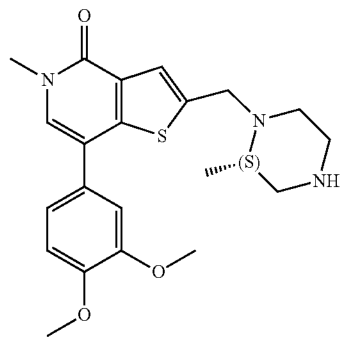 | 30 | 32 | 414 | 0.78 |
| 101 | 2-((3-aminopyrrolidin-1-yl)methyl)-7-(3,4-dimethoxyphenyl)-5-methylthieno[3,2-c]pyridin-4(5H)-one | 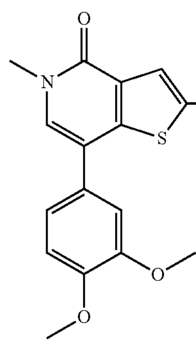 | 37 | 40 | 400 | 0.75 |
| 102 | 2-((4-aminopiperidin-1-yl)methyl)-7-(3,4-dimethoxyphenyl)-5-methylthieno[3,2-c]pyridin-4(5H)-one | 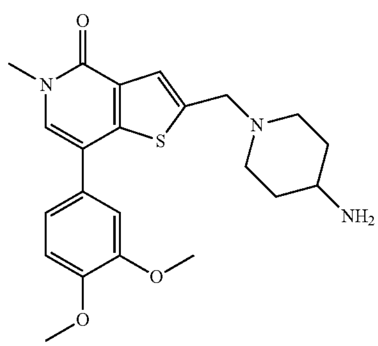 [SMILES: COc1ccc(-c2cn(C)c(=O)c3cc(CN4CCC(N)CC4)sc23)cc1OC] | 33 | 35 | 414 | 0.75 |
| 103* | 2-(((2-amino-ethyl)(methyl)amino)methyl)-7-(3,4-dimethoxyphenyl)-5-methylthieno[3,2-c]pyridin-4(5H)-one | 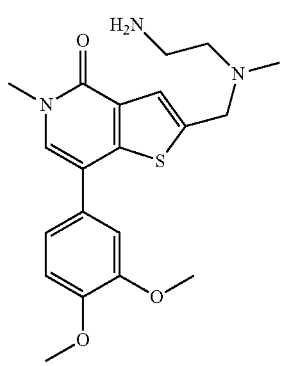 | 16 | 17 | 388 | 0.75 |

All LCMS were conducted using the High pH method.

*Note

Example 97 and Example 103 were subjected to additional purification by MDAP on Xbridge C18 column using a gradient of solvents 10 mM ammonium carbonate in water adjusted to pH 10 with ammonia solution and acetonitrile.

Examples 104-110

The residues for Examples 92, 94, 95, 97, 98, 100 and 101 (see table below for weights) were dissolved in DCM (0.2 mL) and pyridine (0.2 mL). The solutions were treated with methanesulfonyl chloride (see table below for volumes) and the reaction mixtures left to stand at rt in stoppered vessels for 5 hr. The reaction mixtures were evaporated in a vacuum centrifuge and partitioned between DCM (2 mL) and water (2 mL). The organic layers were dried through hydrophobic frits and the solvent evaporated under a stream of nitrogen. The residues were purified by MDAP on Xbridge C18 column using a gradient of solvents 10 mM ammonium carbonate in water adjusted to pH10 with ammonia solution and acetonitrile to give the sulfonamide products.

| Ex. No | Amine Ex No. | Amine Mass (mg) | CH$_3$SO$_2$Cl volume (μL) | Name & Structure | Mass (mg) | % Yield | MH$^+$ | RT (min) |
|---|---|---|---|---|---|---|---|---|
| 104 | 92 | 16 | 31 | (R)-7-(3,4-dimethoxyphenyl)-5-methyl-2-((2-methyl-4-(methylsulphonyl)piperazin-1-yl)methyl)thieno[3,2-c]pyridin-4(5H)-one | 6.6 | 35 | 492 | 0.95 |
| 105 | 94 | 26 | 51 | (S)-7-(3,4-dimethoxyphenyl)-5-methyl-2-((3-methyl-4-(methylsulphonyl)piperazin-1-yl)methyl)thieno[3,2-c]pyridin-4(5H)-one | 6.2 | 20 | 492 | 0.98 |
| 106 | 95 | 11 | 20 | methyl 1-((7-(3,4-dimethoxyphenyl)-5-methyl-4-oxo-4,5-dihydrothieno[3,2-c]pyridin-2-yl)methyl)-4-(methylsulphonyl)piperazine-2-carboxylate | 4.1 | 31 | 536 | 0.96 |

| Ex. No | Amine Ex No. | Amine Mass (mg) | CH₃SO₂Cl volume (μL) | Name & Structure | Mass (mg) | % Yield | MH⁺ | RT (min) |
|---|---|---|---|---|---|---|---|---|
| 107 | 97 | 23 | 41 | (R)-2-((3-butyl-4-(methylsulphonyl)piperazin-1-yl)methyl)-7-(3,4-dimethoxyphenyl)-5-methylthieno[3,2-c]pyridin-4(5H)-one | 7.0 | 26 | 534 | 1.13 |
| 108 | 98 | 27 | 51 | (S)-7-(3,4-dimethoxyphenyl)-2-((3-ethyl-4-(methylsulphonyl)piperazin-1-yl)methyl)-5-methylthieno[3,2-c]pyridin-4(5H)-one | 7.0 | 22 | 506 | 1.03 |
| 109 | 100 | 19 | 38 | (S)-7-(3,4-dimethoxyphenyl)-5-methyl-2-((2-methyl-4-(methylsulphonyl)piperazin-1-yl)methyl)thieno[3,2-c]pyridin-4(5H)-one | 10.1 | 44 | 492 | 0.95 |

-continued

| Ex. No | Amine Ex No. | Amine Mass (mg) | CH₃SO₂Cl volume (μL) | Name & Structure | Mass (mg) | % Yield | MH⁺ | RT (min) |
|---|---|---|---|---|---|---|---|---|
| 110 | 101 | 27 | 55 | N-(1-((7-(3,4-dimethoxyphenyl)-5-methyl-4-oxo-4,5-dihydrothieno[3,2-c]pyridin-2-yl)methyl)pyrrolidin-3-yl)methanesulphonamide | 4.5 | 14 | 478 | 0.85 |

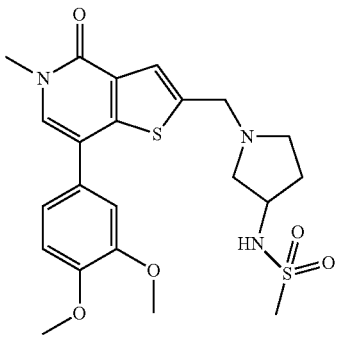 [SMILES: COc1ccc(-c2cn(C)c(=O)c3cc(CN4CCC(NS(C)(=O)=O)C4)sc23)cc1OC]

All LCMS were conducted using the High pH method.

Example 111

7-(4-((2-methoxyethyl)(methyl)amino)pyridin-2-yl)-5-methyl-2-((4-(methylsulphonyl)piperazin-1-yl)methyl)thieno[3,2-c]pyridin-4(5H)-one

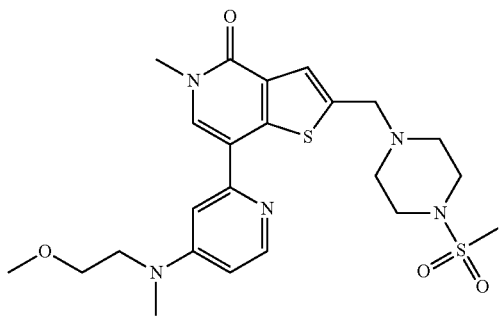

Stage (i). A mixture of 7-bromo-5-methyl-2-((4-(methylsulphonyl)piperazin-1-yl)methyl)thieno[3,2-c]pyridin-4(5H)-one (for a preparation see Intermediate 69, 100 mg, 0.24 mmol), bis(pinacolato)boron (302 mg, 1.19 mmol), potassium acetate (93 mg, 0.95 mmol) and PdCl₂(dppf) (17 mg, 10 mol %) in 1,4-dioxane (4 mL) was heated in a microwave at 110° C. for 30 minutes. The cooled reaction mixture was diluted with ethyl acetate (25 mL) and filtered through Celite. The filtrate was dried over sodium sulphate, and evaporated to leave a black oily residue.

Stage (ii). A mixture of the stage (i) product, 2-chloro-N-(2-methoxyethyl)-N-methylpyridin-4-amine (for a preparation see Intermediate 86, 48 mg, 0.24 mmol), potassium carbonate (99 mg, 0.71 mmol), and bis(triphenylphosphine)palladium(II) chloride (17 mg, 10 mol %) in 1,2-dimethoxyethane (3 mL) and water (0.5 mL) was heated in a microwave at 120° C. for 20 minutes. The cooled reaction mixture was diluted with ethyl acetate (20 mL). The mixture was dried over sodium sulphate and the solvent evaporated. The residue was chromatographed [5% methanol/dichloromethane] then re-purified by MDAP to give 7-(4-((2-methoxyethyl)(methyl)amino)pyridin-2-yl)-5-methyl-2-((4-(methylsulphonyl)piperazin-1-yl)methyl)thieno[3,2-c]pyridin-4(5H)-one (9 mg, 7% yield) as a colourless glass.

LCMS (2 min, Formic Acid): Rt=0.45 min, MH⁺=506.

Example 112

5-methyl-2-((4-(methylsulphonyl)piperazin-1-yl)methyl)-7-(pyridin-3-yl)thieno[3,2-c]pyridin-4(5H)-one

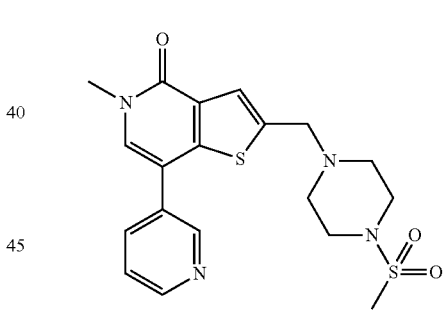

To a solution of 7-bromo-5-methyl-2-((4-(methylsulphonyl)piperazin-1-yl)methyl)thieno[3,2-c]pyridin-4(5H)-one (for a preparation see Intermediate 69, 148 mg, 0.352 mmol) and pyridin-3-ylboronic acid (64.9 mg, 0.528 mmol), in isopropanol (1.5 mL) in a microwave vial were successively added potassium carbonate (0.880 mL, 1.760 mmol) and PEPPSI (23.92 mg, 0.035 mmol). The reaction mixture was stirred at 110° C. in the microwave for 30 minutes. The reaction mixture was concentrated in vacuo and partitioned between water and EtOAc. The phases were separated and the aqueous phase was extracted with EtOAc, The combined organic layers were washed with brine, dried over MgSO₄, filtered and concentrated in vacuo. The crude residue was dissolved in a 1:1 MeOH/DMSO mixture and was purified via MDAP. The collected fractions were combined and concentrated in vacuo to give 5-methyl-2-((4-(methylsulphonyl)piperazin-1-yl)methyl)-7-(pyridin-3-yl)thieno[3,2-c]pyridin-4(5H)-one (29 mg, 20% yield) as a yellow solid.

LCMS (2 min, Formic Acid): Rt=0.43 min, MH⁺=419

Example 113

7-(3,4-dichlorophenyl)-5-methyl-2-((4-(methylsulphonyl)piperazin-1-yl)methyl)thieno[3,2-c]pyridin-4(5H)-one

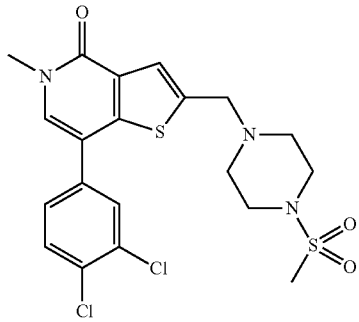 [SMILES: Cn1cc(-c2ccc(Cl)c(Cl)c2)c2sc(CN3CCN(S(C)(=O)=O)CC3)cc2c1=O]

To a mixture of 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), (3,4-dichlorophenyl)boronic acid (38.1 mg, 0.200 mmol) and potassium carbonate (55.2 mg, 0.400 mmol) in isopropanol (2 mL) and water (1 mL) was added PEPPSI catalyst (34.0 mg, 0.05 mmol). The reaction mixture was heated in the microwave at 130° C. for 30 minutes, whereupon it was diluted with a saturated aqueous solution of ammonium sulphate (approx. 15 mL) and DCM (approx. 10 mL). The mixture was filtered through Celite and the filtrate transferred to a separatory funnel. The layers were separated and the aqueous phase was then extracted with DCM (4×10 mL). The combined organic layers were dried over magnesium sulphate, filtered and concentrated under reduced pressure to give a brown-green solid. The crude residue was purified by chromatography on silica gel eluting with 0-5% MeOH in DCM to give an impure yellow oil. The latter was re-purified by MDAP to give 7-(3,4-dichlorophenyl)-5-methyl-2-((4-(methylsulphonyl)piperazin-1-yl)methyl)thieno[3,2-c]pyridin-4(5H)-one (9 mg, 11% yield) as a light yellow solid.

$^1$H NMR (400 MHz, CDCl$_3$) δ-ppm 2.61-2.66 (m, 4H), 2.77 (s, 3H), 3.23-3.27 (m, 4H), 3.67 (s, 3H), 3.80 (s, 2H), 7.16 (s, 1H), 7.40-7.43 (m, 1H), 7.55 (s, 1H), 7.65 (m, 1H), 7.99 (s, 1H).

Example 114

7-(4-(aminomethyl)phenyl)-5-methyl-2-((4-(methylsulphonyl)piperazin-1-yl)methyl)thieno[3,2-c]pyridin-4(5H)-one dihydrochloride

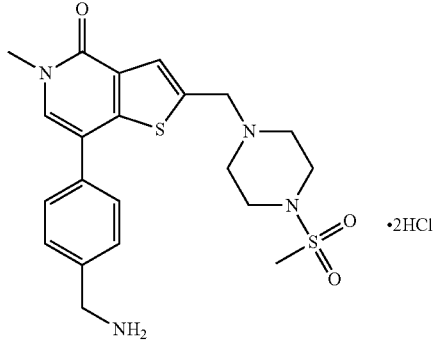 [SMILES: Cn1cc(-c2ccc(CN)cc2)c2sc(CN3CCN(S(C)(=O)=O)CC3)cc2c1=O]

To a solution of tert-butyl 4-(5-methyl-2-((4-(methylsulphonyl)piperazin-1-yl)methyl)-4-oxo-4,5-dihydrothieno[3,2-c]pyridin-7-yl)benzylcarbamate (for a preparation see Intermediate 85, 118 mg, 0.216 mmol) in 1,4-dioxane (3.00 mL) was added 4N HCl in 1,4-dioxane (3 mL). The resulting mixture was stirred at room temperature for 3 hours. The reaction mixture was concentrated in vacuo, the residue was triturated in Et$_2$O, filtered and dried to give 7-(4-(aminomethyl)phenyl)-5-methyl-2-((4-(methylsulphonyl)piperazin-1-yl)methyl)thieno[3,2-c]pyridin-4(5H)-one dihydrochloride (112 mg, 100% yield) as a white solid.

LCMS (2 min, Formic Acid): Rt=0.40 min, MH$^+$=447

Example 115

7-(3-(benzyloxy)-4-methoxyphenyl)-5-methyl-2-((4-(methylsulphonyl)piperazin-1-yl)methyl)thieno[3,2-c]pyridin-4(5H)-one formic acid salt

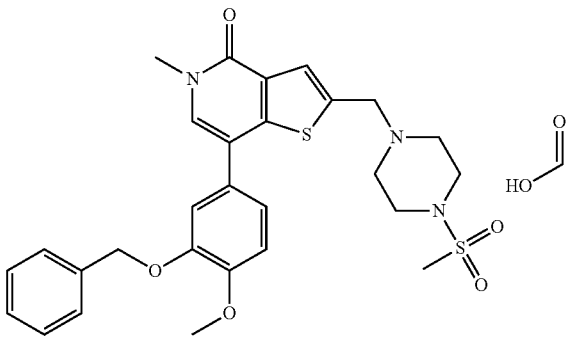

To a solution of 7-bromo-5-methyl-2-((4-(methylsulphonyl)piperazin-1-yl)methyl)thieno[3,2-c]pyridin-4(5H)-one (for a preparation see Intermediate 69, 60 mg, 0.143 mmol) and (3-(benzyloxy)-4-methoxyphenyl)boronic acid (55.3 mg, 0.214 mmol) in isopropanol (3 mL) were successively added potassium carbonate (0.357 mL, 0.714 mmol) and PEPPSI (9.70 mg, 0.014 mmol). The reaction mixture was heated in the microwave at 110° C., whereupon it was allowed to cool to rt. The reaction mixture was concentrated in vacuo, and the residue was partitioned between EtOAc and water. The aqueous phase was extracted three times with EtOAc and the combined organic layers were washed with brine, dried over MgSO4, filtered and concentrated in vacuo. The crude residue was purified via MDAP using a formic acid modifier and the appropriate fractions were combined and concentrated in vacuo to give 7-(3-(benzyloxy)-4-methoxyphenyl)-5-methyl-2-((4-(methylsulphonyl)piperazin-1-yl)methyl)thieno[3,2-c]pyridin-4(5H)-one formic acid salt (19 mg, 22% yield) as a white solid.

LCMS (2 min, Formic Acid): Rt=0.90 min, MH$^+$=554

Example 116

(R)-7-(4-methoxyphenyl)-5-methyl-2-((2-methyl-4-(methylsulphonyl)piperazin-1-yl)methyl)thieno[3,2-c]pyridin-4(5H)-one

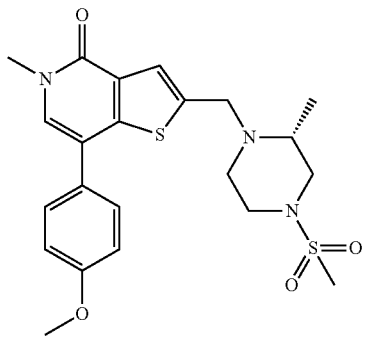 [SMILES: COc1ccc(-c2cn(C)c(=O)c3cc(CN4CCN(S(C)(=O)=O)C[C@H]4C)sc23)cc1]

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.23 mmol), (4-methoxyphenyl)boronic acid (53 mg, 0.35 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (R)-7-(4-methoxyphenyl)-5-methyl-2-((2-methyl-4-(methylsulphonyl)piperazin-1-yl)methyl)thieno[3,2-c]pyridin-4(5H)-one (40 mg, 0.087 mmol, 37.6% yield) as an off white solid.

LCMS (2 min, Formic Acid): Rt=0.73 min, MH$^+$=462

Example 117

5-methyl-2-(((R)-2-methyl-4-(methylsulphonyl)piperazin-1-yl)methyl)-7-(5-(1-(pyridin-2-yl)ethoxy)pyridin-3-yl)thieno[3,2-c]pyridin-4(5H)-one

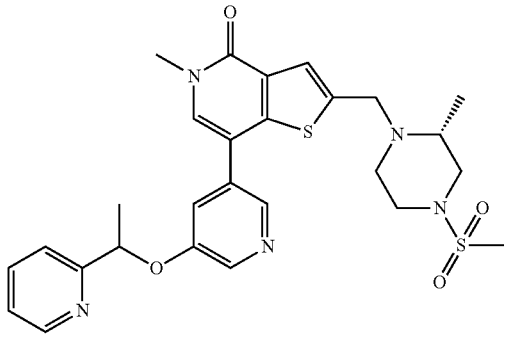 [SMILES: CC(Oc1cncc(-c2cn(C)c(=O)c3cc(CN4CCN(S(C)(=O)=O)C[C@H]4C)sc23)c1)c1ccccn1]

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 340 mg, 0.783 mmol), potassium carbonate (325 mg, 2.348 mmol), PEPPSI (53.2 mg, 0.078 mmol) and (±)-(5-(1-(pyridin-2-yl)ethoxy)pyridin-3-yl)boronic acid (for a preparation see Intermediate 7, 319 mg, 1.307 mmol) in isopropanol (6 mL) and water (2 mL) was heated in a sealed vial at 130° C. for 30 minutes in a microwave reactor. The mixture was diluted with saturated sodium bicarbonate (50 mL) and the aqueous layer extracted with DCM (3×50 mL). The organic layers were combined, filtered through a cartridge fitted with a hydrophobic frit and evaporated in vacuo. The residue was loaded onto a 50 g silica cartridge and purified using a gradient of 0-10% methanol:DCM. Followed by a further gradient of 10-20% methanol:DCM. The required fractions were combined and evaporated in vacuo. The product was dissolved in a mixture of 50:50 methanol:DMSO (3 mL) and further purified by MDAP. The required fractions were combined and evaporated in vacuo to give 5-methyl-2-(((R)-2methyl-4-(methylsulphonyl)piperazin-1-yl)methyl)-7-(5-(1-(pyridin-2-yl)ethoxy)pyridin-3-yl)thieno[3,2-c]pyridin-4(5H)-one (149.6 mg, 0.270 mmol, 34.5% yield) as a yellow gum.

LCMS (2 min, Formic Acid): Rt=0.64 min, MH$^+$=554

Example 118

(R)-7-(3-methoxyphenyl)-5-methyl-2-((2-methyl-4-(methylsulphonyl)piperazin-1-yl)methyl)thieno[3,2-c]pyridin-4(5H)-one

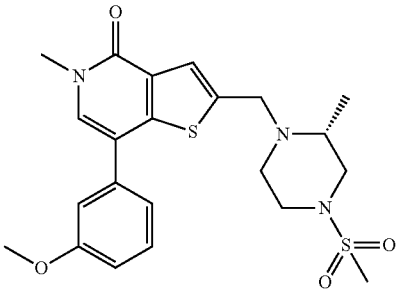 [SMILES: COc1cccc(-c2cn(C)c(=O)c3cc(CN4CCN(S(C)(=O)=O)C[C@H]4C)sc23)c1]

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.23 mmol), (3-methoxyphenyl)boronic acid (53 mg, 0.35 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (R)-7-(3-methoxyphenyl)-5-methyl-2-((2-methyl-4-(methylsulphonyl)piperazin-1-yl)methyl)thieno[3,2-c]pyridin-4(5H)-one (65 mg, 0.141 mmol, 61.2% yield) as an off white solid.

LCMS (2 min, Formic Acid): Rt=0.74 min, MH$^+$=462

Example 119

(R)-N-(4-(5-methyl-2-((2-methyl-4-(methylsulphonyl)piperazin-1-yl)methyl)-4-oxo-4,5-dihydrothieno[3,2-c]pyridin-7-yl)pyridin-2-yl)acetamide

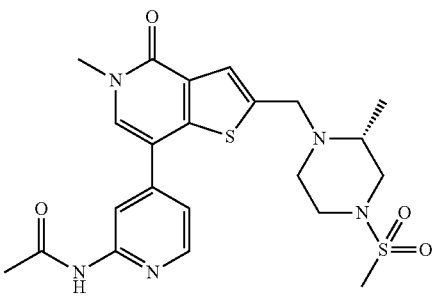 [SMILES: CC(=O)Nc1cc(-c2cn(C)c(=O)c3cc(CN4CCN(S(C)(=O)=O)C[C@H]4C)sc23)ccn1]

To a stirred solution of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.230 mmol) in Isopropanol (2 mL) and water (2 mL) was added N-(4-(4,4,5,5-tetramethyl-1,3,2-dioxaborolan-2-yl)pyridin-2-yl)acetamide (121 mg, 0.460 mmol) [PCT Int. Appl WO2012021615(A1)] followed by potassium carbonate (127 mg, 0.921 mmol), and PEPPSI (15.64 mg, 0.023 mmol) catalyst. The reaction was heated to 80° C. and stirred under an atmosphere of nitrogen for 16 hrs. Further N-(4-(4,4,5,5-tetramethyl-1,3,2-dioxaborolan-2-yl)pyridin-2-yl)acetamide (61 mg, 0.115 mmol) was added and the mixture heated at 80° C. overnight. The mixture was diluted with chloroform (30 mL) and saturated ammonium chloride solution (30 mL) before being passed through a 2.5 g Celite cartridge. The filtrate phases were separated and the aqueous phase was back extracted with chloroform (30 mL). The organic phases were combined, dried over magnesium sulphate, and concentrated under reduced pressure. The crude material was triturated with diethyl ether to give a solid which was suspended in MeOH (2 mL) and refluxed at 70° C. for 30 minutes. The suspension was allowed to cool to room temperature and left to stand overnight. The solid was filtered through a small glass filter funnel and washed with methanol. The product was again suspended in MeOH (1 mL) and refluxed for 30 minutes. The suspension was allowed to cool to room temperature and left to stand overnight. The product was filtered and washed with methanol (3×10 mL) to give (R)-N-(4-(5-methyl-2-((2-methyl-4-(methylsulphonyl)piperazin-1-yl)methyl)-4-oxo-4,5-dihydrothieno[3,2-c]pyridin-7-yl)pyridin-2-yl)acetamide (45 mg, 0.092 mmol, 39.9% yield) as a pale yellow solid.

LCMS (2 min, Formic Acid): Rt=0.51 min, MH$^+$=490

Example 120

(R)-5-methyl-2-((2-methyl-4-(methylsulphonyl)piperazin-1-yl)methyl)-7-phenylthieno[3,2-c]pyridin-4(5H)-one

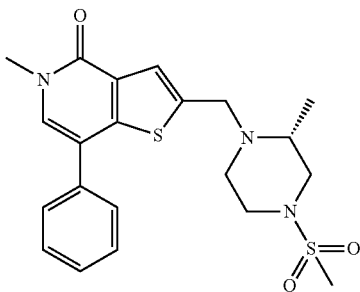

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.23 mmol), phenylboronic acid (42 mg, 0.34 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (R)-5-methyl-2-((2-methyl-4-(methylsulphonyl)piperazin-1-yl)methyl)-7-phenylthieno[3,2-c]pyridin-4(5H)-one (65 mg, 0.151 mmol, 65.4% yield) as an off white solid.

LCMS (2 min, Formic Acid): Rt=0.73 min, MH$^+$=432

Example 121

5-methyl-2-((4-(methylsulphonyl)piperazin-1-yl)methyl)-7-(p-tolyl)thieno[3,2-c]pyridin-4(5H)-one

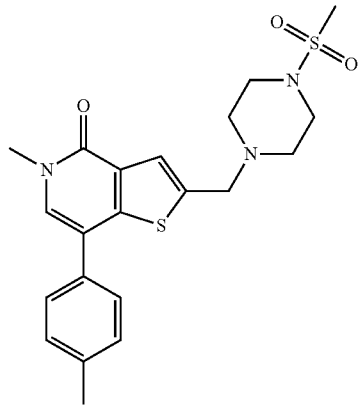 [SMILES: Cc1ccc(-c2cn(C)c(=O)c3cc(CN4CCN(S(C)(=O)=O)CC4)sc23)cc1]

To a 2-5 mL microwave reaction was added 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), p-tolylboronic acid (27.2 mg, 0.200 mmol), and potassium carbonate (55.2 mg, 0.400 mmol) in a solution of isopropanol (2 mL) and water (1 mL). Lastly to the reaction was added PEPPSI (34.0 mg, 0.05 mmol). The reaction vessel was sealed and heated in Biotage Initiator microwave reactor to 130° C. for 30 minutes with 10 seconds of pre-stirring. After cooling, the reaction was quenched with saturated ammonium chloride solution (15 mL) and DCM (15 mL) and passed through Celite to remove the palladium catalyst. The filtrate was transferred to a separating funnel. The organic layer was collected and the aqueous layer was extracted with DCM (2×10 mL). The organic fractions were combined and dried over MgSO$_4$. The filtrate was collected by vacuum filtration and concentrated under reduced pressure to give a brown oil. The residue was loaded onto a 12 g silica gel column and eluted in 0-5% MeOH in DCM over 20 column volumes. The purest fractions were combined and concentrated under reduced pressure to give a yellow oil. The oil was triturated with diethyl ether and oven dried overnight to give 5-methyl-2-((4-(methylsulphonyl)piperazin-1-yl)methyl)-7-(p-tolyl)thieno[3,2-c]pyridin-4(5H)-one (42.3 mg, 59% yield) a yellow solid, LCMS (2 min, Formic Acid): Rt=0.77 min, MH$^+$=432

Example 122

(R)-7-(2-methoxypyridin-4-yl)-5-methyl-2-((2-methyl-4-(methylsulphonyl)piperazin-1-yl)methyl)thieno[3,2-c]pyridin-4(5H)-one

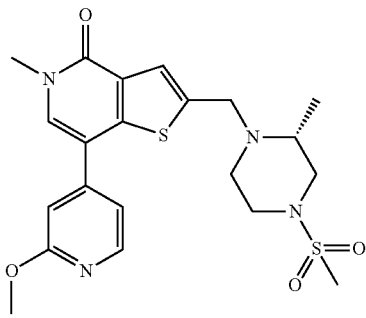 [SMILES: COc1cc(-c2cn(C)c(=O)c3cc(CN4CCN(S(C)(=O)=O)C[C@H]4C)sc23)ccn1]

A mixture of (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.23 mmol), (2-methoxypyridin-4-yl)boronic acid (52 mg, 0.34 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (R)-7-(2-methoxypyridin-4-yl)-5-methyl-2-((2-methyl-4(methylsulphonyl)piperazin-1-yl)methyl)thieno[3,2-c]pyridin-4(5H)-one (71 mg, 0.153 mmol, 66.7% yield) as a colourless solid.

LCMS (2 min, Formic Acid): Rt=0.64 min, MH$^+$=463

Example 123

(R)-7-(5-methoxypyridin-3-yl)-5-methyl-2-((2-methyl-4-(methylsulphonyl)piperazin-1-yl)methyl)thieno[3,2-c]pyridin-4(5H)-one

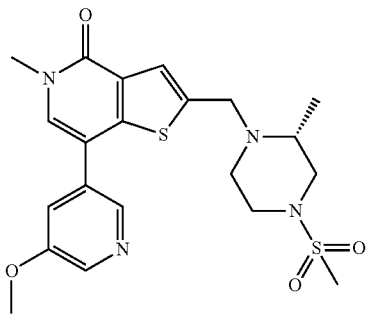

A mixture of (R)-7-bromo-5-methyl-2-((2-methyl-4-(methylsulphonyl)piperazin-1-yl)methyl)thieno[3,2-c]pyridin-4(5H)-one (Intermediate 21, 100 mg, 0.23 mmol), (5-methoxypyridin-3-yl)boronic acid (52 mg, 0.34 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (R)-7-(5-methoxypyridin-3-yl)-5-methyl-2-((2-methyl-4-(methylsulphonyl)piperazin-1-yl)methyl)thieno[3,2-c]pyridin-4(5H)-one (58 mg, 0.125 mmol, 54.5% yield) as a colourless solid.

LCMS (2 min, Formic Acid): Rt=0.56 min, MH$^+$=463

Example 124

(R)-7-(6-methoxypyridin-3-yl)-5-methyl-2-((2-methyl-4-(methylsulphonyl)piperazin-1-yl)methyl)thieno[3,2-c]pyridin-4(5H)-one hydrochloride

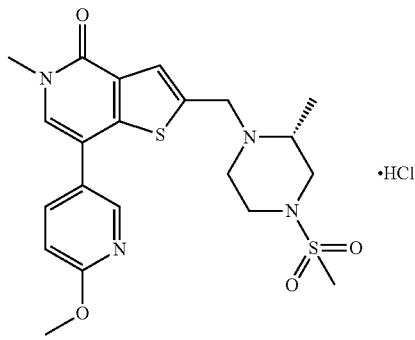 [SMILES: COc1ccc(-c2cn(C)c(=O)c3cc(CN4CCN(S(C)(=O)=O)C[C@H]4C)sc23)cn1 ; Cl]

A mixture of (R)-7-bromo-5-methyl-2-((2-methyl-4-(methylsulphonyl)piperazin-1-yl)methyl)thieno[3,2-c]pyridin-4(5H)-one (Intermediate 21, 100 mg, 0.23 mmol), (6-methoxypyridin-3-yl)boronic acid (52 mg, 0.34 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane]. The product was further purified by MDAP.

The product was dissolved in ethyl acetate (0.5 mL) and treated with 1.0M hydrogen chloride in diethyl ether (0.5 mL). The solid was filtered off, washed with ether and dried to give (R)-7-(6-methoxypyridin-3-yl)-5-methyl-2-((2-methyl-4-(methylsulphonyl)piperazin-1-yl)methyl)thieno[3,2-c]pyridin-4(5H)-one hydrochloride (50 mg, 0.100 mmol, 43.5% yield) as a colourless solid.

LCMS (2 min, Formic Acid): Rt=0.65 min, MH$^+$=463

Example 125

(R)-5-methyl-2-((2-methyl-4-(methylsulphonyl)piperazin-1-yl)methyl)-7-(pyridin-2-yl)thieno[3,2-c]pyridin-4(5H)-one

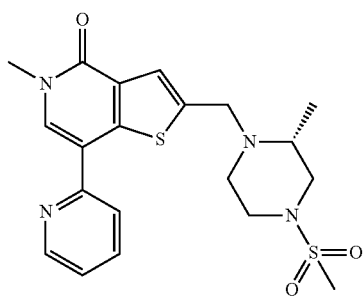 [SMILES: C[C@@H]1CN(S(C)(=O)=O)CCN1Cc1cc2c(=O)n(C)cc(-c3ccccn3)c2s1]

A mixture of (R)-7-bromo-5-methyl-2-((2-methyl-4-(methylsulphonyl)piperazin-1-yl)methyl)thieno[3,2-c]pyridin-4(5H)-one (Intermediate 21, 100 mg, 0.23 mmol), 6-phenyl-2-(pyridin-2-yl)-1,3,6,2-dioxazaborocane (309 mg, 1.15 mmol), potassium orthophosphate (147 mg, 0.69 mmol), copper(I) iodide (22 mg, 0.12 mmol) and bis(triphenylphosphine)palladium(II) chloride (16 mg, 10 mol %) in dry, degassed DMF (4 mL) was heated in the microwave at 150° C. for 45 minutes. The cooled reaction mixture was diluted with ethyl acetate (20 mL) and washed with water (x2) and brine. The organic phase was dried and evaporated. The residue was chromatographed [0-5% methanol/dichloromethane]. The product was triturated with diethyl ether to give (R)-5-methyl-2-((2-methyl-4-(methylsulphonyl)piperazin-1-yl)methyl)-7-(pyridin-2-yl)thieno[3,2-c]pyridin-4(5H)-one (17 mg, 0.039 mmol, 17.07% yield) as a colourless solid.

LCMS (2 min, Formic Acid): Rt=0.61 min, MH$^+$=433

Example 126

5-methyl-2-((4-(methylsulphonyl)piperazin-1-yl)methyl)-7-(3-(trifluoromethyl)phenyl)thieno[3,2-c]pyridin-4(5H)-one

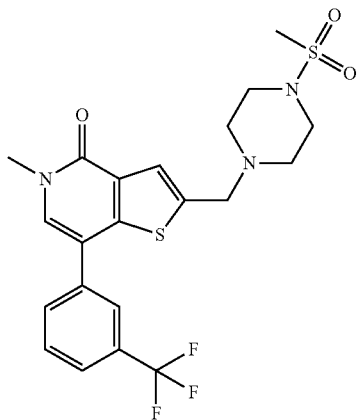 [SMILES: Cn1cc(-c2cccc(C(F)(F)F)c2)c2sc(CN3CCN(S(C)(=O)=O)CC3)cc2c1=O]

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 63 mg, 0.150 mmol), (3-(trifluoromethyl)phenyl)boronic acid (34.2 mg, 0.180 mmol), and potassium carbonate (49.7 mg, 0.360 mmol) in a solution of isopropanol (2 mL) and water (1 mL). To the reaction was then added PEPPSI (34.0 mg, 0.05 mmol). The reaction vessel was sealed and heated in the Biotage Initiator microwave reactor to 130° C. for 30 minutes with 10 seconds of pre-stirring. After cooling, the reaction was quenched with saturated ammonium chloride solution (15 mL) and mixed with DCM (10 mL). The solution was passed through Celite to remove the palladium. The filtrate was transferred to a separating funnel and the organic layer was collected. The aqueous layer was extracted with DCM (2×10 mL). The organic layers were combined and dried over MgSO$_4$. The filtrate was collected using vacuum filtration and the solvent was removed under reduced pressure to give a yellow oil. The oil was triturated with diethyl ether and oven dried overnight to give 5-methyl-2-((4-(methylsulphonyl)piperazin-1-yl)methyl)-7-(3-(trifluoromethyl)phenyl)thieno[3,2-c]pyridin-4(5H)-one (44.1 mg, 61% yield) as a pale pink solid, LCMS (2 min, Formic Acid): Rt=0.86 min, MH$^+$=486

Example 127

N-benzyl-3-(5-methyl-2-((4-(methylsulphonyl)piperazin-1-yl)methyl)-4-oxo-4,5-dihydrothieno[3,2-c]pyridin-7-yl)benzamide

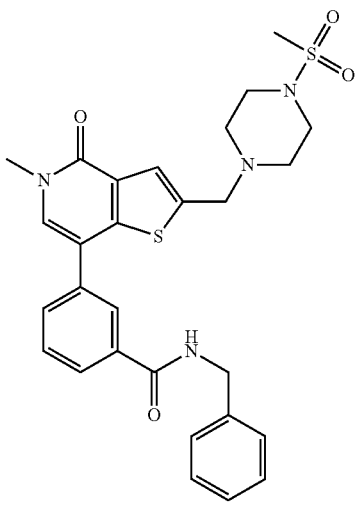 [SMILES: Cn1cc(-c2cccc(C(=O)NCc3ccccc3)c2)c2sc(CN3CCN(S(C)(=O)=O)CC3)cc2c1=O]

To a 2-5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 100 mg, 0.238 mmol) followed by (3-(benzylcarbamoyl)phenyl)boronic acid (Combi-Blocks Inc., 72.8 mg, 0.285 mmol), potassium carbonate (79 mg, 0.571 mmol) and lastly PEPPSI (34.0 mg, 0.05 mmol) in a solution of isopropanol (2 mL) and water (1 mL). The reaction vessel was sealed and heated in the Biotage Initiator microwave reactor to 130° C. for 30 minutes with 10 seconds of pre-stirring. The reaction was diluted with saturated sodium bicarbonate solution (20 mL) and shaken with DCM (20 mL). The solution was passed through Celite to remove the palladium.

The filtrate was transferred to a separating funnel and the organic layer was collected. The aqueous phase was extracted with DCM (3×20 mL). The organic fractions were combined, dried over MgSO$_4$ and concentrated under reduced pressure to give a light brown foam. The crude material was loaded onto a 25 g silica gel column and the product was eluted in 0-5% MeOH in DCM over 25 column volumes to give a pale yellow oil. The oil was triturated with diethyl ether to give N-benzyl-3-(5-methyl-2-((4-(methylsulphonyl)piperazin-1-yl)methyl)-4-oxo-4,5-dihydrothieno[3,2-c]pyridin-7-yl)benzamide (93 mg, 0.169 mmol, 71.0% yield) as an off-white solid, LCMS (2 min, Formic Acid): Rt=0.75 min, MH$^+$=551.

Example 128

(R)-7-(6-hydroxypyrimidin-4-yl)-5-methyl-2-((2-methyl-4-(methylsulphonyl)piperazin-1-yl)methyl)thieno[3,2-c]pyridin-4(5H)-one

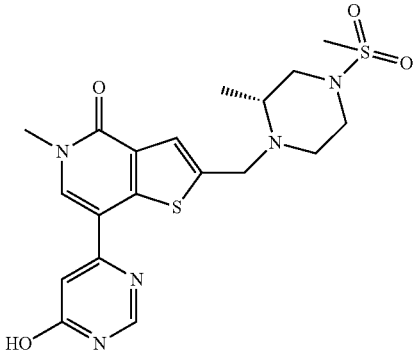 [SMILES: C[C@@H]1CN(S(C)(=O)=O)CCN1Cc1cc2c(=O)n(C)cc(-c3cc(O)ncn3)c2s1]

To a microwave reaction vial was added (R)-7-bromo-5-methyl-2-((2-methyl-4-(methylsulphonyl)piperazin-1-yl)methyl)thieno[3,2-c]pyridin-4(5H)-one (for a preparation see Intermediate 21, 100 mg, 0.230 mmol) followed by bis(pinacolato)boron (292 mg, 1.151 mmol), potassium acetate (90 mg, 0.921 mmol), and PdCl$_2$(dppf) (16.85 mg, 0.023 mmol) catalyst in a solution of 1,4-dioxane (4 mL). The vial was sealed and heated to 130° C. for 30 minutes in a microwave reactor. The reaction mixture was filtered through a 2.5 g Celite cartridge and the filtrate concentrated under reduced pressure. The residue was added to a microwave reaction vial containing 6-bromopyrimidin-4-ol (40.3 mg, 0.230 mmol), potassium carbonate (95 mg, 0.691 mmol). PdCl$_2$(dppf) (16.85 mg, 0.023 mmol) catalyst was added along with 1,2-dimethoxyethane (3 mL) and water (0.5 mL). The reaction vessel was sealed and heated to 120° C. for 20 minutes in a microwave reactor. The reaction was quenched with saturated ammonium chloride solution (25 mL) and the product was extracted from the aqueous phase with DCM (3×25 mL). The organic phases were combined, dried over magnesium sulphate, and concentrated under reduced pressure. The crude material was loaded on to a 12 g silica gel column and was eluted in 0-10% MeOH in DCM to give (R)-7-(6-hydroxypyrimidin-4-yl)-5-methyl-2-((2-methyl-4-(methylsulphonyl)piperazin-1-yl)methyl)thieno[3,2-c]pyridin-4(5H)-one (10 mg, 0.022 mmol, 9.66% yield), as a light brown solid.

LCMS (2 min, Formic Acid): Rt=0.44 min, MH$^+$=450

Example 129

5-methyl-2-((4-(methylsulphonyl)piperazin-1-yl)methyl)-7-(o-tolyl)thieno[3,2-c]pyridin-4(5H)-one

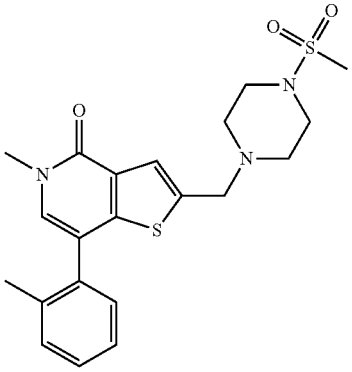

To a 5 mL microwave reaction vial was added 7-bromo-5-methyl-2-((4-(methylsulphonyl)piperazin-1-yl)methyl)thieno[3,2-c]pyridin-4(5H)-one (for a preparation see Intermediate 69, 70 mg, 0.167 mmol), o-tolylboronic acid (27.2 mg, 0.200 mmol), potassium carbonate (55.2 mg, 0.400 mmol), isopropanol (2 mL), and water (1 mL). Lastly was added PEPPSI (34.0 mg, 0.05 mmol) catalyst. The reaction vessel was sealed and heated in Biotage Initiator microwave reactor with 10 seconds of pre-stirring to 130° C. for 30 minutes. After cooling, the reaction was diluted with ammonium chloride solution (15 mL) and DCM (15 mL) and vacuum filtered through Celite. The filtrate was transferred to a separating funnel. The organic layer was collected and the aqueous layer was extracted with DCM (2×15 mL). The organic layers were combined and dried over MgSO$_4$. The filtrate was collected using vacuum filtration and the solvent was removed under reduced pressure to give a pale brown oil. The residue was loaded on to a 12 g silica gel column and eluted in 0-10% MeOH in DCM to give 5-methyl-2-((4-(methylsulphonyl)piperazin-1-yl)methyl)-7-(o-tolyl)thieno[3,2-c]pyridin-4(5H)-one (66 mg, 92% yield) as a light brown solid.

LCMS (2 min, Formic Acid): Rt=0.77 min, MH$^+$=432

Example 130

(S)-7-(6-methoxypyridin-3-yl)-5-methyl-2-((2-methyl-4-(methylsulphonyl)piperazin-1-yl)methyl)thieno[3,2-c]pyridin-4(5H)-one

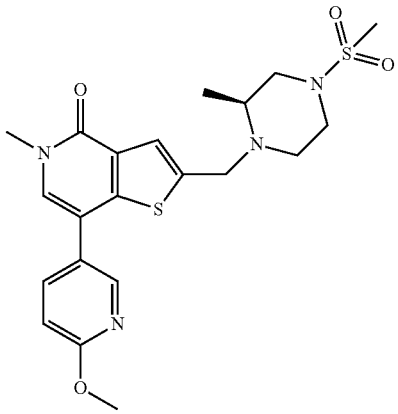 [SMILES: COc1ccc(-c2cn(C)c(=O)c3cc(CN4CCN(S(C)(=O)=O)C[C@@H]4C)sc23)cn1]

A mixture of (S)-7-bromo-5-methyl-2-((2-methyl-4-(methylsulphonyl)piperazin-1-yl)methyl)thieno[3,2-c]pyridin-4(5H)-one (for a preparation see Intermediate 88, 150 mg, 0.34 mmol), (6-methoxypyridin-3-yl)boronic acid (66 mg, 0.43 mmol), potassium carbonate (143 mg, 1.04 mmol) and bis(triphenylphosphine)palladium(II) chloride (25 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-4% methanol/dichloromethane] and the product triturated with diethyl ether to give (S)-7-(6-methoxypyridin-3-yl)-5-methyl-2-((2-methyl-4-(methylsulphonyl)piperazin-1-yl)methyl)thieno[3,2-c]pyridin-4(5H)-one (83 mg, 0.179 mmol, 52.0% yield) as an off white solid.

LCMS (2 min, Formic Acid): Rt=0.66 min, MH$^+$=463

Example 131

(S)-5-methyl-2-((2-methyl-4-(methylsulphonyl)piperazin-1-yl)methyl)-7-(pyridin-4-yl)thieno[3,2-c]pyridin-4(5H)-one

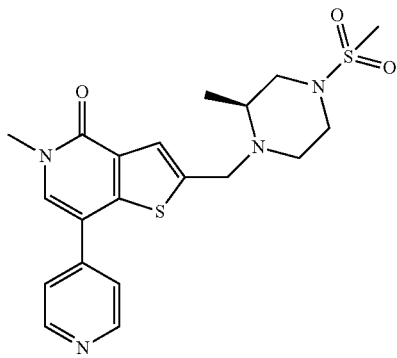 [SMILES: C[C@H]1CN(S(C)(=O)=O)CCN1Cc1cc2c(=O)n(C)cc(-c3ccncc3)c2s1]

A mixture of (S)-7-bromo-5-methyl-2-((2-methyl-4-(methylsulphonyl)piperazin-1-yl)methyl)thieno[3,2-c]pyridin-4(5H)-one (for a preparation see Intermediate 88, 150 mg, 0.34 mmol), pyridin-4-ylboronic acid (53 mg, 0.43 mmol), potassium carbonate (143 mg, 1.04 mmol) and bis(triphenylphosphine)palladium(II) chloride (25 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (S)-5-methyl-2-((2-methyl-4-(methylsulphonyl)piperazin-1-yl)methyl)-7-(pyridin-3,2-c]pyridin-4(5H)-one (83 mg, 0.192 mmol, 55.6% yield) as an off white solid.

LCMS (2 min, Formic Acid): Rt=0.41 min, MH$^+$=433

Example 132

(S)-5-methyl-2-((2-methyl-4-(methylsulphonyl)piperazin-1-yl)methyl)-7-(pyridin-3-yl)thieno[3,2-c]pyridin-4(5H)-one

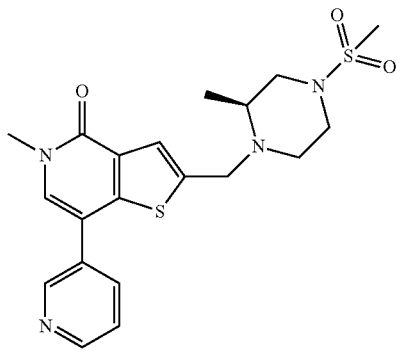 [SMILES: C[C@H]1CN(S(C)(=O)=O)CCN1Cc1cc2c(=O)n(C)cc(-c3cccnc3)c2s1]

A mixture of (S)-7-bromo-5-methyl-2-((2-methyl-4-(methylsulphonyl)piperazin-1-yl)methyl)thieno[3,2-c]pyridin-4(5H)-one (for a preparation see Intermediate 88, 150 mg, 0.34 mmol), pyridin-3-ylboronic acid (53 mg, 0.43 mmol), potassium carbonate (143 mg, 1.04 mmol) and bis(triphenylphosphine)palladium(II) chloride (25 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (S)-5-methyl-2-((2-methyl-4-(methylsulphonyl)piperazin-1-yl)methyl)-7-(pyridin-3-yl)thieno[3,2-c]pyridin-4(5H)-one (54 mg, 0.125 mmol, 36.2% yield) as an off white solid.

LCMS (2 min, Formic Acid): Rt=0.45 min, MH$^+$=433

Example 133

(S)-7-(5-methoxypyridin-3-yl)-5-methyl-2-((2-methyl-4-(methylsulphonyl)piperazin-1-yl)methyl)thieno[3,2-c]pyridin-4(5H)-one

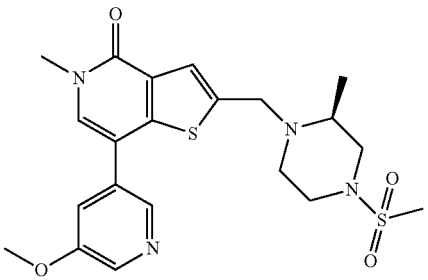

A mixture of (S)-7-bromo-5-methyl-2-((2-methyl-4-(methylsulphonyl)piperazin-1-yl)methyl)thieno[3,2-c]pyridin-4(5H)-one (for a preparation see Intermediate 88, 100 mg, 0.23 mmol), (5-methoxypyridin-3-yl)boronic acid (55 mg, 0.36 mmol), potassium carbonate (95 mg, 0.69 mmol) and bis(triphenylphosphine)palladium(II) chloride (16 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-4% methanol/dichloromethane] and the product triturated with diethyl ether to give (S)-7-(5-methoxypyridin-3-yl)-5-methyl-2-((2-methyl-4-(methylsulphonyl)piperazin-1-yl)methyl)thieno[3,2-c]pyridin-4(5H)-one (52 mg, 0.112 mmol, 48.8% yield) as a grey solid.

LCMS (2 min, Formic Acid): Rt=0.56 min, MH$^+$=463

Example 134

(S)-7-(4-methoxy-2-methylphenyl)-5-methyl-2-((2-methyl-4-(methylsulphonyl)piperazin-1-yl)methyl)thieno[3,2-c]pyridin-4(5H)-one

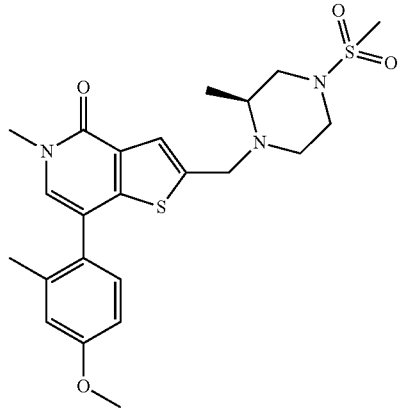 [SMILES: COc1ccc(-c2cn(C)c(=O)c3cc(CN4CCN(S(C)(=O)=O)C[C@@H]4C)sc23)c(C)c1]

A mixture of (S)-7-bromo-5-methyl-2-((2-methyl-4-(methylsulphonyl)piperazin-1-yl)methyl)thieno[3,2-c]pyridin-4(5H)-one (for a preparation see Intermediate 88, 150 mg, 0.34 mmol), (4-methoxy-2-methylphenyl)boronic acid (73 mg, 0.44 mmol), potassium carbonate (143 mg, 1.04 mmol) and bis(triphenylphosphine)palladium(II) chloride (24 mg, 10 mol %) in 1,2-dimethoxyethane (3 mL) and water (0.5 mL) was heated in a microwave at 120° C. for 20 minutes. The cooled reaction mixture was diluted with ethyl acetate (25 mL). The solution was dried over sodium sulphate and evaporated. The residue was chromatographed [0-5% methanol/dichloromethane] and the product triturated with diethyl ether to give (S)-7-(4-methoxy-2-methylphenyl)-5-methyl-2-((2-methyl-4-(methylsulphonyl)piperazin-1-yl)methyl)thieno[3,2-c]pyridin-4(5H)-one (49 mg, 0.103 mmol, 29.8% yield) as a colourless solid.

LCMS (2 min, Formic Acid): Rt=0.78 min, MH+=476

Example 135

(S)-7-(3-(benzyloxy)-4-methoxyphenyl)-5-methyl-2-((2-methylpiperazin-1-yl)methyl)thieno[3,2-c]pyridin-4(5H)-one hydrochloride

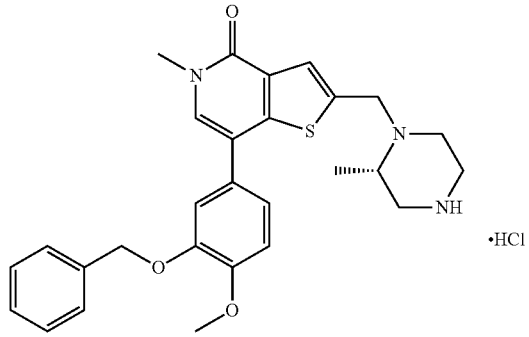 [SMILES: COc1ccc(-c2cn(C)c(=O)c3cc(CN4CCNC[C@@H]4C)sc23)cc1OCc1ccccc1 ; Cl]

To a solution of (S)-tert-butyl 4-((7-(3-(benzyloxy)-4-methoxyphenyl)-5-methyl-4-oxo-4,5-dihydrothieno[3,2-c]pyridin-2-yl)methyl)-3-methylpiperazine-1-carboxylate (Intermediate 68, 1.9 mg, 3.22 μmol) in 1,4-dioxane (1.0 mL) was added 4M HCl in 1,4-dioxane (1 mL). The reaction mixture was stirred at room temperature for 2 hours, whereupon it was concentrated in vacuo. The resulting residue was triturated in ether, filtered and dried in vacuo to give (S)-7-(3-(benzyloxy)-4-methoxyphenyl)-5-methyl-2-((2-methylpiperazin-1-yl)methyl)thieno[3,2-c]pyridin-4(5H)-one hydrochloride (1.6 mg) as a beige solid.

LCMS (2 min, Formic Acid): Rt=0.83 min, MH+=490

Example 136

5-ethyl-2-((4-(methylsulphonyl)piperazin-1-yl)methyl)-7-phenylthieno[3,2-c]pyridin-4(5H)-one

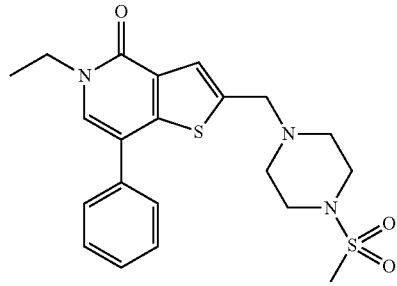 [SMILES: CCn1cc(-c2ccccc2)c2sc(CN3CCN(S(C)(=O)=O)CC3)cc2c1=O]

To a 25 mL round bottom flask under nitrogen and fitted with a reflux condenser and stirrer bar was added 5-ethyl-4-oxo-7-phenyl-4,5-dihydrothieno[3,2-c]pyridine-2-carbaldehyde (Intermediate 31, 95 mg, 0.335 mmol) in DCM (5 mL). To the reaction was then added 1-(methylsulphonyl)piperazine (83 mg, 0.503 mmol) and acetic acid (0.029 mL, 0.503 mmol) and the mixture was stirred at room temperature under nitrogen for 1 hour. The reaction mixture quickly became a yellow suspension. To the reaction mixture was then added sodium triacetoxyborohydride (355 mg, 1.676 mmol) and the temperature was increased to 40° C. After 1 hour the reaction was allowed to cool to room temperature.

The reaction was diluted with saturated sodium bicarbonate solution (20 mL) and transferred to a separating funnel. The product was extracted with DCM (3×10 mL). The organic layers were combined and washed with brine (approx. 10 mL). The organic layer was collected and dried over magnesium sulphate. The filtrate was collected in a 150 mL round bottom flask using a filter cup and the solvent was removed under reduced pressure to give an yellow oily-solid.

The residue was insoluble in a small volume of MeOH so a small volume of DCM was added. The solution was transferred to a 1 g SCX column and allowed to filter through by gravity. The column was then flushed with MeOH (3 column volumes) to remove impurities. The product was then collected by flushing the column with 2.0M ammonia in MeOH (3 column volumes) and the solvent was removed under reduced pressure to give a pale yellow oil. This was placed in the vacuum oven overnight to give a yellow solid, 5-ethyl-2-((4-(methylsulphonyl)piperazin-1-yl)methyl)-7-phenylthieno[3,2-c]pyridin-4(5H)-one (102.4 mg, 0.237 mmol, 70.8% yield).

LCMS (2 min, Formic Acid): Rt=0.83 min, MH+=432.

Example 137

7-(3,4-dimethoxyphenyl)-5-ethyl-2-((4-(methylsulphonyl)piperazin-1-yl)methyl)thieno[3,2-c]pyridin-4(5H)-one

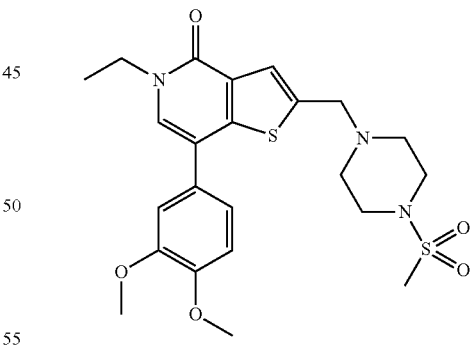

To a 25 mL round bottom flask was added 7-(3,4-dimethoxyphenyl)-5-ethyl-4-oxo-4,5-dihydrothieno[3,2-c]pyridine-2-carbaldehyde (Intermediate 32, 95 mg, 0.277 mmol) dissolved in dichloromethane (5 mL). To the solution was then added 1-(methylsulphonyl)piperazine (68.1 mg, 0.415 mmol) and acetic acid (0.024 mL, 0.415 mmol). The reaction was stirred under nitrogen at room temperature for 1 hour. To the reaction was then added sodium triacetoxyborohydride (293 mg, 1.383 mmol) and it was heated to 40° C. for several hours and then allowed to cool to room temperature.

The reaction was diluted with saturated sodium bicarbonate solution (20 mL) and transferred to a separating funnel. The product was extracted with DCM (3×10 mL). The organic layers were combined and washed once with brine. The organic layer was collected and dried over magnesium sulphate and the filtrate was collected using vacuum filtration. The solvent was removed under reduced pressure to yield a yellow oil.

The crude material was dissolved in a small volume of DCM and MeOH and transferred to a 1 g SCX column. The product was allowed to elute through the column by gravity. The column was flushed with MeOH (3 column volumes) to remove impurities. The product was eluted in 2.0M ammonia in MeOH (3 column volumes) and the solvent was removed under reduced pressure to give a while solid with oily residue. The product was dried in a vacuum oven to give a pale yellow solid, 7-(3,4-dimethoxyphenyl)-5-ethyl-2-((4-(methylsulphonyl)piperazin-1-yl)methyl)thieno[3,2-c]pyridin-4(5H)-one (108.1 mg, 0.220 mmol, 79% yield).

LCMS (2 min, Formic Acid): Rt=0.74 min, MH$^+$=492.

Example 138

2-((4-acetylpiperazin-1-yl)methyl)-5-ethyl-7-phenylthieno[3,2-c]pyridin-4(5H)-one

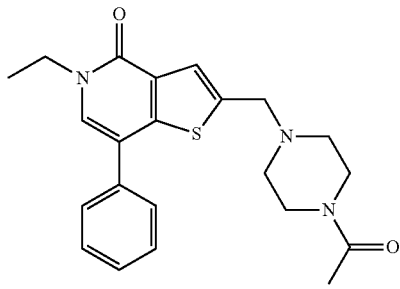 [SMILES: CCn1cc(-c2ccccc2)c2sc(CN3CCN(C(C)=O)CC3)cc2c1=O]

To a 25 mL round bottom flask under nitrogen and equipped with a stirrer bar and reflux condenser was added 5-ethyl-4-oxo-7-phenyl-4,5-dihydrothieno[3,2-c]pyridine-2-carbaldehyde (Intermediate 31, 95 mg, 0.335 mmol) in dichloromethane (5 mL). To the reaction was then added 1-(piperazin-1-yl)ethanone (64.5 mg, 0.503 mmol) and acetic acid (0.029 mL, 0.503 mmol). The reaction was left to stir at room temperature under nitrogen for 1 hour. Finally, sodium triacetoxyborohydride (355 mg, 1.676 mmol) was added to the reaction mixture and it was heated at 40° C. for an hour.

The product was diluted with saturated sodium bicarbonate solution (20 mL) and transferred to a separating funnel. The product was extracted with DCM (3×10 mL). The organic layers were combined and washed with brine. The organic layer was collected and dried over magnesium sulphate and filtered. The filtrate was evaporated under reduced pressure to give a yellow oil. The crude material was dissolved in a small volume of MeOH and DCM and transferred to a 1 g SCX column. The product was allowed to elute with gravity. The column was then flushed with MeOH (3 column volumes) to remove impurities. The product was then eluted with 2.0M ammonia in MeOH (3 column volumes) and the solvent was removed under reduced pressure to give a yellow oil. The product was placed in the vacuum oven overnight to give a yellow solid, 2-((4-acetylpiperazin-1-yl)methyl)-5-ethyl-7-phenylthieno[3,2-c]pyridin-4(5H)-one (96.5 mg, 0.244 mmol, 72.8% yield).

LCMS (2 min, Formic Acid): Rt=0.70 min, MH$^+$=396.

Example 139

2-((4-acetylpiperazin-1-yl)methyl)-7-(3,4-dimethoxyphenyl)-5-ethylthieno[3,2-c]pyridin-4(5H)-one

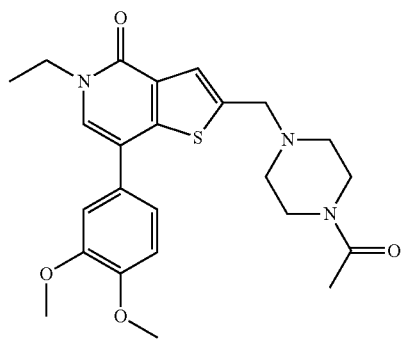 [SMILES: CCn1cc(-c2ccc(OC)c(OC)c2)c2sc(CN3CCN(C(C)=O)CC3)cc2c1=O]

To a 25 mL round bottom flask was added 7-(3,4-dimethoxyphenyl)-5-ethyl-4-oxo-4,5-dihydrothieno[3,2-c]pyridine-2-carbaldehyde (Intermediate 32, 95 mg, 0.277 mmol) dissolved in DCM (5 mL). To the solution was added 1-(piperazin-1-yl)ethanone (53.2 mg, 0.415 mmol) and acetic acid (0.024 mL, 0.415 mmol). The reaction was stirred under nitrogen at room temperature for 1 hour. To the reaction was then added sodium triacetoxyborohydride (293 mg, 1.383 mmol) and it was heated at 40° C. for 2 hours and then allowed to cool to room temperature.

The reaction was diluted with saturated sodium bicarbonate solution (20 mL) and transferred to a separating funnel. The product was extracted with DCM (3×10 mL). The organic layers were combined and washed with brine. The organic layer was collected and dried over magnesium sulphate. The filtrate was collected using vacuum filtration and the solvent was removed under reduced pressure to give a yellow oil.

The crude material was dissolved in a small volume of MeOH and DCM (approx. 2 mL) and transferred to a 1 g SCX column. The product was allowed to elute by gravity. The column was then flushed with MeOH (3 column volumes) to remove impurities. The product was eluted in 2.0M ammonia in MeOH (3 column volumes) to give a yellow oil. To the product was added a few drops of diethyl ether and it was scratched gently with a metal spatula which promoted precipitation of a yellow solid. The diethyl ether was then blown off under nitrogen at 40° C. and the product was dried in the oven overnight to give a pale yellow solid 2-((4-acetylpiperazin-1-yl)methyl)-7-(3,4-dimethoxyphenyl)-5-ethylthieno[3,2-c]pyridin-4(5H)-one (83.5 mg, 0.183 mmol, 66.3% yield).

LCMS (2 min, Formic Acid): Rt=0.70 min, MH$^+$=456.

Example 140

(R)-N-(4-(2-((4-(ethylsulfonyl)-2-methylpiperazin-1-yl)methyl)-5-methyl-4-oxo-4,5-dihydrothieno[3,2-c]pyridin-7-yl)pyridin-2-yl)acetamide

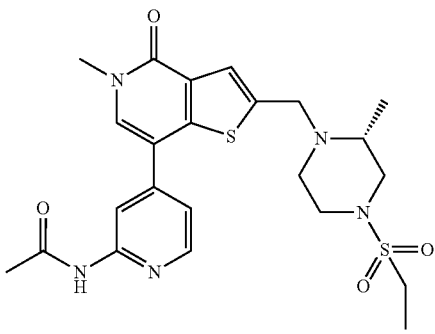 [SMILES: CCS(=O)(=O)N1CCN(Cc2cc3c(=O)n(C)cc(-c4ccnc(NC(C)=O)c4)c3s2)[C@H](C)C1]

To a microwave reaction vial was added (R)-7-bromo-2-((4-(ethylsulfonyl)-2-methylpiperazin-1-yl)methyl)-5-methylthieno[3,2-c]pyridin-4(5H)-one (Intermediate 92) (102 mg, 0.227 mmol) followed by N-(4-(4,4,5,5-tetramethyl-1,3,2-dioxaborolan-2-yl)pyridin-2-yl)acetamide (119 mg, 0.455 mmol), potassium carbonate (126 mg, 0.910 mmol) and bis(triphenylphosphine)palladium(II) chloride (15.97 mg, 0.023 mmol) in a solution of 1,2-DME (3 mL) and water (0.5 mL). The reaction vessel was sealed and heated to 120° C. for 20 min in the Biotage Initiator microwave reactor with 10 seconds of pre-stirring. After cooling, the reaction was diluted with saturated ammonium chloride solution (20 mL) and the product was extracted in DCM (3×20 mL). The organic fractions were combined, dried over magnesium sulfate, and concentrated under reduced pressure to give a yellow solid. The crude material was loaded on to a 12 g silica gel column and was eluted in 0-5% MeOH in DCM to give a yellow oil. The material was triturated with diethyl ether to give the title compound (105 mg, 0.208 mmol, 92% yield), as a pale yellow solid LCMS (2 min, Formic Acid): Rt=0.55 min, MH$^+$=504.

Examples 141-155

The following examples (141-155) were prepared as part of an array using the method exemplified below.

An aliquot (0.4 mL, 0.1 mmol) of stock solution of N-(4-(2-(bromomethyl)-5-methyl-4-oxo-4,5-dihydrothieno[3,2-c]pyridin-7-yl)pyridin-2-yl)acetamide (Intermediate 94) in DMSO (706 mg, 1.8 mmol in 7.2 mL) was dispensed to each of a set of appropriate pre-weighed amines (0.120 mmol) in microwave vials. Finally potassium carbonate (0.041 g, 0.300 mmol) was added to each vial and the reactions were sealed and heated in a microwave reactor at 110° C. for 30 min. After cooling the reactions, the samples were purified by MDAP on an Xbridge column using MeCN/water with an ammonium carbonate modifier. The solvent was removed under a stream of nitrogen to give the required product. LCMS (2 min, High pH).

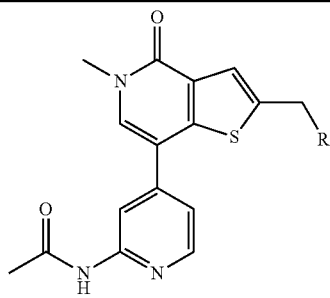

| Example | Name | R | Rt min | MH$^+$ |
|---|---|---|---|---|
| 141 | N-(4-(2-((3-isopropylmorpholino)methyl)-5-methyl-4-oxo-4,5-dihydrothieno[3,2-c]pyridin-7-yl)pyridin-2-yl)acetamide | | 0.52 | 441 |
| 142 | (R)-N-(4-(2-((3-fluoropyrrolidin-1-yl)methyl)-5-methyl-4-oxo-4,5-dihydrothieno[3,2-c]pyridin-7-yl)pyridin-2-yl)acetamide | | 0.43 | 401 |
| 143 | (R)-N-(4-(2-((3-hydroxypyrrolidin-1-yl)methyl)-5-methyl-4-oxo-4,5-dihydrothieno[3,2-c]pyridin-7-yl)pyridin-2-yl)acetamide | | 0.41 | 399 |

-continued

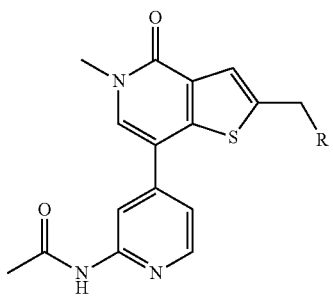

| Example | Name | R | Rt min | MH+ |
|---|---|---|---|---|
| 144 | N-(4-(2-((3-fluoropiperidin-1-yl)methyl)-5-methyl-4-oxo-4,5-dihydrothieno[3,2-c]pyridin-7-yl)pyridin-2-yl)acetamide | piperidine with F at 3-position | 0.44 | 415 |
| 145 | N-(4-(5-methyl-4-oxo-2-((3-(trifluoromethyl)pyrrolidin-1-yl)methyl)-4,5-dihydrothieno[3,2-c]pyridin-7-yl)pyridin-2-yl)acetamide | pyrrolidine with CF3 | 0.52 | 451 |
| 146 | 1-((7-(2-acetamidopyridin-4-yl)-5-methyl-4-oxo-4,5-dihydrothieno[3,2-c]pyridin-2-yl)methyl)piperidine-2-carboxamide | piperidine-2-carboxamide | 0.43 | 440 |
| 147 | N-(4-(5-methyl-2-((2-methylmorpholino)methyl)-4-oxo-4,5-dihydrothieno[3,2-c]pyridin-7-yl)pyridin-2-yl)acetamide | 2-methylmorpholine | 0.46 | 413 |
| 148 | N-(4-(2-((2,6-dimethylmorpholino)methyl)-5-methyl-4-oxo-4,5-dihydrothieno[3,2-c]pyridin-7-yl)pyridin-2-yl)acetamide | 2,6-dimethylmorpholine | 0.49 | 427 |
| 149 | N-(4-(2-((3,5-dimethylmorpholino)methyl)-5-methyl-4-oxo-4,5-dihydrothieno[3,2-c]pyridin-7-yl)pyridin-2-yl)acetamide | 3,5-dimethylmorpholine | 0.47 | 427 |
| 150 | N-(4-(2-(((3R,5S)-3,5-dimethylmorpholino)methyl)-5-methyl-4-oxo-4,5-dihydrothieno[3,2-c]pyridin-7-yl)pyridin-2-yl)acetamide | (3R,5S)-3,5-dimethylmorpholine | 0.46 | 427 |

-continued

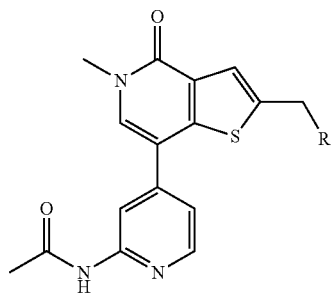

| Example | Name | R | Rt min | MH+ |
|---|---|---|---|---|
| 151 | N-(4-(2-(((2R,3R)-2,3-dimethylmorpholino)methyl)-5-methyl-4-oxo-4,5-dihydrothieno[3,2-c]pyridin-7-yl)pyridin-2-yl)acetamide | | 0.47 | 427 |
| 152 | N-(4-(2-((3-fluoropyrrolidin-1-yl)methyl)-5-methyl-4-oxo-4,5-dihydrothieno[3,2-c]pyridin-7-yl)pyridin-2-yl)acetamide | | 0.43 | 401 |
| 153 | N-(4-(2-(((2S,6R)-2,6-dimethylmorpholino)methyl)-5-methyl-4-oxo-4,5-dihydrothieno[3,2-c]pyridin-7-yl)pyridin-2-yl)acetamide | | 0.49 | 427 |
| 154 | N-(4-(5-methyl-4-oxo-2-((2-(trifluoromethyl)pyrrolidin-1-yl)methyl)-4,5-dihydrothieno[3,2-c]pyridin-7-yl)pyridin-2-yl)acetamide | | 0.90 | 451 |
| 155 | N-(4-(2-((2,5-dimethylmorpholino)methyl)-5-methyl-4-oxo-4,5-dihydrothieno[3,2-c]pyridin-7-yl)pyridin-2-yl)acetamide | | 0.48 | 427 |

Example 144

N-(4-(2-((3-fluoropiperidin-1-yl)methyl)-5-methyl-4-oxo-4,5-dihydrothieno[3,2-c]pyridin-7-yl)pyridin-2-yl)acetamide

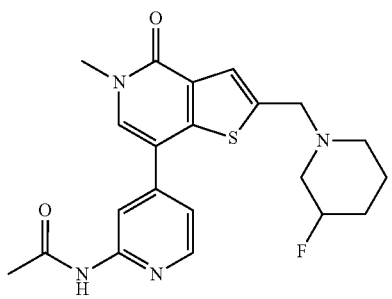 [SMILES: CC(=O)Nc1cc(-c2cn(C)c(=O)c3cc(CN4CCCC(F)C4)sc23)ccn1]

Alternative Preparation

A mixture of 7-bromo-2-((3-fluoropiperidin-1-yl)methyl)-5-methylthieno[3,2-c]pyridin-4(5H)-one (Intermediate 96) (200 mg, 0.56 mmol), N-(4-(4,4,5,5-tetramethyl-1,3,2-dioxaborolan-2-yl)pyridin-2-yl)acetamide (219 mg, 0.84 mmol), potassium carbonate (385 mg, 2.78 mmol) and bis(triphenylphosphine)palladium(II) chloride (20 mg, 5 mol %) in toluene (2 mL) and ethanol (2 mL) was heated in a microwave at 120° C. for 20 minutes. The cooled reaction mixture was diluted with EtOAc (20 mL). The mixture was dried over sodium sulfate then filtered. The solvent was evaporated from the filtrate and the residue was purified by column chromatography on silica gel [0-5% MeOH/DCM] to give the title compound (127 mg, 0.306 mmol, 55.0% yield) as a pale yellow solid.

LCMS (2 min, Formic Acid): Rt=0.48 minutes, MH$^+$=415.

This material was separated into its two component enantiomers by preparative chiral HPLC. 150 mg of racemate was dissolved at a rate of 30 mg per 2 mL of EtOH and 2 mL portions were injected onto a 2 cm×25 cm Chiralpak IC column. The column was eluted with 30% EtOH/Hexane, flow rate=15 mL/min, wavelength 230 nm. Appropriate fractions were combined, concentrated, re-dissolved in DCM and re-concentrated to give the two enantiomers:

Example 144A: 37 mg. LCMS (2 min, Formic Acid): Rt=0.48 min, MH$^+$=415. Enantiomeric purity by chiral HPLC=>99% e.e.

Example 144B: 38 mg. LCMS (2 min, Formic Acid): Rt=0.48 min, MH$^+$=415. Enantiomeric purity by chiral HPLC=95% e.e.

Absolute stereochemistry was not assigned.

Examples 156-161

The following examples (156-161) were prepared as part of an array using the method exemplified by that outlined below.

An aliquot (0.4 mL, 0.1 mmol) of stock solution of N-(4-(2-(bromomethyl)-5-methyl-4-oxo-4,5-dihydrothieno[3,2-c]pyridin-7-yl)pyridin-2-yl)acetamide (Intermediate 94) in DMF (235 mg, 0.6 mmol in 2.4 mL) was dispensed to each of a set of appropriate pre-weighed amines (0.120 mmol) in microwave vials. Finally DIPEA (50 uL, 0.286 mmol) was added to each vial and the reactions were sealed and heated in a microwave reactor at 110° C. for 30 min. After cooling the reactions, the samples were purified by MDAP on an Xbridge column using MeCN/water with an ammonium carbonate modifier. The solvent was removed under a stream of nitrogen to give the required product. LCMS (2 min, High pH). * DMSO was used as solvent for Example 161

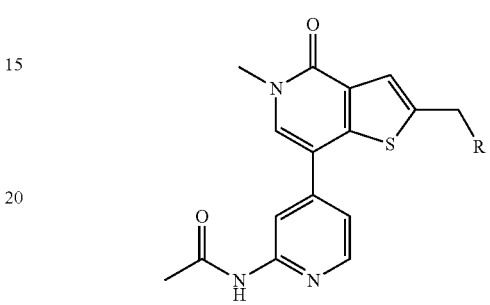

| Example | Name | Product | Rt min | MH$^+$ |
|---|---|---|---|---|
| 156 | (S)-N-(4-(2-((3-hydroxypiperidin-1-yl)methyl)-5-methyl-4-oxo-4,5-dihydrothieno[3,2-c]pyridin-7-yl)pyridin-2-yl)acetamide | | 0.43 | 413 |
| 157 | (S)-N-(4-(2-((3-hydroxypyrrolidin-1-yl)methyl)-5-methyl-4-oxo-4,5-dihydrothieno[3,2-c]pyridin-7-yl)pyridin-2-yl)acetamide | | 0.42 | 399 |
| 158 | (R)-N-(4-(2-((3-hydroxypiperidin-1-yl)methyl)-5-methyl-4-oxo-4,5-dihydrothieno[3,2-c]pyridin-7-yl)pyridin-2-yl)acetamide | | 0.43 | 413 |
| 159 | (S)-N-(4-(2-((3-fluoropyrrolidin-1-yl)methyl)-5-methyl-4-oxo-4,5-dihydrothieno[3,2-c]pyridin-7-yl)pyridin-2-yl)acetamide | | 0.44 | 401 |
| 160 | N-(4-(2-((3-methoxypiperidin-1-yl)methyl)-5-methyl-4-oxo-4,5-dihydrothieno[3,2-c]pyridin-7-yl)pyridin-2-yl)acetamide | | 0.48 | 427 |
| 161* | N-(4-(2-((3-hydroxyazetidin-1-yl)methyl)-5-methyl-4-oxo-4,5-dihydrothieno[3,2-c]pyridin-7-yl)pyridin-2-yl)acetamide | | 0.42 | 385 |

Example 162

N-(4-(2-((3,3-difluoropiperidin-1-yl)methyl)-5-methyl-4-oxo-4,5-dihydrothieno[3,2-c]pyridin-7-yl)pyridin-2-yl)acetamide

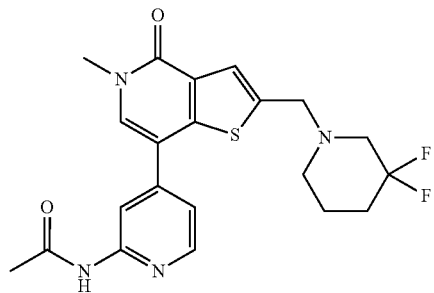 [SMILES: CC(=O)Nc1cc(-c2cn(C)c(=O)c3cc(CN4CCCC(F)(F)C4)sc23)ccn1]

7-Bromo-2-((3,3-difluoropiperidin-1-yl)methyl)-5-methylthieno[3,2-c]pyridin-4(5H)-one (Intermediate 95) (100 mg, 0.265 mmol), N-(4-(4,4,5,5-tetramethyl-1,3,2-dioxaborolan-2-yl)pyridin-2-yl)acetamide (104 mg, 0.398 mmol), potassium carbonate (183 mg, 1.325 mmol) and bis(triphenylphosphine)palladium(II) chloride (9.30 mg, 0.013 mmol), were dissolved in ethanol (2 mL) and toluene (2 mL) and heated in a microwave reactor for 20 min at 120° C. EtOAc (20 mL) was added, the mixture was dried over MgSO4, filtered and the solvent evaporated. The crude product was dissolved in a small amount of DCM and purified by silica gel column chromatography using 0-5% MeOH/DCM. The appropriate fractions were combined and evaporated under vacuum to give a yellow oil. This was triturated with diethyl ether to give the title compound (59 mg, 0.136 mmol, 51.5% yield) as a yellow solid.

LCMS (2 min, High pH): Rt=0.89 min, MH$^+$=433.

Example 163

(R)-7-(2-ethoxypyridin-4-yl)-5-methyl-2-((2-methyl-4-(methylsulfonyl)piperazin-1-yl)methyl)thieno[3,2-c]pyridin-4(5H)-one

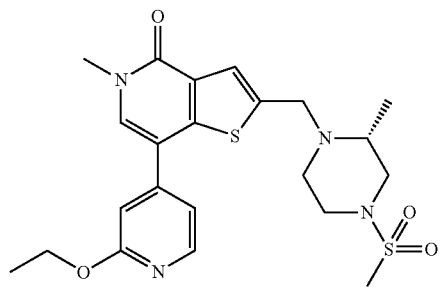 [SMILES: CCOc1cc(-c2cn(C)c(=O)c3cc(CN4CCN(S(C)(=O)=O)C[C@H]4C)sc23)ccn1]

Tetrakis(triphenylphosphine) palladium(0) (19.07 mg, 0.017 mmol), (R)-7-bromo-5-methyl-2-((2-methyl-4-(methylsulfonyl)piperazin-1-yl)methyl)thieno[3,2-c]pyridin-4(5H)-one (Intermediate 21) (143 mg, 0.33 mmol), sodium carbonate (280 mg, 2.64 mmol), and 2-ethoxy-4-(4,4,5,5-tetramethyl-1,3,2-dioxaborolan-2-yl)pyridine (Intermediate 107) (93 mg, 0.371 mmol) in 1,2-DME (4 mL) were mixed and heated in the microwave for 2 hr at 120° C. Further tetrakis(triphenylphosphine) palladium(0) (19.07 mg, 0.017 mmol) was added and the reaction was heated in the microwave to 120° C. for 3 hr. Further tetrakis(triphenylphosphine) palladium(0) (19.07 mg, 0.017 mmol) was added the reaction was heated in the microwave to 120° C. for 4 hr. The reaction was diluted with EtOAc and water, filtered and the organic layer was separated and concentrated in vacuo. The crude product was purified by chromatography [0-5% MeOH in DCM] and fractions containing product were concentrated then further purified by MDAP. The fractions containing product were concentrated in vacuo and once more purified by MDAP. The product containing fractions were concentrated in vacuo then dissolved in MeOH and passed through a Ig aminopropyl column, eluting with MeOH.

The solvent was removed in vacuo to give the title compound as a white solid (13 mg, 0.027 mmol, 8.3% yield).

LCMS (2 min, Formic Acid): Rt=0.72 min, MH$^+$=477

Example 164

(R)-7-(2-(cyclopropyl methoxy)pyridin-4-yl)-5-methyl-2-((2-methyl-4-(methylsulfonyl)piperazin-1-yl)methyl)thieno[3,2-c]pyridin-4(5H)-one

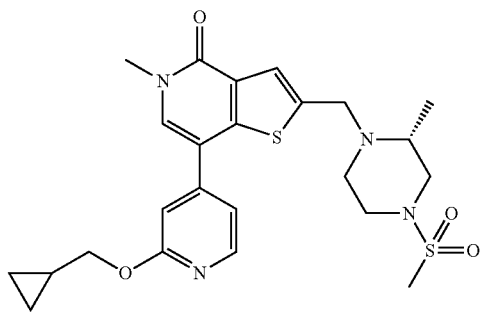 [SMILES: C[C@@H]1CN(S(C)(=O)=O)CCN1Cc1cc2c(=O)n(C)cc(-c3ccnc(OCC4CC4)c3)c2s1]

Tetrakis(triphenylphosphine) palladium(0) (18.62 mg, 0.016 mmol), (R)-7-bromo-5-methyl-2-((2-methyl-4-(methylsulfonyl)piperazin-1-yl)methyl)thieno[3,2-c]pyridin-4(5H)-one (Intermediate 21) (140 mg, 0.322 mmol), aqueous sodium carbonate (1.289 mL, 2.58 mmol), and 2-(cyclopropylmethoxy)-4-(4,4,5,5-tetramethyl-1,3,2-dioxaborolan-2-yl)pyridine (Intermediate 108) (111 mg, 0.403 mmol) in 1,2-DME (3 mL) were mixed and heated in the microwave for 2 hr at 120° C. The reaction was diluted with EtOAc and water, filtered and the organic layer was separated and concentrated in vacuo. The crude product was purified by chromatography [0-5% MeOH in DCM] and fractions containing product were combined and concentrated further purified by MDAP to give the title compound as a white solid (16 mg, 0.032 mmol, 9.9% yield).

LCMS (2 min, High pH): Rt=1.10 min, MH$^+$=503.

Example 165

(R)-5-methyl-2-((2-methyl-4-(methylsulfonyl)piperazin-1-yl)methyl)-7-(2-(2-(pyrrolidin-1-yl)ethoxy)pyridin-4-yl)thieno[3,2-c]pyridin-4(5H)-one

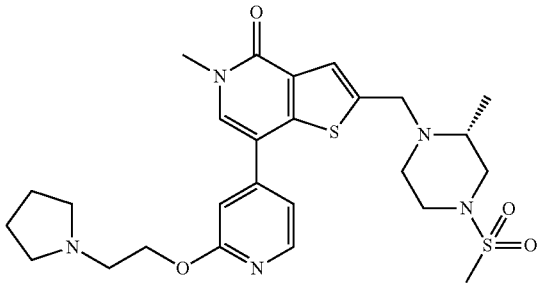 [SMILES: C[C@@H]1CN(S(C)(=O)=O)CCN1Cc1cc2c(=O)n(C)cc(-c3ccnc(OCCN4CCCC4)c3)c2s1]

The title compound was prepared from Intermediates 21 and 109 using a method similar to that described for Example 164 (39 mg, 0.071 mmol, 21.7% yield).
LCMS (2 min, High pH): Rt=0.96 min, MH$^+$=546.

Example 166

(R)-7-(2-(2-methoxyethoxy)pyridin-4-yl)-5-methyl-2-((2-methyl-4-(methylsulfonyl)piperazin-1-yl)methyl)thieno[3,2-c]pyridin-4(5H)-one

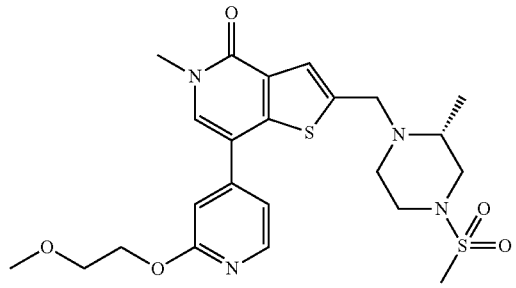 [SMILES: COCCOc1cc(-c2cn(C)c(=O)c3cc(CN4CCN(S(C)(=O)=O)C[C@H]4C)sc23)ccn1]

The title compound was prepared from Intermediates 21 and 110 using a method similar to that described for Example 164 (28 mg, 0.055 mmol, 18.5% yield).
LCMS (2 min, High pH): Rt=0.91 min, MH$^+$=507.

Example 167

(R)-7-(3-methoxypyridin-4-yl)-5-methyl-2-((2-methyl-4-(methylsulfonyl)piperazin-1-yl)methyl)thieno[3,2-c]pyridin-4(5H)-one

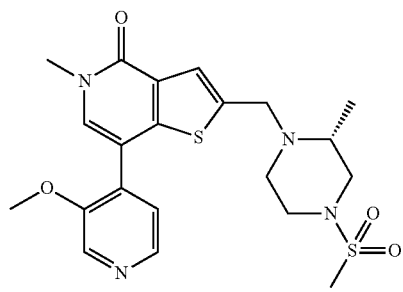 [SMILES: COc1cnccc1-c1cn(C)c(=O)c2cc(CN3CCN(S(C)(=O)=O)C[C@H]3C)sc12]

(3-Methoxypyridin-4-yl)boronic acid (Combi-Blocks) (100 mg, 0.654 mmol), (R)-7-bromo-5-methyl-2-((2-methyl-4-(methylsulfonyl)piperazin-1-yl)methyl)thieno[3,2-c]pyridin-4(5H)-one (Intermediate 21) (250 mg, 0.576 mmol), tetrakis(triphenylphosphine) palladium(0) (33.3 mg, 0.029 mmol) and aqueous sodium carbonate (2.302 mL, 4.60 mmol) were mixed in 1,2-DME (3 mL) and heated in the microwave for 2 hr at 120° C. Further (3-methoxypyridin-4-yl)boronic acid (40 mg, 0.262 mmol) and tetrakis(triphenylphosphine) palladium(0) (33.3 mg, 0.029 mmol) were added and the reaction heated again to 120° C. for 2 hr in the microwave. The reaction was diluted with EtOAc and water, filtered and the organic layer was separated and concentrated in vacuo. The residue was dissolved in ethanol and passed through a 10 g SCX column, eluting with MeOH, then ammonia (2 M in MeOH). The solvent was evaporated off to give the crude product which was purified by silica gel column chromatography [5-40% EtOH in EtOAc] and fractions containing product were combined and concentrated in vacuo to give the title compound as a white solid (36 mg, 0.078 mmol, 13.5% yield).
LCMS (2 min, High pH): Rt=0.76 min, MH$^+$=463.

Example 168

(R)-7-(3-(cyclopropylmethoxy)pyridin-4-yl)-5-methyl-2-((2-methyl-4-(methylsulfonyl)piperazin-1-yl)methyl)thieno[3,2-c]pyridin-4(5H)-one

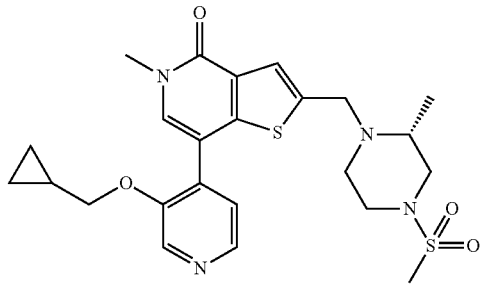 [SMILES: C[C@@H]1CN(S(C)(=O)=O)CCN1Cc1cc2c(=O)n(C)cc(-c3ccncc3OCC3CC3)c2s1]

3-(Cyclopropylmethoxy)-4-(4,4,5,5-tetramethyl-1,3,2-dioxaborolan-2-yl)pyridine (Intermediate 111) (73.7 mg, 0.268 mmol), (R)-7-bromo-5-methyl-2-((2-methyl-4-(methylsulfonyl)piperazin-1-yl)methyl)thieno[3,2-c]pyridin-4(5H)-one (Intermediate 21) (100 mg, 0.230 mmol), tetrakis(triphenylphosphine) palladium(0) (13.30 mg, 0.012 mmol) and aqueous sodium carbonate (0.921 mL, 1.842 mmol) were mixed in 1,2-DME (3 mL) and heated in the microwave for 2 hr at 120° C. The reaction was diluted with EtOAc and water and filtered. The organic layer was separated and concentrated in vacuo and the crude product was purified by MDAP. Fractions containing product were concentrated in vacuo and further purified by MDAP. Fractions containing product were concentrated in vacuo, dissolved in MeOH and eluted with MeOH through a 10 g aminopropyl cartridge. The solvent was evaporated to give the title compound as a beige solid (58 mg, 0.115 mmol, 50.1% yield).
LCMS (2 min, Formic): Rt=0.59 min, MH$^+$=503.

Example 169

(R)-5-methyl-2-((2-methyl-4-(methylsulfonyl)piperazin-1-yl)methyl)-7-(2-(2-(2-oxopyrrolidin-1-yl)ethoxy)pyridin-4-yl)thieno[3,2-c]pyridin-4(5H)-one

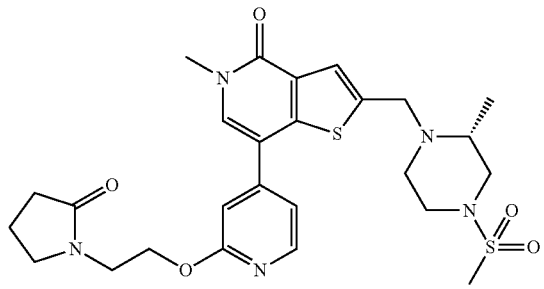 [SMILES: C[C@@H]1CN(S(C)(=O)=O)CCN1Cc1cc2c(=O)n(C)cc(-c3ccnc(OCCN4CCCC4=O)c3)c2s1]

To a suspension of (R)-7-bromo-5-methyl-2-((2-methyl-4-(methylsulfonyl)piperazin-1-yl)methyl)thieno[3,2-c]pyridin-4(5H)-one (Intermediate 21) (100 mg, 0.230 mmol), crude 1-(2-((4-(4,4,5,5-tetramethyl-1,3,2-dioxaborolan-2-yl)pyridin-2-yl)oxy)ethyl)pyrrolidin-2-one (Intermediate 116) (361 mg, 42% w/w, 0.456 mmol) and potassium carbonate (95 mg, 0.691 mmol) in 1,2-DME (3 mL) in a microwave vial, was added tetrakis(triphenylphosphine)palladium(0) (13.30 mg, 0.012 mmol). The vial was sealed and placed in a Biotage Initiator microwave for 2 hr to 120° C. The mixture was diluted with EtOAc (20 mL) and water (20 mL). Two layers separated and the aqueous phase was extracted by EtOAc (3×20 mL). The combined organics were dried using a hydrophobic frit and concentrated in vacuo to give a brown oil. The residue was dissolved in DMSO (3 mL) and purified by MDAP. Appropriate fractions were combined and concentrated in vacuo. The residue was dissolved in DMSO (1 mL) and again purified by MDAP. Appropriate fractions were combined and reduced in vacuo to give the title compound as a clear oil (14 mg, 10.9% yield).

LCMS (2 min, High pH): Rt=0.82 min, MH$^+$=560.

Example 170

(R)-7-(5-(cyclopropyl methoxy)pyridin-3-yl)-5-methyl-2-((2-methyl-4-(methylsulfonyl)piperazin-1-yl)methyl)thieno[3,2-c]pyridin-4(5H)-one

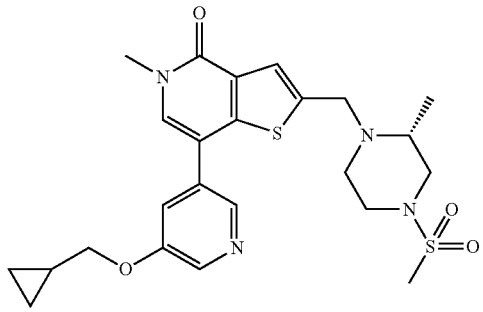

To a stirred suspension of crude (3-(cyclopropylmethoxy)-5-(4,4,5,5-tetramethyl-1,3,2-dioxaborolan-2-yl)pyridine (Intermediate 117) (619 mg, 23% w/w, 0.517 mmol) in 1,2-DME (4 mL), was added potassium carbonate (293 mg, 2.118 mmol), (R)-7-bromo-5-methyl-2-((2-methyl-4-(methylsulfonyl)piperazin-1-yl)methyl)thieno[3,2-c]pyridin-4(5H)-one (Intermediate 21) (130 mg, 0.3 mmol) and tetrakis(triphenylphosphine) palladium (0) (0.015 g, 0.013 mmol). This was sealed in a microwave vial and heated in a Biotage microwave for 120° C. for 2 hr. Further (R)-7-bromo-5-methyl-2-((2-methyl-4-(methylsulfonyl)piperazin-1-yl)methyl)thieno[3,2-c]pyridin-4(5H)-one (50 mg) was then added together with tetrakis(triphenylphosphine) palladium (0) (5 mg). The reaction was heated in the microwave at 120° C. for a further 1 hr. The reaction was diluted with EtOAc (30 mL) and water (30 mL). Two layers separated and the aqueous layer was re-extracted with EtOAc (3×30 mL). The solvent was evaporated to dryness under reduced pressure. The residue was dissolved in DMSO (5 mL) and purified by MDAP. Appropriate fractions were combined and concentrated in vacuo. The residue was dissolved in MeOH and loaded on an SCX cartridge (1 g). The product was eluted with 2M ammonia in MeOH. Appropriate fractions were combined and concentrated in vacuo to give the title compound as a brown oil (26.4 mg, 17.5%).

LCMS (2 min, High pH): Rt=0.97 min, MH$^+$=503.

Example 171

2-((3-hydroxypiperidin-1-yl)methyl)-7-(2-methoxypyridin-4-yl)-5-methylthieno[3,2-c]pyridin-4(5H)-one

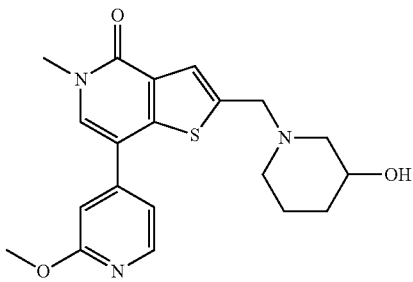 [SMILES: COc1cc(-c2cn(C)c(=O)c3cc(CN4CCCC(O)C4)sc23)ccn1]

7-Bromo-2-((3-hydroxypiperidin-1-yl)methyl)-5-methylthieno[3,2-c]pyridin-4(5H)-one (Intermediate 118) (125 mg, 0.35 mmol), 2-methoxy-4-(4,4,5,5-tetramethyl-1,3,2-dioxaborolan-2-yl)pyridine (Intermediate 112) (94 mg, 0.4 mmol), bis(triphenylphosphine)palladium(II) chloride (12.28 mg, 0.018 mmol) and potassium carbonate (145 mg, 1.050 mmol) in 1,2-DME (3 mL) and water (0.5 mL) were mixed together and heated in the microwave for 1 hr to 120° C. Further bis(triphenylphosphine)palladium(II) chloride (12.28 mg, 0.018 mmol) was added and the reaction was heated in the microwave to 120° C. for 3 hr. The solution was extracted with EtOAc and washed with water. The aqueous and organic layers were filtered together and then separated. The organic layer was filtered through a hydrophobic frit and concentrated in vacuo and purified by MDAP. Fractions containing product were combined and concentrated in vacuo then dissolved in MeOH and loaded onto a 2 g aminopropyl column which was eluted with MeOH. The eluent was concentrated then re-dissolved in MeOH then loaded onto 500 mg SCX cartridge. Elution with 2M ammonia in MeOH then concentration in vacuo gave the title compound as a colourless solid (10 mg, 0.026 mmol, 7.4% yield).

LCMS (2 min, Formic Acid): Rt=0.55 min, MH$^+$=386.

Example 172

7-(2-ethoxypyridin-4-yl)-2-((3-hydroxypiperidin-1-yl)methyl)-5-methylthieno[3,2-c]pyridin-4(5H)-one

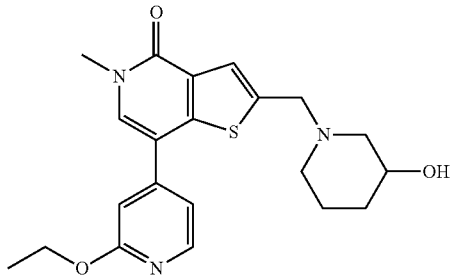 [SMILES: CCOc1cc(-c2cn(C)c(=O)c3cc(CN4CCCC(O)C4)sc23)ccn1]

7-Bromo-2-((3-hydroxypiperidin-1-yl)methyl)-5-methylthieno[3,2-c]pyridin-4(5H)-one (Intermediate 118) (118 mg, 0.33 mmol), tetrakis(triphenylphosphine) palladium (0) (19.07 mg, 0.017 mmol), sodium carbonate (280 mg, 2.64 mmol) and 2-ethoxy-4-(4,4,5,5-tetramethyl-1,3,2-dioxaborolan-2-yl)pyridine (Intermediate 107) (92 mg, 0.371 mmol) in 1,2-DME (4 mL) were mixed and heated in the microwave for 2 hr at 120° C. PEPPSI (11.24 mg, 0.017 mmol) was added and the reaction was heated to 120° C. for 1.5 hr. The reaction was diluted with EtOAc and water and filtered then the organic layer was separated and concentrated in vacuo to give the crude product which was purified by silica gel column chromatography [0-5% MeOH in DCM]. Fractions containing product were concentrated in vacuo then further purified by MDAP. Fractions containing product were concentrated in vacuo then dissolved in MeOH, loaded onto a 2 g aminopropyl column. Elution with MeOH then concentration in vacuo gave the title compound as a white solid (10 mg, 0.025 mmol, 7.6% yield).

LCMS (2 min, Formic Acid): Rt=0.61 min, MH$^+$=400.

Example 173

(R)-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)propionamide

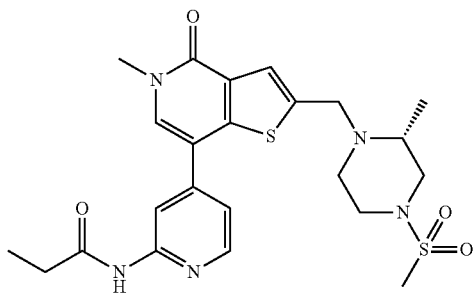 [SMILES: CCC(=O)Nc1cc(-c2cn(C)c(=O)c3cc(CN4CCN(S(C)(=O)=O)C[C@H]4C)sc23)ccn1]

N-(4-(4,4,5,5-Tetramethyl-1,3,2-dioxaborolan-2-yl)pyridin-2-yl)propionamide (Intermediate 113) (80 mg, 0.291 mmol), (R)-7-bromo-5-methyl-2-((2-methyl-4-(methylsulfonyl)piperazin-1-yl)methyl)thieno[3,2-c]pyridin-4(5H)-one (Intermediate 21) (115 mg, 0.265 mmol), tetrakis(triphenylphosphine) palladium (0) (15.30 mg, 0.013 mmol) and aqueous sodium carbonate (1.059 mL, 2.118 mmol) were mixed and heated in the microwave for 2 hr at 120° C. The reaction was diluted with EtOAc and water and filtered then the organic layer was separated and concentrated in vacuo to give the crude product which was purified by MDAP. Fractions containing product were concentrated in vacuo then further purified by MDAP twice. Fractions containing product were combined, concentrated in vacuo, dissolved in MeOH and eluted through a 1 g aminopropyl cartridge with MeOH. The solvent was removed in vacuo to give the title compound (23 mg, 0.046 mmol, 17.25% yield).

LCMS (2 min, Formic Acid): Rt=0.58 min, MH$^+$=504.

Example 174

(R)-2-cyclopropyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide

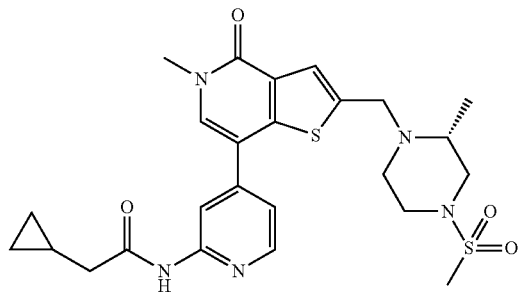 [SMILES: C[C@@H]1CN(S(C)(=O)=O)CCN1Cc1cc2c(=O)n(C)cc(-c3ccnc(NC(=O)CC4CC4)c3)c2s1]

N-(4-(4,4,5,5-Tetramethyl-1,3,2-dioxaborolan-2-yl)pyridin-2-yl)cyclopropanecarboxamide (Intermediate 114) (93 mg, 0.322 mmol), (R)-7-bromo-5-methyl-2-((2-methyl-4-(methylsulfonyl)piperazin-1-yl)methyl)thieno[3,2-c]pyridin-4(5H)-one (Intermediate 21) (120 mg, 0.276 mmol), tetrakis(triphenylphosphine) palladium (0) (15.96 mg, 0.014 mmol) and aqueous sodium carbonate (1.105 mL, 2.210 mmol) were mixed in 1,2-DME (3 mL), and heated in the microwave for 2 hr at 120° C. The reaction was diluted with EtOAc and water then filtered. The organic layer was separated and concentrated in vacuo to give the crude product which was purified by MDAP. Fractions containing product were concentrated in vacuo to give the title compound as a white solid (25 mg, 0.048 mmol, 17.6% yield).

LCMS (2 min, High pH): Rt=0.84 min, MH$^+$=516.

Example 175

(R)-N-methyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide

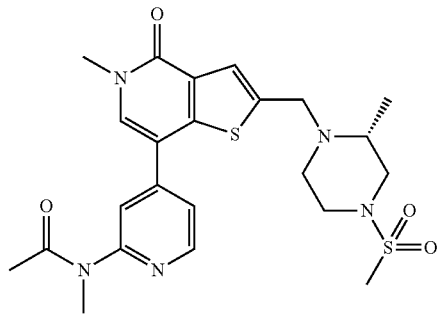 [SMILES: CC(=O)N(C)c1cc(-c2cn(C)c(=O)c3cc(CN4CCN(S(C)(=O)=O)C[C@H]4C)sc23)ccn1]

(N-Methyl-N-(4-(4,4,5,5-tetramethyl-1,3,2-dioxaborolan-2-yl)pyridin-2-yl)acetamide (Intermediate 115) (85 mg, 0.309 mmol), (R)-7-bromo-5-methyl-2-((2-methyl-4-(methylsulfonyl)piperazin-1-yl)methyl)thieno[3,2-c]pyridin-4(5H)-one (Intermediate 21) (115 mg, 0.265 mmol), tetrakis(triphenylphosphine) palladium (0) (15.30 mg, 0.013 mmol) and aqueous sodium carbonate (1.059 mL, 2.118 mmol) were mixed in 1,2-DME (3 mL), and heated in the microwave for 2 hr at 120° C. The reaction was diluted with EtOAc and water then filtered. The organic layer was separated and concentrated in vacuo to give the crude product which was purified by MDAP. Fractions containing product were concentrated in vacuo, dissolved in MeOH and passed down a 5 g aminopropyl column eluting with MeOH. The solvent was evaporated and the resulting solid was purified by MDAP to give the title compound as a colourless solid (12 mg, 0.024 mmol, 9.0% yield).

LCMS (2 min, High pH): Rt=0.75 min, MH$^+$=504.

Example 176

(R)-N-(6-(cyclopropylmethoxy)-4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide

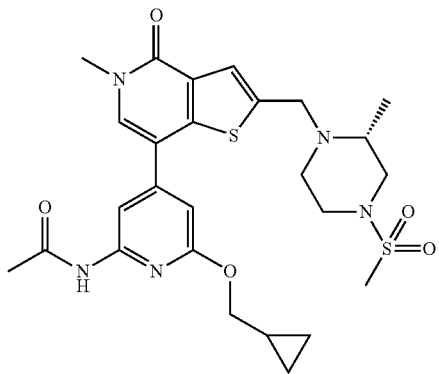 [SMILES: CC(=O)Nc1cc(-c2cn(C)c(=O)c3cc(CN4CCN(S(C)(=O)=O)C[C@H]4C)sc23)cc(OCC2CC2)n1]

To a stirred suspension of (R)-7-(2-chloro-6-(cyclopropylmethoxy)pyridin-4-yl)-5-methyl-2-((2-methyl-4-(methylsulfonyl)piperazin-1-yl)methyl)thieno[3,2-c]pyridin-4(5H)-one (Intermediate 121) (30 mg, 0.056 mmol), cesium carbonate (24 mg), acetamide (4 mg) and Xantphos (3 mg) in 1-4-dioxane (1 mL), was added Pd$_2$(dba)$_3$ (2 mg). The reaction was left to reflux for 24 hr. Further cesium carbonate (24 mg), acetamide (4 mg), Xantphos (3 mg) and Pd$_2$(dba)$_3$ (2 mg) were added and the reaction was refluxed for an additional 18 hr. The mixture was then placed into a microwave vial and heated to 120° C. for 2 hr in a microwave reactor.

Further cesium carbonate (24 mg), acetamide (4 mg) and Xantphos (3 mg) and Pd$_2$(dba)$_3$ (2 mg) were added and the reaction was heated in the microwave at 160° C. for 2 hr. The mixture was dissolved in water (20 mL) and DCM (20 mL) and the two layers were separated. The aqueous phase was re-extracted with DCM (3×20 mL). All phases were re-combined combined and concentrated in vacuo. The residue was dissolved in DMSO (1 mL) and purified by MDAP.

Appropriate fractions were combined and concentrated in vacuo. The residue was dissolved in DMSO (1 mL) and again purified by MDAP. Appropriate fractions were combined and reduced in vacuo to give the title compound as a yellow oil (8 mg, 34.6%).

LCMS (2 min, High pH): Rt=1.01 min, MH$^+$=560.

Example 177

2-((1,4-oxazepan-4-yl)methyl)-5-methyl-7-(2-((tetrahydro-2H-pyran-4-yl)methoxy)pyridin-4-yl)thieno[3,2-c]pyridin-4(5H)-one

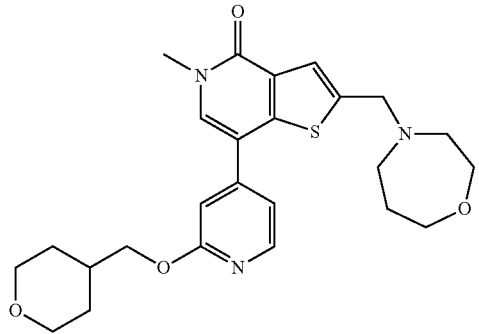 [SMILES: Cn1cc(-c2ccnc(OCC3CCOCC3)c2)c2sc(CN3CCCOCC3)cc2c1=O]

A mixture of 2-((1,4-oxazepan-4-yl)methyl)-7-bromo-5-methylthieno[3,2-c]pyridin-4(5H)-one (Intermediate 42) (150 mg, 0.42 mmol), 2-((tetrahydro-2H-pyran-4-yl)methoxy)-4-(4,4,5,5-tetramethyl-1,3,2-dioxaborolan-2-yl)pyridine hydrochloride (ex. BoroPharm Inc.) (224 mg, 0.63 mmol), potassium carbonate (290 mg, 2.10 mmol) and bis(triphenylphosphine)palladium(II) chloride (30 mg, 10 mol %) in ethanol (2 mL) and toluene (2 mL) was heated in a microwave at 130° C. for 45 minutes. The reaction mixture was cooled and another portion of bis(triphenylphosphine)palladium(II) chloride (31 mg, 10 mol %) was added. The reaction mixture was heated in a microwave at 130° C. for 45 minutes. The cooled reaction mixture was filtered through Celite. The filtrate was treated with potassium carbonate (290 mg, 2.10 mmol) and bis(triphenylphosphine)palladium(II) chloride (30 mg, 10 mol %) and the mixture heated in the microwave at 130° C. for 45 minutes. The cooled reaction mixture was diluted with EtOAc (20 mL). The mixture was dried over sodium sulphate, filtered and the solvent was evaporated from the filtrate. The residue was purified by silica gel column chromatography [0-2% MeOH/EtOAc]. The product was triturated with diethyl ether to give the title compound as a white solid (157 mg, 0.334 mmol, 80% yield).

LCMS (2 min, Formic Acid): Rt=0.65 min, MH$^+$=470.

Example 178

5-methyl-2-(morpholinomethyl)-7-(2-((tetrahydro-2H-pyran-4-yl)methoxy)pyridin-4-yl)thieno[3,2-c]pyridin-4(5H)-one

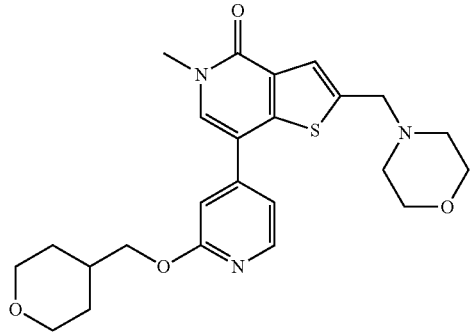 [SMILES: Cn1cc(-c2ccnc(OCC3CCOCC3)c2)c2sc(CN3CCOCC3)cc2c1=O]

A mixture of 7-bromo-5-methyl-2-(morpholinomethyl)thieno[3,2-c]pyridin-4(5H)-one (Intermediate 122) (150 mg, 0.44 mmol), 2-((tetrahydro-2H-pyran-4-yl)methoxy)-4-(4,4,5,5-tetramethyl-1,3,2-dioxaborolan-2-yl)pyridine hydrochloride (233 mg, 0.66 mmol), potassium carbonate (302 mg, 2.18 mmol) and bis(triphenylphosphine)palladium(II) chloride (31 mg, 10 mol %) in ethanol (2 mL) and toluene (2 mL) was heated in a microwave at 130° C. for 45 minutes. The reaction mixture was cooled and another portion of bis(triphenylphosphine)palladium(II) chloride (31 mg, 10 mol %) was added. The reaction mixture was heated in a microwave at 130° C. for 45 minutes. The cooled reaction mixture was diluted with EtOAc (20 mL). The mixture was dried over sodium sulphate, filtered and the solvent was evaporated from the filtrate. The residue was purified by silica gel column chromatography [0-2% MeOH/EtOAc]. The product was triturated with diethyl ether to give the title compound as an off-white solid (35 mg, 0.077 mmol, 17.6% yield).

LCMS (2 min, Formic Acid): Rt=0.64 min, MH+=456.

Example 179

2-((1,4-diazepan-1-yl)methyl)-5-methyl-7-(2-((tetrahydro-2H-pyran-4-yl)methoxy)pyridin-4-yl)thieno[3,2-c]pyridin-4(5H)-one

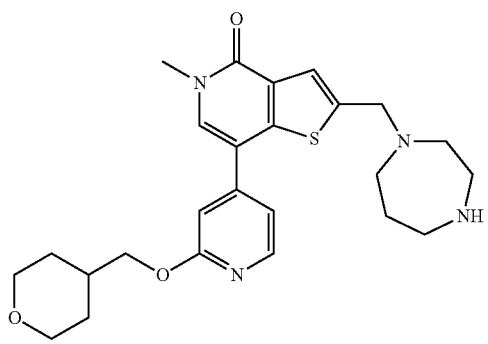 [SMILES: Cn1cc(-c2ccnc(OCC3CCOCC3)c2)c2sc(CN3CCCNCC3)cc2c1=O]

To a solution of tert-butyl 4-((5-methyl-4-oxo-7-(2-((tetrahydro-2H-pyran-4-yl)methoxy)pyridin-4-yl)-4,5-dihydrothieno[3,2-c]pyridin-2-yl)methyl)-1,4-diazepane-1-carboxylate (Intermediate 125) (400 mg, 0.703 mmol) in MeOH (30 mL) was added a solution of hydrogen chloride in 1,4-dioxane (2 mol/L, 10.0 mL) and the solution was stirred at rt for 2 hr. The solvent was evaporated. The residue was dissolved in DCM (50 mL). The organic phase was washed with saturated sodium carbonate (3×50 mL) and dried over sodium sulphate to give the crude product as a yellow oil. The crude product was purified by silica gel column chromatography eluting with DCM/MeOH (20/1) to give the title compound (231 mg, 0.493 mmol, 70.1% yield) as yellow solid.

LCMS: MH+=469

Example 180

5-methyl-2-((4-methyl-1,4-diazepan-1-yl)methyl)-7-(2-((tetrahydro-2H-pyran-4-yl)methoxy)pyridin-4-yl)thieno[3,2-c]pyridin-4(5H)-one

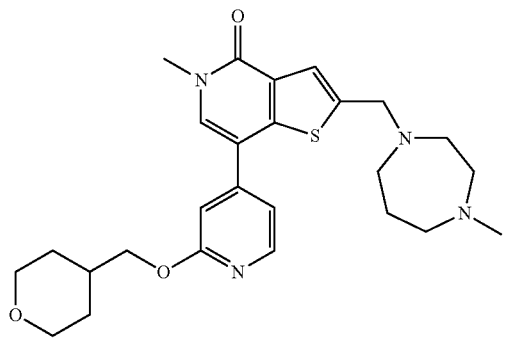 [SMILES: CN1CCCN(Cc2cc3c(=O)n(C)cc(-c4ccnc(OCC5CCOCC5)c4)c3s2)CC1]

To a solution of 2-((1,4-diazepan-1-yl)methyl)-5-methyl-7-(2-((tetrahydro-2H-pyran-4-yl)methoxy)pyridin-4-yl)thieno[3,2-c]pyridin-4(5H)-one (Example 179) (115 mg, 0.245 mmol) in MeOH (20 mL) was added formaldehyde (36.8 mg, 1.227 mmol) and acetic acid (0.2 mL). The solution was stirred for 1.5 hr, then NaCNBH3 (154 mg, 2.454 mmol) was added and the solution was stirred for 2 hr. The reaction mixture was combined with that from an additional experiment (using 100 mg starting material Example 179) and concentrated. The crude product was purified by silica gel column chromatography eluting with DCM/MeOH (20/1) to give the title compound (101 mg, 0.209 mmol, 85% yield) as a light yellow solid.

LCMS: MH+=483

Example 181

2-((1,4-diazepan-1-yl)methyl)-5-methyl-7-(2-((pyridin-2-ylmethyl)amino)pyridin-4-yl)thieno[3,2-c]pyridin-4(5H)-one

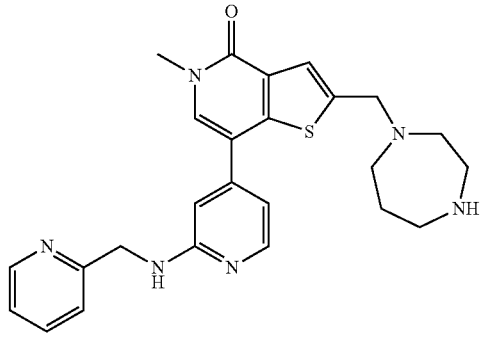 [SMILES: Cn1cc(-c2ccnc(NCc3ccccn3)c2)c2sc(CN3CCCNCC3)cc2c1=O]

To a solution of tert-butyl 4-((5-methyl-4-oxo-7-(2-((pyridin-2-ylmethyl)amino)pyridin-4-yl)-4,5-dihydrothieno[3,2-c]pyridin-2-yl)methyl)-1,4-diazepane-1-carboxylate (Intermediate 128) (280 mg, 0.499 mmol) in EtOAc (10 mL) stirred under nitrogen at rt was added a solution of hydrogen chloride (1460 mg, 40 mmol) in 1,4-dioxane (10 mL). The reaction mixture was stirred at rt for 20 hr. Some solid precipitated. The mixture was filtered and the filtered cake was washed with EtOAc (10 mL) and dried in vacuo to obtain a crude product. The crude product was purified by Pre-HPLC using water and MeCN as solvents with a formic acid modifier. This did not give clean purification, so the residue from this was purified by Pre-HPLC using water and MeCN as solvents with a TFA modifier [on a Waters Gemini C18 (150×21.2 mm, 5 um), eluting with 0.1% v/v solution of TFA in water (Solvent A) and MeCN (Solvent B), using the following elution gradient of 0-30% Solvent B over 15 min at a flow rate of 20 mL/min. The UV detection wavelength: 214 nm]. The product containing fraction was treated with 0.5 mL conc. HCl, and then concentrated to afford the 2HCl salt of the title compound (170 mg, 0.319 mmol, 63.8% yield) as an off-white solid.

LCMS: MH+=461

Example 182

2-((1,4-diazepan-1-yl)methyl)-5-methyl-7-(3-(pyridin-2-ylmethoxy)phenyl)thieno[3,2-c]pyridin-4(5H)-one

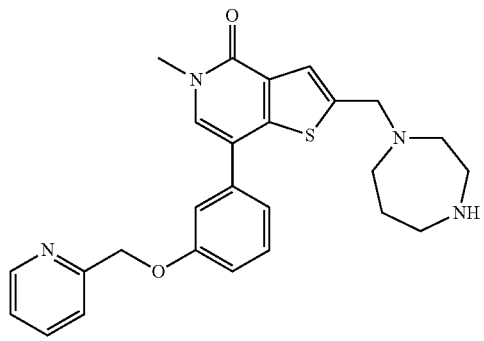 [SMILES: Cn1cc(-c2cccc(OCc3ccccn3)c2)c2sc(CN3CCCNCC3)cc2c1=O]

The 2HCl salt of the title compound was prepared from Intermediate 131 as a pale yellow solid using a method similar to that described for Example 181 (180 mg, 0.337 mmol, 67.6% yield).

LCMS: MH+=461

Example 183

2-((1,4-diazepan-1-yl)methyl)-5-methyl-7-(2-(pyridin-2-ylmethoxy)pyridin-4-yl)thieno[3,2-c]pyridin-4(5H)-one

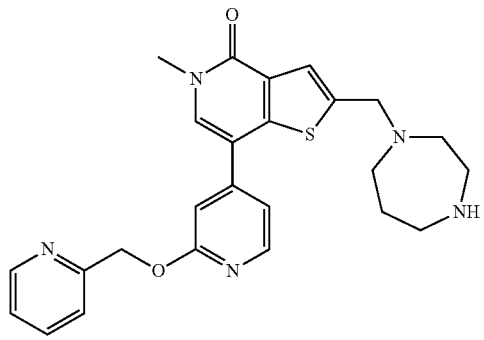 [SMILES: Cn1cc(-c2ccnc(OCc3ccccn3)c2)c2sc(CN3CCCNCC3)cc2c1=O]

To a solution of tert-butyl 4-((5-methyl-4-oxo-7-(2-(pyridin-2-ylmethoxy)pyridin-4-yl)-4,5-dihydrothieno[3,2-c]pyridin-2-yl)methyl)-1,4-diazepane-1-carboxylate (Intermediate 134) (340 mg, 0.424 mmol) in DCM (10 mL) stirred under nitrogen at rt was added trifluoroacetic acid (5 mL, 64.9 mmol). The reaction mixture was stirred at rt for 2 hr. The reaction mixture was concentrated and to the residue was added DCM (100 mL). The organic phase was washed with saturated sodium bicarbonate solution 50 mL, saturated brine 50 mL, dried over sodium sulphate and evaporated in vacuo to give the crude product which was purified by Pre-HPLC on a Waters Gemini C18 (150×21.2 mm, 5 um) eluting with 0.05% v/v solution of NH3 in Water (Solvent A) and MeCN (Solvent B), using the following elution gradient of 20-70% Solvent B over 15 min at a flow rate of 20 mL/min.

The UV detection wavelength: 214 nm. The appropriate fractions were combined and evaporated in vacuo to give the title compound (121 mg, 0.262 mmol, 61.9% yield) as a yellow glass.

LCMS: MH+=462.

Example 184

2-((1,4-diazepan-1-yl)methyl)-7-(2-(benzyloxy)pyridin-4-yl)-5-methylthieno[3,2-c]pyridin-4(5H)-one

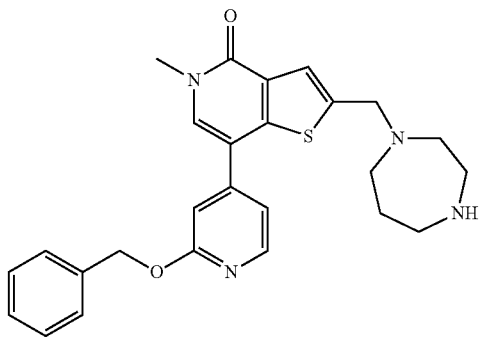 [SMILES: Cn1cc(-c2ccnc(OCc3ccccc3)c2)c2sc(CN3CCCNCC3)cc2c1=O]

To a solution of tert-butyl 4-((7-(2-(benzyloxy)pyridin-4-yl)-5-methyl-4-oxo-4,5-dihydrothieno[3,2-c]pyridin-2-yl)methyl)-1,4-diazepane-1-carboxylate (Intermediate 137) (340 mg, 0.606 mmol) in DCM (10 mL) stirred under nitrogen at rt was added trifluoroacetic acid (5 mL, 64.9 mmol). The reaction mixture was stirred at rt for 2 hr. The reaction mixture was concentrated and to the residue was added DCM (100 mL). The organic phase was washed with saturated sodium bicarbonate solution (50 mL) and saturated brine (50 mL), then dried over sodium sulphate and evaporated in vacuo. The crude product was purified by Pre-HPLC on a chiralpak-IA (250×20 mm, 5 um) column eluting with 0.2% v/v solution of diethylamine in EtOH (Solvent A) and Hexane (Solvent B), using the following elution gradient of 50-50% Solvent B over 30 min at a flow rate of 14 mL/min. The UV detection wavelength: 214 nm. The appropriate fractions were combined and evaporated in vacuo to give the title compound (171 mg, 0.371 mmol, 61.2% yield) as a yellow glass.

LCMS: MH+=461.

Example 185

1-((7-(3,4-dimethoxyphenyl)-5-methyl-4-oxo-4,5-dihydrothieno[3,2-c]pyridin-2-yl)methyl)-N,3-dimethylpiperidine-3-carboxamide

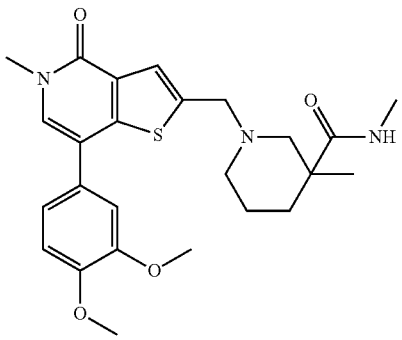

A solution of 7-(3,4-dimethoxyphenyl)-5-methyl-4-oxo-4,5-dihydrothieno[3,2-c]pyridine-2-carbaldehyde (Intermediate 25) (100 mg, 0.304 mmol), N,3-dimethylpiperidine-3-carboxamide (95 mg, 0.607 mmol) and sodium triacetoxyborohydride (193 mg, 0.911 mmol) in 1,2-DCE (20 mL) was stirred under nitrogen at rt for 17 hr. The mixture was washed with NaHCO$_3$ solution (5 mL) and the organic layer was dried over Na$_2$SO$_4$. The solvent was evaporated in vacuo to give the crude product. The crude product was purified by silica gel column chromatography eluting with DCM/MeOH (20:1) to give the title compound (60 mg, 0.126 mmol, 41.7% yield) as a white solid.

LCMS: MH$^+$=470.

Example 186

7-(3,4-dimethoxyphenyl)-2-((3-(hydroxymethyl)-3-methylpiperidin-1-yl)methyl)-5-methylthieno[3,2-c]pyridin-4(5H)-one

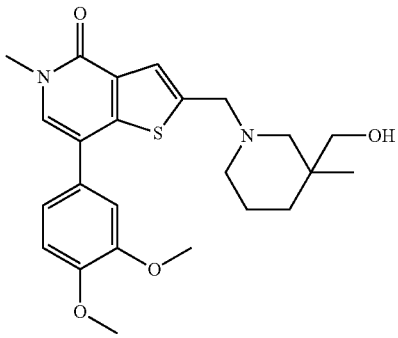 [SMILES: COc1ccc(-c2cn(C)c(=O)c3cc(CN4CCCC(C)(CO)C4)sc23)cc1OC]

A solution of 7-(3,4-dimethoxyphenyl)-5-methyl-4-oxo-4,5-dihydrothieno[3,2-c]pyridine-2-carbaldehyde (Intermediate 25) (200 mg, 0.607 mmol), (3-methylpiperidin-3-yl)methanol (Intermediate 140) (78 mg, 0.607 mmol) and sodium triacetoxyhydroborate (386 mg, 1.822 mmol) in 1,2-DCE (30 mL) was stirred under nitrogen at rt for 17 hr. The mixture was washed with NaHCO$_3$ solution (5 mL) and the organic layer was dried with Na$_2$SO$_4$, concentrated in vacuo and purified by MDAP. 0.1 mL HCl (2M) was added to the appropriate fractions which were combined and the solvent was removed by rotary evaporation to give the title compound as a hydrochloride salt (20 mg, 0.045 mmol, 7.4% yield).

LCMS: MH$^+$=443.

Example 187

7-(3,4-dimethoxyphenyl)-2-(((1,1-dioxidotetrahydrothiophen-3-yl)amino)methyl)-5-methylthieno[3,2-c]pyridin-4(5H)-one

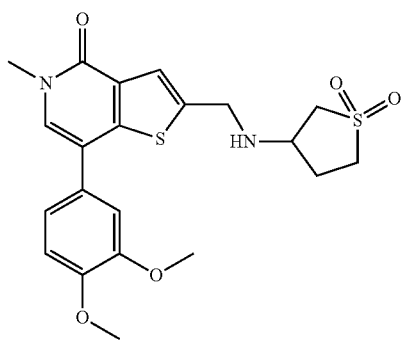 [SMILES: COc1ccc(-c2cn(C)c(=O)c3cc(CNC4CCS(=O)(=O)C4)sc23)cc1OC]

A solution of 7-bromo-2-(((1,1-dioxidotetrahydrothiophen-3-yl)amino)methyl)-5-methylthieno[3,2-c]pyridin-4(5H)-one (Intermediate 138) (233 mg, 0.595 mmol), (3,4-dimethoxyphenyl)boronic acid (130 mg, 0.715 mmol), potassium carbonate (181 mg, 1.310 mmol) and PEPPSI (37 mg, 0.054 mmol) in water (2 mL) and isopropanol (6 mL) was stirred for 30 min at 120° C. in the microwave. The reaction mixture was allowed to cool to rt, diluted with EtOAc (50 mL), filtered through Celite, passed through a hydrophobic frit and concentrated in vacuo. The resulting residue was diluted in DMSO (4.0 mL) and purified by MDAP. The appropriate fractions were combined and concentrated in vacuo to give the title compound (156 mg, 0.35 mmol, 58%) as a pale orange solid.

LCMS (2 min, Formic Acid): Rt=0.78 min, MH$^+$=449.

Example 188

7-(3,4-dimethoxyphenyl)-2-(((1,1-dioxidotetrahydro-2H-thiopyran-4-yl)amino)methyl)-5-methylthieno[3,2-c]pyridin-4(5H)-one

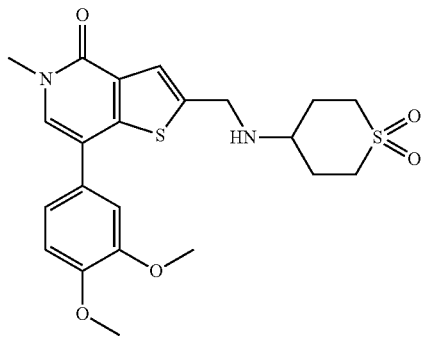 [SMILES: COc1ccc(-c2cn(C)c(=O)c3cc(CNC4CCS(=O)(=O)CC4)sc23)cc1OC]

A solution of 7-bromo-2-(((1,1-dioxidotetrahydro-2H-thiopyran-4-yl)amino)methyl)-5-methylthieno[3,2-c]pyridin-4(5H)-one (Intermediate 139) (204 mg, 0.503 mmol), (3,4-dimethoxyphenyl)boronic acid (110 mg, 0.604 mmol), PEPPSI (31 mg, 0.046 mmol) and potassium carbonate (153 mg, 1.107 mmol) in isopropanol (6 mL) and water (2 mL) was heated to 120° C. in a microwave reactor for 30 minutes. The solution was allowed to cool to rt, diluted with EtOAc (50 mL), filtered through Celite, passed through a hydrophobic frit and concentrated in vacuo. The resulting residue was dissolved in DMSO (3×1.0 mL) and purified by MDAP. The appropriate fractions were combined and concentrated in vacuo to give the title compound (118 mg, 0.26 mmol, 51%) as an off white solid.

LCMS (2 min, Formic Acid): Rt=0.60 min, MH+=463.

Example 189

7-(3,4-dimethoxyphenyl)-5-methyl-2-((methylamino)methyl)thieno[3,2-c]pyridin-4(5H)-one

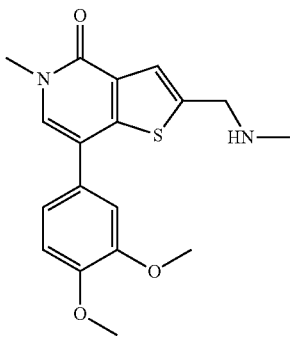

A solution of 7-bromo-5-methyl-2-((methylamino)methyl)thieno[3,2-c]pyridin-4(5H)-one (Intermediate 34) (126 mg, 0.439 mmol), (3,4-dimethoxyphenyl)boronic acid (96 mg, 0.527 mmol), PEPPSI (27 mg, 0.040 mmol) and potassium carbonate (133 mg, 0.965 mmol) in water (1 mL) and isopropanol (3 mL) was left to stir at 120° C. for 30 min in a microwave reactor. The reaction mixture was allowed to cool to rt, diluted with EtOAc (30 mL), filtered through Celite, passed through a hydrophobic frit and concentrated in vacuo. The resultant residue was dissolved in MeOH (3 mL) and passed through an Isolute NH₂ column. The appropriate fractions were collected and concentrated in vacuo.

The resultant residue was dissolved in DMSO (3×1.0 mL) and purified by MDAP. The appropriate fractions were combined and concentrated in vacuo to give the title compound (66 mg, 0.19 mmol, 44%) as a pale yellow oil.

LCMS (2 min, Formic Acid): Rt=0.58 min, MH+=345.

Example 190

7-(3,4-dimethoxyphenyl)-2-((3-(methoxymethyl)-3-methylpiperidin-1-yl)methyl)-5-methylthieno[3,2-c]pyridin-4(5H)-one

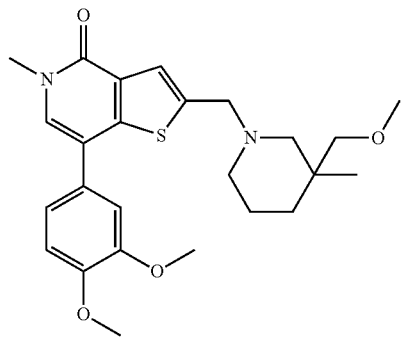

To a solution of 7-(3,4-dimethoxyphenyl)-5-methyl-4-oxo-4,5-dihydrothieno[3,2-c]pyridine-2-carbaldehyde (Intermediate 25) (460 mg, 1.396 mmol) and 3-(methoxymethyl)-3-methylpiperidine (Intermediate 143) (200 mg, 1.396 mmol) in 1,2-DCE (30 mL) stirred under nitrogen at rt, was added sodium triacetoxyborohydride (888 mg, 4.19 mmol) in 1,2-DCE (30 mL). The reaction mixture was stirred at 85° C. for 24 hr. The suspension was concentrated in vacuo and purified by MDAP. 0.1 mL HCl (2 M) was added to the fractions and the appropriate fractions were combined and the solvent was removed by rotary evaporation to give the hydrocholoride salt of the title compound (100 mg, 0.194 mmol, 13.9% yield) as an orange solid.

LCMS: MH+=457.

Example 191

2-((3-((cyclopropylmethoxy)methyl)-3-methylpiperidin-1-yl)methyl)-7-(3,4-dimethoxyphenyl)-5-methylthieno[3,2-c]pyridin-4(5H)-one

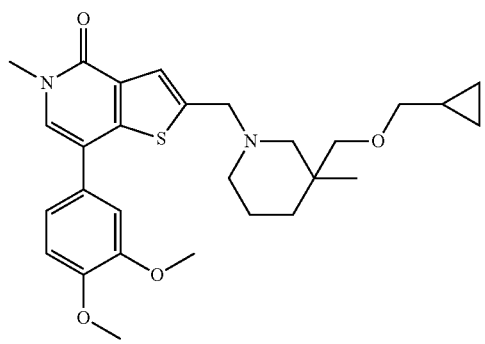 [SMILES: COc1ccc(-c2cn(C)c(=O)c3cc(CN4CCCC(C)(COCC5CC5)C4)sc23)cc1OC]

The title compound was prepared as the hydrochloride salt from Intermediates 25 and 145 using a method similar to that described for Example 190. White solid (95.6 mg, 0.175 mmol, 21.39% yield).

LCMS: MH+=497.

The following compounds of Formula (I) were also prepared:

| Example No. | Structure | Name |
|---|---|---|
| 192 | 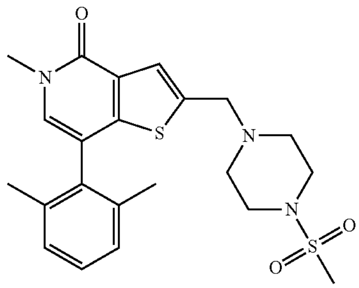 [SMILES: Cc1cccc(C)c1-c1cn(C)c(=O)c2cc(CN3CCN(S(C)(=O)=O)CC3)sc12] | 7-(2,6-dimethylphenyl)-5-methyl-2-((4-(methylsulfonyl)piperazin-1-yl)methyl)thieno[3,2-c]pyridin-4(5H)-one |
| 193 | 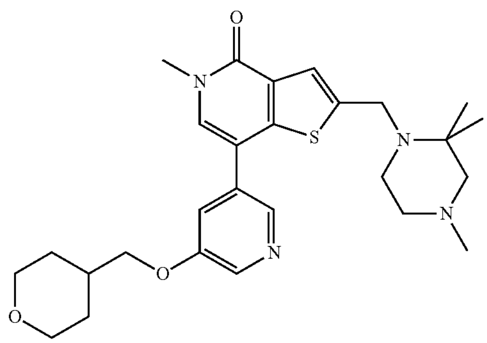 [SMILES: CN1CCN(Cc2cc3c(=O)n(C)cc(-c4cncc(OCC5CCOCC5)c4)c3s2)C(C)(C)C1] | 5-methyl-7-(5-((tetrahydro-2H-pyran-4-yl)methoxy)pyridin-3-yl)-2-((2,2,4-trimethylpiperazin-1-yl)methyl)thieno[3,2-c]pyridin-4(5H)-one |
| 194 | 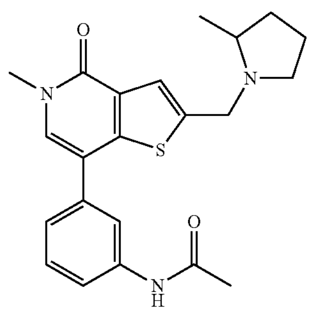 [SMILES: CC(=O)Nc1cccc(-c2cn(C)c(=O)c3cc(CN4CCCC4C)sc23)c1] | N-(3-(5-methyl-2-((2-methylpyrrolidin-1-yl)methyl)-4-oxo-4,5-dihydrothieno[3,2-c]pyridin-7-yl)phenyl)acetamide |
| 195 | 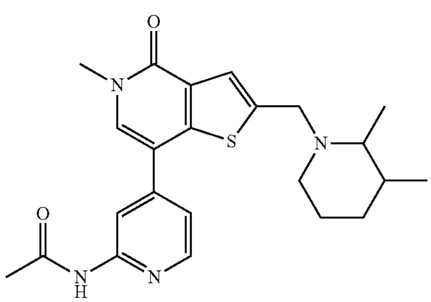 [SMILES: CC(=O)Nc1cc(-c2cn(C)c(=O)c3cc(CN4CCCC(C)C4C)sc23)ccn1] | N-(4-(2-((2,3-dimethylpiperidin-1-yl)methyl)-5-methyl-4-oxo-4,5-dihydrothieno[3,2-c]pyridin-7-yl)pyridin-2-yl)acetamide |
| 196 | 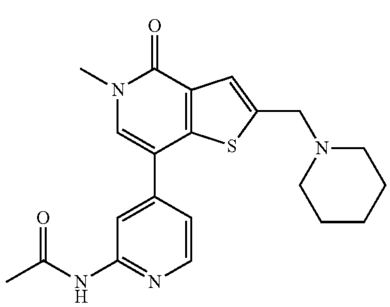 [SMILES: CC(=O)Nc1cc(-c2cn(C)c(=O)c3cc(CN4CCCCC4)sc23)ccn1] | N-(4-(5-methyl-4-oxo-2-(piperidin-1-ylmethyl)-4,5-dihydrothieno[3,2-c]pyridin-7-yl)pyridin-2-yl)acetamide |

-continued

| Example No. | Structure | Name |
|---|---|---|
| 197 | 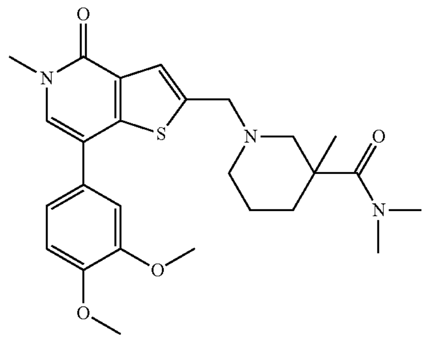 | 1-((7-(3,4-dimethoxyphenyl)-5-methyl-4-oxo-4,5-dihydrothieno[3,2-c]pyridin-2-yl)methyl)-N,N,3-trimethylpiperidine-3-carboxamide hydrochloride |
| 207 | 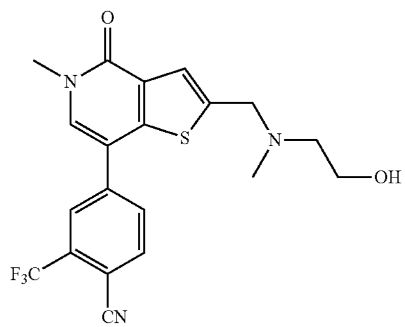 [SMILES: CN(CCO)Cc1cc2c(=O)n(C)cc(-c3ccc(C#N)c(C(F)(F)F)c3)c2s1] | 4-(2-(((2-hydroxyethyl)(methyl)amino)methyl)-5-methyl-4-oxo-4,5-dihydrothieno[3,2-c]pyridin-7-yl)-2-(trifluoromethyl)benzonitrile |

Example 198

2-((3-((cyclopropylmethoxy)methyl)-3-methylpyrrolidin-1-yl)methyl)-7-(3,4-dimethoxyphenyl)-5-methylthieno[3,2-c]pyridin-4(5H)-one To a solution of 3-((cyclopropylmethoxy)methyl)-3-methylpyrrolidine (Intermediate 149) (100 mg, 0.591 mmol) and 7-(3,4-dimethoxyphenyl)-5-methyl-4-oxo-4,5-dihydrothieno[3,2-c]pyridine-2-carbaldehyde (Intermediate 25) (214 mg, 0.650 mmol) in 1,2-DCE (5 mL) stirred under nitrogen at room temperature was added AcOH (0.1 mL) dropwise during 1 min. The reaction mixture was stirred at rt for 30 min, sodium triacetoxyborohydride (188 mg, 0.886 mmol) was added portionwise during 1 min and stirred at room temperature overnight. The reaction mixture was quenched with water and partitioned with DCM (2×50 mL). The organic phase was dried over sodium sulphate and evaporated in vacuo. The crude product was loaded onto a silica gel column that was eluted with DCM/MeOH (15:1) to give the title compound (90 mg, 0.186 mmol, 31.6% yield) as a yellow oil.
LCMS: MH+=483.

Example 199

2-((1,4-diazepan-1-yl)methyl)-5-methyl-7-(3-((pyridin-2-ylmethyl)amino)phenyl) thieno[3,2-c]pyridin-4(5H)-one hydrochloride To tert-butyl 4-((5-methyl-4-oxo-7-(3-((pyridin-2-ylmethyl)amino)phenyl)-4,5-dihydrothieno[3,2-c]pyridin-2-yl)methyl)-1,4-diazepane-1-carboxylate (Intermediate 151) (320 mg, 0.400 mmol) in DCM (50 mL) was added TFA (0.154 mL, 2.001 mmol) and the mixture was stirred overnight at rt. The solvent was removed and the residue was purified by Pre-HPLC on a Waters Gemini C18 (150×21.2 mm, 5 um) eluting with 0.1% v/v solution of formic acid in water (Solvent A) and acetonitrile(Solvent B), using the following elution gradient of 2-30% B over 20 min at a flow rate of 50 ml/min. The UV detection wavelength was 214 nm. The product containing fraction was treated with 0.5 mL conc. HCl, and then concentrated to afford the title compound (190 mg, 0.379 mmol, 95% yield) as a light orange solid.

LCMS: MH$^+$=460

Example 200

5-methyl-2-((4-methyl-1,4-diazepan-1-yl)methyl)-7-(3-((pyridin-2-ylmethyl)amino)phenyl)thieno[3,2-c]pyridin-4(5H)-one hydrochloride

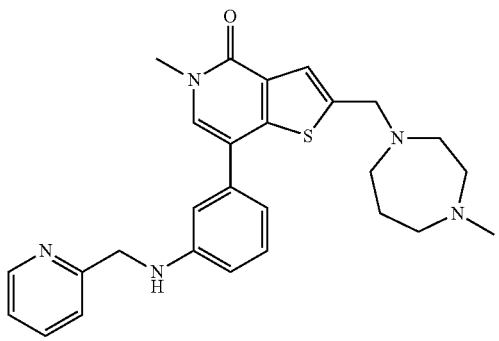 [SMILES: CN1CCCN(Cc2cc3c(=O)n(C)cc(-c4cccc(NCc5ccccn5)c4)c3s2)CC1]

A mixture of 2-((1,4-diazepan-1-yl)methyl)-5-methyl-7-(3-((pyridin-2-ylmethyl)amino)phenyl) thieno[3,2-c]pyridin-4(5H)-one (Example 199) (75 mg, 0.163 mmol), formaldehyde (4.50 μL, 0.163 mmol) and AcOH (0.934 μL, 0.016 mmol) in MeOH (30 mL) was stirred at 25° C. for 2 h. NaCNBH3 (103 mg, 1.632 mmol) was added and the mixture was stirred overnight. The mixture was concentrated in vacuo. The crude product was purified by MDAP and 0.5 mL HCl (1 M) was added to the product containing fractions which were combined and the solvent was removed by rotary evaporation to give the title compound (6 mg, 0.013 mmol, 7.76% yield) as a yellow solid.

LCMS: MH$^+$=474.

Example 201

N-(3-(2-((1,4-diazepan-1-yl)methyl)-5-methyl-4-oxo-4,5-dihydrothieno[3,2-c]pyridin-7-yl)phenyl) picolinamide hydrochloride

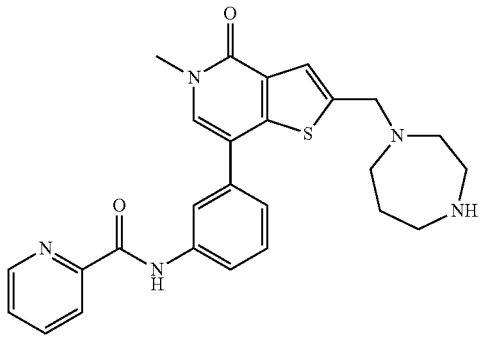 [SMILES: Cn1cc(-c2cccc(NC(=O)c3ccccn3)c2)c2sc(CN3CCCNCC3)cc2c1=O]

To a solution of tert-butyl 4-((5-methyl-4-oxo-7-(3-(picolinamido)phenyl)-4,5-dihydrothieno[3,2-c]pyridin-2-yl)methyl)-1,4-diazepane-1-carboxylate (Intermediate 153) (90 mg, 0.157 mmol) in DCM (10 mL) was added TFA (0.121 mL, 1.569 mmol). The mixture was stirred at 25° C. for 2 h. The mixture was concentrated in vacuo. The crude product was purified by MDAP and 0.5 mL HCl (1 M) was added to the product containing fractions which were combined and the solvent was removed by rotary evaporation to give the title compound (12 mg, 0.025 mmol, 16.15% yield) as a yellow solid.

LCMS: MH$^+$=474.

Example 202

2-((4-acetyl-2-methylpiperazin-1-yl)methyl)-5-methyl-7-(2-((tetrahydro-2H-pyran-4-yl)methoxy) pyridin-4-yl)thieno[3,2-c]pyridin-4(5H)-one hydrochloride

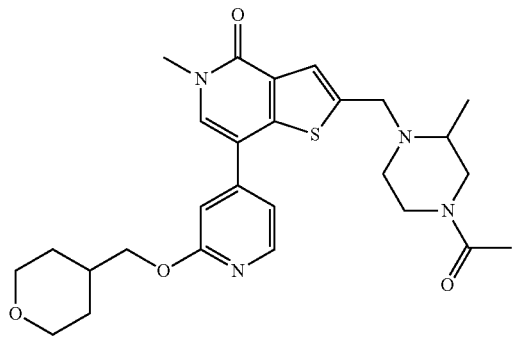 [SMILES: CC(=O)N1CCN(Cc2cc3c(=O)n(C)cc(-c4ccnc(OCC5CCOCC5)c4)c3s2)C(C)C1]

A mixture of crude 2-((4-acetyl-2-methylpiperazin-1-yl)methyl)-7-bromo-5-methylthieno[3,2-c]pyridin-4(5H)-one (Intermediate 156) (300 mg, 46% w/w, 0.346 mmol), 2-((tetrahydro-2H-pyran-4-yl)methoxy)-4-(4,4,5,5-tetramethyl-1,3,2-dioxaborolan-2-yl)pyridine (Intermediate 124) (111 mg, 0.346 mmol), tetrakis(triphenylphosphine) palladium (0) (40.0 mg, 0.035 mmol) and potassium carbonate (96 mg, 0.693 mmol) in 1,4-dioxane (50 mL) and water (10.00 mL) was stirred for 4 h at 100° C. The organic phase was extracted with DCM (200 mL), washed with saturated brine (100 mL) and water (50 mL), dried over magnesium sulphate and evaporated in vacuo to give the crude product as a orange oil. The residue was purified by Pre-HPLC on a Waters Gemini C18 (150×21.2 mm, 5 um) eluting with 0.1% v/v solution of formic acid in water (Solvent A) and acetonitrile (Solvent B), using the following elution gradient of 2-30% B over 20 min at a flow rate of 50 mL/min. The UV detection wavelength was 214 nm. The appropriate fraction was treated with 0.5 mL conc. HCl, and then concentrated to afford the title compound (118 mg, 0.214 mmol, 61.6% yield) as a yellow solid.

LCMS: MH$^+$=511.

Example 203

5-methyl-2-((2-oxopiperazin-1-yl)methyl)-7-(2-((tetrahydro-2H-pyran-4-yl)methoxy)pyridin-4-yl)thieno[3,2-c]pyridin-4(5H)-one hydrochloride

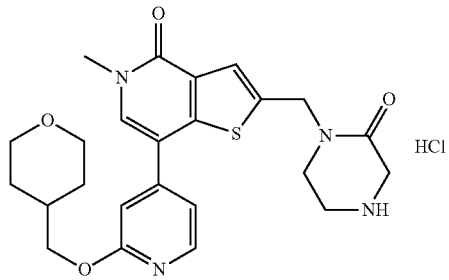 [SMILES: Cn1cc(-c2ccnc(OCC3CCOCC3)c2)c2sc(CN3CCNCC3=O)cc2c1=O ; Cl]

To the solution of tert-butyl 4-((5-methy-4-oxo-(2-(tetrahydro-2H-pyran-4-yl)methoxy)pyridin-4-yl)-4,5-dihydrothieno[3,2-c]pyridin-2-yl)methyl)-3-oxopiperazine-1-carboxylate (Intermediate 158) (750 mg, 1.319 mmol) in DCM (30 mL) was added TFA (1.016 mL, 13.19 mmol). The mixture was stirred at 25° C. for 2 h. The mixture was concentrated in vacuo, then combined with the crude products from two further experiments (carried out on 50 mg and 280 mg scale), and purified by MDAP. 0.5 mL HCl (1 M) was added to the product containing fractions which were combined and the solvent was removed by rotary evaporation to give the title compound (220 mg) as a yellow solid.

LCMS: MH$^+$=469.

Example 204

5-methyl-2-((4-methyl-2-oxopiperazin-1-yl)methyl)-7-(2-((tetrahydro-2H-pyran-4-yl)methoxy)pyridin-4-yl)thieno[3,2-c]pyridin-4(5H)-one hydrochloride

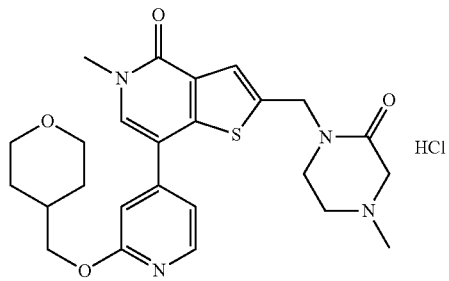 [SMILES: CN1CCN(Cc2cc3c(=O)n(C)cc(-c4ccnc(OCC5CCOCC5)c4)c3s2)C(=O)C1 ; Cl]

A mixture of 5-methyl-2-((2-oxopiperazin-1-yl)methyl)-7-(2-((tetrahydro-2H-pyran-4-yl)methoxy)pyridin-4-yl)thieno[3,2-c]pyridin-4(5H)-one (Example 203) (100 mg, 0.213 mmol), formaldehyde (0.029 mL, 1.067 mmol) and AcOH (1.2 µL, 0.021 mmol) in MeOH (20 mL) was stirred at 25° C. for 2 h. NaCNBH3 (134 mg, 2.134 mmol) was added and stirring was continued overnight. The mixture was concentrated in vacuo then combined with the crude products from a further experiment (carried out on a 10 mg scale), and purified by MDAP. 0.5 mL HCl (1 M) was added to the product containing fractions which were combined and the solvent was removed by rotary evaporation to give the title compound (70 mg, 0.145 mmol, 68.0% yield) as a yellow solid.

LCMS: MH$^+$=483.

Example 205

7-(3-(dimethylamino)phenyl)-2-(((2-hydroxyethyl)(methyl)amino)methyl)-5-methylthieno[3,2-c]pyridin-4(5H)-one

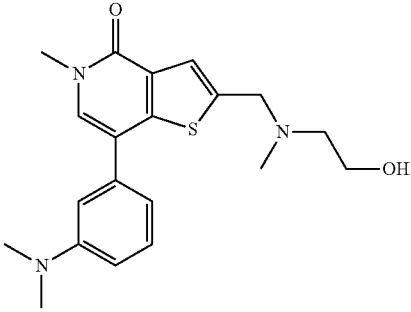 [SMILES: CN(CCO)Cc1cc2c(=O)n(C)cc(-c3cccc(N(C)C)c3)c2s1]

A mixture of 7-bromo-2-(((2-hydroxyethyl)(methyl)amino)methyl)-5-methylthieno[3,2-c]pyridin-4(5H)-one (Intermediate 159) (50 mg, 0.15 mmol), (3-(dimethylamino)phenyl)boronic acid (30 mg, 0.180 mmol), potassium carbonate (50 mg, 0.360 mmol) and PEPPSI-iPr (9.17 mg, 0.014 mmol) in water (0.3 mL) and isopropanol (0.9 mL) was heated to 120° C. in a microwave reactor for 30 min. The solution was allowed to cool to room temperature, diluted with EtOAc (3 mL), passed through a C18 1 g SPE-pre-conditioned column, rinsed with further EtOAc (3 mL) and MeOH (2 mL). The filtrate was collected and blown down under nitrogen at 40° C. and the crude product was purified by MDAP to give the title compound (5 mg, 0.013 mmol, 9% yield).

LCMS (2 min, High pH): Rt=0.93 min, MH$^+$=372.

Example 206

7-(3,4-dichlorophenyl)-2-(((2-hydroxyethyl)(methyl)amino)methyl)-5-methylthieno[3,2-c]pyridin-4(5H)-one

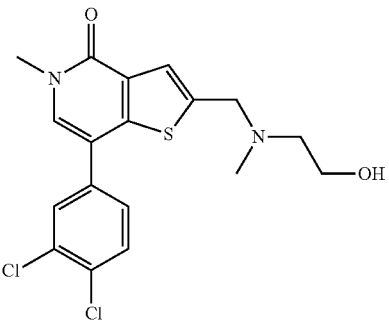 [SMILES: CN(CCO)Cc1cc2c(=O)n(C)cc(-c3ccc(Cl)c(Cl)c3)c2s1]

The title compound was prepared from Intermediate 159 and (3,4-dichlorophenyl)boronic acid using a method similar to that described for Example 205 (11 mg, 0.028 mmol, 18% yield).

LCMS (2 min, High pH): Rt=1.07 min, MH$^+$=397/399/401.

Biological Test Methods

The compounds of formula (I) may be tested in one or more of the following assays:

Time Resolved Fluorescence Resonance Energy Transfer (TR-FRET) assay

Binding was assessed using a time resolved fluorescent resonance energy transfer binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X:

4-((Z)-3-(6-((5-(2-(((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-di methyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

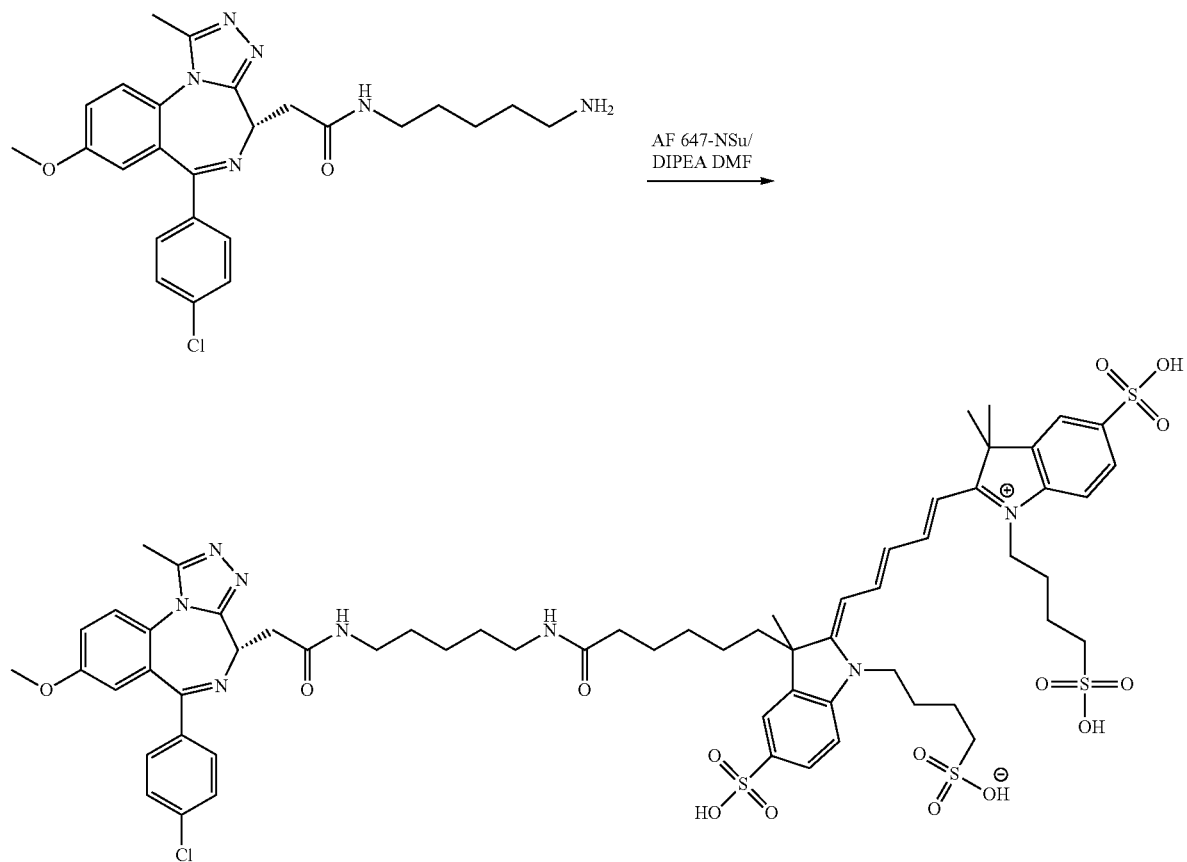

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO02011/054848A1, 1.7 mg, 3.53 μmol) in DMF (40 μl) was added a solution of AlexaFluor647-ONSu (2.16 mg, 1.966 μmol) also in DMF (100 μl). The mixture was basified with DIPEA (1 μl, 5.73 μmol) and agitated overnight on a vortex mixer.

The reaction mixture was evaporated to dryness. The solid was dissolved in acetonitrile/water/acetic acid (5/4/1, <1 mL) filtered and was applied to a Phenomenex Jupiter C18 preparative column and eluted with the following gradient (A=0.1% trifluoroacetic acid in water, B=0.1% TFA/90% acetonitrile/10% water): Flow rate=10 mL/min., AU=20/10 (214 nm): 5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B. Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/-corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle: In the absence of a competing compound, excitation of the Europium causes the donor to emit at λ618 nm which excites the Alexa labelled bromodomain binding compound leading to an increased energy transfer that is measurable at λ647 nM. In the presence of a sufficient concentration of a compound that can bind these proteins, the interaction is disrupted leading to a quantifiable drop in fluorescent resonance energy transfer.

The binding of the compounds of formula (I) to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein Production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1pl/mL protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant Assays: All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 µl of this reaction mixture was added to all wells containing 50nl of various concentrations of test compound or DMSO vehicle (0.5% DMSO final) in Greiner 384 well black low volume microtitre plates and incubated in dark for 30 minutes at room temperature. 5 µl of detection mixture containing 1.5 nM final concentration anti-6His Europium chelate was added to all wells and a further dark incubation of at least 30 minutes was performed. Plates were then read on the Envision platereader, ($\lambda$ex=317 nm, donor $\lambda$em=615 nm; acceptor $\lambda$em=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y = a + ((b-a)/(1+(10^x/10^c)^d)$$

Where 'a' is the minimum, 'b' is the Hill slope, 'c' is the pIC50 and 'd' is the maximum.

Fluorescence Polarization (FP) Assay

Binding was assessed using a fluorescence polarisation binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Assay Principle: The Bromodomain protein, fluorescent ligand (Reference compound X) and a variable concentration of test compound are incubated together to reach thermodynamic equilibrium under conditions such that in the absence of test compound the fluorescent ligand is significantly (>50%) bound and in the presence of a sufficient concentration of a potent inhibitor the fluorescence polarization of the unbound fluorescent ligand is measurably different from the bound value.

The binding of the compounds of formula (I) to Bromodomain BRD4 was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein Production: Recombinant Human Bromodomains [BRD4 (1-477) (Y97A) and (Y390A)] were expressed in *E. coli* cells (in pET15b vector) with a 6-His tag at the N-terminal. The His-tagged Bromodomain pellet was resuspended in 50 mM HEPES (pH7.5), 300 mM NaCl, 10 mM imidazole & 1µ/mL protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD4 BD1 and BD2 Mutant FP Assays: All assay components were dissolved in buffer composition of 50 mM HEPES pH7.4, 150 mM NaCl, and 1 mM CHAPS.

The final concentration of the Bromodomain proteins were 2×Kd and the Alexa Fluor647 ligand was 5 nM. These components were premixed and 10 µl of this reaction mixture was added to all wells containing 50nl of various concentrations of test compound or DMSO vehicle in Greiner 384 well black low volume microtitre plates and incubated in the dark for 45 minutes at room temperature. Plates were then read on the Envision platereader, ($\lambda$ex=620 nm, $\lambda$em=688 nm). The parallel and perpendicular fluorescence intensity were measured, converted to polarization values and used for data analysis. All data was normalized to the mean of 16 high (inhibitor control) and 16 low (DMSO) control wells on each plate. A four parameter curve fit of the following form was then applied:

$$y = a + ((b-a)/(1+(10^x/10^c)^d)$$

Where 'a' is the minimum, 'b' is the Hill slope, 'c' is the pIC50 and 'd' is the maximum.

Examples 1-207 were each tested in at least one of the TR-FRET or FP BRD2, BRD3, BRD4 or BRDT, BD1 or BD2 assays described above and were found to have a $pIC_{50} \geq 4.5$ in at least one assay.

Examples 1-34, 36-59, 61-69, 71-73, 75, 76, 78, 80, 92-113, 115-128, 135, 137, 140-146, 156, 157, 159, 161-176, 179-184, 186-188, 191, 193, 198, 199 and 201 were found to have a $pIC_{50} \geq 6.0$ in the TR-FRET or FP BRD4 BD1 assay.

Examples 1, 2, 4, 16-18, 21, 26, 28-30, 40, 47, 48, 48A, 53, 71, 97, 104-106, 115-119, 135, 164, 168, 173, 176, 181, 182, 184 and 199 were found to have a $pIC_{50} \geq 7.0$ in the TR-FRET or FP BRD4 BD1 assay.

Calculation of Selectivity for BRD4 BD1 over BRD4 BD2

Selectivity for BRD4 BD1 over BRD4 BD2 was calculated as follows:

Selectivity=BRD4BD1pIC$_{50}$–BRD4 BD2 pIC$_{50}$ $pIC_{50}$ values are expressed as $log_{10}$ units.

Examples 1-83, 90-130, 135-137, 140-191 and 198-206 were found to have selectivity for BRD4 BD1 over BRD4 BD2 of >1 log unit in at least one of the FP or TR-FRET assays described above, hence are at least 10 fold selective for BRD4 BD1 over BRD4 BD2.

Quantification of LPS Induced IL-6 Secretion from Human Whole Blood

Activation of monocytic cells by agonists of toll-like receptors such as bacterial lipopolysaccharide (LPS) leads to the activation of intracellular signaling pathways resulting in the production of key pro-inflammatory mediators including IL-6. Such pathways are widely considered to be central to the pathophysiology of a range of auto-immune and inflammatory disorders.

The impact of bromodomain inhibitors on IL-6 release was assessed in an LPS-stimulated human whole blood assay. Briefly, serial dilutions of test compounds were prepared in DMSO and 1 µL of the diluted compounds or vehicle (DMSO) was added to each well in a 96-well cell culture plate. Fresh blood was collected in heparinized tubes by venipuncture from volunteers with consent, and 130 uL/well was added in the culture plate already containing the compounds. The plates were then incubated for 30 min at 37° C. and 5% $CO_2$ before the addition of 10 µl of 2.8 µg/mL LPS diluted in 1% BSA (LPS from *Salmonella typhosa*; Sigma L 6386 at a final concentration of 200 ng/mL). After further incubation for 24 hours at 37° C. and 5% $CO_2$, 140 µl of PBS were added to each well. The plates were then sealed, shaken for 10 minutes and then centrifuged for 10 minutes at 2000 rpm. 100 µl of the supernatant were removed and IL-6 levels quantified using an MSD ELISA (MesoScale Discovery technology). Concentration response curves for each compound were generated and an $IC_{50}$ values were calculated.

Examples 1, 3, 7, 40, 97, 119 and 168 were tested in this assay and were found to have a $pIC_{50} \geq 5.0$. These data demonstrate that bromodomain inhibitors tested in the above whole blood assay inhibited the production of the key inflammatory mediator IL-6.

The invention claimed is:

1. A compound of formula (I):

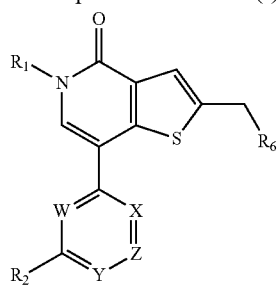

wherein:
W is N or C—$R_8$;
X is N, CH, or C(CH$_3$);
Z is N or C—$R_{14}$;
Y is N or C—$R_5$, wherein no more than 2 of W, X, Y and Z are N;
$R_1$ is $C_{1-4}$alkyl;
$R_2$ is H, OH, $C_{1-4}$alkyl, —N(CH$_3$)$_2$, —NH(CH$_3$), halo, —CF$_3$, —NH$_2$, —OC$_{1-4}$alkyl, —NHC(O)H, —NHC(O)C$_{1-4}$alkyl, —N(CH$_3$)C(O)C$_{1-4}$alkyl, —NHCH(CH$_3$)CH$_2$OCH$_3$, —N(CH$_3$)CH$_2$CH$_2$OCH$_3$, —OCH$_2$CH$_2$OCH$_3$, —OCH$_2$CH$_2$CH$_2$OH, —OCH(CH$_3$)CH$_2$OCH$_3$, or
$R_2$ is a group selected from -G-CH$_2$CH(R$_3$)(R$_4$), -G-CH(R$_3$)(R$_4$), and -G-R$_3$ wherein
G is NH, N(CH$_3$), O, C(O)NH, or NHC(O);
$R_3$ is phenyl, pyridinyl, $C_{3-7}$cycloalkyl, or a heterocycle optionally substituted by =O; and
$R_4$ is H or $C_{1-4}$ alkyl;
$R_5$ is H, $C_{1-4}$alkyl, halo, —CF$_3$, CN, OH, —OC$_{1-4}$ alkyl, —CH$_2$NH$_2$, —OCF$_3$, or —SO$_2$CH$_3$;
$R_6$ is —NR$_{11}$R$_{12}$ or a group

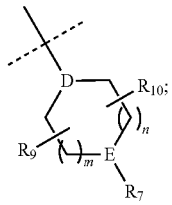

D is CH or N;
E is N, O, CH, or SO$_2$;
$R_7$, when present, is H, OH, $C_{1-4}$alkyl, —NH$_2$, —SO$_2$C$_{1-4}$ alkyl, —SO$_2$phenyl, —SO$_2$benzyl, —SO$_2$N(CH$_3$)$_2$, —NHSO$_2$CH$_3$, —C(O)C$_{1-4}$alkyl, or —C(O)phenyl;
$R_8$ is H, $C_{1-4}$alkyl, halo, —CF$_3$, CN, OH, —OC$_{1-4}$ alkyl, —OCF$_3$, —OCH$_2$phenyl or —OCH$_2$C$_{3-7}$cycloalkyl;
$R_9$ is H, $C_{1-4}$alkyl, —C(O)NH$_2$, —CO$_2$CH$_3$, —CF$_3$, halo, OH, —OC$_{1-4}$alkyl, —CH$_2$OH, —C(O)NHCH$_3$, —C(O)N(CH$_3$)$_2$, —CH$_2$OC$_{1-4}$alkyl, —CH$_2$OCH$_2$C$_{3-7}$ cycloalkyl, or oxo;
$R_{10}$ is H, $C_{1-4}$alkyl, —C(O)NH$_2$, —CO$_2$CH$_3$, —CF$_3$, halo, OH, or —OC$_1$, alkyl;
$R_{11}$ is H, $C_{1-4}$alkyl, or SO$_2$CH$_3$;
$R_{12}$ is H, $C_{1-4}$alkyl, $C_{1-4}$alkyleneNHR$_{13}$, $C_{1-4}$alkyleneOH, SO$_2$CH$_3$, a heterocycle, or a heterocycle comprising SO$_2$;
$R_{13}$ is H or SO$_2$CH$_3$;
$R_{14}$ is H, $C_{1-4}$alkyl, or NHC(O)C$_{1-4}$alkyl; and
n and m are each an integer independently selected from 0, 1 and 2; or a pharmaceutically acceptable salt thereof.

2. The compound or pharmaceutically acceptable salt thereof according to claim 1 wherein $R_8$ is hydrogen, methyl, ethyl, —OCH$_3$, fluoro, —OCH$_2$cyclopropyl, or —OCH$_2$phenyl.

3. The compound or pharmaceutically acceptable salt thereof according to claim 1 wherein X is CH.

4. The compound or pharmaceutically acceptable salt thereof according to claim 1 wherein Y is C—$R_5$.

5. The compound or pharmaceutically acceptable salt thereof according to claim 1 wherein $R_5$ is hydrogen, —OCH$_3$, fluoro, chloro, —CF$_3$, CN, methyl, —SO$_2$CH$_3$, or —CH$_2$NH$_2$.

6. The compound or pharmaceutically acceptable salt thereof according to claim 1 wherein $R_1$ is methyl.

7. The compound or pharmaceutically acceptable salt thereof according to claim 1 wherein $R_2$ is H, OH, methyl, chloro, —CF$_3$, —NH$_2$, —OCH$_3$, —OCH$_2$CH$_3$, —OCH(CH$_3$)$_2$, —NHC(O)H, —NHC(O)CH$_3$, —NHC(O)CH$_2$CH$_3$, —NHCH(CH$_3$)CH$_2$OCH, —N(CH$_3$)CH$_2$CH$_2$OCH$_3$, —N(CH$_3$)C(O)CH$_3$, —OCH$_2$CH$_2$OCH$_3$, —OCH$_2$CH$_2$CH$_2$OH, or —OCH(CH$_3$)CH$_2$OCH$_3$.

8. The compound or pharmaceutically acceptable salt thereof according to claim 1 wherein G is NH, O, or C(O)NH.

9. The compound or pharmaceutically acceptable salt thereof according to claim 1 wherein $R_3$ is phenyl, pyridinyl, cyclopropyl, tetrahydropyranyl, or tetrahydrofuranyl.

10. The compound or pharmaceutically accepatble salt thereof according to claim 1 wherein $R_2$ is a group -G-CH$_2$CH($R_3$)($R_4$).

11. A compound which is 5-methyl-2-((4-(methylsulphonyl)piperazin-1-yl)methyl)-7-(5-(1-phenylethoxy)pyridin-3-yl)thieno[3,2-c]pyridin-4(5H)-one;

5-methyl-2-((4-(methylsulphonyl)piperazin-1-yl)methyl)-7-(3-(1-(pyridin-2-yl)ethoxy)phenyl)thieno[3,2-c]pyridin-4(5H)-one;

5-methyl-2-((4-(methylsulphonyl)piperazin-1-yl)methyl)-7-(5-(1-(pyridin-2-yl)ethoxy)pyridin-3-yl)thieno[3,2-c]pyridin-4(5H)-one;

7-(5-(benzyloxy)pyridin-3-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(3-((tetrahydro-2H-pyran-4-yl)methoxy)phenyl)thieno[3,2-c]pyridin-4(5H)-one;

7-(3-isopropoxyphenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-((tetrahydro-2H-pyran-4-yl)methoxy)pyridin-4-yl)thieno[3,2-c]pyridin-4(5H)-one;

7-(3-(2-methoxyethoxy)phenyl)-5-methyl-2-((4-(methylsulphonyl)piperazin-1-yl)methyl)thieno[3,2-c]pyridin-4(5H)-one;

7-(3-(3-hydroxypropoxy)phenyl)-5-methyl-2-((4-(methysulphonyl)piperazin-1-yl)methyl)thieno[3,2-c]pyridin-4(5H)-one;

7-(3-hydroxyphenyl)-5-methy-2-((4-(methylsuphonyl)piperazin-1-yl)methyl)thieno[3,2-c]pyridin-4(5H)-one;

5-methyl-2-((4-(methylsulphonyl)piperazin-1-yl)methyl)-7-(5-((tetrahydro-2H-pyran-4-yl)methoxy)pyridin-3-yl)thieno[3,2-c]pyridin-4(5H)-one;

7-(5-hydroxyl)pyridin-3-yl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-(1-(pyridin-2-yl)ethoxy)pyridin-4-yl)thieno[3,2-c]pyridin-4(5H)-one;

7-(5-((1-methoxypropan-2-yl)oxy)pyridin-3-yl)-5-methyl-2-((4-(methylsulphonyl)piperazin-1-yl)methyl)thieno[3,2-c]pyridin-4(5H)-one;

7-(3-methoxyphenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(3-(1-phenylethoxy)phenyl)thieno[3,2-c]pyridin-4(5H)-one;

5-methyl-2-((4-(methylsulphonyl)piperazin-1-yl)methyl)-7-(3-((1-phenylethyl)amino)phenyl)thieno[3,2-c]pyridin-4(5H)-one;

(R)-N-(3-(5-methyl-2-((2-methyl-4-(methylsulphonyl)piperazin-1-yl)methyl)-4-oxo-4,5-dihydrothieno[3,2-c]pyridin-7-yl)phenyl)acetamide;

5-methyl-2-((4-(methylsulphonyl)piperazin-1-yl)methyl)-7-(3-(((tetrahydro-2H-2H-pyran-4-yl)methyl)amino)phenyl)thieno[3,2-c]pyridin-4(5H)-one;

N-(3-(5-methyl-2-((4-(methylsulphonyl)piperazin-1-yl)methyl)-4-oxo-4,5-dihydrothieno[3,2-c]pyridin-7-yl)phenyl)acetamide;

7-(2-((2-methoxyethyl)(methyl)amino)pyridin-4-yl)-5-methyl-2-((4-(methylsulphonyl)piperazin-1-yl)methyl)thieno[3,2-c]pyridin-4(5H)-one;

7-(2-((1-methoxypropan-2-yl)amino)pyridin-4-yl)-5-methyl-2-((4-(methylsulphonyl)piperazin-1-yl)methyl)thieno[3,2-c]pyridin-4(5H)-one;

7-(2-((cyclopropylmethyl)amino)pyridin-4-yl)-5-methyl-2-((4-(methylsulphonyl)piperazin-1-yl)methyl)thieno[3,2-c]pyridin-4(5H)-one;

N-(3-(5-methyl-2-((4-(methylsulphonyl)piperazin-1-yl)methyl)-4-oxo-4, 5-dihydrothieno[3,2-c]pyridin-7-yl)phenyl)formamide;

7-(3-aminophenyl)-5-methyl-2-((4-(methylsulphonyl)piperazin-1-yl)methyl)thieno[3,2-c]pyridin-4(5H)-one;

7-(3-(benzylamino)phenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(2-(((tetrahydrofuran-2-yl)methyl)amino)pyridin-4-yl)thieno[3,2-c]pyridin-4(5H)-one;

7-(3-(benzyloxy)phenyl)-2-((4-ethylpiperazin-1-yl)methyl)-5-methylthieno[3,2-c]pyridin-4(5H)-one;

7-(3-(benzyloxy)phenyl)-2-((4-isopropylpiperazin-1-yl)methyl)-5-methylthieno[3,2-c]pyridin-4(5H)-one;

2-((4-benzoylpiperazin-1-yl)methyl)-7-(3,4-dimethoxyphenyl)-5-methylthieno[3,2-c]pyridin-4(5H)-one;

7-(3,4-dimethoxyphenyl)-2-((4-(ethylsulphonyl)piperazin-1-yl)methyl)-5-methylthieno[3,2-c]pyridin-4(5H)-one;

N-(3-(5-methyl-2-((4-methylpiperazin-1-yl)methyl)-4-oxo-4,5-dihydrothieno[3,2-c]pyridin-7-yl)phenyl)acetamide;

2-((4-(benzylsulphonyl)piperazin-1-yl)methyl)-7-(3,4-dimethoxyphenyl)-5-methylthieno[3,2-c]pyridin-4(5H)-one;

7-(3,4-dimethoxyphenyl)-5-methyl-2-((4-(phenylsulphonyl)piperazin-1-yl)methyl)thieno[3,2-c]pyridin-4(5H)-one;

2-((4-acetylpiperazin-1-yl)methyl)-5-methyl-7-phenylthieno[3, 2-c]pyridin-4(5H)-one;

7-(3,4-dimethoxyphenyl)-2-((4-(isopropylsulphonyl)piperazin-1-yl)methyl)-5-methylthieno[3,2-c]pyridin-4(5H)-one;

7-(3,4-dimethoxyphenyl)-5-methyl-2-((4-methylpiperazin-1-yl)methyl)thieno[3,2-c]pyridin-4(5H)-one;

4-((7-(3,4-dimethoxyphenyl)-5-methyl-4-oxo-4, 5-dihydrothieno[3,2-c]pyridin-2-yl)methyl)-N,N-dimethylpiperazine-1-sulphonamide;

2-((4-acetylpiperazin-1-yl)methyl)-7-(3,4-dimethoxyphenyl)-5-methylthieno[3,2-c]pyridin-4(5H)-one;

7-(3-(benzyloxy)phenyl)-5-methyl-2-((4-methyl-1,4-diazepan-1-yl)methyl)thieno[3,2-c]pyridin-4(5H)-one;

N-(3-(5-methyl-2-((1-(methylsulphonyl)piperidin-4-yl)methyl)-4-oxo-4,5-dihydrothieno[3,2-c]pyridin-7-yl)phenyl)acetamide;

7-(2,4-difluorophenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(pyridin-2-yl)thieno[3,2-c]pyridin-4(5H)-one;

5-methyl-2-((4-(methylsulphonyl)piperazin-1-yl)methyl)-7-phenylthieno[3,2-c]pyridin-4(5H)-one;

2-((2,4-dimethylpiperazin-1-yl)methyl)-5-methyl-7-(5-((tetrahydro-2H-2H-pyran-4-yl)methoxy)pyridin-3-yl)thieno[3,2-c]pyridin-4(5H)-one;

2-((1,4-diazepan-1-yl)methyl)-7-(3,4-dimethoxyphenyl)-5-methylthieno[3,2-c]pyridin-4(5H)-one;

2-(((3-aminopropyl)amino)methyl)-7-(3-(benzyloxy)phenyl)-5-methylthieno[3,2-c]pyridin-4(5H)-one;

N-(2-(((7-(3-(benzyloxy)phenyl)-5-methyl-4-oxo-4, 5-dihydrothieno[3,2-c]pyridin-2-yl)methyl)amino)ethyl)methanesulphonamide;

N-((7-(3-(benzyloxy)phenyl)-5-methyl-4-oxo-4,5-dihydrothieno[3,2-c]pyridin-2-yl)methyl)-N-(2-(methylsulfonamido)ethyl)methanesulfonamide;

N-(4-(5-methyl-2-((1-(methylsulphonyl)piperidin-4-yl)methyl)-4-oxo-4,5-dihydrothieno[3,2-c]pyridin-7-yl)pyridin-2-yl)acetamide;

N-(3-(5-methyl-2-((4-methyl-1,4-diazepan-1-yl)methyl)-4-oxo-4,5-dihydrothieno[3,2-c]pyridin-7-yl)phenyl)acetamide;

7-(3,4-di methoxyphenyl)-5-methyl-2-((1-(methylsulphonyl)piperidin-4-yl)methyl)thieno[3,2-c]pyridin-4(5H)-one;

2-(((3-aminopropyl)amino)methyl)-7-(3,4-dimethoxyphenyl)-5-methylthieno[3,2-c]pyridin-4(5H)-one;

2-(((2-aminoethyl)amino)methyl)-7-(3-(benzyloxy)phenyl)-5-methylthieno[3,2-c]pyridin-4(5H)-one;

5-methyl-2-((4-(methylsulphonyl)piperazin-1-yl)methyl)-7-(pyridin-4-yl)thieno[3,2-c]pyridin-4(5H)-one;

7-(3,4-dimethoxyphenyl)-5-methyl-2-((4-(methylsulphonyl)-1,4-diazepan-1-yl)methyl)thieno[3,2-c]pyridin-4(5H)-one;

7-(3,4-dimethoxyphenyl)-5-methyl-2-((3-methyl-4-(methylsulphonyl)piperazin-1-yl)methyl)thieno[3,2-c]pyridin-4(5H)-one;

7-(3,4-dimethoxyphenyl)-5-methyl-2-((4-(methylsulphonyl)piperazin-1-yl)methyl)thieno[3,2-c]pyridin-4(5H)-one;

7-(5-methoxy-2-methylphenyl)-5-methyl-2-((4-(methylsulphonyl)piperazin-1-yl) methyl)thieno[3,2-c]pyridin-4 (5H)-one;

7-(3-methoxy-2-methylphenyl)-5-methyl-2-((4-(methylsulphonyl)piperazin-1-yl)methyl)thieno[3,2-c]pyridin-4(5H)-one;

7-(2-ethylphenyl)-5-methyl-2-((4-(methylsulphonyl)piperazin-1-yl)methyl)thieno[3,2-c]pyridin-4(5H)-one;

N-(3-(5-methyl-2-((N-methylmethylsulphonamido)methyl)-4-oxo-4,5-dihydrothieno[3,2-c]pyridin-7-yl)phenyl)acetamide;

7-(4-methoxyphenyl)-5-methyl-2-((4-(methylsulphonyl)piperazin-1-yl)methyl)thieno[3,2-c]pyridin-4(5H)-one;

5-methyl-7-(4-(methylsulphonyl)phenyl)-2-((4-(methylsulphonyl)piperazin-1-yl)methyl)thieno[3,2-c]pyridin-4(5H)-one;

7-(3,4-dimethoxyphenyl)-5-methyl-2-(piperazin-1-ylmethyl)thieno[3,2-c]pyridin-4(5H)-one;

2-(((2-aminoethyl)amino)methyl)-7-(3,4-dimethoxyphenyl)-5-methylthieno[3,2-c]pyridin-4(5H)-one;

7-(3,4-dimethoxyphenyl)-5-methyl-2-((3-methylpiperazin-1-yl)methyl)thieno[3,2-c]pyridin-4(5H)-one;

N-(2-(((7-(3,4-dimethoxyphenyl)-5-methyl-4-oxo-4,5-dihydrothieno[3, 2-c]pyridin-2-yl)methyl)amino)ethyl)methanesulphonamide;

N-((7-(3,4-dimethoxyphenyl)-5-methyl-4-oxo-4,5-dihydrothieno[3,2-c]pyridin-2-yl)methyl)-N-(2-(methylsulfonamido)ethyl)methanesulfonamide;

5-methyl-2-((4-(methylsulphonyl)piperazin-1-yl)methyl)-7-(m-tolyl)thieno[3,2-c]pyridin-4(5H)-one;

7-(3,4-dimethoxyphenyl)-2-((1,1-dioxidothiomorpholino)methyl)-5-methylthieno[3,2-c]pyridin-4(5H)-one;

(R)-7-(3,4-dimethoxyphenyl)-5-methyl-2-((3-methylmorpholino)methyl)thieno[3,2-c]pyridin-4(5H)-one;

7-(2-(benzyloxy)phenyl)-5-methyl-2-((4-(methylsulphonyl)piperazin-1-yl)methyl)thieno[3,2-c]pyridin-4(5H)-one;

5-methyl-2-((4-(methylsulphonyl)piperazin-1-yl)methyl)-7-(4-(trifluoromethyl)phenyl)thieno[3,2-c]pyridin-4(51)-one;

2-((1,4-oxazepan-4-yl)methyl)-7-(2-((2-methoxyethyl)(methyl)amino)pyridin-4-yl)-5-methylthieno[3,2-c]pyridin-4(5H)-one;

7-(3,4-dimethoxyphenyl)-2-((4-hydroxypiperidin-1-yl)methyl)-5-methylthieno[3,2-c]pyridin-4(5H)-one;

7-(4-methoxy-2-methylphenyl)-5-methyl-2-((4-(methylsulphonyl)piperazin-1-yl)methyl)thieno[3,2-c]pyridin-4(5H)-one;

4-(5-methyl-2-((4-(methylsulphonyl)piperazin-1-yl)methyl)-4-oxo-4,5-dihydrothieno[3,2-c]pyridin-7-yl)benzonitrile;

N-(4-(5-methyl-2-((3-methylmorpholino)methyl)-4-oxo-4,5-dihydrothieno[3,2-c]pyridin-7-yl)pyridin-2-yl)acetamide;

(S)-7-(3-(benzyloxy)phenyl)-5-methyl-2-((3-methylmorpholino)methyl)thieno[3,2-c]pyridin-4(5H)-one;

N-(3-(5-methyl-2-((3-methylmorpholino)methyl)-4-oxo-4,5-dihydrothieno[3,2-c]pyridin-7-yl)phenyl)acetamide;

7-(2-((2-methoxyethyl)(methyl)amino)pyridin-4-yl)-5-methyl-2-((4-(methylsulphonyl)piperidin-1-yl)methyl)thieno[3,2-c]pyridin-4(5H)-one;

(S)-7-(3-hydroxyphenyl)-5-methyl-2-((3-methylmorpholino)methyl)thieno[3,2-c]pyridin-4(5H)-one;

(S)-7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-((3-methylmorpholino)methyl)thieno[3,2-c]pyridin-4(5H)-one;

7-(3,4-dimethoxyphenyl)-5-methyl-2-(piperidin-1-ylmethyl)thieno[3,2-c]pyridin-4(5H)-one;

2-((1,4-oxazepan-4-yl)methyl)-7-(2-chloropyridin-4-yl)-5-methylthieno[3,2-c]pyridin-4(5H)-one;

7-(2-aminopyridin-4-yl)-5-methyl-2-((3-methylmorpholino)methyl)thieno[3,2-c]pyridin-4(5H)-one;

5-methyl-2-((methylamino)methyl)-7-(2-((tetrahydro-2H-2H-pyran-4-yl)methoxy)pyridin-4-yl)thieno[3,2-c]pyridin-4(5H)-one;

7-(3,4-dimethoxyphenyl)-5-methyl-2-(pyrrolidin-1-ylmethyl)thieno[3,2-c]pyridin-4(5H)-one;

N-((7-(3,4-dimethoxyphenyl)-5-methyl-4-oxo-4,5-dihydrothieno[3,2-c]pyridin-2-yl)methyl)-N-methylmethanesulphonamide;

7-(3,4-dimethoxyphenyl)-2-((3,5-dimethylpiperazin-1-yl)methyl)-5-methylthieno[3,2-c]pyridin-4(5H)-one;

(S)-5-methyl-2-((3-methylmorpholino)methyl)-7-(3-((tetrahydro-2H-2H-pyran-4-yl)methoxy)phenyl)thieno[3,2-c]pyridin-4(5H)-one;
(R)-7-(3,4-dimethoxyphenyl)-5-methyl-2-((2-methylpiperazin-1-yl)methyl)thieno[3,2-c]pyridin-4(5H)-one;
(R)-1-((7-(3,4-dimethoxyphenyl)-5-methyl-4-oxo-4,5-dihydrothieno[3,2-c]pyridin-2-yl)methyl)piperazine-2-carboxamide;
(S)-7-(3,4-dimethoxyphenyl)-5-methyl-2-((3-methylpiperazin-1-yl)methyl)thieno[3,2-c]pyridin-4(5H)-one;
methyl 1-((7-(3,4-dimethoxyphenyl)-5-methyl-4-oxo-4,5-dihydrothieno[3,2-c]pyridin-2-yl)methyl)piperazine-2-carboxylate;
7-(3,4-dimethoxyphenyl)-2-((cis-2,6-dimethylpiperazin-1-yl)methyl)-5-methylthieno[3,2-c]pyridin-4(5H)-one;
(R)-2-((3-butylpiperazin-1-yl)methyl)-7-(3,4-dimethoxyphenyl)-5-methylthieno[3,2-c]pyridin-4(5H)-one;
(S)-7-(3,4-dimethoxyphenyl)-2-((3-ethylpiperazin-1-yl)methyl)-5-methylthieno[3,2-c]pyridin-4(5H)-one;
7-(3,4-dimethoxyphenyl)-5-methyl-2-((piperidin-4-ylamino)methyl)thieno[3,2-c]pyridin-4(5H)-one;
(S)-7-(3,4-dimethoxyphenyl)-5-methyl-2-((2-methylpiperazin-1-yl)methyl)thieno[3,2-c]pyridin-4(5H)-one;
2-((3-aminopyrrolidin-1-yl)methyl)-7-(3,4-dimethoxyphenyl)-5-methylthieno[3,2-c]pyridin-4(5H)-one;
2-((4-aminopipendin-1-yl)methyl)-7-(3,4-dimethoxyphenyl)-5-methylthieno[3,2-c]pyridin-4(5H)-one;
2-(((2-aminoethyl)(methyl)amino)methyl)-7-(3,4-dimethoxyphenyl)-5-methylthieno[3,2-c]pyridin-4(5H)-one;
(R)-7-(3,4-dimethoxyphenyl)-5-methyl-2-((2-methyl-4-(methylsulphonyl)piperazin-1-yl)methyl)thieno[3,2-c]pyridin-4(5H)-one;
(S)-7-(3,4-dimethoxyphenyl)-5-methyl-2-((3-methyl-4-(methylsulphonyl)piperazin-1-yl)methyl)thieno[3,2-c]pyridin-4(5H)-one;
methyl 1-((7-(3,4-dimethoxyphenyl)-5-methyl-4-oxo-4,5-dihydrothieno[3,2-c]pyridin-2-yl)methyl)-4-(methylsulphonyl)piperazine-2-carboxylate;
(R)-2-((3-butyl-4-(methylsulphonyl)piperazin-1-yl)methyl)-7-(3,4-dimethoxyphenyl)-5-methylthieno[3,2-c]pyridin-4(5H)-one;
(S)-7-(3,4-dimethoxyphenyl)-2-((3-ethyl-4-(methylsulphonyl)piperazin-1-yl)methyl)-5-methylthieno[3,2-c]pyridin-4(5H)-one;
(S)-7-(3,4-dimethoxyphenyl)-5-methyl-2-((2-methyl-4-(methylsulphonyl)piperazin-1-yl)methyl)thieno[3,2-c]pyridin-4(5H) one;
N-(1-((7-(3,4-dimethoxyphenyl)-5-methyl-4-oxo-4,5-dihydrothieno[3,2-c]pyridin-2-yl)methyl)pyrrolidin-3-yl)methanesulphonamide;
7-(4-((2-methoxyethyl)(methyl)amino)pyridin-2-yl)-5-methyl-2-((4-(methylsulphonyl)piperazin-1-yl)methyl)thieno[3,2-c]pyridin-4(5H)-one;
5-methyl-2-((4-(methylsulphonyl)piperazin-1-yl)methyl)-7-(pyridin-3-yl)thieno[3,2-c]pyridin-4(5)-one;
7-(3,4-dichlorphenyl)-5-methyl-2-((4-(methylsulphonyl)piperazin-1-yl)methyl)thieno[3,2-c]pyridin-4(5H)-one;
7-(4-(aminomethyl)phenyl)-5-methyl-2-((4-(methylsulphonyl)piperazin-1-yl)methyl)thieno[3,2-c]pyridin-(5H)-one;
7-(3-(benzyloxy)-4-methoxyphenyl)-5-methyl-2-((4-(methylsulphonyl)piperazin-1-yl)methyl)thieno[3,2-c]pyridin-4(5H)-one;
(R)-7-(4-methoxyphenyl)-5-methyl-2-((2-methyl-4-(methylsulphonyl)piperazin-1-yl)methyl)thieno[3,2c]pyridin-4(5H)-one;
5-methyl-2-(((R)2-methyl-4-(methylsulphonyl)piperazin-1-yl)methyl)-7-(5-(1-(pyridine-2-yl)ethoxy)pyridine-3-yl)thieno[3,2-c]pyridin-4(5H)-one;
(R)-7-(3-methoxyphenyl)-5-methyl-2-((2-methyl-4-(methylsulphonyl)piperazin-1-yl)methyl)thieno[3,2-c]pyridin-4(5H)-one;
(R)-N-(4-(5-methyl-2-((2-methyl-4-(methylsuphonyl)piperazin-1-yl)methyl)-4-oxo-4,5-dihydrothieno[3,2-c]pyridin-7-yl)pyridine-2-acetamide;
(R)-5-methyl-2-((2-methyl-4-(methylsulphonyl)piperazin-1-yl)methyl)-7-phenylthieno[3,2-c]pyridin-4(5H)-one;
5-methyl-2-((4-(methylsulphonyl)piperazin-1-yl)methyl)-7-(p-tolyl)thieno[3,2-c]pyridin-4(5H)-one;
(R)-7-(2-methoxypyridin-4-yl)-5-methyl-2-((2-methyl-4-(methylsulphonyl)piperazin-1-yl)methyl)thieno[3,2-c]pyridin-4(5H)-one;
(R)-7-(5-methoxypyridin-3-yl)-5-methyl-2-((2-methyl-4-(methylsulphonyl)piperazin-1-yl)methyl)thieno[3,2-c]pyridin-4(5H)-one;
(R)-7-(6-methoxypyridin-3-yl)-5-methyl-2-((2-methyl-4-(methylsulphonyl)piperazin-1-yl)methyl)thieno[3,2-c]pyridin-4(5H)-one;
(R)-5-methyl-2-((2-methyl-4-(methylsulphonyl)piperazin-1-yl)methyl)-7-(pyridin-2-yl)thieno[3,2-c]pyridin-4(5H)-one;
5-methyl-2-((4-(methylsulphonyl)piperazin-1-yl)methyl)-7-(3-(trifluoromethyl)phenyl)thieno[3,2-c]pyridin-4(5H)-one;
N-benzyl-3-(5-methyl-2-((4-(methylsulphonyl)piperazin-1-yl)methyl)-4-oxo-4,5-dihydrothieno[3,2-c]pyridin-7-yl)benzamide;
(R)-7-(6-hydroxypyridin-4-yl)-5-methyl-2-((2-methyl-4-(methylsulphonyl)piperazin-1-yl)methyl)thieno[3,2-c]pyridin-4(5H)-one;
5-methyl-2-((4-(methylsulphonyl)piperazin-1-yl)methyl)-7-(o-tolyl)thieno[3,2-c]pyridin-4(5H)-one;
(S)-7-(6-methoxypyridin-3-yl)-5-methyl-2-((2-methyl-4-(methylsulphonyl)piperazin-1-yl)methyl)thieno[3,2-c]pyridin-4(5H)-one;
(S)-5-methyl-2-((2-methyl-4-(methylsulphonyl)piperazin-1-yl)methyl)-7-(pyridin-4-yl)thieno[3,2-c]pyridin-4(5H)-one;
(S)-5-methyl-2-((2-methyl-4-(methylsulphonyl)piperazin-1-yl)methyl)-7-(pyridin-3-yl)thieno[3,2-c]pyridin-4 (5H)-one;
(S)-7-(5-methoxypyridin-3-yl)-5-methyl-2-((2-methyl-4-(methylsulphonyl)piperazin-1-yl)methyl)thieno[3,2-c]pyridin-4(5H)-one;
(S)-7-(4-methoxy-2-methylphenyl)-5-methyl-2-((2-methyl-4-(methylsulphonyl)piperazin-1-yl)methyl)thieno[3,2-c]pyridin-4(5H)-one;
(S)-7-(3-(benzyloxy)-4-methoxyphenyl)-5-methyl-2-((2-methylpiperazin-1-yl)methyl)thieno[3,2-c]pyridin-4 (5H)-one;
5-ethyl-2-((4-(methylsulphonyl)piperazin-1-yl)methyl)-7-phenylthieno[3,2-c]pyridin-4(5H)-one;
7-(3,4-dimethoxyphenyl)-5-ethyl-2-((4-(methylsulphonyl)piperazin-1-yl)methyl)thieno[3,2-c]pyridin-4 (5H)-one;
2-((4-acetylpiperazin-1-yl)methyl)-5-ethyl-7-phenylthieno[3,2-c]pyridin-4(5H)-one;
2-((4-acetylpiperazin-1-yl)methyl)-7-(3,4-dimethoxyphenyl)-5-ethylthieno[3,2-c]pyridin-4(5H)-one;
(R)-N-(4-(2-((4-(ethylsulfonyl)-2-methylpiperazin-1-yl)methyl)-5-methyl-4-oxo-4,5-dihydrothieno[3,2-c]pyridin-7-yl)pyridin-2-yl)acetamide;

N-(4-(2-((3-isopropylmorpholine)methyl)-5-methyl-4-oxo-4,5-dihydrothieno[3,2-c]pyridin-7-yl)pyridin-2-yl)acetamide;

(R)-N-(4-(2-((3-fluoropyrrolidin-1-yl)methyl)-5-methyl-4-oxo-4,5-dihydrothieno[3,2-c]pyridin-7-yl)pyridin-2-yl)acetamide;

(R)-N-(4-(2-((3-hydroxypyrrolidin-1-yl)methyl)-5-methyl-4-oxo-4,5-dihydrothieno[3,2-c]pyridin-7-yl)pyridin-2-yl)acetamide;

N-(4-(2-((3-fluoropiperidin-1-yl)methyl)-5-methyl-4-oxo-4,5-dihydrothieno[3,2-c]pyridin-7-yl)pyridin-2-yl)acetamide;

N-(4-(5-methyl-4-oxo-2-((3-(trifluoromethyl)pyrrolidin-1-yl)methyl)-4,5-dihydrothieno[3,2-c]pyridin-7-yl)pyridin-2-yl)acetamide;

1-((7-(2-acetamidopyridin-4-yl)-5-methyl-4-oxo-4,5-dihydrothieno[3,2-c]pyridin-2-yl)methyl)piperidine-2-carboxamide;

N-(4-(5-methyl-2-((2-methylmorpholino)methyl)-4-oxo-4,5-dihydrothieno[3,2-c]pyridin-7-yl)pyridin-2-yl)acetamide;

N-(4-(2-((2,6-dimethylmorpholino)methyl)-5-methyl-4-oxo-4,5-dihydrothieno[3,2-c]pyridin-7-yl)pyridin-2-yl)acetamide;

N-(4-(2-((3,5-dimethylmorpholino)methyl)-5-methyl-4-oxo-4,5-dihydrothieno[3, 2-c]pyridin-7yl)pyridin-2-yl)acetamide;

N-(4-(2-(((2R,3R)-2,3-dimethylmorpholino)methyl)-5-methyl-4-oxo-4,5-dihydrothieno[3,2-c]pyridin-7-yl)pyridin-2-yl)acetamide;

N-(4-(2-((3-fluoropyrrolidin-1-yl)methy)-5-methy-4-oxo-4,5-dihydrothieno[3,2-c]pyridin-7-yl)pyridin-2-yl)acetamide;

N-(4-(2-(((2S,6R)-2,6-dimethylmorpholino)methyl)-5-methyl-4-oxo-4,5-dihydrothieno[3,2-c]pyridin-7-yl)pyridin-2-yl)acetamide;

N-(4-(5-methyl-4-oxo-2-((2-(trifluoromethyl)pyrrolidin-1-yl)methyl)-4,5-dihydrothieno[3,2-c]pyridin-7-yl)pyridin-2-yl)acetamide;

N-(4-(2-((2,5-dimethylmorpholino)methyl)-5-methyl-4-oxo-4,5-dihydrothieno[3,2-c]pyridin-7-yl)pyridin-2-yl)acetamide;

(S)-N-(4-(2-((3-hydroxypiperidin-1-yl)methyl)-5-methyl-4-oxo-4,5-dihydrothieno[3,2-c]pyridin-7-yl)pyridin-2-yl)acetamide;

(S)-N-(4-(2-((3-hydroxypyrrolidin-1-yl)methyl)-5-methyl-4-oxo-4,5-dihydrothieno[3,2-c]pyridin-7-yl)pyridin-2-yl)acetamide;

(R)-N-(4-(2-((3-hydroxypiperidin-1-yl)methyl)-5-methyl-4-oxo-4,5-dihydrothieno[3,2-c]pyridin-7-yl)pyridin-2-yl)acetamide;

(S)-N-(4-(2-((3-fluoropyrrolidin-1-yl)methyl)-5-methyl-4-oxo-4,5-dihydrothieno[3,2-c]pyridin-7-yl)pyridin-2-yl)acetamide;

N-(4-(2-((3-methoxypipendin-1-yl)methyl)-5-methyl-4-oxo-4,5-dihydrothieno[3,2-c]pyridin-7-yl)pyridin-2-yl)acetamide;

N-(4-(2-((3-hydroxyazetidine-1-yl)methyl)-5-methyl-4-oxo-4,5-dihydrothieno[3,2-c]pyridin-7-yl)pyridin-2-yl)acetamide;

N-(4-(2-((3,3-difluoropipenidin-1-yl)methyl)-5-methyl-4-oxo-4,5-dihydrothieno[3,2-c]pyridin-7-yl)pyridin-2-yl)acetamide;

(R)-7-(2-ethoxy)pyridin-4-yl)-5-methyl-2-((2-methyl-4-(methylsulfonyl)piperazin-1-yl)methyl)thieno[3,2-c]pyridin-4(5H)-one;

(R)-7-(2-(cyclopropylmethoxy)pyridin-4-yl)-5-methy-2-((2-methyl-4-(methylsulfonyl)piperazin-1-yl)methyl)thieno[3,2-c]pyridin-4(5H)-one;

(R)-5-methyl-2-((2-methyl-4-(methylsulfonyl)piperazin-1-yl)methyl)-7-(2-(2-(pyrrolidin-1-yl)ethoxy)pyridin-4-yl)thieno[3,2-c]pyridin-4(5H)-one;

(R)-7-(2-(2-methoxyethoxy)pyridin-4-yl)-5-methyl-2-((2-methyl-4-(methylsulfonyl)piperazin-1-yl)methyl)thieno[3,2-c]pyridin-4(5H)-one;

(R)-7-(3-methoxypyridin-4-yl)-5-methyl-2-((2-methyl-(methylsulfonyl)piperazin-1-yl)methyl)thieno[3,2-c]pyridin-4(5H)-one;

(R)-7-(3-(cyclopropylmethoxy)pyridin-4-yl)-5-methyl-2-((2-methyl-4-(methylsulfonyl)piperazin-1-yl)methyl)thieno[3,2-c]pyridin-4(5H)-one;

(R)-5-methyl-2-((2-methyl-4-(methylsulfonyl)piperazin-1-yl)methyl)-7-(2-(2-(2-oxopyrrolidin-1-yl)ethoxy)pyridin-4-yl)thieno[3,2-c]pyridin-4(5H)-one;

(R)-7-(5-(cyclopropylmethoxy)pyridin-3-yl)-5-methyl-2-((2-methyl-4-(methylsulfonyl)piperazin-1-yl)methyl)thieno[3,2-c]pyridin-4(5H)-one;

2-((3-hydroxypiperidin-1-yl)methyl)-7-(2-methoxypyridin-4-yl)-5-methylthieno[3,2-c]pyridin-4(5H)-one;

7-(2-ethoxypyridin-4-yl)-2-((3-hydroxypiperidin-1-yl)methyl)-5-methylthieno[3,2-c]pyridin-4(5H)-one;

(R)-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)propionamide;

(R)-2-cyclopropyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

(R)-N-methyl-N-(4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

(R)-N-(6-(cyclopropyl methoxy)-4-(5-methyl-2-((2-methyl-4-(methylsulfonyl)piperazin-1-yl)methyl)-4-oxo-4,5-dihydrothieno[3,2-c]pyridin-7-yl)pyridin-2-yl)acetamide;

2-((1,4-oxazepan-4-yl)methyl)-5-methyl-7-(2-((tetrahydro-2H-2H-pyran-4-yl)methoxy)pyridin-4-yl)thieno[3,2-c]pyridin-4(5H)-one;

5-methyl-2-(morpholinomethyl)-7-(2-((tetrahydro-2H-pyran-4-yl)methoxy)pyridin-4-yl)thieno[3,2-c]pyridin-4(5H)-one;

2-((1,4-diazepan-1-yl)methyl)-5-methyl-7-(2-((tetrahydro-2H-pyran-4-yl)methoxy)pyridin-4-yl)thieno[3,2-c]pyridin-4(5H)-one;

5-methyl-2-((4-methyl-1,4-diazepan-1-yl)methyl)-7-(2-((tetrahydro-2H-pyran-4-yl)methoxy)pyridin-4-yl)thieno[3,2-c]pyridin-4(5H)-one;

2-((1,4-diazepan-1-yl)methyl)-5-methyl-7-(2-((pyridin-2-ylmethyl)amino)pyridin-4-yl)thieno[3,2-c]pyridin-4(5H)-one;

2-((1,4-diazepan-1-yl)methyl)-5-methyl-7-(3-(pyridin-2-ylmethoxy)phenyl)thieno[3,2-c]pyridin-4(5H)-one;

2-((1,4-diazepan-1-yl)methyl)-5-methyl-7-(2-(pyridin-2-ylmethoxy)pyridin-4-yl)thieno[3,2-c]pyridin-4(5H)-one;

2-((1,4-diazepan-1-yl)methyl)-7-(2-(benzyloxy)pyridin-4-yl)-5-methylthieno[3,2-c]pyridin-4(5H)-one;

1-((7-(3,4-dimethoxyphenyl)-5-methyl-4-oxo-4,5-dihydrothieno[3,2-c]pyridin-2-yl)methyl)-N,3-dimethylpiperidine-3-carboxamide;

7-(3,4-dimethoxyphenyl)-2-((3-(hydroxymethyl)-3-methylpiperidin-1-yl)methyl)-5-methylthieno[3,2-c]pyridin-4(5H)-one;

7-(3,4-dimethoxyphenyl)-2-(((1,1-dioxidotetrahydrothiophen-3-yl)amino)methyl)-5-methylthieno[3,2-c]pyridin-4(5H)-one;

7-(3,4-dimethoxyphenyl)-2-(((1, I-dioxidotetrahydro-2H-thiopyran-4-yl)amino)methyl)-5-methylthieno[3,2-c]pyridin-4(5H)-one;

7-(3,4-dimethoxyphenyl)-5-methyl-2-((methylamino)methyl)thieno[3,2-c]pyridin-4(5H)-one;

7-(3,4-dimethoxyphenyl)-2-((3-(methoxymethyl)-3-methylpiperidin-1-yl)methyl)-5-methylthieno[3,2-c]pyridin-4(5H)-one;

2-((3-((cyclopropylmethoxy)methyl)-3-methylpiperidin-1-yl)methyl)-7-(3,4-dimethoxyphenyl)-5-methylthieno[3,2-c]pyridin-4 (5H)-one;

7-(2,6-dimethylphenyl)-5-methyl-2-((4-(methylsulfonyl)piperazin-1-yl)methyl)thieno[3,2-c]pyridin-4(5H)-one;

5-methyl-7-(5-((tetrahydro-2H-pyran-4-yl) methoxy)pyridin-3-yl)-2-((2,2,4-trimethylpiperazine-1-yl)methyl)thieno[3,2-c]pyridin-4(5H)-one;

N-(3-(5-methyl-2-((2-methylpyrrolidin-1-yl)methyl)-4-oxo-4,5-dihydrothieno[3,2-c]pyridin-7-yl)phenyl)acetamide;

N-(4-(2-((2, 3-dimethylpiperidine-1-yl)methyl)-5-methyl-4-oxo-4,5-dihydrothieno[3,2-c]pyridin-7-yl)pyridin-2-yl)acetamide;

N-(4-(5-methyl-4-oxo-2-(piperidin-1-ylmethyl)-4,5-dihydrothieno[3,2-c]pyridin-7-yl)pyridin-2-yl)acetamide;

1-((7-(3,4-dimethoxyphenyl)-5-methyl-4-oxo-4,5-dihydrothieno[3,2-c]pyridin-2-yl)methyl)-N,N,3-trimethylpipendine-3-carboxamide;

2-((3-((cyclopropylmethoxy)methyl)-3-methylpyrrolidin-1-yl)methyl)-7-(3,4-dimethoxyphenyl)-5-methylthieno[3,2-c]pyridin-4(5h)-one;

2-((1,4-diazepan-1-yl)methyl)-5-methyl-7-(3-((pyridin-2-ylmethyl)amino)phenyl)thieno[3,2-c]pyridin-4(5H)-one;

5-methyl-2-((4-methyl-1,4-diazepan-1-yl)methyl)-7-(3-((pyridin-2-ylmethyl)amino)phenyl)thieno[3,2-c]pyridin-4(5H)-one;

N-(3-(2-((1,4-diazepan-1-yl)methyl)-5-methyl-4-oxo-4, 5-dihydrothieno[3,2-c]pyridin-7-yl)phenyl)picolinamide;

2-((4-acetyl-2-methylpiperazin-1-yl)methyl)-5-methyl-7-(2-((tetrahydro-2H-pyran-4-yl)methoxy)pyridin-4-yl)thieno[3,2-c]pyridin-4(5H)-one;

5-methyl-2-((2-oxopiperazin-1-yl)methyl)-7-(2-((tetrahydro-2H-pyran-4-yl)methoxy)pyridin-4-yl)thieno[3,2-c]pyridin-4(5H)-one;

5-methyl-2-((4-methyl-2-oxopiperazin-1-yl)methyl)-7-(2-((tetrahydro-2H-pyran-4-yl)methoxy)pyridin-4-yl)thieno[3,2-c]pyridin-4(5H)-one;

7-(3-(dimethylamino)phenyl)-2-(((2-hydroxyethyl)(methyl)amino)methyl)-5-methylthieno[3,2-c]pyridin-4(5H)-one;

7-(3,4-dichlorophenyl)-2-(((2-hydroxyethyl)(methyl)amino)methyl)-5-methylthieno[3,2-c]pyridin-4(5H)-one;

4-(2-(((2-hydroxyethyl)(methyl)amino)methyl)-5-methyl-4-oxo-4,5-dihydrothieno[3,2-c]pyridin-7-yl)-2-(trifluoromethyl)benzonitrile;

or a pharmaceutically acceptable salt thereof.

12. A pharmaceutical composition comprising the compound or a pharmaceutically acceptable salt thereof as defined in claim 1 and one or more pharmaceutically acceptable carriers, diluents, or excipients.

13. The compound according to claim 1 which is (R)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one;

(S)-5-methyl-2-((4-(methylsulfonyl)piperazin-1-yl)methyl)-7-(5-(1-(pyridin-2-yl)ethoxy)pyridin-3-yl)thieno[3,2-c]pyridin-4(5H)-one;

(R)-N-(4-(2-(((3-fluoropiperidin-1-yl)methyl)-5-methyl-4-oxo-4,5-dihydrothieno[3,2-c]pyridin-7-yl)pyridin-2-yl)acetamide;

(S)-N-(4-(2-(((3-fluoropiperidin-1-yl)methyl)-5-methyl-4-oxo-4,5-dihydrothieno[3,2-c]pyridin-7-yl)pyridin-2-yl)acetamide;

N-(4-(2-(((3R,5S)-3,5-dimethylmorpholino)methyl)-5-methyl-4-oxo-4,5-dihydrothieno[3,2-c]pyridin-7-yl)pyridin-2-yl)acetamide;

or a pharmaceutically acceptable salt thereof.

\* \* \* \* \*